US012594292B2

(12) United States Patent
Hostetler et al.

(10) Patent No.: US 12,594,292 B2
(45) Date of Patent: Apr. 7, 2026

(54) ANTIVIRAL PRODRUGS, INTERMEDIATE-AND LONG-ACTING FORMULATIONS AND METHODS

(71) Applicant: The Regents of the University of California, Oakland, CA (US)

(72) Inventors: Karl Y. Hostetler, Oakland, CA (US); James Beadle, Oakland, CA (US); Nadejda Valiaeva, Oakland, CA (US); Robert T. Schooley, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/833,747

(22) PCT Filed: Jan. 26, 2023

(86) PCT No.: PCT/US2023/011639
§ 371 (c)(1),
(2) Date: Jul. 26, 2024

(87) PCT Pub. No.: WO2023/146974
PCT Pub. Date: Aug. 3, 2023

(65) Prior Publication Data

US 2025/0177428 A1 Jun. 5, 2025

Related U.S. Application Data

(60) Provisional application No. 63/303,376, filed on Jan. 26, 2022.

(51) Int. Cl.
*A61K 31/7068* (2006.01)
*A61K 31/7064* (2006.01)
*C07F 9/6558* (2006.01)
*C07F 9/6561* (2006.01)
*C07H 7/06* (2006.01)

(52) U.S. Cl.
CPC ...... *A61K 31/7068* (2013.01); *A61K 31/7064* (2013.01); *C07F 9/65586* (2013.01); *C07F 9/65616* (2013.01); *C07H 7/06* (2013.01)

(58) Field of Classification Search
None
See application file for complete search history.

(56) References Cited

U.S. PATENT DOCUMENTS

| | | | |
|---|---|---|---|
| 5,484,908 | A | 1/1996 | Froehler |
| 5,645,985 | A | 7/1997 | Froehler |
| 5,830,653 | A | 11/1998 | Froehler |
| 5,990,303 | A | 11/1999 | Seela |
| 6,303,315 | B1 | 10/2001 | Skouv |
| 6,639,059 | B1 | 10/2003 | Kochkine |
| 8,835,630 | B1 | 9/2014 | Hostetler |
| 2003/0092905 | A1 | 5/2003 | Kochkine |
| 2013/0029940 | A1 | 1/2013 | Hostetler et al. |
| 2014/0364397 | A1 | 12/2014 | Hostetler et al. |
| 2019/0083520 | A1 | 3/2019 | Painter et al. |
| 2020/0197422 | A1 | 6/2020 | Axt et al. |
| 2022/0081455 | A1 | 3/2022 | Lazerwith |
| 2022/0143052 | A1 | 5/2022 | Lazerwith |

FOREIGN PATENT DOCUMENTS

| | | | | |
|---|---|---|---|---|
| WO | WO-2015038596 | A1 * | 3/2015 | ......... A61K 31/7068 |
| WO | 2016044281 | A1 | 3/2016 | |
| WO | 2017048956 | A1 | 3/2017 | |
| WO | 2019053696 | A1 | 3/2019 | |
| WO | 2021222535 | A1 | 11/2021 | |
| WO | 2022020793 | A1 | 1/2022 | |
| WO | 2022046631 | A1 | 3/2022 | |
| WO | 2022081973 | A1 | 4/2022 | |
| WO | 2022265964 | A1 | 12/2022 | |
| WO | 2023146974 | A2 | 8/2023 | |
| WO | 2024159117 | A1 | 8/2024 | |

OTHER PUBLICATIONS

Beadle et al. Journal of Medicinal Chemistry (2006), 49(6), 2010-2015.*

PCT International Search Report and Written Opinion for PCT/US2023/011639, mailed Apr. 30, 2024 (14 pages).

Carlin, et al., "1-O-Octadecyl-2-O-benzyl-sn-glyceryl-3-phospho-GS-441524 (V2043). Evaluation of Oral V2043 in a Mouse Model of SARS-CoV-2 Infection and Synthesis and Antiviral Evaluation of Additional Phospholipid Esters with Enhanced Anti-SARS-CoV-2 Activity", J. Med. Chem. 2023, 66, 5802-5819.

De Wit, et al., "Prophylactic and therapeutic remdesivir (GS-5734) treatment in the rhesus macaque model of MERS-CoV infection", PNAS, Mar. 24, 2020, vol. 117, No. 12, 6771-6776.

Gordon, et al., "The antiviral compound remdesivir potently inhibits RNA-dependent RNA polymerase from Middle East respiratory syndrome coronavirus" J. Biol. Chem. (2020) 295(15), 4773-4779.

Halldorsson, et al., "Lipase-catalysed kinetic resolution of 1-O-alkylglycerols by sequential transesterification", Tetrahedron: Assymmetry, 15 (2004) 2893-2899.

Pruijssers, et al., "Remdesivir Inhibits SARS-CoV-2 in Human Lung Cells and Chimeric SARS-CoV Expressing the SARSCoV-2 RNA Polymerase in Mice", Cell Reports 32, 107940, Jul. 21, 2020.

Ruiz, et al., "Synthesis and antiviral evaluation of alkoxyalkyl-phosphate conjugates of cidofovir and adefovir", ScienceDirect, Antiviral Research, 75 (2007) 87-90.

(Continued)

*Primary Examiner* — Patrick T Lewis

(74) *Attorney, Agent, or Firm* — Eversheds-Sutherland (US) LLP

(57) ABSTRACT

Compounds and pharmaceutical formulations including a compound and an oil, which may be formulated for intermediate- or long-acting intramuscular injection. Methods for treating respiratory syncytial virus (RSV), human immunodeficiency virus (HIV), coronavirus, SARS CoV-2, and other RNA virus infections in mammals.

8 Claims, 18 Drawing Sheets

Specification includes a Sequence Listing.

(56) References Cited

OTHER PUBLICATIONS

Schooley, et al., "Rethinking Remdesivir: Synthesis, Antiviral Activity, and Pharmacokinetics of Oral Lipid Prodrugs", Antimicrobial Agents and Chemotherapy, Oct. 2021, vol. 65, Issue 10, e01155-21.
Tempestilli, et al., "Pharmacokinetics of remdesivir and GS-441524 in two critically ill patients who recovered from COVID-19", J. Antimicrob Chemother, 2020, 75:2977-2980.
Warren, et al., "Therapeutic efficacy of the small molecule GS-5734 against Ebola virus in rhesus monkeys", Nature, vol. 531, Mar. 17, 2016, 381-399.
Yan, et al., "Advantages of the Parent Nucleoside GS-441524 over Remdesivir for Covid-19 Treatment", ACS Med. Chem. Lett., 2020, 11, 1361-1366.
International Search Report and the Written Opinion for International Application No. PCT/US2021/043094, mailed Dec. 29, 2021, 10 pages.
Carlin, et al., "Oral pharmacokinetics and efficacy of oral phospholipid remdesivir nucleoside prodrugs against SARS-CoV-2 in mice", Antimicrobial Agents and Chemotherapy, American Society for Microbiology, pp. 1-13; Downloaded from https://journals.asm.org/journal/aac on Sep. 6, 2024.
Schooley et al, Rethinking Remdesivir: Synthesis of Lipid Prodrugs that Substantially 2 Enhance Anti-Coronavirus Activity, ioRxiv preprint doi: https://doi.org/10.1101/2020.08.26.269159; posted on Aug. 27, 2020.
Extended European Search Report issued in European application No. 23747606.4, dated Sep. 8, 2025 (14 pages).

* cited by examiner

ANTIVIRAL PRODRUGS, INTERMEDIATE-AND LONG-ACTING FORMULATIONS AND METHODS

CROSS REFERENCE TO RELATED APPLICATIONS

This application claims the priority benefit of PCT/US2023/011639, filed on Jan. 26, 2023, which claims the priority to U.S. Provisional Patent Application No. 63/303,376, filed Jan. 26, 2022, which is incorporated by reference herein.

GOVERNMENT SPONSORSHIP

This invention was made with government support under AI131424 and AI161348 awarded by the National Institutes of Health. The government has certain rights in the invention.

SEQUENCE LISTING

The instant application contains a Sequence Listing which has been submitted electronically in ST.26 XML format and is hereby incorporated by reference in its entirety. Said ST.26 XML copy, created on Mar. 16, 2023, is named Sequence_Listing.xml and is 5,000 bytes in size.

TECHNICAL FIELD

The present disclosure relates to antiviral prodrugs, methods for producing antiviral prodrugs, methods of treatment, and pharmaceutical formulations, such as long- or intermediate-acting formulations, of antiviral prodrugs for treatment of various diseases, such as SARS CoV-2 infections or human immunodeficiency infections, in mammals.

BACKGROUND

Over the past 18 years, spillover events have introduced the highly transmissible beta-coronavirus strains SARS CoV, MERS CoV, SARS CoV-2 into the human population (see, e.g., Zhong N. S., et. al. *Lancet* 2003; 362:1353-1358; Zaki, A. M., et. al., *N Engl J Med* 2012; 367:1814-1820; and Zhu N., et. al. *N Engl J Med.* 2020; 382:727-733). Although case fatality ratios have varied, each has demonstrated the ability to induce substantial morbidity and mortality—especially among those over 55 and/or those with underlying co-morbid medical conditions (see, e.g., Wu C., et. al., *JAMA Intern Med* 2020; 180: 934-943; and Zhou F. et. al. *Lancet* 2020; 395:1054-1062). Although SARS CoV and MERS CoV were largely contained by epidemiological interventions, the current outbreak evolved into a global pandemic responsible for hundreds of millions of infections and over five million deaths (see, e.g., Johns Hopkins Coronavirus Resource Center https://coronavirus.jhu.edu/map.html (accessed Jan. 16, 2022). Intensive efforts to develop COVID vaccines have resulted in the development of a number of highly effective vaccines that provide substantial levels of protection from severe disease and death (see, e.g., Polack F. P. et. al. *N Engl J Med* 2021; 383; 2603-2615, and Baden L. R. *N Engl J Med.* 2021; 384:403-416). In the case of even the most effective vaccines, immunity begins to wane within 5 months (see, e.g., Keehner J. et. al, *N Engl J Med.* 2021; 384:1774-1775). Despite their effectiveness, vaccine hesitancy is widespread and up to 50% of people in many parts of the world have declined vaccination (see, e.g., Daniel C. N. et. al. *Vaccine.* 2022: S0264-410X(21)01667-4). Substantial subgroups of the population are immunocompromised and/or have underlying conditions that limit vaccine effectiveness. Thus, despite major successes in vaccine development, the SARS CoV-2 infection rate remains high and COVID-related morbidity and mortality should be anticipated to persist in the years to come without effective antiviral therapeutics.

Antiviral therapeutic efforts have included both monoclonal antibodies directed at neutralizing epitopes on the viral spike protein and small molecules directed at the viral RNA-dependent RNA polymerase or the virus' 3-CL like protease enzyme. Remdesivir nucleoside triphosphate (RVn triphosphate) potently inhibits enzymatic activity of the polymerase of every coronavirus tested thus far, including SARS CoV-2. Remdesivir also inhibits the polymerases of a number of other pathogenic RNA viruses, including Ebola virus, Nipah virus and respiratory syncytial virus (see, e.g., Wang M., et. al., *Cell Res* 2020; 30:269-271; Yan V. C, e.g., *ACS Med Chen Lett.* 2020; 11:1361-1366; and Mulangu S. et. al, *N Engl J Med* 2019; 381:2293-2303).

Clinical trials of antiviral agents for COVID-19 (including remdesivir) have demonstrated maximal benefit when employed prior to hospitalization (see, e.g., Gotttlieb R L *New Engl J Med,* 2021 Dec. 22: NEJMoa2116846). Remdesivir can reduce hospitalization or death by 85-90% when administered as three daily intravenous infusions prior to hospitalization. This approach, while highly effective, is extremely challenging to take to scale since it requires three sequential days of intravenous infusion of SARS CoV-2 infected patients. The approach, nonetheless, is a proof of concept that early remdesivir can have a substantial impact on the disease if employed early enough in the illness. The availability of a remdesivir prodrug that could be administered orally for a week or intramuscularly on a single occasion to outpatients with SARS CoV-2 who are at risk for severe COVID-19 disease would greatly extend the clinical reach of this agent in the treatment of COVID-19 and, potentially, for the treatment of Ebola, Nipah, and RSV infection. Sustained release injectable formulations of remdesivir prodrugs are of interest because RDV is not highly bioavailable following oral administration and must be administered intravenously, thereby, in many instances, severely complicating its administration to high-risk patients prior to hospitalization with relatively advanced disease. A long-acting formulation of remdesivir nucleoside monophosphate, which might enable plasma antiviral activity above the 90% effective concentration for at least about 5 to about 10 days after a single intramuscular or subcutaneous dose, would be particularly useful.

Antiretroviral therapy (ART) has resulted in enormous reductions in HIV-1 related morbidity and mortality in the US and globally (see, e.g., Walensky R. P. et. al., *J Infect Dis* 2006; 194:11-19; and April M. D., et. al. *J Infect Dis.* 2014; 209:491-9). By 2021, 28 million of the 38 million people with HIV infection were receiving antiretroviral therapy (see, e.g., https://www.unaids.org/en/resources/fact-sheet (accessed Jan. 19, 2022)). Of those in antiretroviral therapy, it is estimated that as many as 90% may be fully virally suppressed in resource rich settings. Since plasma HIV-1 RNA levels are not routinely measured in sub-Saharan Africa, the fraction of the HIV-1 infected population currently on fully effective therapy is not known but is likely substantially lower. Prevention of transmission of HIV-1 is also an urgent global priority. With the demonstration that the likelihood of transmission of HIV is directly related to plasma (and by extension genital) levels of HIV-1 (see, e.g.

Quinn T. C., et. al., *N Engl J Med* 2000; 342:921-929), there has been increasing optimism that the epidemic might be ended by an aggressive global expansion of antiretroviral therapy used for both treatment and prevention (see, e.g., Granich R. M., et. al., *N Engl J Med* 2000; 342:921-929). Indeed, reductions in incident infections related to treatment of HIV-1 infected individuals been demonstrated both in clinical trials and at the population level (see, e.g., Cohen M. S., et. al., *N Engl J Med.* 2011; 365:493-505; Montaner J. S., et. al., *Lancet* 2010; 376: 532-539; Montaner J. S., et. al., *PLoS One* 2014; 9: e87872; and Tanser J. F., et. al., *Science* 2013. 339: 966-971). One and a half million people were newly infected in 2020. Despite early optimism about the development of an effective AIDS vaccine, there are few real insights into how to elicit protective responses with scalable commercial vaccine products. Treatment of high risk. HIV-1 uninfected persons (termed pre-exposure prophylaxis or "PrEP") has been effective in some populations, but not in others with protection rates ranging from 0-62% (see, e.g., Grant R. M. *N Engl J Med* 2010; 363:2587-2599; Baeten J. M., et. al., *N Engl J Med* 2012; 367:399-410; Thigpen M C. *N Engl J Med.* 2012; 367:423-434; Choopanya K, et al. *Lancet* 2013; 381:2083-90; Van Damme L, et. al, *N Engl J Med.* 2012; 367:411-22; and Marrazzo J. M., et. al., *N Engl J Med* 2015; 372:509-18). PrEP is effective if adherence is high but persons at the highest risk for HIV-1 infection are often those facing the greatest barriers to adherence. The failure of the large FEM PrEP and VOICE trials to demonstrate any degree of protection despite concurrent assessments of 88-90% adherence by self-report and returned product counts has only underlined the adherence challenges posed by oral PrEP (see, e.g., Van Damme L, et. al., *N Engl J Med.* 2012; 367:411-22; and Marrazzo J. M., et. al., *N Engl J Med* 2015; 372:509-18). Nonetheless, the results from the oral and topical PrEP trials involving TFV were perhaps more consistent than they might seem: high levels of protection can be achieved when active concentrations of drug are present at the time of exposure. The dual benefits of ART that include improving the health of HIV-1 infected persons receiving therapy and reducing the likelihood of viral transmission have made rapid expansion of antiretroviral therapy a major global priority (see, e.g., UNAIDS. 90-90-90 An Ambitious Treatment Target to help end the AIDS epidemic. Geneva, Switzerland 2014. Available at: http://www.unaids.org/sites/default/files/media_asset/90-90-90_en_0.pdf).

With mitigation of many of the acute and chronic toxicities of first generation ARVs by several currently available once-a-day single tablet regimens (STR), treatment adherence has emerged as the greatest barrier to long-term treatment success. Although most patients can adhere to daily regimens, many of the most vulnerable populations (for prevention and therapy) include those whose adherence is challenged by mental health issues, substance use, and stigma. The development of effective, inexpensive, well-tolerated, convenient modalities that maintain active concentrations at sites of viral replication and exposure for prolonged periods of time would represent a major advance for ART for both treatment and prevention. Long-acting injectable products such as cabotegravir, rilpivirine and islatravir have provided a proof of concept of this approach (see, e.g., Margolis D. A., et. al., *Lancet Infect Dis.* 2015; 15:1145-55; Verloes R, et. al., *HIV Med.* 2015; 16:477-84; and Mattthers R. P., et. al., *Nature Med.* 2021; 27, 1712-1717). The recent decision of the FDA to place trials of islatravir on clinical hold because of leucopenia in a subset of patients underlines the need to develop agents within multiple classes if long-acting ART is to be of widespread use in patient populations vulnerable to different toxicities and with viruses of differing drug susceptibility.

There remains a need for pharmaceutical formulations that can be delivered in various ways, such as intramuscularly. There also remains a need for pharmaceutical formulations that are long-acting, such as formulations that can provide effective plasma levels for extended periods after infrequent administration, such as once monthly.

BRIEF SUMMARY

Provided herein are compounds, such as antiviral prodrugs, and pharmaceutical formulations that overcome one or more of the disadvantages of currently used drugs and/or formulations. For example, embodiments of the compounds and pharmaceutical formulations provided herein include orally useful antiviral prodrugs that may specifically target organs where viral replication is maximal and be conveniently administered at scale in any disease stage. For oral use and enhanced lung exposure, some embodiments of the prodrugs of RVn or formulations provided herein can accomplish one or more of the following: 1) kinase bypass of the first nucleoside phosphorylation, 2) provide increased oral bioavailability, 3) deliver antivirally significant concentrations to lung and gastrointestinal tract and formulations which may provide for sustained levels in plasma for 5 to 30 days following a single injection. Also provided herein are methods for the synthesis and antiviral evaluation of the compounds, including novel lipophilic prodrugs of RVn-monophosphate that are substantially more active than remdesivir in Vero E6 cells infected with SARS-CoV-2. Not wishing to be bound by any particular theory, embodiments of the compounds herein are prodrugs that may allow earlier and/or more effective treatment at the time of diagnosis of SARS-CoV-2 infection. The prodrugs herein may represent an approach that may be able to target the antiviral to the lung and away from the liver where remdesivir's major dose limiting is directed.

In one aspect, compounds, including antiviral prodrugs, are provided herein. In some embodiments, the compounds have a structure according to formula (I):

formula (I)

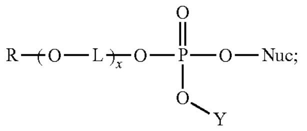

wherein Nuc is selected from the group consisting of an antiviral nucleoside and an antiviral nucleoside analog; Y is independently selected from the group consisting of hydrogen, a $C_1$-$C_{30}$ hydrocarbyl, a pharmaceutically acceptable cation, and a covalent bond to a carbon atom of a five-carbon sugar moiety of the antiviral nucleoside or the antiviral nucleoside analog; x is 0 or 1; L is independently a $C_1$-$C_{30}$ hydrocarbyl (such as a $C_1$-$C_6$ hydrocarbyl); and R is independently selected from the group consisting of a $C_{10}$-$C_{30}$ hydrocarbyl and a substituent of formula (A);

formula (A)

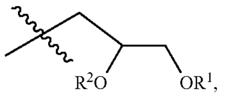

wherein $R^1$ and $R^2$ are independently selected from the group consisting of hydrogen and a $C_1$-$C_{30}$ hydrocarbyl.

In another aspect, pharmaceutical formulations are provided. In some embodiments, the pharmaceutical formulations include an oil and one or more compounds described herein. The pharmaceutical formulations may be formulated for injection, such as intramuscular injection or subcutaneous injection. The pharmaceutical formulations may be orally bioavailable.

In a further aspect, methods of treatment are provided, such as methods for treating a virus (e.g., coronavirus), including virus infections in mammals. In some embodiments, the methods include administering an effective amount of a compound described herein, or a pharmaceutical formulation described herein.

In a still further aspect, methods of producing a compound, such as a prodrug, are provided. In some embodiments, the methods include (i) providing a compound of formula (a)— formula (a)

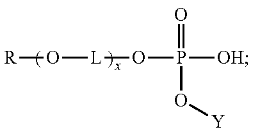

(ii) providing a compound of formula (b)— formula (b)

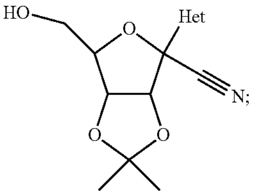

(iii) contacting the compound of formula (a) and the compound of formula (b) to form a compound of formula (c)— formula (c)

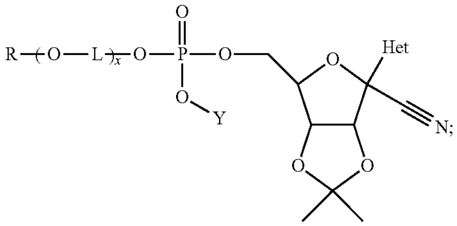

and (iv) contacting the compound of formula (c) with an acid to form a compound of formula (d)— formula (d)

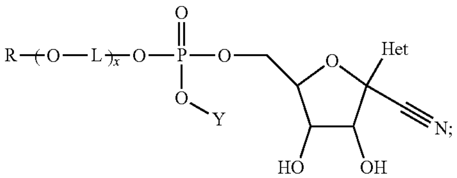

wherein Het is a $C_1$-$C_{30}$ hydrocarbyl including at least one heteroatom; Y is selected from the group consisting of hydrogen, a $C_1$-$C_{30}$ hydrocarbyl, and a pharmaceutically acceptable cation; x is 0 or 1; L is a $C_1$-$C_{30}$ hydrocarbyl (such as a $C_1$-$C_6$ hydrocarbyl); and R is selected from the group consisting of a $C_{10}$-$C_{30}$ hydrocarbyl and a substituent of formula (A);

formula (A)

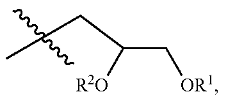

wherein $R^1$ and $R^2$ are independently selected from the group consisting of hydrogen and a $C_1$-$C_{30}$ hydrocarbyl. The methods may include performing an intramolecular esterification reaction of a product, such as a phosphodiester, to form a cyclic phosphate, such as a 3',5'-cyclic phosphate.

In yet another aspect, methods of producing a drug triphosphate also are provided. In some embodiments, the methods include providing a plurality of cells, contacting the plurality of cells with an amount of a drug, incubating the plurality of cells and the amount of the drug for period effective to form the drug triphosphate.

Additional aspects will be set forth in part in the description which follows, and in part will be obvious from the description, or may be learned by practice of the aspects described herein. The advantages described herein may be realized and attained by means of the elements and combinations particularly pointed out in the appended claims. It is to be understood that both the foregoing general description and the following detailed description are exemplary and explanatory only and are not restrictive.

DETAILED DESCRIPTION

Figure 1A:
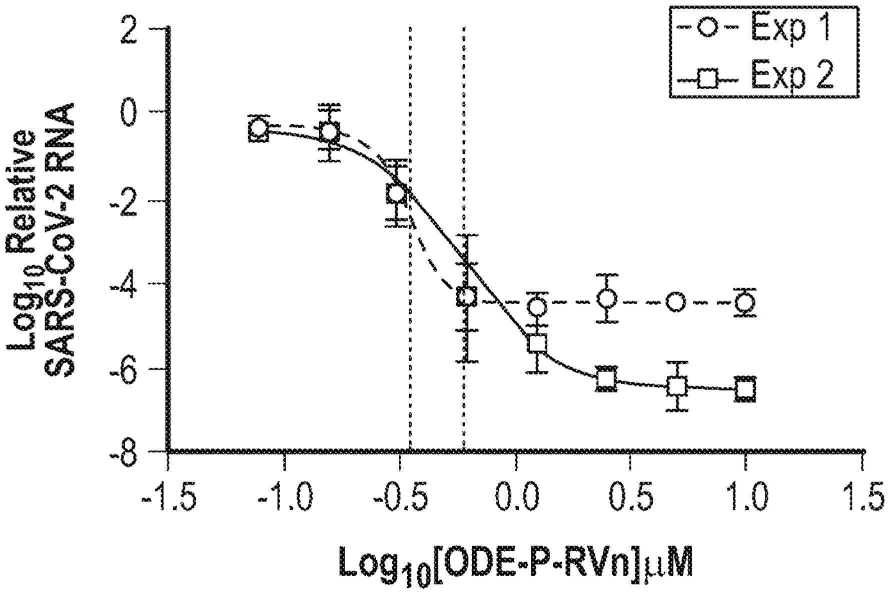
FIG. 1A-FIG. 1F depict concentration-response curves for ODBG-P-RVn, ODE-P-RVn, and HDP-P-RVn (4b), remdesivir (RDV), and remdesivir nucleoside (RVn) for SARS-CoV-2 infection in Vero E6 cells in two separate experiments performed in duplicate.
Figure 1B:
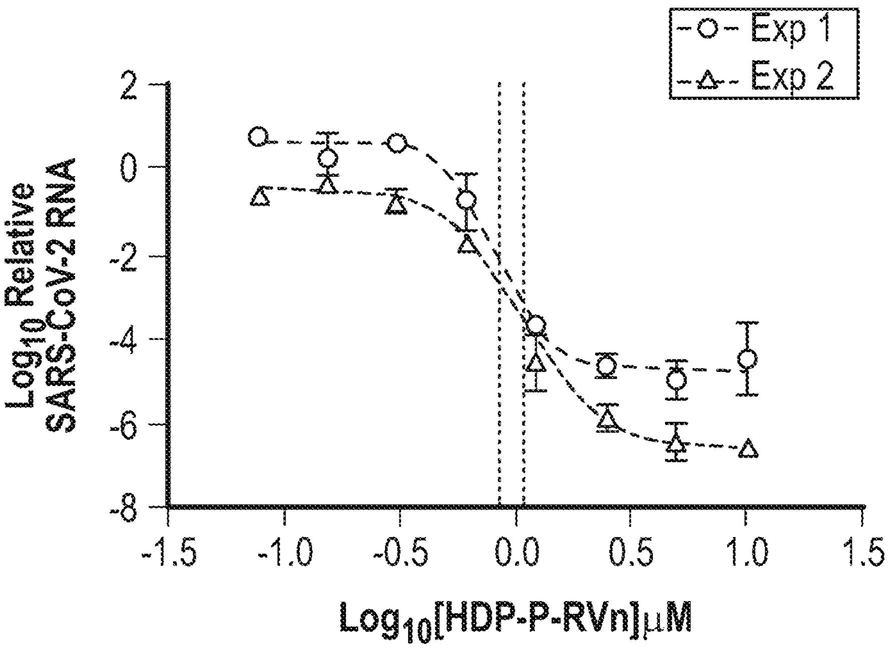
Figure 1C:
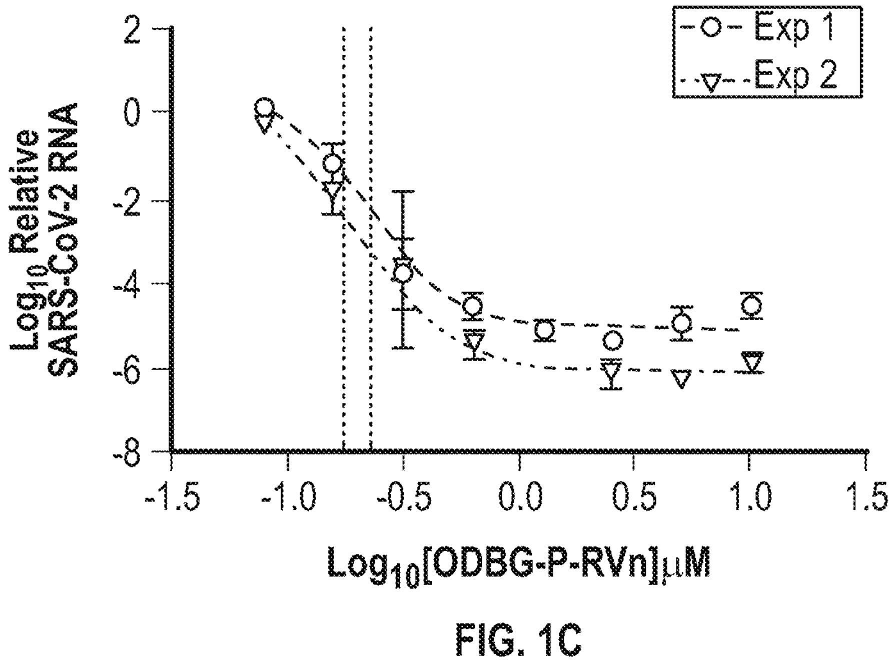
Figure 1D:
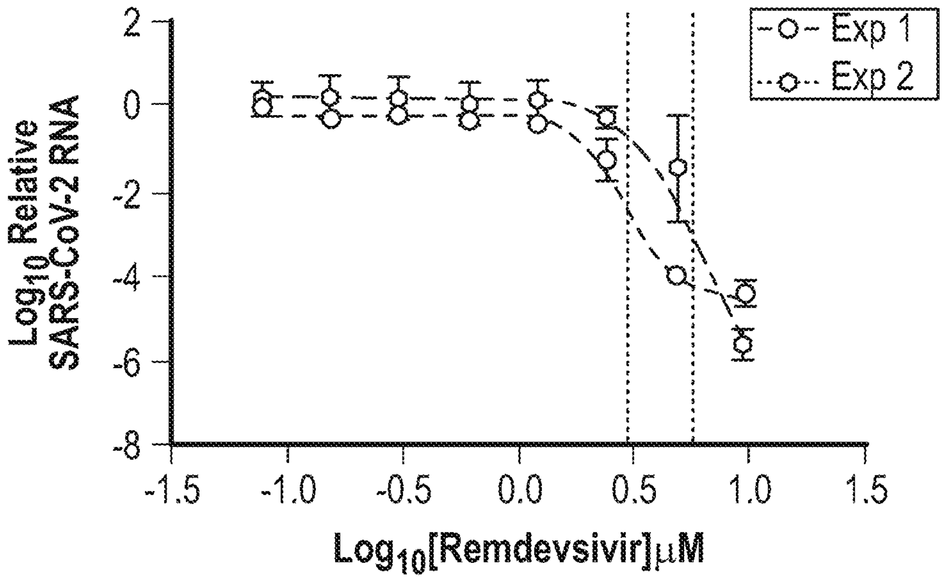
Figure 1E:
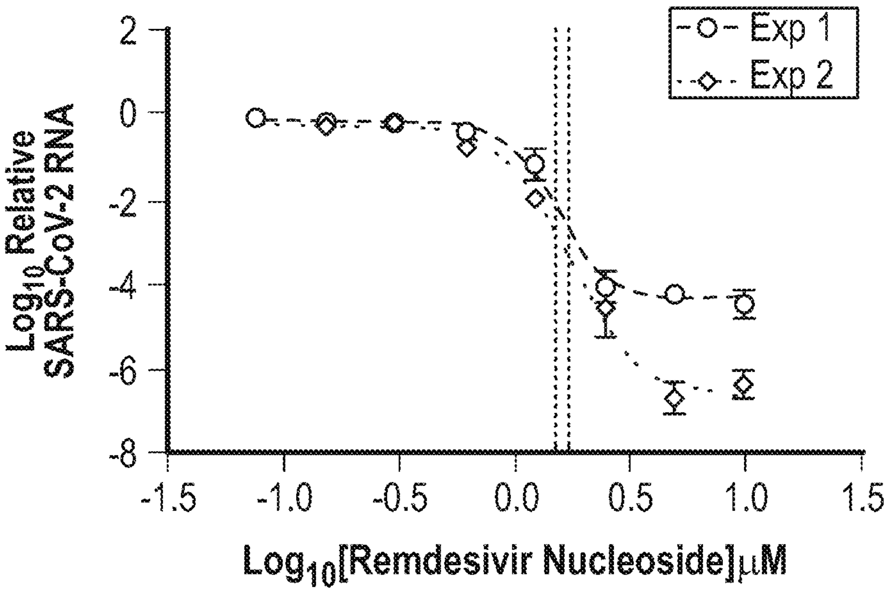

In one aspect, pharmaceutical formulations are provided herein. The pharmaceutical formulations may include (i) an oil, and (ii) a compound of formula (I), as described herein. In some embodiments, the pharmaceutical formulations also include benzyl alcohol, benzyl benzoate, ethyl alcohol, or a combination thereof.

As used herein, the term "oil" refers to a non-polar compound or a mixture of two or more non-polar compounds that is insoluble in water (e.g., a solubility of less than 1 g per liter of water), such as a non-polar compound that includes an at least partially saturated carbon chain (e.g., hydrocarbons, fatty acids, etc.).

Any known oil may be used in the pharmaceutical formulations provided herein. In some embodiments, an oil is selected from the group consisting of sesame oil, triglycerides (e.g., medium chain triglycerides), and a combination thereof.

An oil may be present at any effective concentration in the pharmaceutical formulations provided herein. For example, an oil may be present in a pharmaceutical formulation at an amount of about 60% to about 95%, about 65% to about 95%, about 70% to about 95%, about 75% to about 95%, about 80% to about 95%, or about 85% to about 95%, by weight, based on the weight of the pharmaceutical formulation.

In some embodiments, the pharmaceutical formulations also include benzyl alcohol, benzyl benzoate, ethyl alcohol, or a combination thereof. When present, benzyl alcohol, ethyl alcohol, benzyl benzoate or the combination thereof may be present at a total amount of about 0.01% to about 25%, about 0.01% to about 20%, about 0.01% to about 15%, about 0.01% to about 10%, or about 5% to about 10%, by weight, based on the weight of the pharmaceutical formulation.

A compound of formula (I) may be present at any effective concentration in the pharmaceutical formulations provided herein. For example, a compound of formula (I) may be present at an amount of about 0.01% to about 40%, about 0.01% to about 30%, about 0.01% to about 20%, about 0.01% to about 10%, about 0.01% to about 5%, by weight, based on the weight of the pharmaceutical formulation.

The pharmaceutical formulations provided herein may be configured for any route of administration. In some embodiments, the pharmaceutical formulations are configured for oral administration. In some embodiments, the pharmaceutical formulations are configured for injection, such as intramuscular injection or subcutaneous injection.

The pharmaceutical formulations provided herein may be configured to be administered as a single dose. For example, a pharmaceutical formulation may be configured to be administered as a single, long-acting treatment, as described herein. The single dose may provide an effective amount of the pharmaceutical formulation, such as a compound of formula (I) that is present in the pharmaceutical formulation. The pharmaceutical formulations provided herein may be configured to be administered as a series of two or more doses, wherein each dose is administered at least 7 days, at least 14 days, at least 21 days, or at least 28 days after the preceding dose. For example, each of the two or more doses may be a long-acting treatment, as described herein.

In some embodiments, the pharmaceutical formulations include one or more of the components of any of formulations F3, F4, F7, or F8:

| Components | F3 | F4 | F7 | F8 |
|---|---|---|---|---|
| Sesame oil | 92.65 | 73.67 | — | — |
| Medium chain triglycerides | — | — | 92.65 | 73.67 |
| Benzyl alcohol | 1.22 | 10.67 | 1.22 | 10.67 |
| Benzyl benzoate | — | 15.67 | — | 15.67 |
| Ethyl alcohol | 6.12 | — | 6.12 | — |

In some embodiments, the pharmaceutical formulation is a long-acting treatment. As used herein, the phrase "long-acting treatment", "long-acting dose", and the like refers to a treatment or dose, respectively, that facilitates plasma antiviral activity above the 90% effective concentration for about 5 days to about 30 days, about 5 days to about 28 days, about 5 days to about 21 days, about 5 days to about 14 days, or about 5 days to about 7 days after the administration of a single dose.

The pharmaceutical formulations described herein may include one or more additives that do not undesirably affect one or more features of the pharmaceutical formulations, such as the activity of a compound of formula (I), bioavailability, etc. Non-limiting examples of additives include excipients, coloring agents, flavoring agents, buffers, preservatives, surfactants, other active ingredients, such as anti-inflammatory agents, pain reducing agents, etc.

In one aspect, compounds are provided herein, including compounds of formula (I):

formula (I)

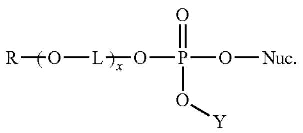

The "Nuc" of formula (I) may be any suitable nucleoside. The nucleoside may be bonded to a compound in any manner. For example, a 5'-hydroxyl of a nucleoside may be joined to a phosphate moiety as an ester bond.

The nucleoside, in some embodiments, is an antiviral nucleoside. The antiviral nucleoside may be an antiviral ribonucleoside. The nucleoside, in some embodiments, is an antiviral nucleoside analog. The antiviral nucleoside analog may be an antiviral ribonucleoside analog.

In some embodiments, Nuc is RVn (GS-441524), beta-D-$N^4$-hydroxycytidine (NHC), or (2'R)-2-amino-2'-deoxy-2'-fluoro-N,2'-dimethyladenosine (CAS #is 1998705-62-6). In some embodiments, Nuc is GS-441524, and the compound of formula (I) has the following structure:

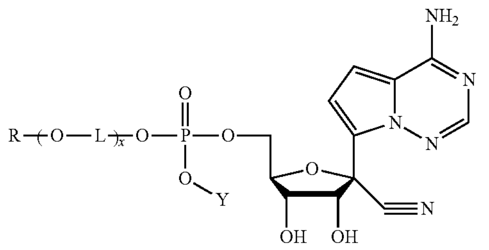

Other antivirals for coronavirus infection can also be modified in the manner provided herein. For example, $N^4$-hydroxy-cytidine (NHC) is an antiviral candidate entering clinical Phase I evaluation. Other nucleoside analogs known to inhibit RNA viruses are also suitable for modification according to this disclosure.

The "Y" of formula (I) may be any of the substituents described herein. In some embodiments, Y is hydrogen, a $C_1$-$C_{30}$ hydrocarbyl, a pharmaceutically acceptable cation, or a covalent bond to a carbon atom of a five-carbon sugar moiety of the antiviral nucleoside or the antiviral nucleoside analog.

When Y is a covalent bond to a carbon atom of a five-carbon sugar moiety of the antiviral nucleoside or the antiviral nucleoside analog, the covalent bond may be a covalent bond to any carbon atom of a five-carbon sugar moiety of the antiviral nucleoside or the antiviral nucleoside analog (e.g., the 1' carbon, the 2' carbon, the 3' carbon, or the 4' carbon). In other words, the covalent bond may be a covalent bond between (i) the oxygen to which Y is bonded in formula (I), and (ii) any carbon atom of a five-carbon sugar moiety of the antiviral nucleoside or the antiviral nucleoside analog (e.g., the 1' carbon, the 2' carbon, the 3' carbon, or the 4' carbon). For example, Nuc may be GS-441524; the covalent bond may be between the oxygen to which Y is bonded in formula (I), and the 3' carbon of five-carbon sugar moiety of GS-441524, and the compound of formula (I) has the following structure:

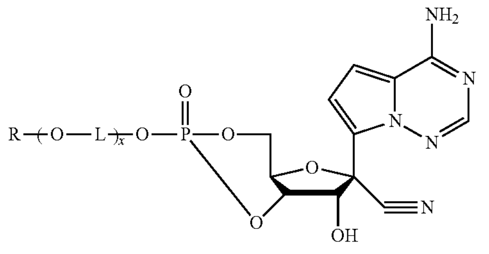

When Y is a pharmaceutically acceptable cation, the pharmaceutically acceptable cation may be $Na^+$.

In some embodiments, Y is a $C_1$-$C_{20}$ hydrocarbyl, a $C_1$-$C_{10}$ hydrocarbyl, or a $C_1$-$C_6$ hydrocarbyl. In some embodiments, Y is a $C_1$-$C_6$ alkyl, which may be unsubstituted. In some embodiments, Y includes at least one cyclic moiety. The at least one cyclic moiety may be a monocyclic moiety or a multicyclic moiety, e.g., a bicyclic moiety, a spiro moiety, etc. In some embodiments, Y is aryl, arylalkyl, heteroaryl, heteroarylalkyl, or heterocycloalkyl, each of which may be unsubstituted or substituted. In some embodiments, Y is an unsubstituted or substituted pyridinyl. In some embodiments. Y is an unsubstituted or substituted benzyl. The unsubstituted or substituted benzyl may have a structure according to formula (B):

formula (B)

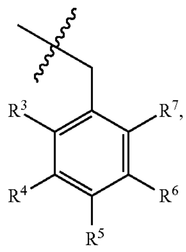

wherein $R^3$, $R^4$, $R^5$, $R^6$, and $R^7$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino. In some embodiments, $R^3$, $R^4$, $R^5$, $R^6$, and $R^7$ are hydrogen. In some embodiments, at least two of $R^3$, $R^4$, $R^5$, $R^6$, and $R^7$ are hydrogen. In some embodiments, at least three of $R^3$, $R^4$, $R^5$, $R^6$, and $R^7$ are hydrogen. In some embodiments, at least four of $R^3$, $R^4$, $R^5$, $R^6$, and $R^7$ are hydrogen.

When Y is an unsubstituted or substituted benzyl of formula (B), the compound of formula (I) has the following structure:

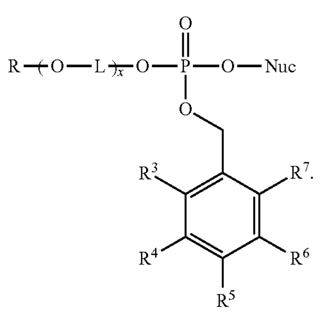

In formula (I), x may be 1 or 0. When x is 1, the "—O-L-" moiety is present in the compounds of formula (I). When x is 0, R is bonded directed to the oxygen of the phosphonate moiety, as shown in the following structure:

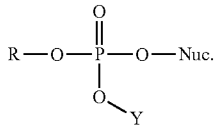

When "L" is present in the compounds of formula (I), the "L" may be selected from any of the substituents described herein. In some embodiments, L is a $C_1$-$C_{30}$ hydrocarbyl, a $C_1$-$C_{20}$ hydrocarbyl, a $C_1$-$C_{10}$ hydrocarbyl, a $C_1$-$C_6$ hydrocarbyl, a $C_1$-$C_5$ hydrocarbyl, a $C_1$-$C_4$ hydrocarbyl, a $C_1$-$C_3$ hydrocarbyl, or a $C_1$-$C_2$ hydrocarbyl. In some embodiments, L is an ethyl, which may be unsubstituted. In some embodiments, L is a methyl, which may be unsubstituted. In some embodiments, L is a propyl, which may be unsubstituted.

The "R" of formula (I) may be selected from any of the substituents described herein. In some embodiments, R is a $C_1$-$C_{30}$ hydrocarbyl, a $C_5$-$C_{30}$ hydrocarbyl, a $C_{10}$-$C_{30}$ hydrocarbyl, a $C_{12}$-$C_{24}$ hydrocarbyl, a $C_{13}$-$C_{29}$ hydrocarbyl, a $C_{15}$-$C_{24}$ hydrocarbyl, or a $C_{20}$-$C_{24}$ hydrocarbyl. R, in some embodiments, is a heteroalkyl. R may include 0 to 6 unsaturated bonds, 1 to 6 unsaturated bonds, 2 to 6 unsaturated bonds, 3 to 6 unsaturated bonds, or 4 to 6 unsaturated bonds. The "unsaturated bonds" described herein may include any non-single bond, and when more than one unsaturated bond is present, the two or more unsaturated bonds may be selected independently from a double bond or a triple bond. When one or more double bonds are present, the one or more double bonds may be cis-, trans-, or a combination thereof. R may include a cyclopropyl moiety, such as a terminal cyclopropyl moiety.

In some embodiments, R is—

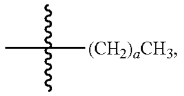

wherein a is 1 to 29. In some embodiments, a is 15 to 25. In some embodiments, a is 18 to 22. In some embodiments, a is 19. In some embodiments, a is 6 to 10. In some embodiments, a is 8.

In some embodiments R is—

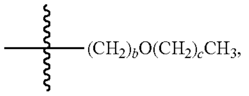

wherein b is 1 to 29, c is 0 to 28, and a sum of b and c is 29 or less. In some embodiments, b is 1 to 4 and c is 15 to 20. In some embodiments, b is 3 and c is 15. In some embodiments, b is 2 and c is 17.

In some embodiments, R is a substituent of formula (A);

formula (A)

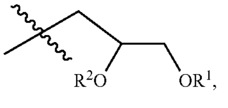

wherein $R^1$ and $R^2$ are hydrogen or a $C_1$-$C_{30}$ hydrocarbyl, such as a $C_{10}$-$C_{30}$ hydrocarbyl, or a $C_{12}$-$C_{24}$ hydrocarbyl. $R^1$, $R^2$, or both $R^1$ and $R^2$ may include at least one cyclic moiety, which may be a monocyclic moiety or a multicyclic moiety, e.g., a bicyclic moiety, a spiro moiety, etc. $R^1$, $R^2$, or both $R^1$ and $R^2$ may include 0 to 6 unsaturated bonds, 1 to 6 unsaturated bonds, 2 to 6 unsaturated bonds, 3 to 6 unsaturated bonds, or 4 to 6 unsaturated bonds. When one or more double bonds are present, the one or more double bonds may be cis-, trans-, or a combination thereof. $R^1$, $R^2$, or both $R^1$ and $R^2$ may include a branched hydrocarbyl, such as a penultimate branched hydrocarbyl. In some embodiments, at least one of $R^1$ and $R^2$ are hydrogen. In some embodiments, both $R^1$ and $R^2$ are independently selected from a $C_1$-$C_{30}$ hydrocarbyl.

In some embodiments, $R^1$, $R^2$, or both $R^1$ and $R^2$ are independently selected from the group consisting of aryl, arylalkyl, heteroaryl, heteroarylalkyl, and heterocycloalkyl, each of which may be unsubstituted or substituted. The arylalkyl may be an unsubstituted or substituted benzyl. The unsubstituted or substituted benzyl may have a structure according to formula (C):

formula (C)

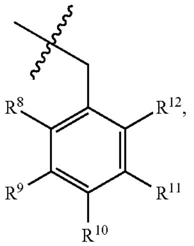

wherein $R^8$, $R^9$, $R^{10}$, $R^{11}$, and $R^{12}$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido. N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino. In some embodiments, each of $R^8$, $R^9$, $R^{10}$, $R^{11}$, and $R^{12}$ are hydrogen. In some embodiments, at least two of $R^8$, $R^9$, $R^{10}$, $R^{11}$, and $R^{12}$ are hydrogen. In some embodiments, at least three of $R^8$, $R^9$, $R^{10}$, $R^{11}$, and $R^{12}$ are hydrogen. In some embodiments, at least four of $R^8$, $R^9$, $R^{10}$, $R^{11}$, and $R^{12}$ are hydrogen. In some embodiments, at least five of $R^8$, $R^9$, $R^{10}$, $R^{11}$, and $R^{12}$ are hydrogen.

In some embodiments, $R^1$ is—

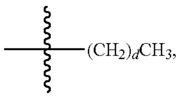

wherein d is 1 to 29. In some embodiments, d is 5 to 29, 10 to 29, 15 to 29, 20 to 29, 25 to 29, 1 to 25, 1 to 20, 1 to 15, 1 to 10, or 1 to 5.

In some embodiments, $R^1$ is

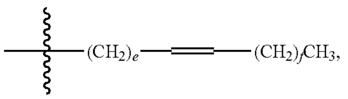

wherein e is 1 to 27, f is 0 to 26, and a sum of e and f is 27 or less.

In some embodiments, $R^2$ is selected from the group consisting of—

(A)

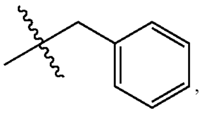

(B)

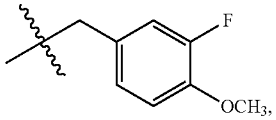

(C)

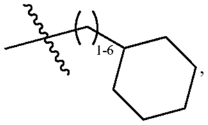

(D)

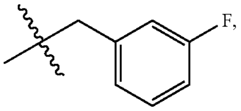

(E)

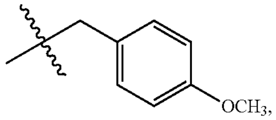

(F)

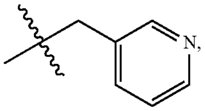

(G)

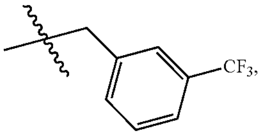

(H)

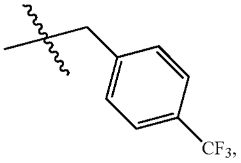

(I)

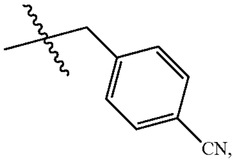

-continued (J)

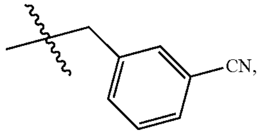

(K)

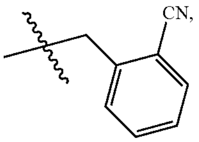

and (L)

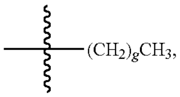

wherein g is 1 to 29. In some embodiments, g is 5 to 10. In some embodiments, g is 7.

The substituent of formula (A) may be a racemate, an sn-1 stereoisomer, or an sn-3 stereoisomer. Throughout this disclosure, when a formula, such as formula (A), is depicted with no indication(s) of spatial orientation, then the formula reads on all isomers, e.g., stereoisomers, of the compounds of the formula. For example, in some embodiments, a compound may have a structure according to formula (I), wherein x is 0, and R is a substituent of formula (A):

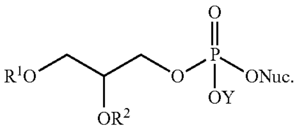

This formula lacks any indication of spatial orientation, and therefore reads on the sn-3 isomer thereof, the sn-1 isomer thereof, and mixtures of the sn-3 and sn-1 isomers, including racemic mixtures thereof:

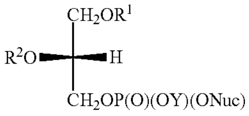

sn-3 isomer

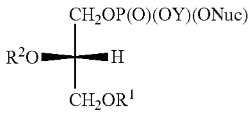

sn-1 isomer

Further non-limiting embodiments of compounds of formula (I) are provided at the following table:

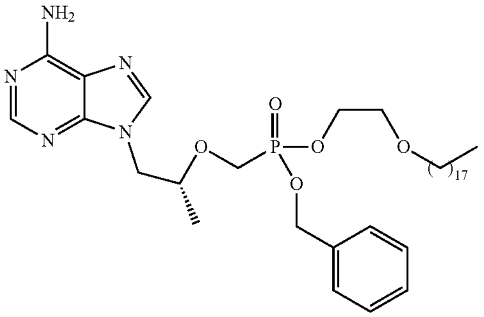
Octadecyloxyethyl benzyl tenofovir (ODE-Bn-TFV)
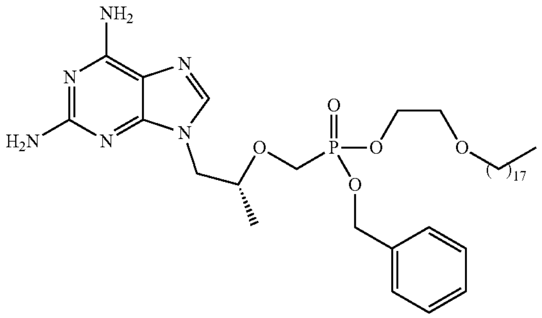
Octadecyloxyethyl benzyl 9-(R)-[(2-phosphonomethoxy)propyl]-2,6-diaminopurine (ODE-Bn-PMPDAP)
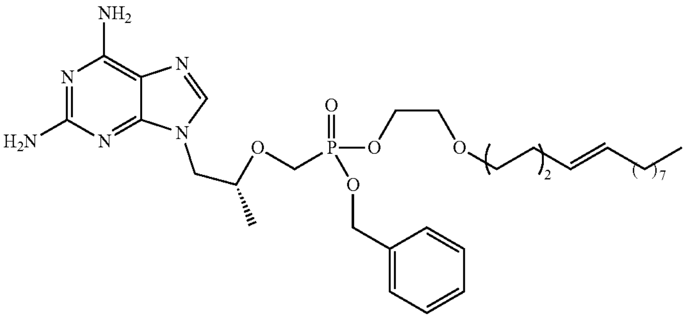
Oleyloxyethyl benzyl 9-(R)-[(2-phosphonomethoxy)propyl]-2,6-diaminopurine (OLE-Bn-PMPDAP)
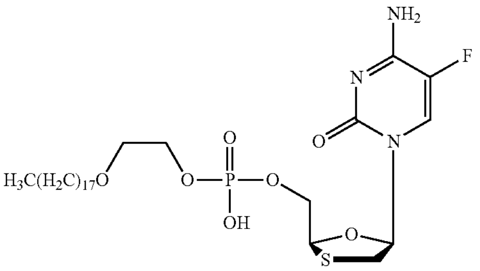
Octadecyloxyethyl-phospho-emtricitabine (ODE-P-FTC)

-continued
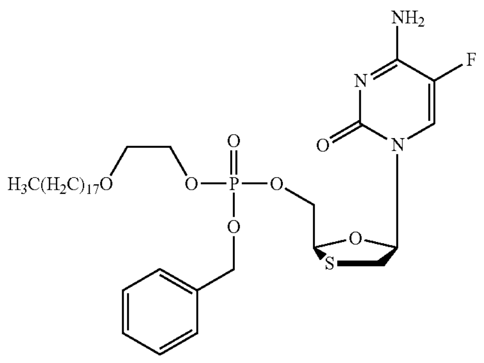
Octadecyloxyethyl benzyl-phospho-emtricitabine (ODE-Bn-P-FTC)
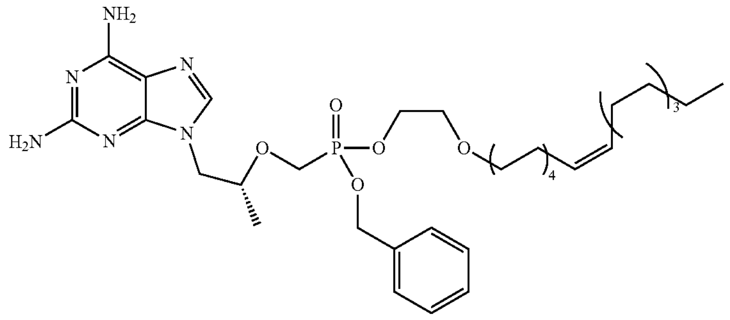
Oleyloxyethyl benzyl 9-(R)-[2-phosphono-methoxy ]propyl]-2,6-diaminopurine (OLE-Bn-PMPDAP)
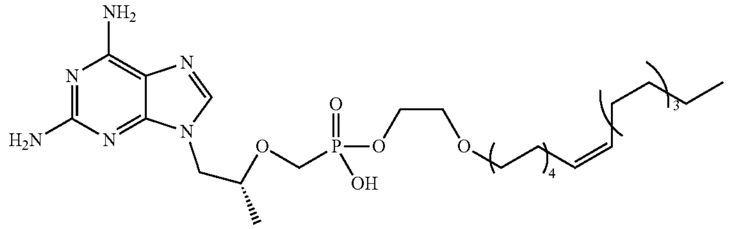
Oleyloxyethyl 9-(R)-[(2-phosphonomethoxy)propyl]-2,6-diaminopurine (OLE-(R)-PMPDAP)
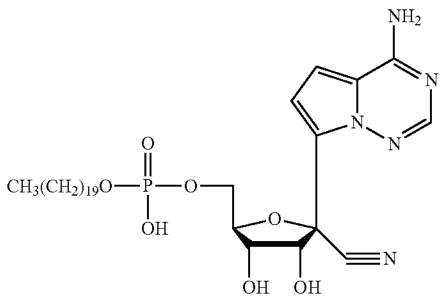
Eicosyl-phospho-RVn -continued
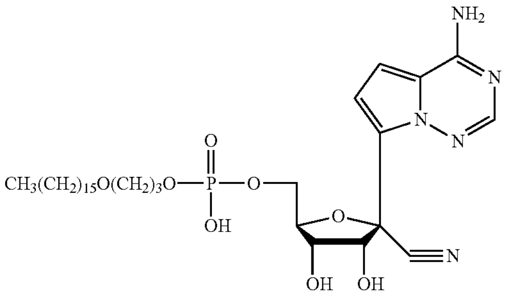
Hexadecy loxypropyl-phospho-RVn
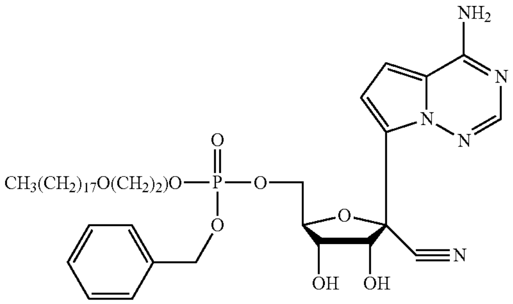
Octadecyloxyethyl-benzyl-phospho-RVn
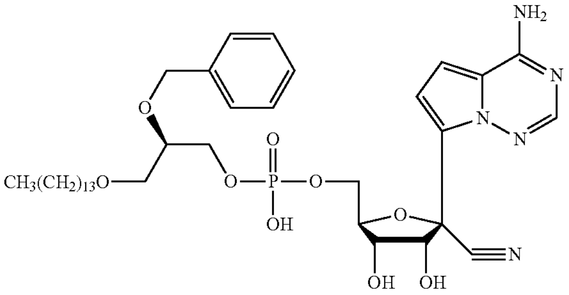
1-O-tetradecyl-2-O-benzyl-sn-glyceryl-phospho-RVn
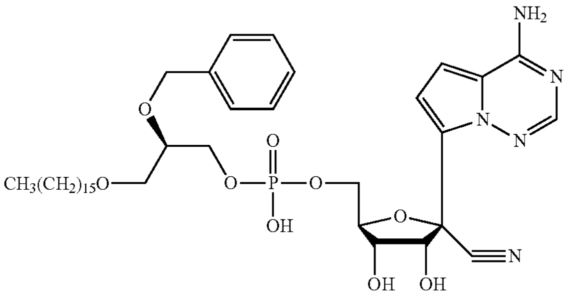
1-O-hexadecyl-2-O-benzyl-sn-glyceryl-phospho-RVn -continued
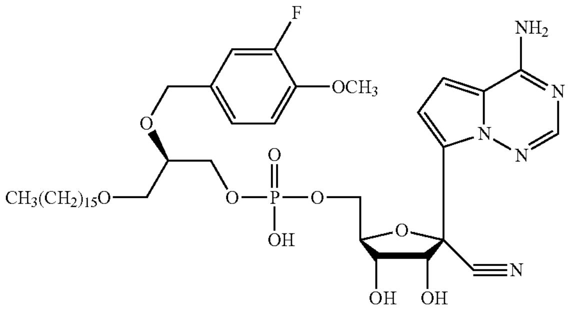
1-O-hexadecyl-2-O-(3-fluoro, 4-methoxybenzyl)-sn-glyceryl-phospho-RVn
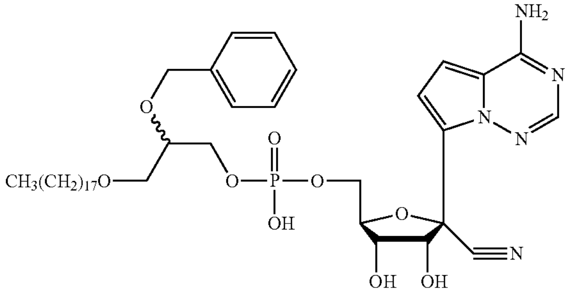
1-O-octadecyl-2-O-benzyl-rac-glyceryl-phospho-RVn
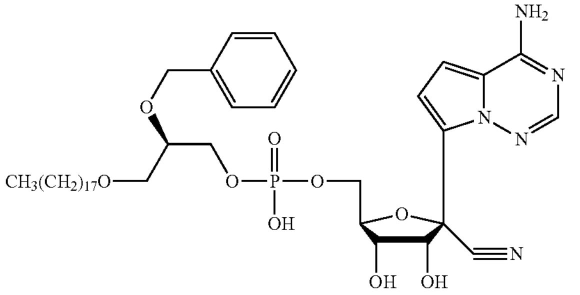
1-O-octadecyl-2-O-benzyl-sn-glyceryl-phospho-RVn
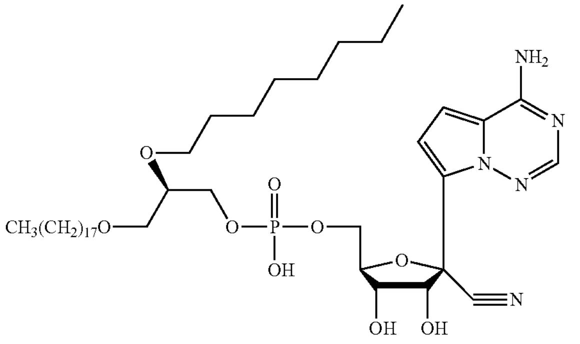
1-O-octadecyl-2-O-octyl-sn-glyceryl-phospho-RVn -continued
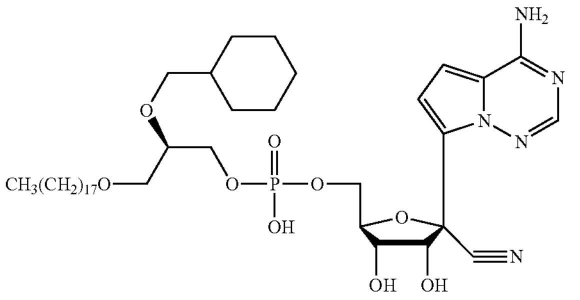
1-O-octadecyl-2-O-(methylcyclohexyl)-
sn-glyceryl-phospho-RVn
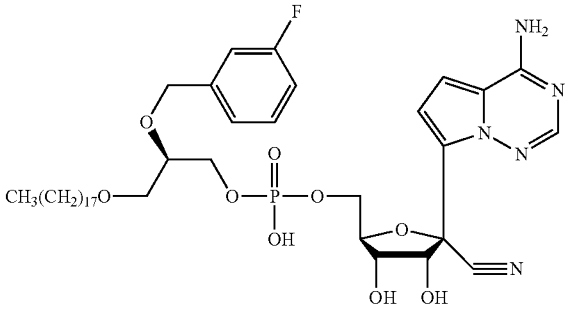
1-O-octadecyl-2-O-(3-fluorobenzyl)-
sn-glyceryl-phospho-RVn
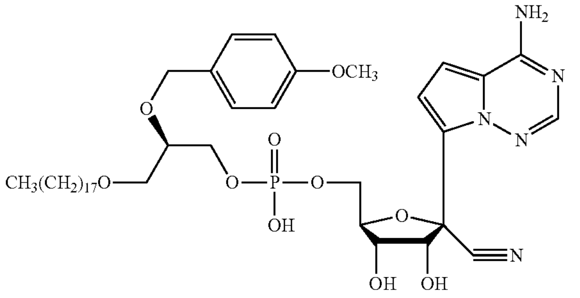
1-O-octadecyl-2-O-(4-methoxybenzyl)-
sn-glyceryl-phospho-RVn
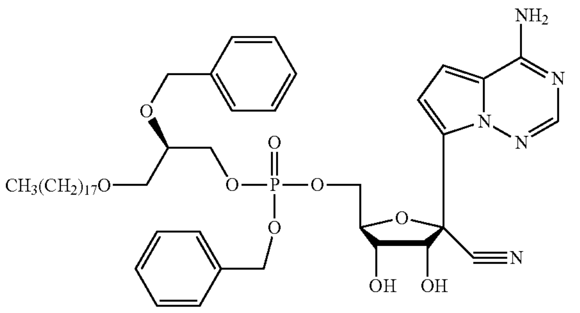
1-O-octadecyl-2-O-benzyl-benzyl-sn-glyceryl-phospho-RVn -continued
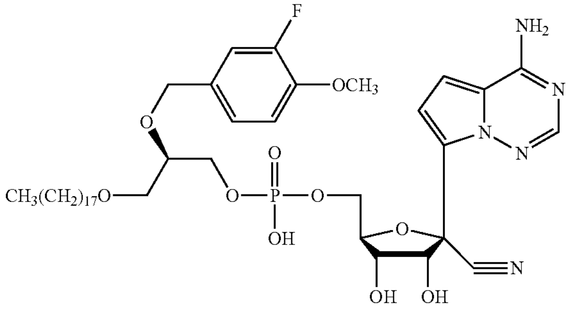
1-O-octadecyl-2-O-(3-fluoro, 4-methoxybenzyl)-sn-glyceryl-phospho-RVn
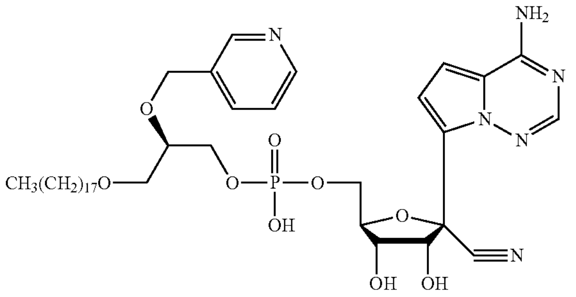
1-O-octadecyl-2-O-(methylpyridinyl)-sn-glyceryl-phospho-RVn
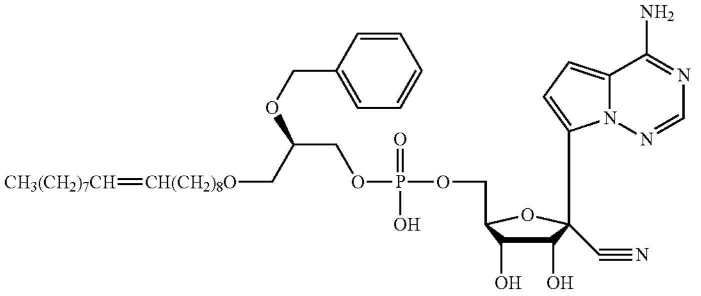
1-O-oleyl-2-O-benzyl-sn-glyceryl-phospho-RVn
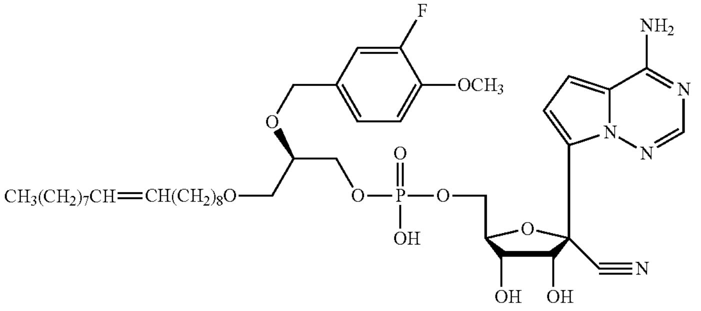
1-O-oleyl-2-O-(3-fluoro, 4-methoxybenzyl)-sn-glyceryl-phospho-RVn -continued
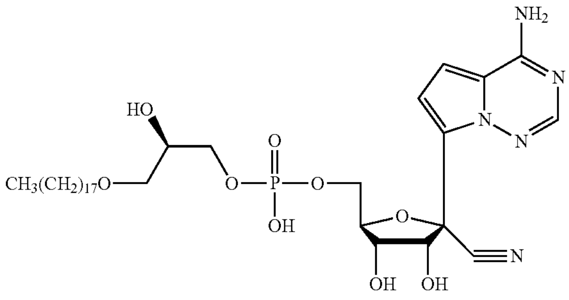
1-O-octadecyl-sn-glyceryl-phospho-RVn
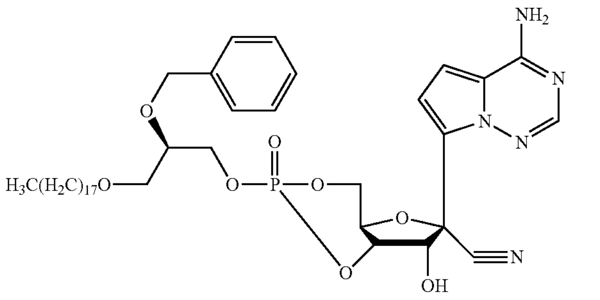
GS-441524-3',5'-cyclic monophosphate, 1-O-octadecyl-2-O-benzyl-sn-glyceryl ester
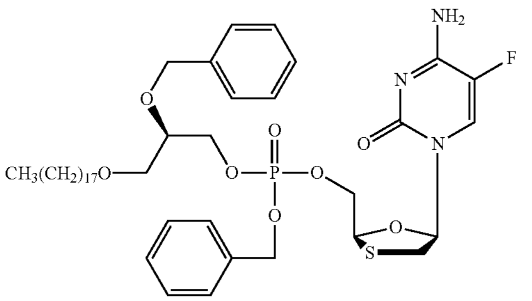
ODBG-benzyl-phospho-emtricitabine
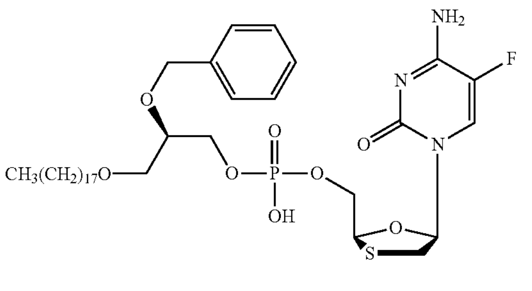
ODBG-phospho-emtricitabine -continued
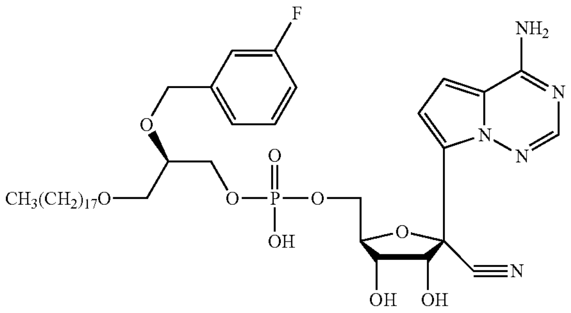
1-O-octadecyl-2-O-(3-trifluoromethyl)-sn-glyceryl-phospho-RVn
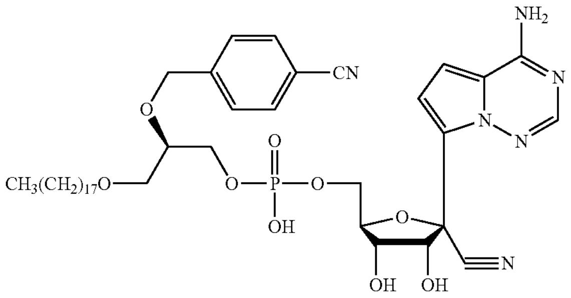
1-O-octadecyl-2-O-(4-trifluoromethyl)-sn-glyceryl-phospho-RVn
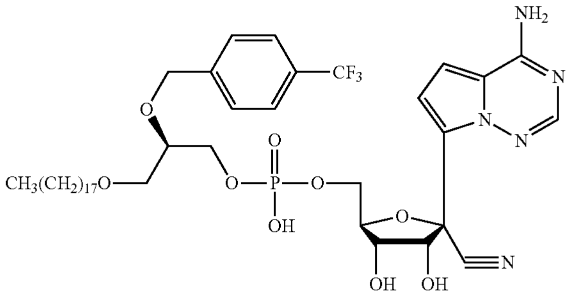
1-O-octadecyl-2-O-(4-cyano)-sn-glyceryl-phospho-RVn
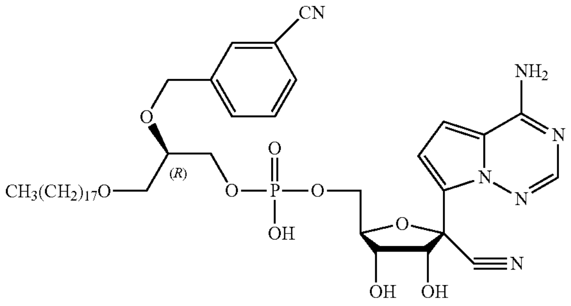
1-O-octadecyl-2-O-(2-cyanobenzyl)-sn-glyceryl-phospho-RVn -continued

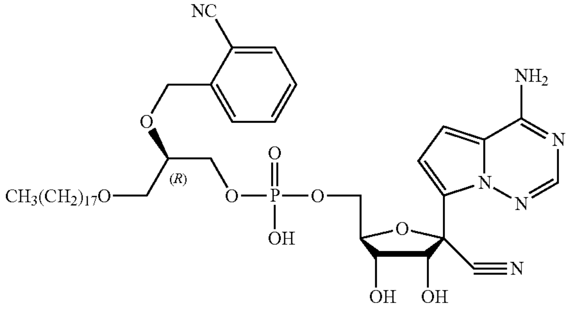

1-O-octadecyl-2-O-(3-cyanobenzyl)-sn-glyceryl-phospho-RVn

When used herein with regard to the selection of a substituent, the term "independently" indicates that (i) a substituent at a particular location may be the same or different for each molecule of a formula (e.g., (i) a compound of formula (I) may include two molecules of formula (I), with each molecule having the same or a different $C_1$-$C_{30}$ hydrocarbyl selected for R; and/or (ii) two differently labeled substituents selected from the same pool of substituents may be the same or different (e.g., R and Y of a molecule of a compound of formula (I) may both be selected from "a $C_1$-$C_{30}$ hydrocarbyl", and the $C_1$-$C_{30}$ hydrocarbyls selected for R and Y may be the same or different)).

The phrases "$C_1$-$C_{30}$ hydrocarbyl," "$C_{10}$-$C_{30}$ hydrocarbyl", and the like, as used herein, generally refer to aliphatic, aryl, or arylalkyl groups containing 1 to 30 carbon atoms, or 10 to 30 carbon atoms, respectively, including unsubstituted groups and substituted derivatives thereof, which, as explained herein, may include, but are not limited to, heteroaryl, heteroarylalkyl, heterocycloalkyl groups, etc. Therefore, when a substituent herein is characterized, for example, as a "$C_1$-$C_{30}$ hydrocarbyl", the phrase "$C_1$-$C_{30}$ hydrocarbyl" refers to and includes unsubstituted and substituted $C_1$-$C_{30}$ hydrocarbyls, unless expressly noted otherwise. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and/or linear analogs or derivatives thereof, in each instance having 1 to 30 total carbon atoms or 10 to 30 total carbon atoms for a "$C_1$-$C_{30}$ hydrocarbyl" and "$C_{10}$-$C_{30}$ hydrocarbyl", respectively. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl, including any heteroatom substituted derivative thereof. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl. 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, anthracenyl, tolyl, xylyl, mesityl, benzyl, and the like, including any heteroatom substituted derivative thereof.

Unless otherwise indicated, the term "substituted," when used to describe a chemical structure or moiety, refers to a derivative of that structure or moiety wherein (i) a multivalent non-carbon atom (e.g., oxygen, nitrogen, sulfur, phosphorus, etc.) is bonded to one or more carbon atoms of the chemical structure or moiety (e.g., a "substituted" $C_4$ hydrocarbyl may include, but is not limited to, a pyrimidinyl moiety, a pyridinyl moiety, a dioxanyl moiety, a diethyl ether moiety, a methyl propionate moiety, an N,N-dimethylacetamide moiety, a butoxy moiety, etc., and a "substituted" aryl Cu hydrocarbyl may include, but is not limited to, an oxydibenzene moiety, a benzophenone moiety, etc.) or (ii) one or more of its hydrogen atoms (e.g., chlorobenzene may be characterized generally as an aryl $C_6$ hydrocarbyl "substituted" with a chlorine atom) is substituted with a chemical moiety or functional group such as acyl, alcohol, alkoxy, alkanoyloxy, alkoxycarbonyl, alkenyl, alkyl (e.g., methyl, ethyl, propyl, t-butyl), alkynyl, alkylcarbonyloxy (—OC(O) alkyl), amide (—C(O)NH-alkyl- or -alkylNHC(O)alkyl), primary, secondary, and tertiary amino (such as alkylamino, arylamino, arylalkylamino), aryl, arylalkyl, aryloxy, azo, azido, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, cycloalkyl, cycloalkenyl, ester, ether (e.g., methoxy, ethoxy), halo, haloalkyl (e.g., $—CCl_3$, $—CF_3$, $—C(CF_3)_3$), haloalkoxy, trihalomethanesulfonyl, trihalomethanesulfonamido, heteroalkyl, heterocycloalkyl, heteroaryl, heteroarylalkyl, isocyanate, isothiocyanate, nitrile, nitro, oxo, phosphodiester, silyl, sulfide, sulfonamido (e.g., $SO_2NH_2$), sulfone, sulfenyl, sulfinyl, sulfonyl (including alkylsulfonyl, arylsulfonyl and arylalkylsulfonyl), sulfoxide, thiocarbonyl, thiocarbamyl, thiocyanato, thiol (e.g., sulfhydryl, thioether) or urea (—NHCONH-alkyl-).

Methods of Treatment

Also provided herein are methods of treatment, including methods of treating a virus infection, such as a coronavirus infection. The virus infection may be an infection in a mammal.

In some embodiments, the methods include administering to a mammal an effective amount of a compound described herein or a pharmaceutical formulation described herein.

The virus infection may be an RNA virus infection. In some embodiments, the RNA virus infection is caused by a RNA virus of a viral family selected from the group consisting of Filoviridae, Orthomyxoviridae, Paramyxoviridae. Pneumoviridae, Phenuiviridae, Nairoviridae, Arenaviridae, Flaviviridae, and Coronaviridae.

Compounds, including prodrugs, provided herein may be screened for inhibitory activity against SARS-CoV-2 and related coronaviruses (or other viruses), using conventional techniques for evaluating anti-coronavirus activity and cytotoxicity. Typically, compounds are first screened for inhibition of coronavirus in vitro, and those showing significant antiviral activity are then screened for efficacy in vivo.

Non-limiting examples of potentially useful in vitro assays including the following: a) Using the OC43 betacoronavirus strain (ATCC 1558) in the human adenocarcinoma cell line, HCT-8 (ATCC CCL-244), or using coronavirus 229E in MRC-5 human lung fibroblasts. Endpoints can include semiquantitative RT-PCR and pfu as determined by triplicate serial dilution. b) The activity of compounds may be studied using laboratory and clinical isolates of SARS-CoV-2 in Vero E6 cells, Caco-2, Calu-3, HPSC human lung cells, or Huh7.5 cells. Initial SARS CoV-2 growth inhibition assays can quantify plaque reduction on Vero cells grown in 12 well plates using a commercial murine anti-SARS CoV-2 spike protein detection antibody (Item 40021-MM07, Sino-Biological.com). Virus can also be quantified in culture supernatants by serial dilution on Vero cell lawns and by RT-PCR. Laboratory strains that can be obtained, for example, from BEI Resources (Strains NR52281 and NR522282), and clinical strains that can be isolated from patients participating in clinical trials can be used. Cytotoxicity can be measured by commercially MTT or Cell Titer Glo. Compounds with the lowest 90% inhibitory concentrations and that require the highest concentrations to induce cellular cytotoxicity may be selected for further evaluation. Anti-coronavirus compounds may also be evaluated in a lung explant model for SARS CoV infection. To determine activity in primary cells from the organ most clinically impacted by the virus, candidate molecules with the highest therapeutic indices in Vero E6 cells can be advanced to studies in human lung explants.

Methods of Producing a Compound

Also provided herein are methods of producing a compound, such as a compound described herein, which may be a prodrug.

The compounds provided herein may be prepared by a variety of processes, including the processes described herein. In some embodiments, protected analogs of remdesivir nucleoside, RVn, 2 are prepared and then coupled to suitable alkoxyalkyl phosphates to form phosphodiesters. Removal of the protecting groups can afford compounds of Formula (I).

1

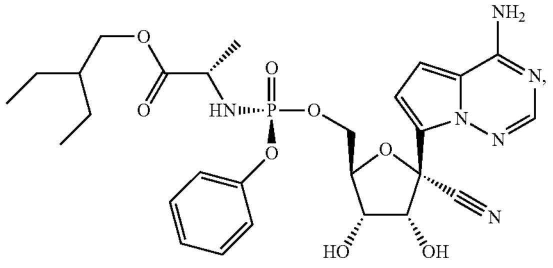

remdesivir, RDV

2

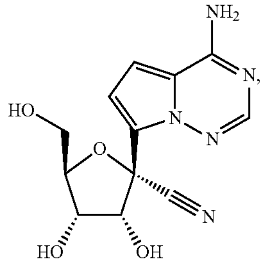

remdesivir nucleoside, RVn

In some embodiments, 2-C-(4-aminopyrrolo[2,1-f][1,2,4]triazin-7-yl)-2,5-anhydro-D-altrononitrile (RVn, 2) is first converted to its 2',3'-isopropylidene derivative. Mixtures of alkoxyalkyl phosphates and protected RVn may then be treated with N,N-dicyclohexylcarbodiimide (DCC) and N,N-dimethylaminopyridine (DMAP) under conditions suitable to prepare the phosphodiesters. Removal of the isopropylidene protecting group by treatment with dilute HCl or other suitable acid may provide compounds of Formula (I) in suitable yield and purity.

In some embodiments, the methods include providing a compound of formula (a)— formula (a)

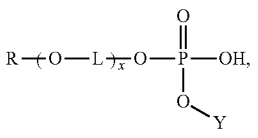

wherein x, R, L, and Y are as defined herein.

In some embodiments, the methods include providing a compound of formula (b)— formula (b)

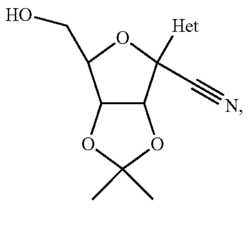

wherein Het is as defined herein. In some embodiments, Het is selected from the group consisting of—

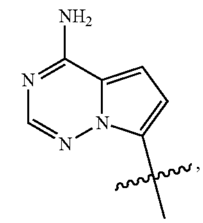,
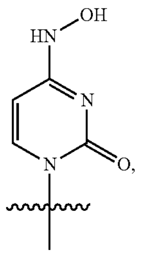, and

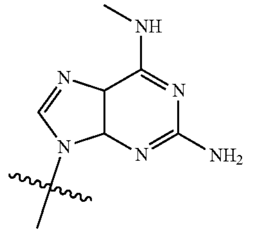

Also, as explained herein, formula (b) does not include any stereochemical indication(s), and therefore, reads on at least the following stereoisomer of formula (b):

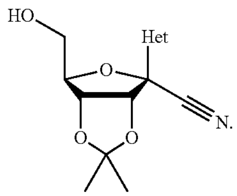

In some embodiments, the methods include contacting a compound of formula (a) and a compound of formula (b) to form a compound of formula (c)— formula (c)

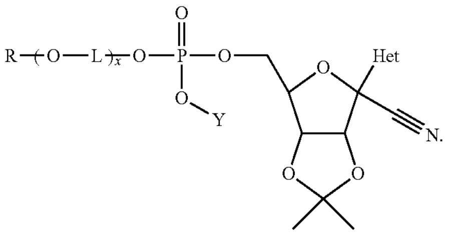

The contacting of a compound of formula (a) and a compound of formula (b) may occur at any temperature or pressure, and may occur in the presence of any suitable liquid. The liquid may include a $C_1$-$C_{30}$ hydrocarbyl, such as a $C_1$-$C_{30}$ hydrocarbyl that includes at least one cyclic moiety, at least one heteroatom, such as nitrogen, or a combination thereof. In some embodiments, the liquid is N,N-dicyclohexylcarbodiimide, 4-dimethylaminopyridine, or a combination thereof.

In some embodiments, the methods contacting a compound of formula (c) with an acid to form a compound of formula (d)— formula (d)

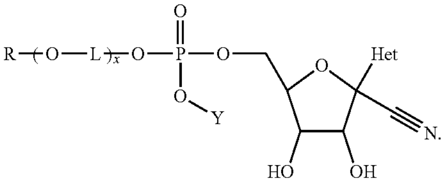

The acid may include any acid that is capable of facilitating the formation of a compound of formula (d). The acid may be an organic acid or inorganic acid. The acid may include a hydrogen halide, such as hydrogen chloride. The contacting of a compound of formula (c) with an acid may occur in the presence of any suitable liquid. The liquid may be a $C_1$-$C_{30}$ hydrocarbyl, such as a $C_1$-$C_{30}$ hydrocarbyl including at least one cyclic moiety, at least one heteroatom, or a combination thereof. In some embodiments, the liquid is tetrahydrofuran.

In some embodiments, the methods include performing an intramolecular esterification reaction of a compound of formula (d) to form a cyclic phosphate, such as a 3',5'-cyclic phosphate.

Methods of Producing a Drug Triphosphate

Also provided herein are methods of producing a drug triphosphate. In some embodiments, the methods include providing a plurality of cells, contacting the plurality of cells with an amount of a drug, incubating the plurality of cells and the amount of the drug for period effective to form the drug triphosphate. The plurality of cells may include any suitable cells. The plurality of cells, in some embodiments, includes Vero E6 cells, Calu-2 cells, Caco-2 cells, MRC5 human lung fibroblasts, Huh7.5 cells and PSC human lung cells. In some embodiments, the drug includes remdesivir or the remdesivir nucleoside (GS441524).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

As used herein, the terms "comprises," "comprising," "includes," "including," "has," "having," "contains", "containing," "characterized by," or any other variation thereof, are intended to encompass a non-exclusive inclusion, subject to any limitation explicitly indicated otherwise, of the recited components. For example, a fusion protein, a pharmaceutical composition, and/or a method that "comprises" a list of elements (e.g., components, features, or steps) is not necessarily limited to only those elements (or components or steps), but may include other elements (or components or steps) not expressly listed or inherent to the fusion protein, pharmaceutical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a compound, pharmaceutical formulations, and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

It is understood that aspects and embodiments of the invention described herein include "consisting" and/or "consisting essentially of" aspects and embodiments.

The terms "a," "an," and "the" are intended to include plural alternatives, e.g., at least one. For instance, the disclosure of "a compound", "a pharmaceutical formulation", "an acid", and the like, is meant to encompass one, or mixtures or combinations of more than one compound, pharmaceutical formulation, acid, and the like, unless otherwise specified.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone. A and B in combination, A and C in combination, B and C in combination or A, B, and C in combination.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that "a is 15 to 25". This range should be interpreted as encompassing 15 and 25, and further encompasses each of 16, 17, 18, 19, 20, 21, 22, 23, and 24, including any ranges and sub-ranges between any of these values.

When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein the term "pharmaceutical composition" refers to pharmaceutically acceptable compositions, wherein the composition comprises a pharmaceutically active agent, and in some embodiments further comprises a pharmaceutically acceptable carrier. In some embodiments, the pharmaceutical composition may be a combination of pharmaceutically active agents and carriers.

The term "combination" refers to either a fixed combination in one dosage unit form, or a kit of parts for the combined administration where one or more active compounds and a combination partner (e.g., another drug as explained below, also referred to as "therapeutic agent" or "co-agent") may be administered independently at the same time or separately within time intervals. In some circumstances, the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a compound and a combination partner, are both administered to a patient simultaneously in the form of a single entity or dosage. The term "non-fixed combination" means that the active ingredients, e.g., a compound and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy, 20th ed., (Lippincott, Williams & Wilkins 2003). Except insofar as any conventional media or agent is incompatible with the active compound, such use in the compositions is contemplated.

As used herein, "therapeutically effective amount" refers to an amount of a pharmaceutically active compound(s) that is sufficient to treat or ameliorate, or in some manner reduce the symptoms associated with diseases and medical conditions. When used with reference to a method, the method is sufficiently effective to treat or ameliorate, or in some manner reduce the symptoms associated with diseases or conditions. For example, an effective amount in reference to diseases is that amount which is sufficient to block or prevent onset; or if disease pathology has begun, to palliate, ameliorate, stabilize, reverse or slow progression of the disease, or otherwise reduce pathological consequences of the disease. In any case, an effective amount may be given in single or divided doses.

As used herein, the terms "treat," "treatment," or "treating" embraces at least an amelioration of the symptoms associated with diseases in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent. As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human.

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

"Nucleic acid" or "nucleic acid molecule" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid backbone can be made up of a variety of linkages, including one or more of sugar-phosphodiester linkages, peptide-nucleic acid bonds, phosphorothioate linkages, methylphosphonate linkages, or combinations thereof. Sugar moieties of the nucleic acid can be ribose, deoxyribose, or similar compounds having known substitutions (e.g. 2'-methoxy substitutions and 2-halide substitutions). Nitrogenous bases can be conventional bases (A, G, C, T, U) or analogs thereof (e.g., inosine, 5-methylisocytosine, isoguanine). A nucleic acid can comprise only conventional sugars, bases, and linkages as found in RNA and DNA, or can include conventional components and substitutions (e.g., conventional bases linked by a 2'-methoxy backbone, or a nucleic acid including a mixture of conventional bases and one or more base analogs). Nucleic acids can include "locked nucleic acids"

(LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA). Nucleic acids can include modified bases to alter the function or behavior of the nucleic acid (e.g., addition of a 3'-terminal dideoxynucleotide to block additional nucleotides from being added to the nucleic acid). Synthetic methods for making nucleic acids in vitro are well known in the art although nucleic acids can be purified from natural sources using routine techniques. Nucleic acids can be single-stranded or double-stranded.

A nucleic acid is typically single-stranded or double-stranded and will generally contain phosphodiester bonds, although in some cases, as outlined, herein, nucleic acid analogs are included that may have alternate backbones, including, for example and without limitation, phosphoramide (Beaucage et al. (1993) Tetrahedron 49(10):1925 and references therein; Letsinger (1970) J. Org. Chem. 35:3800; Sprinzl et al. (1977) Eur. J. Biochem. 81:579; Letsinger et al. (1986) Nucl. Acids Res. 14: 3487; Sawai et al. (1984) Chem. Lett. 805; Letsinger et al. (1988) J. Am. Chem. Soc. 110: 4470; and Pauwels et al. (1986) Chemica Scripta 26: 1419, which are each incorporated by reference), phosphorothioate (Mag et al. (1991) Nucleic Acids Res. 19:1437; and U.S. Pat. No. 5,644,048, which are both incorporated by reference), phosphorodithioate (Briu et al. (1989) J. Am. Chem. Soc. 111:2321, which is incorporated by reference), O-methylphosphoroamidite linkages (see Eckstein, Oligonucleotides and Analogues: A Practical Approach, Oxford University Press (1992), which is incorporated by reference), and peptide nucleic acid backbones and linkages (see, Egholm (1992) J. Am. Chem. Soc. 114:1895; Meier et al. (1992) Chem. Int. Ed. Engl. 31:1008; Nielsen (1993) Nature 365:566; and Carlsson et al. (1996) Nature 380:207, which are each incorporated by reference). Other analog nucleic acids include those with positively charged backbones (Denpcy et al. (1995) Proc. Natl. Acad. Sci. USA 92:6097, which is incorporated by reference); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem: Lett. 4: 395; Jeffs et al. (1994) J. Biomolecular NMR 34:17; and Tetrahedron Lett. 37:743 (1996), which are each incorporated by reference) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (TO modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

An "oligonucleotide" or "oligomer" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; or the solid support method of U.S. Pat. No. 4,458,066, or other methods known in the art. All of these references are incorporated by reference.

Compounds of the present disclosure and methods of use for inhibiting RNA viruses include the following viral families: Filoviridae, Orthomyxoviridae, Paramyxoviridae, Pneumoviridae, Phenuiviridae, Nairoviridae, Arenaviridae, Flaviviridae and Coronaviridae. The names of exemplary viruses in each family are included in the below table.

RNA Virus Families which may be inhibited by compounds of the disclosure

| Virus Family | Virus |
|---|---|
| Filoviridae | Ebola virus |
| | Sudan virus |
| | Bundibugyo virus |
| | Bombali virus |
| | Reston virus |
| | Marburg virus |
| | Ravn virus |
| Orthomyxoviridae | Influenza viruses |
| Paramyxoviridae | Nipah virus |
| | Hendra virus |
| | Human Parainfluenza viruses |
| | Measles virus |
| | Mumps virus |
| | Sosuga virus |
| Pneumoviridae | Respiratory syncytial viruses |
| | Human metapneumovirus |
| Phenuiviridae | Rift Valley Fever virus |
| | Punta Toro phlebovirus |
| Nairoviridae | Crimean Congo Hemorrhagic Fever virus |
| | Dugbe virus |
| Arenaviridae | Lassa virus |
| | Junin virus |
| | Lymphocytic choriomeningitis virus |
| | Guanarito virus |
| | Machupo virus |
| Flaviviridae | Kyasanur Forest Disease virus |
| | Omsk Hemorrhagic Fever virus |
| | Yellow Fever virus |
| | Japanese Encephalitis virus |
| | Hepatitis C Virus |
| | Zika Virus |
| | Dengue Viruses |
| | West Nile Virus |
| | Tick Borne encephalitis virus |
| | Murray Valley Fever encephalitis Virus |
| | Kunjin Virus |
| | Saint Louis Encephalitis Virus |
| | Bovine viral diarrhea virus |
| Coronaviridae | SARS-CoV-2 |
| | MERS |
| | SARS CoV |
| | OC43 |
| | 229E |
| | NL43 |
| | Evolving Zoonotic and Human Coronaviruses |
| | Feline Infectious Peritonitis virus |

EMBODIMENTS

Embodiments of the compounds, pharmaceutical formulations, and methods described herein are provided at the following listing:

Embodiment 1. A compound of formula (I) or a pharmaceutically acceptable salt thereof:

formula (I)

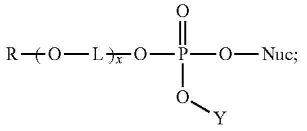

wherein Nuc is selected from the group consisting of an antiviral nucleoside and an antiviral nucleoside analog; Y is independently selected from the group consisting of hydrogen, a $C_1$-$C_{30}$ hydrocarbyl, a pharmaceutically acceptable cation, and a covalent bond to a carbon atom of a five-carbon sugar moiety of the antiviral nucleoside or the antiviral nucleoside analog; x is 0 or 1; L is independently a $C_1$-$C_3M$ hydrocarbyl; and R is independently selected from the group consisting of a $C_{10}$-$C_{30}$ hydrocarbyl and a substituent of formula (A);

formula (A)

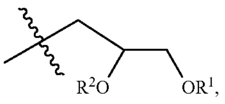

wherein $R^1$ and $R^2$ are independently selected from the group consisting of hydrogen and a $C_1$-$C_{30}$ hydrocarbyl;

wherein optionally the compound of formula (I) (i) achieves kinase bypass of the first nucleoside phosphorylation, (ii) provides increased oral bioavailability, (iii) delivers antivirally significant concentrations to lung and gastrointestinal tract and formulations, (iv) provides sustained levels in plasma for at least about 5 to about 30 days following administration of a single dose, such as intravascularly, or (v) a combination thereof.

Embodiment 2. The compound of Embodiment 1, wherein the antiviral nucleoside or the antiviral nucleoside analog is an antiviral ribonucleoside or an antiviral ribonucleoside analog, respectively.

Embodiment 3. The compound of any one of the previous Embodiments, wherein Nuc is selected from the group consisting of GS-441524, beta-D-$N^4$-hydroxycytidine (NHC), and (2'R)-2-amino-2'-deoxy-2'-fluoro-N,2'-dimethyladenosine.

Embodiment 4. The compound of any one of the previous Embodiments, wherein Nuc is—

(i) GS-441524:

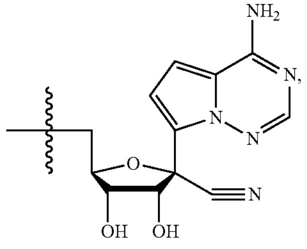

-continued (ii)

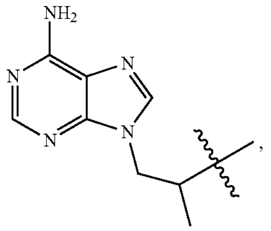

(iii)

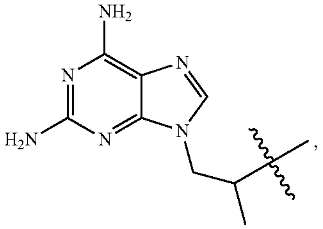

or (iv)

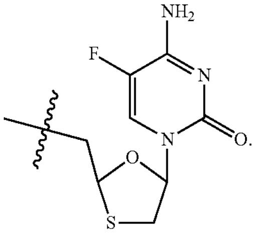

Embodiment 5. The compound of any one of the previous Embodiments, wherein Y is an unsubstituted $C_1$-$C_6$ alkyl, a $C_1$-$C_{20}$ hydrocarbyl, a $C_1$-$C_{10}$ hydrocarbyl, a $C_1$-$C_6$ hydrocarbyl, or $Na^+$.

Embodiment 6. The compound of any one of the previous Embodiments, wherein Y comprises at least one cyclic moiety.

Embodiment 7. The compound of any one of the previous Embodiments, wherein Y is selected from the group consisting of aryl, arylalkyl, heteroaryl, heteroarylalkyl, and heterocycloalkyl, each of which is unsubstituted or substituted.

Embodiment 8. The compound of any one of the previous Embodiments, wherein the heteroaryl is an unsubstituted or substituted pyridinyl.

Embodiment 9. The compound of any one of the previous Embodiments, wherein the arylalkyl is an unsubstituted or substituted benzyl.

Embodiment 10. The compound of any one of the previous Embodiments, wherein the unsubstituted or substituted benzyl has a structure according to formula (B):

formula (B)

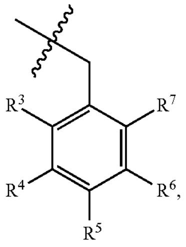

wherein $R^3$, $R^4$, $R^5$, $R^6$, and $R^7$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino.

Embodiment 11. The compound of any one of the previous Embodiments, wherein at least two of $R^3$, $R^4$, $R^5$, $R^6$, and $R^7$ are hydrogen.

Embodiment 12. The compound of any one of the previous Embodiments, wherein R (i) is an unsubstituted or substituted $C_{12}$-$C_{24}$ hydrocarbyl, (ii) comprises 0 to 6 unsaturated bonds, (iii) comprises a cyclopropyl moiety, or (iv) a combination thereof.

Embodiment 13. The compound of any one of the previous Embodiments, wherein R (i) is an unsubstituted or substituted $C_{13}$-$C_{29}$ heteroalkyl, (ii) comprises 0 to 6 unsaturated bonds, or (iii) a combination thereof.

Embodiment 14. The compound of any one of the previous Embodiments, wherein R is selected from the group consisting of—

(i)

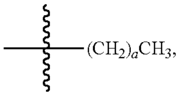

wherein a is 1 to 29; and (ii)

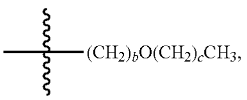

wherein b is 1 to 29, c is 0 to 28, and a sum of b and c is 29 or less.

Embodiment 15. The compound of any one of the previous Embodiments, wherein (i) a is 15 to 25, or (ii) b is 1 to 4 and c is 15 to 20.

Embodiment 16. The compound of any one of the previous Embodiments, wherein (i) a is 19, (ii) b is 3 and c is 15, or (iii) b is 2 and c is 17.

Embodiment 17. The compound of any one of the previous Embodiments, wherein a is 8.

Embodiment 18. The compound of any one of the previous Embodiments, wherein $R^1$ and/or $R^2$, independently, (i) is an unsubstituted or substituted $C_{12}$-$C_{24}$ hydrocarbyl, (ii) comprises 0 to 6 unsaturated bonds, or (iii) a combination thereof.

Embodiment 19. The compound of any one of the previous Embodiments, wherein (i) $R^1$, (ii) $R^2$, or (iii) both $R^1$ and $R^2$ are independently selected from a $C_1$-$C_{30}$ hydrocarbyl comprising at least one cyclic moiety.

Embodiment 20. The compound of any one of the previous Embodiments, wherein (i) $R^1$, (ii) $R^2$, or (iii) both $R^1$ and $R^2$ are independently selected from the group consisting of aryl, arylalkyl, heteroaryl, heteroarylalkyl, and heterocycloalkyl, each of which is unsubstituted or substituted.

Embodiment 21. The compound of any one of the previous Embodiments, wherein the arylalkyl is an unsubstituted or substituted benzyl.

Embodiment 22. The compound of any one of the previous Embodiments, wherein the unsubstituted or substituted benzyl has a structure according to formula (C):

formula (C)

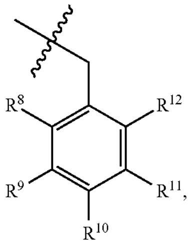

wherein $R^8$, $R^9$, $R^{10}$, $R^{11}$ and $R^{12}$ are independently selected from the group consisting of hydrogen, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, amino, mono-substituted amino, and di-substituted amino.

Embodiment 23. The compound of any one of the previous Embodiments, wherein at least two of $R^8$, $R^9$, $R^{10}$, $R^{11}$, and $R^{12}$ are hydrogen.

Embodiment 24. The compound of any one of the previous Embodiments, wherein the substituent of formula (A) is a racemate, an sn-1 stereoisomer (e.g., glyceryl-sn-1-phospho), or an sn-3 stereoisomer (e.g., glyceryl-sn-3-phospho).

Embodiment 25. The compound of any one of the previous Embodiments, wherein—

(i) $R^1$ and/or $R^2$, independently, is selected from the group consisting of—

(a)

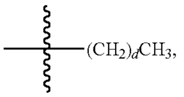

wherein d is 1 to 29; and (b)

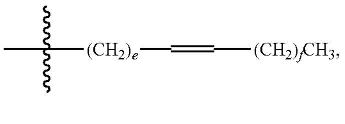

wherein e is 1 to 27, f is 0 to 26, and a sum of e and f is 27 or less;

(ii) $R^1$ and/or $R^2$, independently, is selected from the group consisting of—

(A)

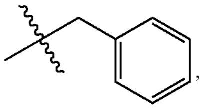

(B)

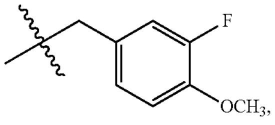

(C)

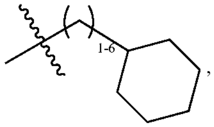

(D)

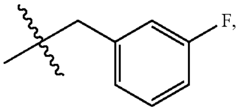

(E)

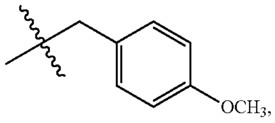

(F)

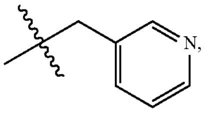

(G)

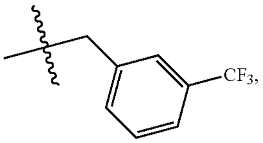

(H)

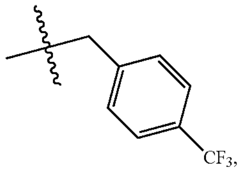

(I)

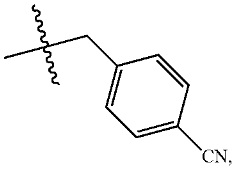

(J)

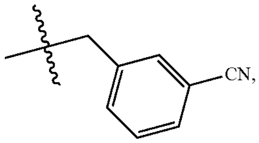

(K)

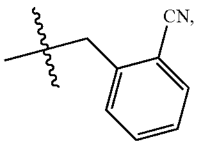

and

-continued (L)

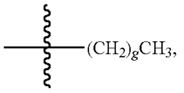

wherein g is 1 to 29; or (iii) a combination thereof.

Embodiment 26. The compound of any one of the previous Embodiments, wherein g is 5 to 10.

Embodiment 27. The compound of any one of the previous Embodiments, wherein g is 7.

Embodiment 28. The compound of any one of the previous Embodiments, wherein x is 1, and L is an unsubstituted or substituted $C_1$-$C_3$ hydrocarbyl.

Embodiment 29. The compound of any one of the previous Embodiments, wherein L is selected from the group consisting of an unsubstituted methyl, an unsubstituted ethyl and an unsubstituted propyl.

Embodiment 30. The compound of any one of the previous Embodiments, wherein the compound of formula (I) is at least one of the following compounds or a pharmaceutically acceptable salt thereof:

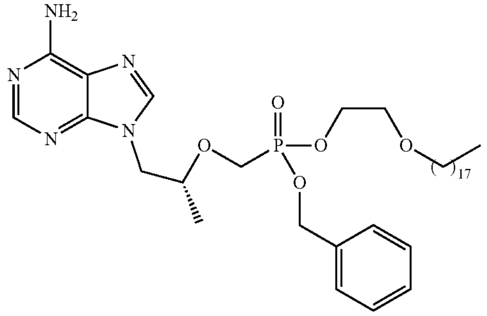

Octadecyloxyethyl benzyl tenofovir (ODE-Bn-TFV)

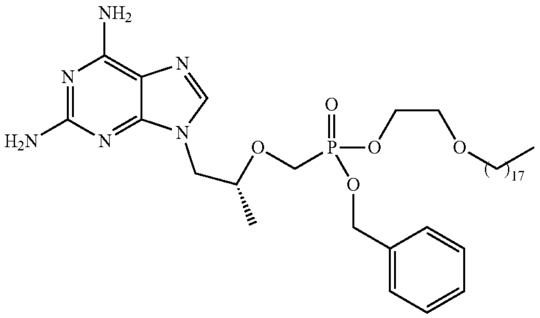

Octadecyloxyethyl benzyl 9-(R)-[(2-phosphonomethoxy)propyl]-2,6-diaminopurine (ODE-Bn-PMPDAP)

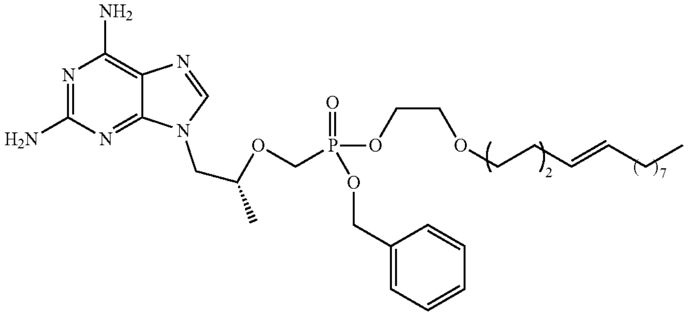

Oleyloxyethyl benzyl 9-(R)-[(2-phosphonomethoxy)propyl]-2,6-diaminopurine (OLE-Bn-PMPDAP)

-continued
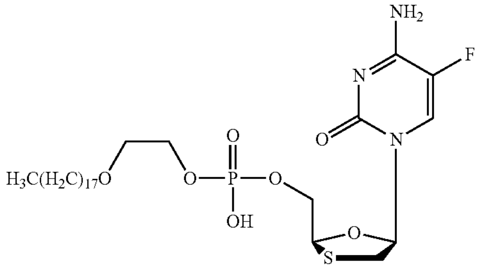
Octadecyloxyethyl-phospho-emtricitabine (ODE-P-FTC)
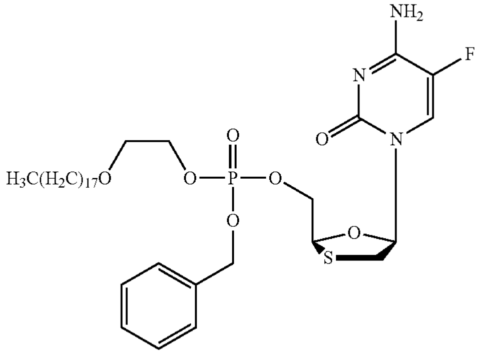
Octadecyloxyethyl benzyl-phospho-emtricitabine (ODE-Bn-P-FTC)
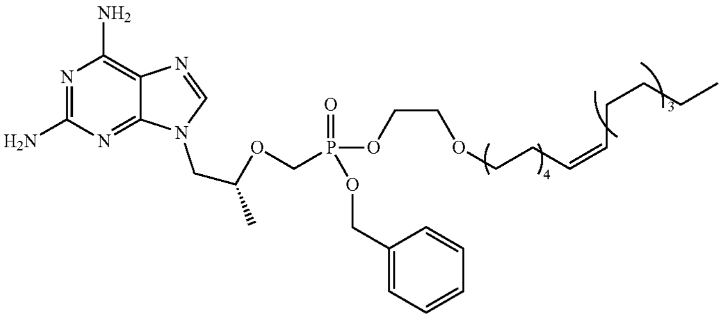
Oleyloxyethyl benzyl 9-(R)-[2-phosphono-methoxy]propyl]-2,6-diaminopurine (OLE-Bn-PMPDAP)
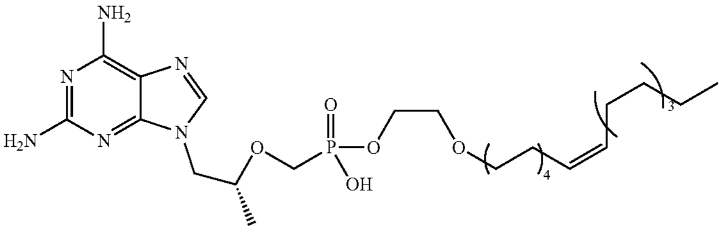
Oleyloxyethyl 9-(R)-[(2-phosphonomethoxy)propyl]-2,6-diaminopurine (OLE-(R)-PMPDAP)

-continued
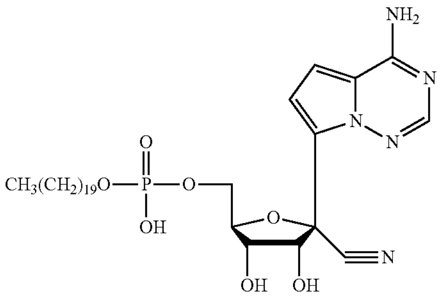
Eicosyl-phospho-RVn
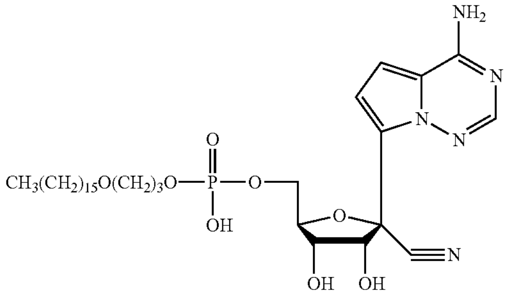
Hexadecyloxypropyl-phospho-RVn
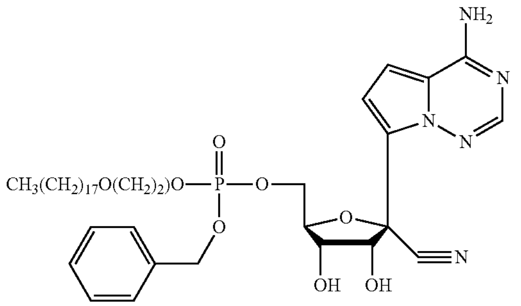
Octadecyloxyethyl-benzyl-phospho-RVn
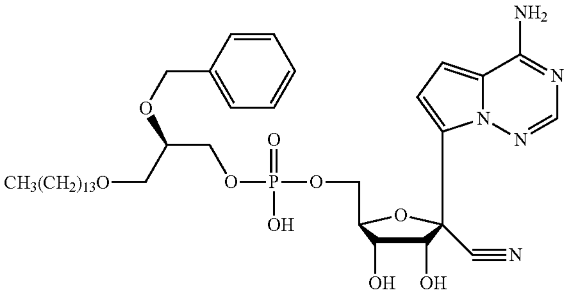
1-O-tetradecyl-2-O-benzyl-sn-glyceryl-phospho-RVn -continued
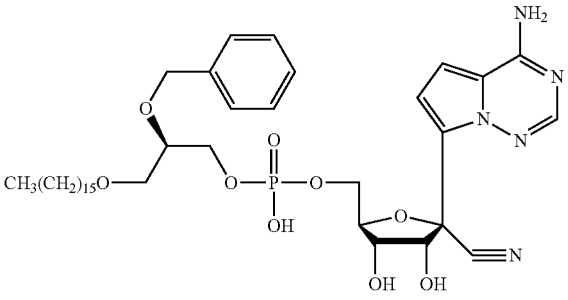
1-O-hexadecyl-2-O-benzyl-sn-glyceryl-phospho-RVn
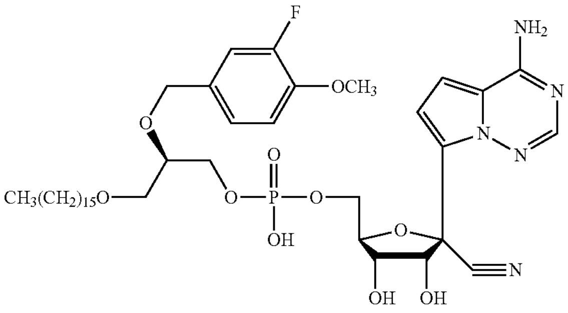
1-O-hexadecyl-2-O-(3-fluoro,4-methoxybenzyl)-sn-glyceryl-phospho-RVn
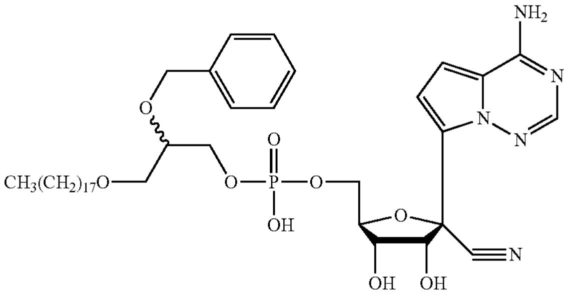
1-O-octadecyl-2-O-benzyl-rac-glyceryl-phospho-RVn
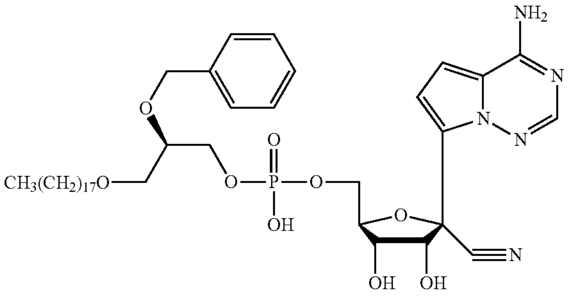
1-O-octadecyl-2-O-benzyl-sn-glyceryl-phospho-RVn -continued
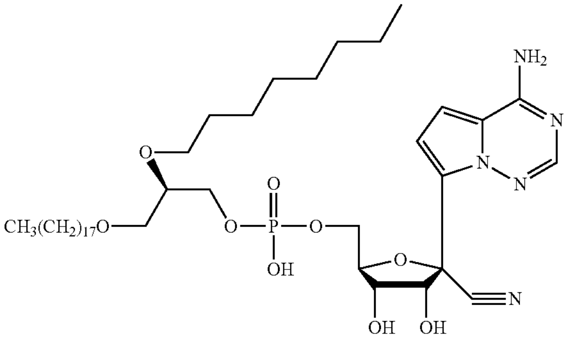
1-O-octadecyl-2-O-(methylcyclohexyl)-sn-glyceryl-phospho-RVn
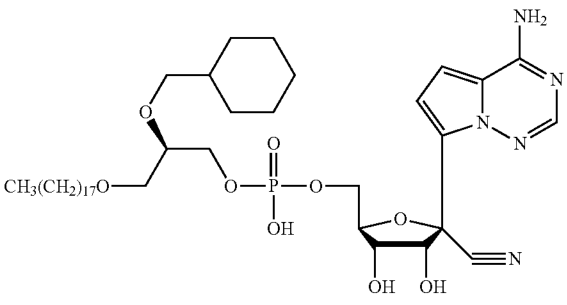
1-O-octadecyl-2-O-octyl-sn-glyceryl-phospho-RVn
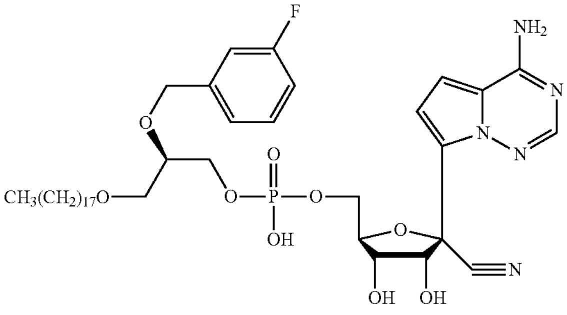
1-O-octadecyl-2-O-(3-fluorobenzyl)-sn-glyceryl-phospho-RVn
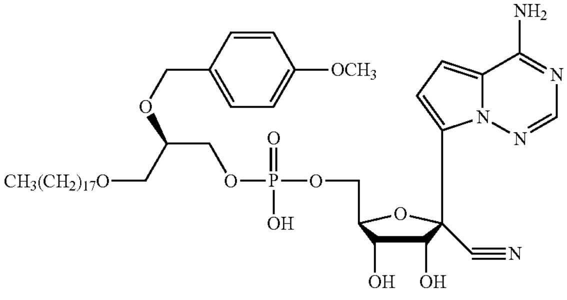
1-O-octadecyl-2-O-(4-methoxybenzyl)-sn-glyceryl-phospho-RVn -continued
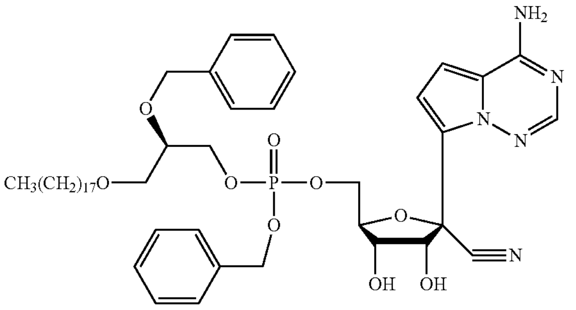
1-O-octadecyl-2-O-benzyl-benzyl-sn-glyceryl-phospho-RVn
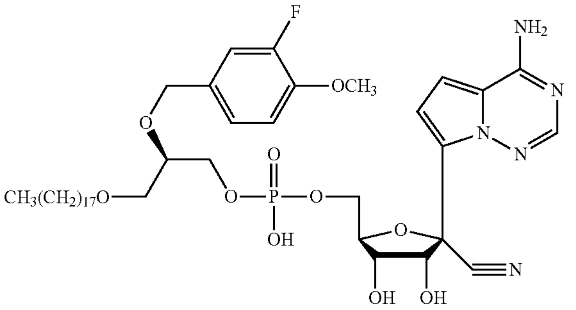
1-O-octadecyl-2-O-(3-fluoro, 4-methoxybenzyl)-sn-glyceryl-phospho-RVn
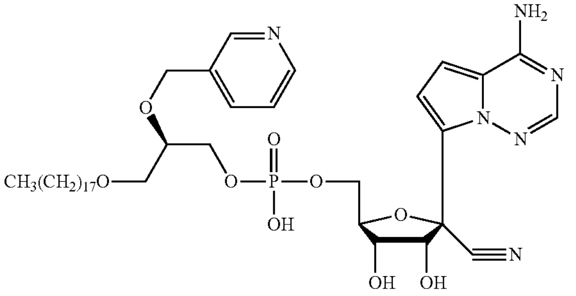
1-O-octadecyl-2-O-(methylpyridinyl)-sn-glyceryl-phospho-RVn
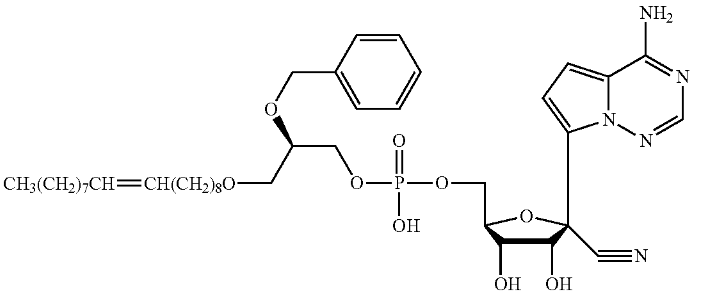
1-O-oleyl-2-O-benzyl-sn-glyceryl-phospho-RVn -continued
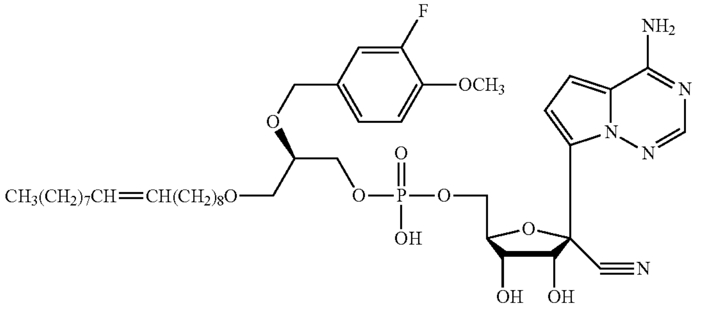
1-O-oleyl-2-O-(3-fluoro, 4-methoxybenzyl)-sn-glyceryl-phospho-RVn
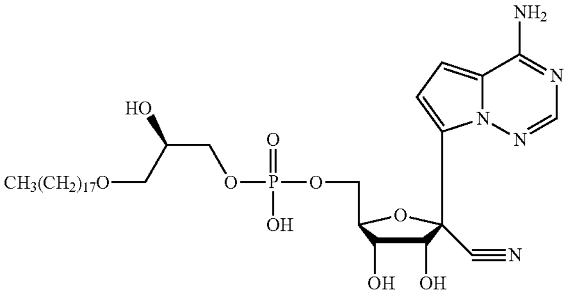
1-O-octadecyl-sn-glyceryl-phospho-RVn
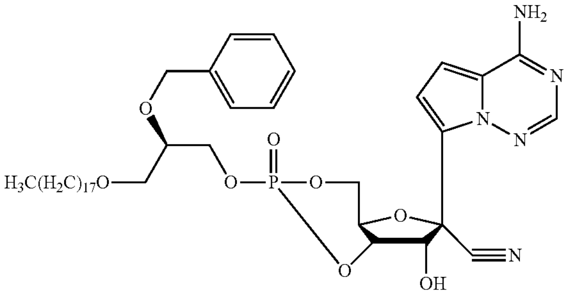
GS-441524-3',5'-cyclic monophosphate, 1-O-octadecyl-2-O-benzyl-sn-glyceryl ester
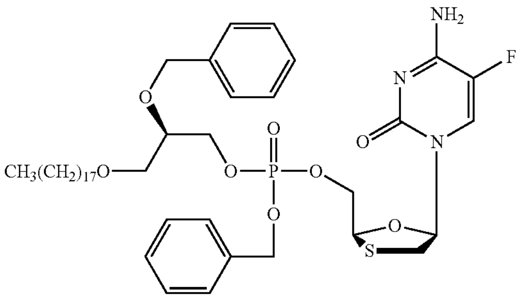
ODBG-benzyl-phospho-emtricitabine -continued
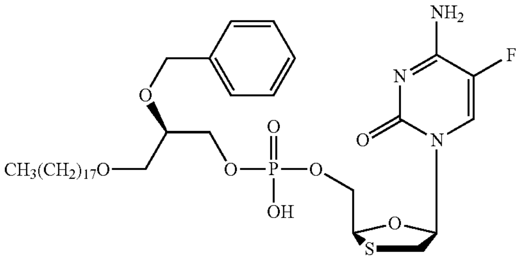
ODBG-phospho-emtricitabine
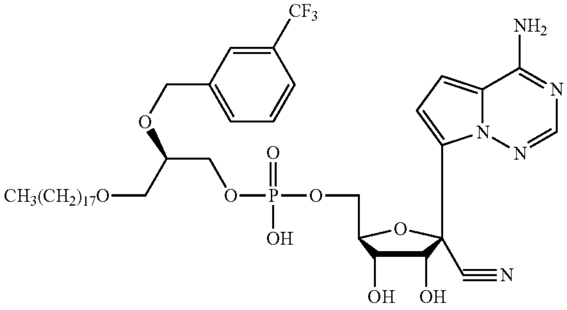
1-O-octadecyl-2-O-(3-trifluoromethyl)-sn-glyceryl-phospho-RVn
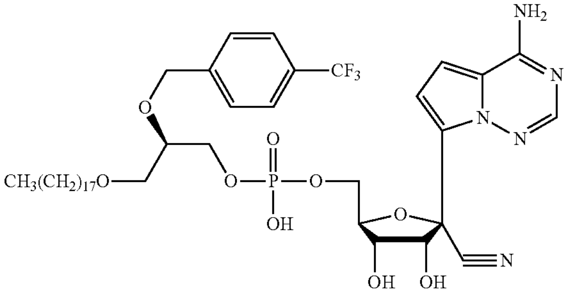
1-O-octadecyl-2-O-(4-trifluoromethyl)-sn-glyceryl-phospho-RVn
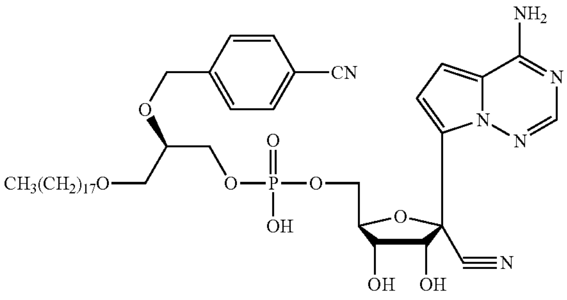
1-O-octadecyl-2-O-(4-cyano)-sn-glyceryl-phospho-RVn -continued
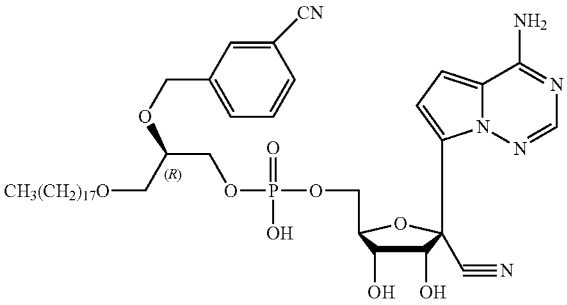
1-O-octadecyl-2-O-(2-cyanobenzyl)-sn-glyceryl-phospho-RVn
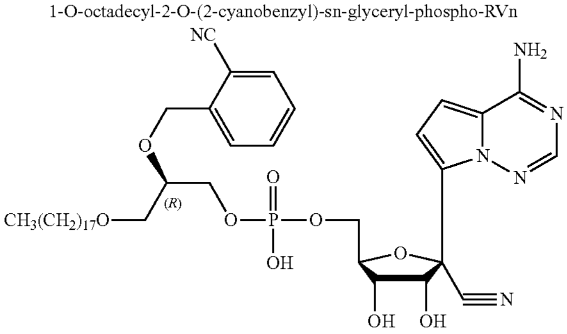
1-O-octadecyl-2-O-(3-cyanobenzyl)-sn-glyceryl-phospho-RVn
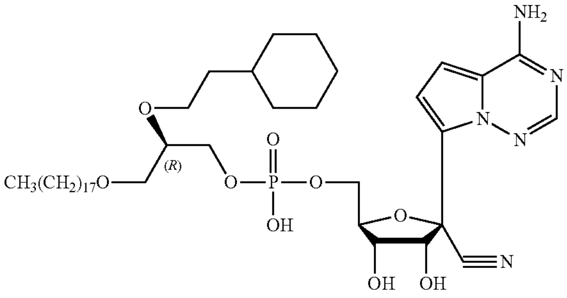
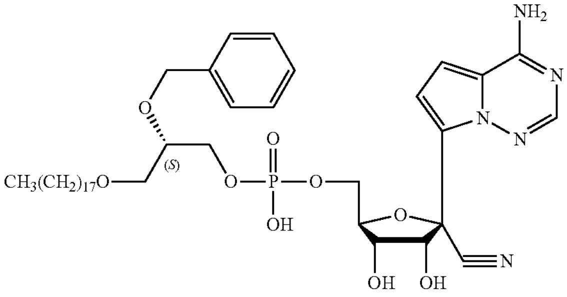
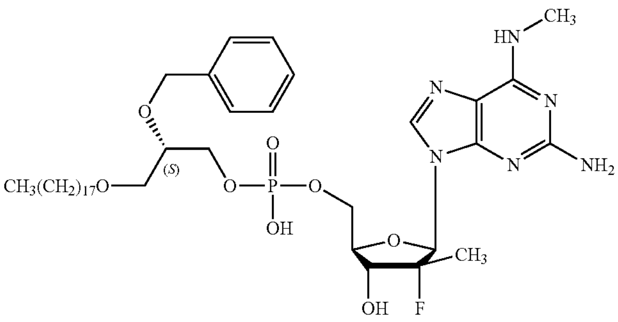

-continued
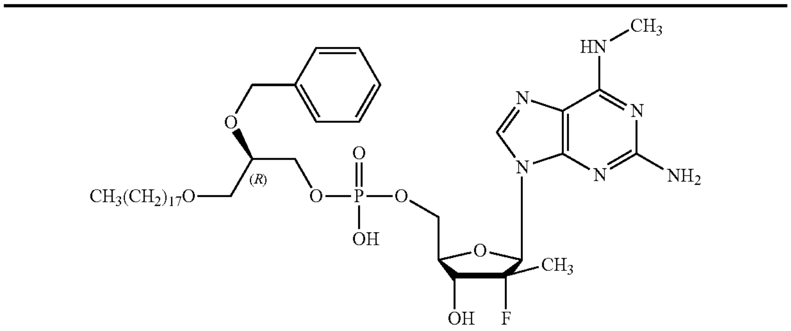
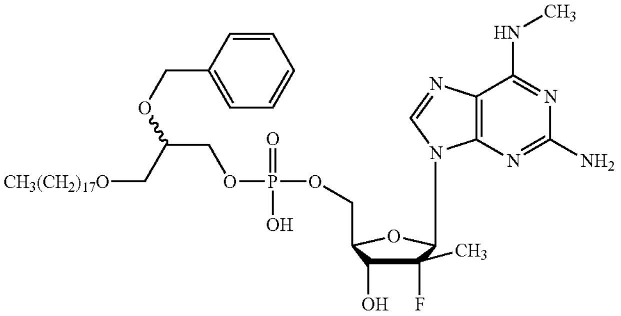
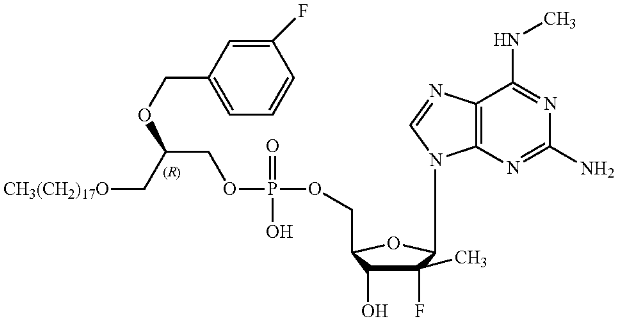
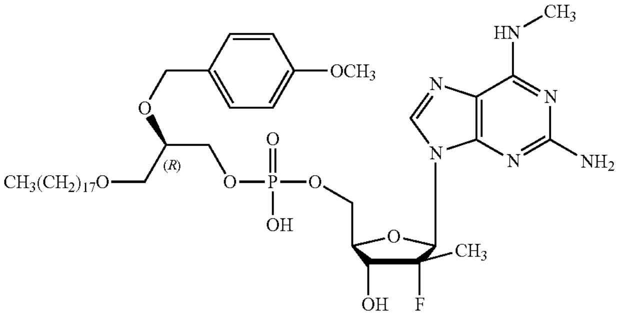
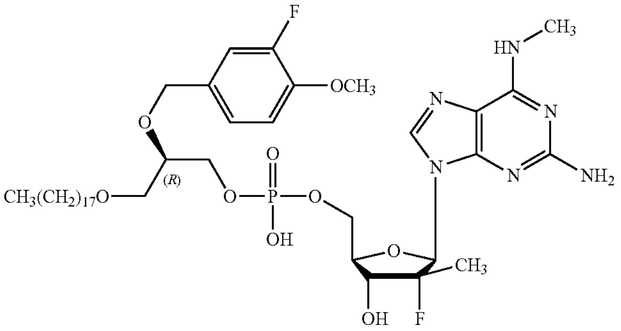

-continued
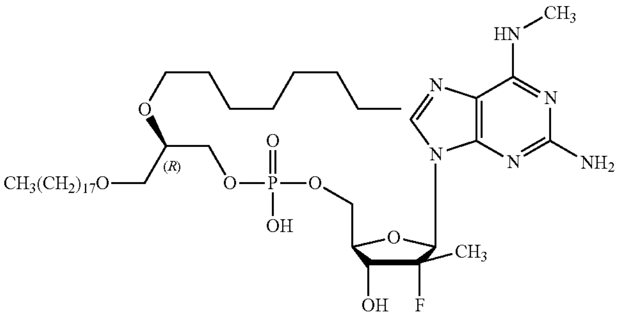
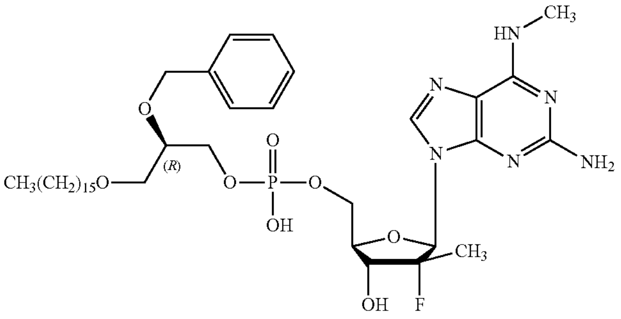
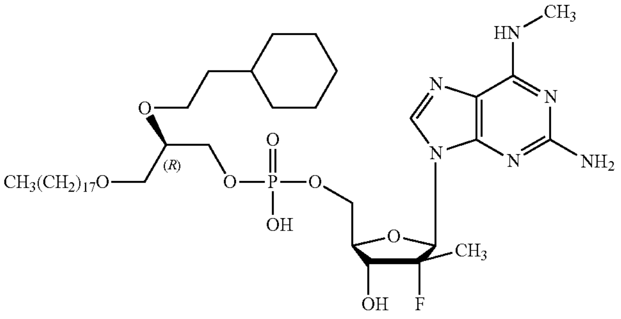
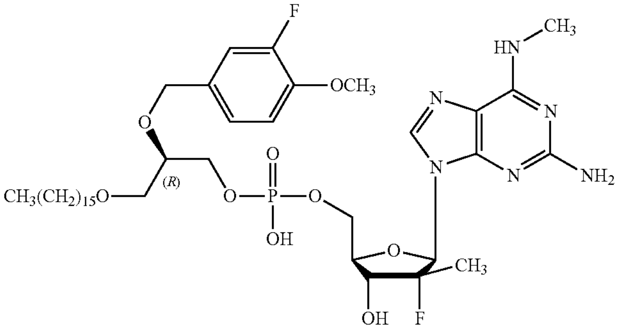
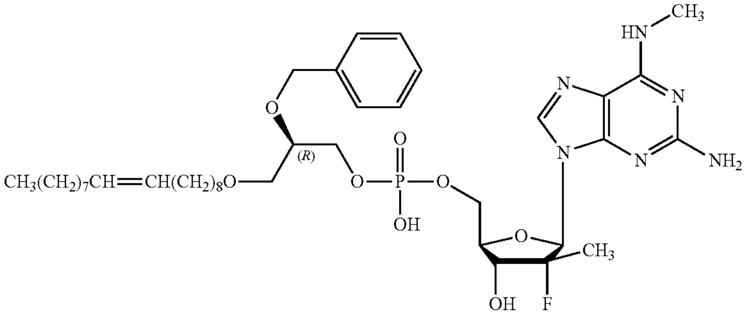

-continued
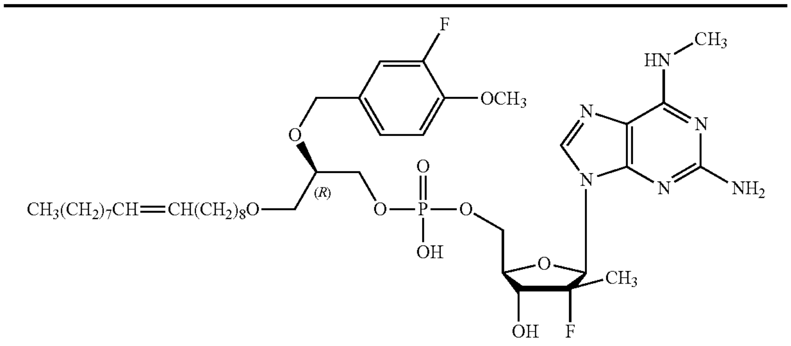
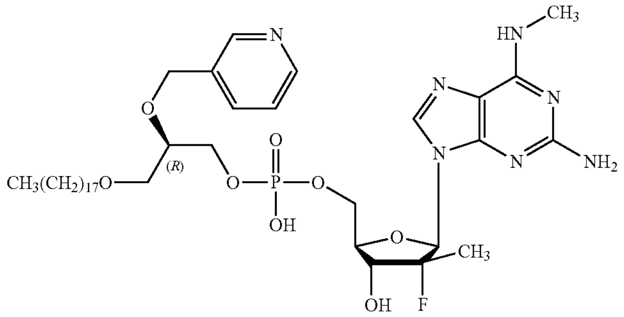
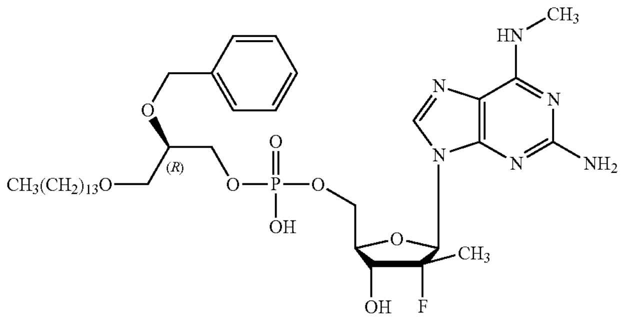
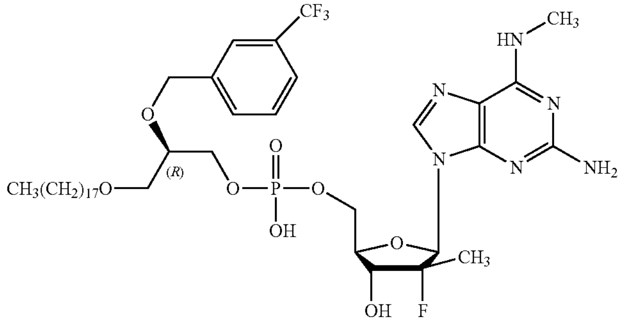
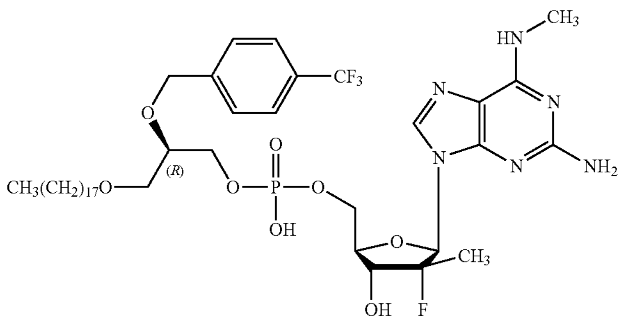

-continued
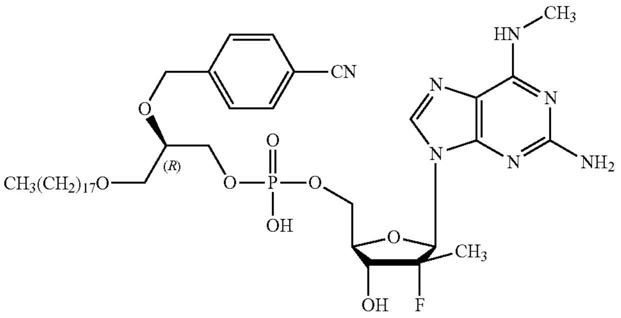
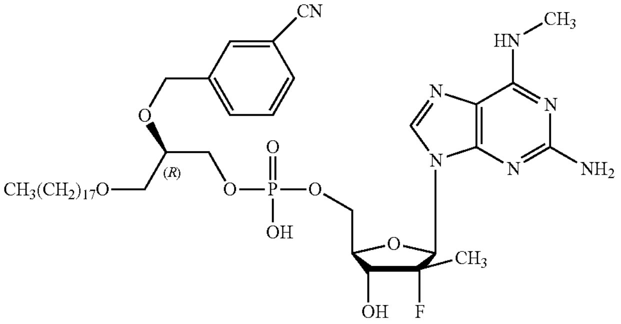
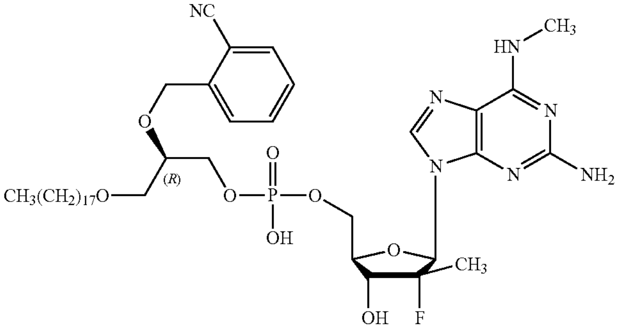
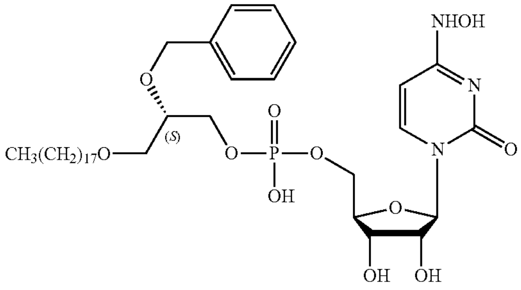
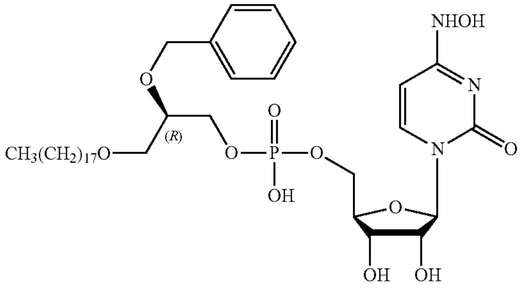

-continued
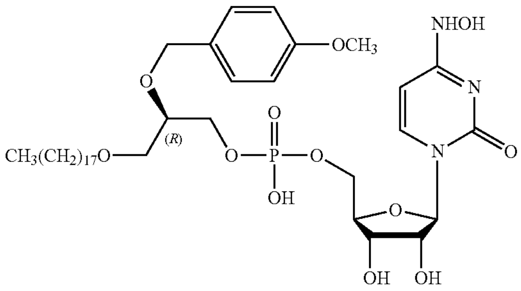
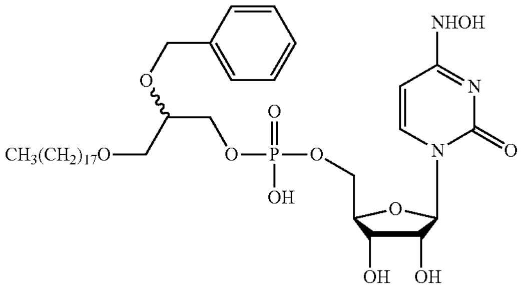
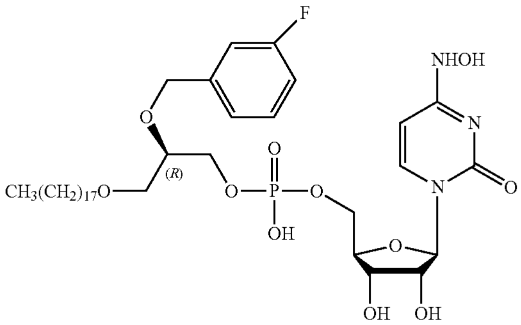
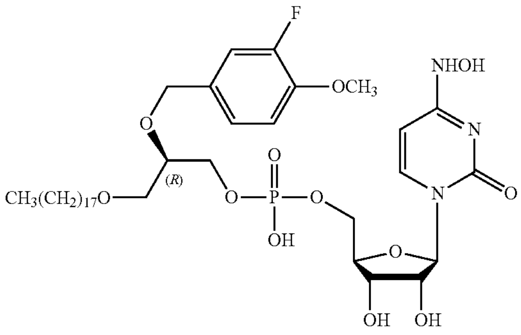
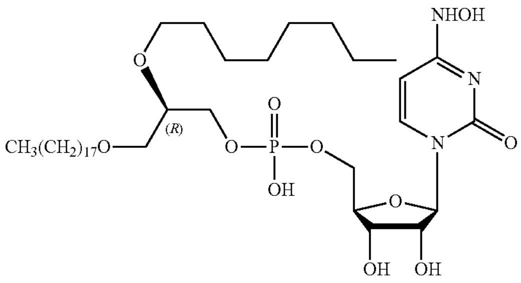

-continued
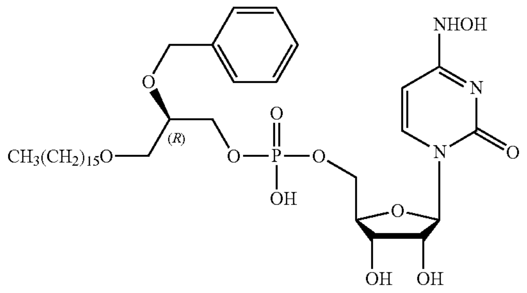
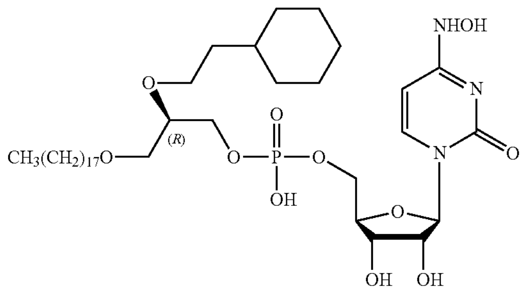
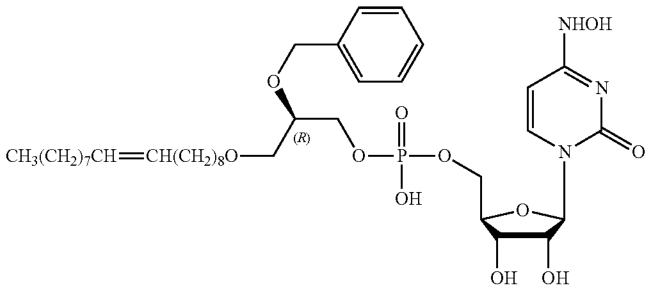
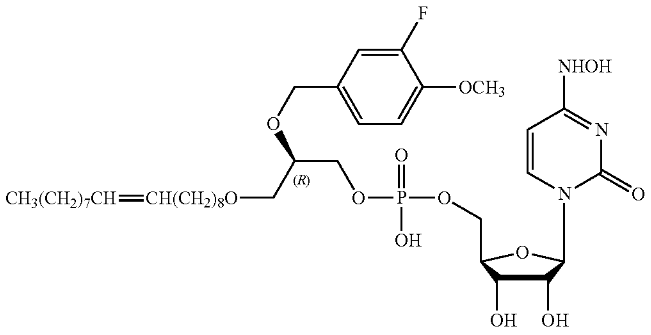
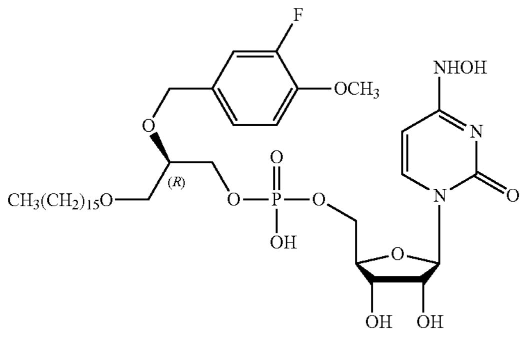

-continued
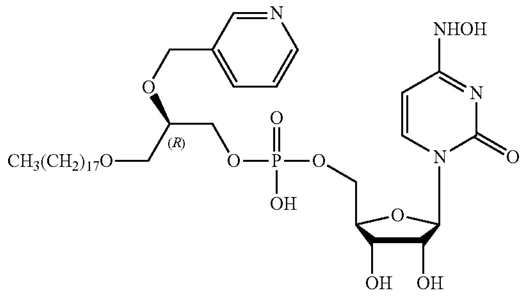
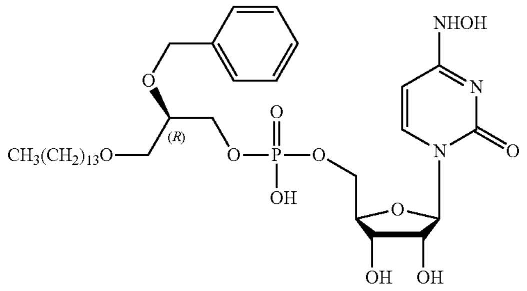
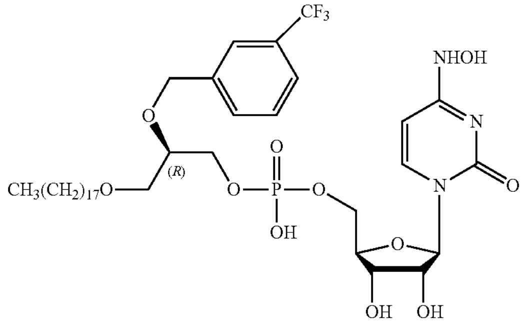
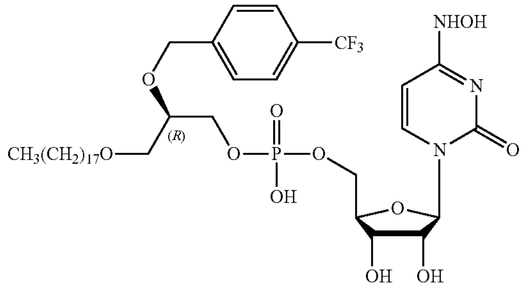
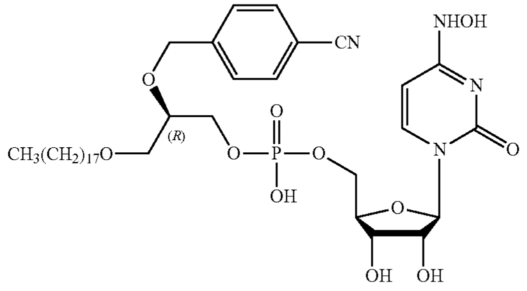

-continued

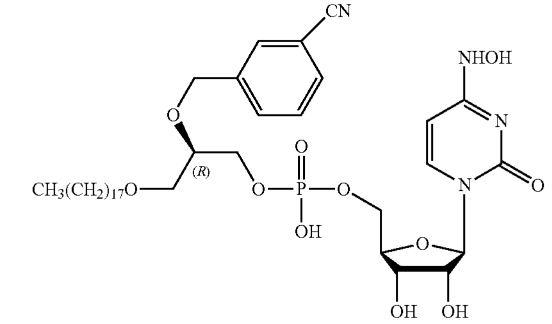

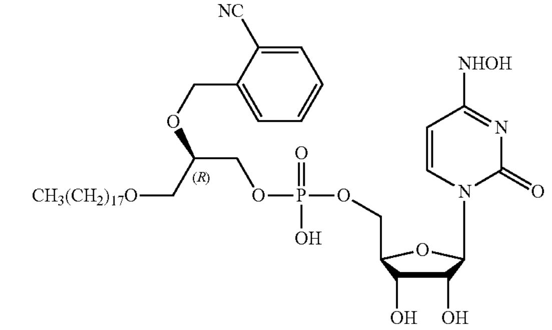

Embodiment 31. A pharmaceutical formulation comprising—

(i) an oil, and (ii) the compound of any one of Embodiments 1 to 30.

Embodiment 32. The pharmaceutical formulation of Embodiment 31, wherein the oil is selected from the group consisting of sesame oil, triglycerides (e.g., medium chain triglycerides), and a combination thereof.

Embodiment 33. The pharmaceutical formulation of Embodiment 31 or 32, wherein (A) the oil is present in the pharmaceutical formulation at an amount of about 60% to about 95%, about 65% to about 95%, about 70% to about 95%, about 75% to about 95%, about 80% to about 95%, or about 85% to about 95%, by weight, based on the weight of the pharmaceutical formulation, (B) the compound of formula (I) is present at an amount of about 0.01% to about 40%, about 0.01% to about 30%, about 0.01% to about 20%, about 0.01% to about 10%, about 0.01% to about 5%, by weight, based on the weight of the pharmaceutical formulation, or (C) a combination thereof.

Embodiment 34. The pharmaceutical formulation of any one of Embodiments 31 to 33, wherein the pharmaceutical formulation further comprises benzyl alcohol, benzyl benzoate, ethyl alcohol, or a combination thereof; wherein, optionally, the benzyl alcohol, ethyl alcohol, benzyl benzoate, or the combination thereof is present at a total amount of about 0.01% to about 25%, about 0.01% to about 20%, about 0.01% to about 15%, about 0.01% to about 10%, or about 5% to about 10%, by weight, based on the weight of the pharmaceutical formulation.

Embodiment 35. The pharmaceutical formulation of any one of Embodiments 31 to 34, wherein the pharmaceutical formulation (A) is formulated for injection, such as intramuscular or subcutaneous injection, (B) is configured to achieve kinase bypass of the first nucleoside phosphorylation, (C) delivers antivirally significant concentrations to lungs and/or gastrointestinal tract, (D) provides sustained levels of active ingredient in plasma for about 5 to about 30 days, about 5 days to about 28 days, about 5 days to about 21 days, about 5 days to about 14 days, or about 5 days to about 7 days following administration of a single dose, such as by intramuscular injection, or (E) a combination thereof.

Embodiment 36. A method for treating coronavirus infection in a mammal (e.g., a human), the method comprising administering to the mammal an effective amount of the pharmaceutical formulation of any one of Embodiments 31 to 35.

Embodiments 37. The method of Embodiment 36, wherein the effective amount of the pharmaceutical formulation is administered as a single dose.

Embodiment 38. The method of Embodiment 36 or 37, wherein the pharmaceutical formulation comprises an intermediate acting oil formulation, such as formulation F8 or formulation F7, as described herein.

Embodiment 39. A method for treating HIV infection in a mammal, the method comprising administering to the mammal an effective amount of the pharmaceutical formulation of any one of Embodiments 31 to 35.

Embodiment 40. The method of Embodiment 39, wherein the pharmaceutical formulation is a long-acting treatment.

Embodiment 41. The method of Embodiment 39 or 40, wherein the pharmaceutical formulation comprises formulation F3 or formulation F4, as described herein.

Embodiment 42. A method for treating and/or inhibiting the replication of respiratory syncytial virus (RSV), the method comprises administering to the mammal an effective amount of the pharmaceutical formulation of any one of Embodiments 31 to 35.

Embodiment 43. A method for treating a virus infection in a mammal, the method comprising administering to the mammal an effective amount of the pharmaceutical formulation of any one of Embodiments 31 to 35, wherein the virus is a RNA virus of a viral family selected from the group consisting of Filoviridae, Orthomyxoviridae, Paramyxoviridae, Pneumoviridae, Phenuiviridae, Nairoviridae, Arenaviridae, Flaviviridae, and Coronaviridae.

Embodiment 44. A method for producing a prodrug, the method comprising:

(i) providing a compound of formula (a)— formula (a)

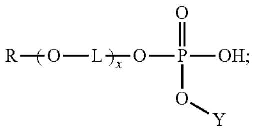

(ii) providing a compound of formula (b)— formula (b)

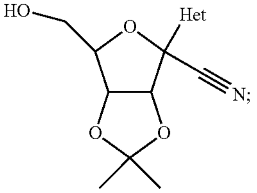

(iii) contacting the compound of formula (a) and the compound of formula (b) to form a compound of formula (c)— formula (c)

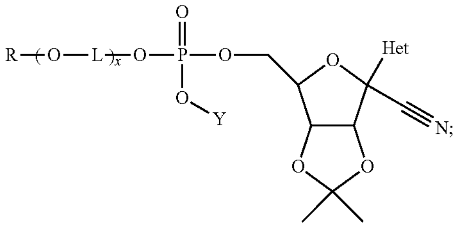

and (iv) contacting the compound of formula (c) with an acid to form a compound of formula (d)— formula (d)

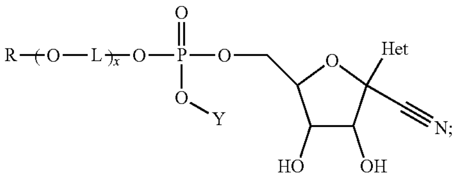

wherein Het is a $C_1$-$C_{30}$ hydrocarbyl comprising at least one heteroatom; Y is selected from the group consisting of hydrogen, a $C_1$-$C_{30}$ hydrocarbyl, and a pharmaceutically acceptable cation; x is 0 or 1; L is independently a $C_1$-$C_{30}$ hydrocarbyl; and R is selected from the group consisting of a $C_{10}$-$C_{30}$ hydrocarbyl and a substituent of formula (A);

formula (A)

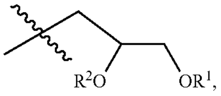

wherein $R^1$ and $R^2$ are independently selected from the group consisting of hydrogen and a $C_1$-$C_{30}$ hydrocarbyl.

Embodiment 45. The method for producing a prodrug of any of the previous Embodiments, wherein the contacting of the compound of formula (a) and the compound of formula (b) occurs in the presence of N,N-dicyclohexylcarbodiimide, 4-dimethylaminopyridine, or a combination thereof.

Embodiment 46. The method for producing a prodrug of any of the previous Embodiments, wherein the acid comprises HCl.

Embodiment 47. The method for producing a prodrug of any of the previous Embodiments, wherein the contacting of formula (c) with the acid occurs in the presence of tetrahydrofuran (THF).

EXAMPLES

The present disclosure is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present disclosure or the scope of the appended claims. Thus, other aspects of this disclosure will be apparent to those skilled in the art from consideration of the specification and practice of the disclosure disclosed herein.

Example 1—Preparation of Compounds

In this example, several general methods were used for producing various products and/or intermediates, but other known synthesis techniques may be used.

A. Synthesis of Alkyl and Alkoxyalkyl Esters of GS-441524 5'-monophosphate the ether layer was recrystallized from hexanes to afford phosphates 2a-c.

Scheme 1. Synthesis of Alkyl and Alkoxyalkyl Esters of GS-441524 5'-Monophosphate.
Reagents: a) $POCl_3$, TEA, THF; b) GS-441524 acetonide, DCC/DMAP or DIC/NMI, pyridine; c) formic acid, rt or con. HCl/THF;d) PyBOP, DIEA, DMF

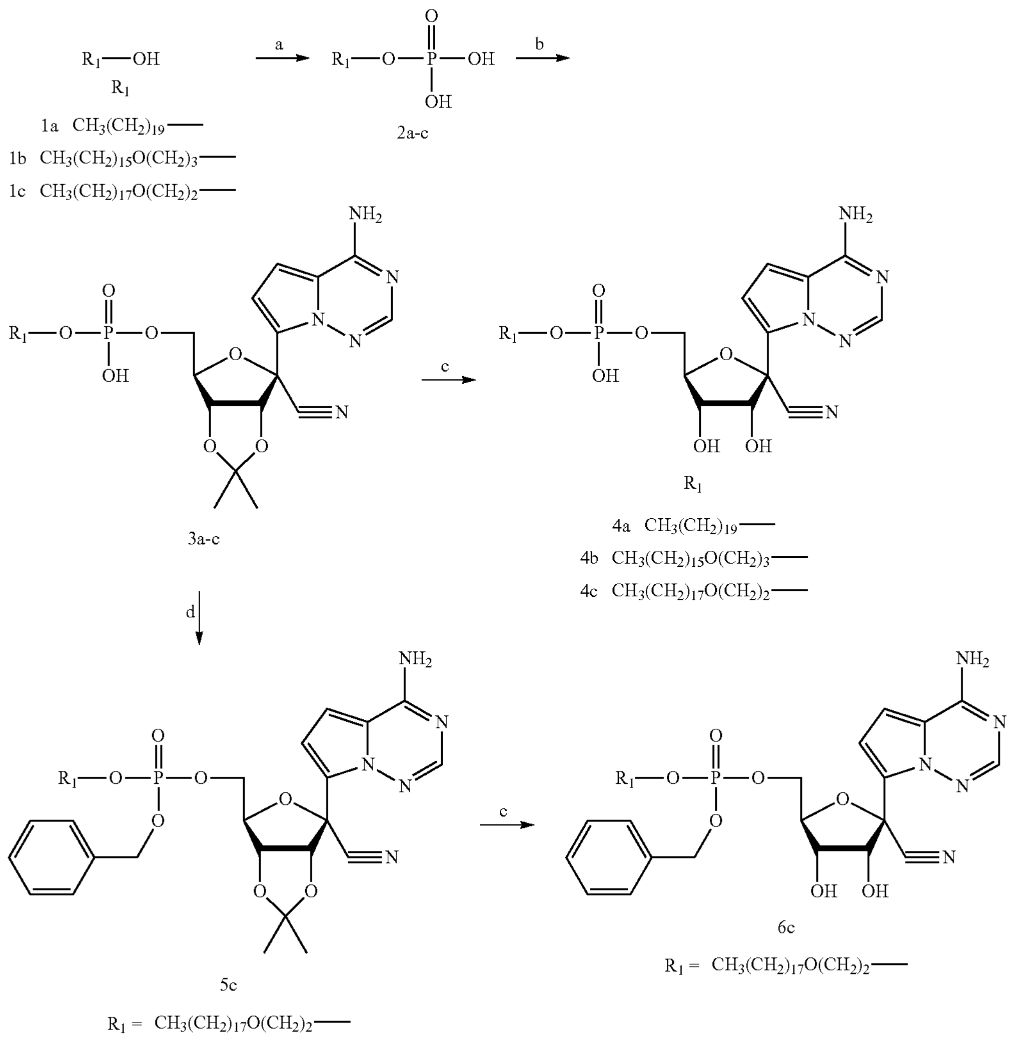

$R_1$
1a $CH_3(CH_2)_{19}$—
1b $CH_3(CH_2)_{15}O(CH_2)_3$—
1c $CH_3(CH_2)_{17}O(CH_2)_2$—

2a-c 3a-c $R_1$
4a $CH_3(CH_2)_{19}$—
4b $CH_3(CH_2)_{15}O(CH_2)_3$—
4c $CH_3(CH_2)_{17}O(CH_2)_2$—

5c
$R_1$ = $CH_3(CH_2)_{17}O(CH_2)_2$—

6c
$R_1$ = $CH_3(CH_2)_{17}O(CH_2)_2$—

Synthesis of Alkyl and Alkoxyalkyl Phosphates (Scheme 1, 2a-c)

General Method A. Long-chain alcohols 1a-c were phosphorylated to afford phosphates 2a-c as previously described (Ruiz, J., Beadle, J. R., Aldern, K. A., Keith, K., Hartline, C., Kem, E., Hostetler, K. Y. (2007). Synthesis and antiviral evaluation of alkoxyalkyl-phosphate conjugates of cidofovir and adefovir. *Antiviral Res.*, 75, 87-90). Briefly, a solution of the long-chain alcohol (1 eq.) and triethylamine (2 eq.) in anhydrous tetrahydrofuran (THF) was added dropwise to a solution of phosphorus oxychloride (1.5 eq.) in THF with stirring while the temperature was maintained below 20° C. Stirring was continued for an additional hour at 0° C., then water was added and the stirring continued overnight followed by extraction with ethyl ether. The crude solid from 2a Eicosyl dihydrogen phosphate $^1H$ (400 MHz, Chloroform-d) δ 8.30 (s, 1H), 3.98 (t, 2H), 1.61 (m, 1H), 1.26 (br s, 16H), 0.86 (t, 1H). ESI-MS 650.38 $[M-H]^-$ 2b 3-(Hexadecyloxy)propyl dihydrogen phosphate $^1H$ NMR (400 MHz, Chloroform-d) δ 4.03 (dt, 2H), 3.49 (t, 2H), 3.40 (t, 2H), 1.94 (p, 2H), 1.59-1.55 (m, 2H), 1.26 (br s, 18H), 0.86 (t, 3H).

2c 2-(Octadecyloxy)ethyl dihydrogen phosphate $^1H$ NMR (400 MHz, Chloroform-d) δ 4.12 (dt, 2H), 3.77 (t, 2H), 3.42 (t, 2H), 1.29 (br s, 20H), 0.94-0.85 (t, 3H).

Coupling of Phosphates 2a-c to GS-441524 Acetonide (Remdesivir Nucleoside, RVn Acetonide)

General Method B. N,N-Dicyclohexylcarbodiimide (DCC, 1.5 eq) was added to a mixture of GS-441524 acetonide (1 eq, CAS #1191237-80-5, purchased from Ontario Chemicals), a long-chain dihydrogen phosphate (1.0 eq), and 4-dimethylaminopyridine (DMAP, 1.0 eq) in dry pyridine, and then the mixture was heated to 90° C. and stirred for 24 h. Water was added to quench the reaction and pyridine was evaporated under vacuum. The residue was adsorbed onto silica gel and purified by flash column chromatography on silica gel 60. Gradient elution ($CH_2Cl_2$/methanol 10-20%) afforded the protected phosphodiester compound.

General Method C. N,N-Diisopropylcarbodiimide (DIC, 3.3 mmol) was added to a mixture of GS-441524 acetonide (1.65 mmol), lipid phosphate (1.65 mmol), and 1-methylimidazole (NMI, 406 mg, 4.95 mmol) in dry pyridine (30 mL), and then the mixture was stirred for 48 hours at room temperature until analysis of the reaction mixture by TLC indicated substantial formation of coupled product Water (5 mL) was then added, and the mixture was concentrated on a rotary evaporator. The residue was adsorbed onto silica gel and purified by flash column chromatography on silica gel 60. Gradient elution (100% $CH_2Cl_2$ to $CH_2Cl_2$/20% methanol) afforded the protected phosphodiester analogs.

3a Eicosyl-phospho-RVn acetonide. GS-441524 acetonide was coupled to 2a according to General Method C. The structure was confirmed by ESI-MS 690.50 $[M-H]^-$.

3b 3-(Hexadecyloxy)propyl-phospho-RVn acetonide. GS-441524 acetonide was coupled to 2b according to General Method B. N,N-Dicyclohexylcarbodiimide (DCC, 619 mg, 3 mmol) was added to a mixture of GS-441524 acetonide (300 mg, 0.91 mmol), 3-(hexadecyloxy)propyl phosphate (2b, 414 mg, 1.10 mmol), and 4-dimethylaminopyridine (DMAP, 122 mg, 1.0 mmol) in 25 mL of dry pyridine, and then the mixture was heated to 90° C. and stirred for 24 hours. Pyridine was then evaporated and the residue was purified by flash column chromatography on silica gel 60. Gradient elution ($CH_2Cl_2$/methanol 10-20%) afforded 423 mg (67% yield) of Compound 3b. $^1H$ NMR (500 MHz, chloroform-d) δ 8.42 (s, 1H), 7.98 (s, 1H), 7.70 (s, 2H), 6.22 (d, J=6.0 Hz, 1H), 5.68 (d, J=6.2 Hz, 1H), 5.15 (d, J=1.0 Hz, 1H), 4.70 (dd, J=3.8, 0.9 Hz, 1H), 4.48-4.42 (m, 1H), 4.26 (ddd, J=11.2, 8.5, 2.6 Hz, 1H), 4.15 (ddd, J=11.1, 8.5, 2.6 Hz, 1H), 4.02 (dt, J=8.5, 6.3 Hz, 2H), 3.49 (t, J=6.1 Hz, 2H), 3.40 (t, J=6.1 Hz, 2H), 1.95 (p, J=6.2 Hz, 2H), 1.54 (tt, J=7.4, 6.1 Hz, 2H), 1.31 (s, 3H), 1.32-1.24 (m, 26H), 0.94-0.85 (m, 3H). ESI-MS 691.6 $[M-H]^-$.

3c 2-(Octadecyloxy)ethyl-phospho-RVn acetonide. GS-441524 acetonide was coupled to 2c according to General Method B. N,N-Dicyclohexylcarbodiimide (DCC, 0.3 g, 1.4 mmol) was added to a mixture of GS-441524 acetonide (0.23 g, 0.7 mmol), phosphate 2c (0.27 g, 0.68 mmol), and 4-dimethylaminopyridine (DMAP, 0.07 g, 0.6 mmol) in 10 mL of dry pyridine, and then the mixture was heated to 90° C. and stirred for 3 days. Pyridine was then evaporated, and the residue was purified by flash column chromatography on silica gel 60. Gradient elution ($CH_2Cl_2$/methanol 10-20%) afforded 0.22 g (45% yield) of phosphodiester 3c.

Synthesis of 4a-c: Removal of the Acetonide Protecting Group

General Method D. (HCl/THF) Concentrated HCl (0.1 mL) in tetrahydrofuran (THF, 1 mL) was added to a stirred solution of acetonide-protected (2',3'-isopropylidene) phosphodiesters (0.25 mmol) in THF (10 mL) at room temperature. The mixture was stirred for 3 hours and then sodium bicarbonate (50 mg) and water (2 mL) were added. After stirring an additional 15 minutes the solvents were evaporated and cold water (10 mL) was added to the residue. The crude product was collected by vacuum filtration and dried under vacuum. Purification by flash column chromatography (100% $CH_2Cl_2$ to $CH_2Cl_2$/35% methanol) yielded pure phosphodiester analogs.

General Method E. Acetonide analogs (1 mmol) were added to formic acid (25 mL) at room temperature and stirred. The reaction was monitored by TLC until deprotection was complete at about 4 hours. Formic acid was removed by rotary evaporation and the residue was co-evaporated with EtOH (2×25 mL), then adsorbed onto silica gel and purified by flash column chromatography. Gradient elution (100% $CH_2Cl_2$ to $CH_2Cl_2$/35% methanol) afforded products.

4a Eicosyl-phospho-RVn—Prepared from 3a according to General Method E. The structure was confirmed by ESI-MS 650.38 $[M-H]^-$.

4b 3-(Hexadecyloxy)propyl-phospho-RVn. Prepared from 3b according to General Method D. Concentrated HCl (0.1 mL) in tetrahydrofuran (THF, 1 mL) was added to a stirred solution of 3b (100 mg, 0.14 mmol) in THF (10 mL) at room temperature. The mixture was stirred for 3 hours and then sodium bicarbonate (50 mg) and water (2 mL) were added. After stirring an additional 15 minutes the solvents were evaporated and cold water (10 mL) was added to the residue. The solid product was collected by vacuum filtration and dried under vacuum to yield 4b (79 mg, 87% yield) as an off-white solid. $^1H$ NMR (500 MHz, $CDCl_3$-methanol-$d_4$) δ 8.42 (s, 1H), 7.98 (s, 1H), 7.70 (s, 1H), 6.22 (d, J=6.0 Hz, 1H), 5.70 (d, J=6.0 Hz, 1H), 5.12 (d, J=4.2 Hz, 1H), 4.55 (ddd, J=5.5, 2.7, 0.9 Hz, 1H), 4.40 (dtd, J=6.8, 2.6, 0.8 Hz, 1H), 4.33-4.27 (m, 2H), 4.25 (ddd, J=11.1, 8.4, 2.6 Hz, 1H), 4.16 (ddd, J=11.3, 8.5, 2.6 Hz, 1H), 4.02 (dt, J=8.5, 6.3 Hz, 2H), 3.49 (t, J=6.1 Hz, 2H). 3.40 (t. J=6.1 Hz, 2H), 1.95 (p, J=6.2 Hz, 2H), 1.59-1.50 (m, 1H), 1.34-1.24 (m, 23H), 0.94-0.85 (m, 3H). ESI MS: 652.39 $[M-H]^-$. Purity by HPLC: 99.7%

4c 2-(Octadecyloxy)ethyl-phospho-RVn Prepared from 3c according to General Method D. Concentrated HCl (0.3 mL) was added slowly to a stirred solution of 3c (0.2 g, 0.28 mmol) in THF (10 mL) at 0° C. The mixture was allowed to warm to room temperature overnight and then was diluted with water (2 mL) and adjusted to pH=8 by adding saturated sodium bicarbonate. The product was extracted with chloroform (3×30 mL) and the organic layer was concentrated under reduced pressure. The residue was purified by flash chromatography on silica gel. Elution with 20% MeOH/$CH_2Cl_2$ gave 0.10 g (55% yield) of compound 4c. $^1H$ NMR (400 MHz, $CDCl_3$-methanol-$d_4$) δ ppm 7.89 (s, 1H), 6.94 (d, J=4.65 Hz, 1H), 6.89 (d, J=4.65 Hz, 1H), 4.40 (d, J=4.65 Hz, 2H), 4.21-4.28 (m, 1H), 4.12-4.20 (m, 1H), 4.04-4.12 (m, 1H), 3.91 (d, J=4.89 Hz, 2H), 3.46-3.57 (m, 2H), 3.42 (td, J=6.85, 1.96 Hz, 2H), 3.34 (dt, J=3.18, 1.59 Hz, 2H), 1.53 (d, J=6.85 Hz, 2H), 1.20-1.37 (m, 30H), 0.89 (t, J=6.97 Hz, 3H). ESI MS: 666.43 $[M-H]^-$. Purity by HPLC 98.4%.

B. Synthesis of 2-(Octadecyloxy)ethyl benzyl phospho-RVn (Long-Acting Formulation) (Scheme 1, 6c)

Compound 3c (160 mg, 0.22 mmol), benzyl alcohol (48 mg, 0.45 mmol), diisopropylethylamine (DIEA, 58 mg, 0.45 mmol), and (TH-benzotriazol-1-yloxy)-tripyrrolidinophosphonium hexafluorophosphate (PyBOP, 230 mg, 0.45 mmol) in dry DMF (5 mL) were stirred at room temperature for 3 h. DMF was then evaporated, and the residue was dissolved in ethyl acetate (50 mL) and washed with saturated $NaHCO_3$ (3×10 mL). The organic layer was dried over $MgSO_4$ and concentrated. The residue was purified by column chromatography on silica gel, eluting with chloroform/methanol (0-15%) to yield 5c (60 mg, 35% yield). $^1H$ NMR (400 MHz, $CDCl_3$-$CD_3OD$) δ ppm 7.87 (d, J=4.03 Hz, 1H), 7.27-7.37 (m, 5H), 6.91-6.95 (m, 1H), 6.83-6.89 (m, 1H), 5.41 (d, J=6.97 Hz, 1H), 4.92-5.06 (m, 3H), 4.54-4.60 (m, 1H), 4.24-4.31 (m, 2H), 4.07-4.15 (m, 2H), 3.53-3.60 (m, 2H), 3.38-3.51 (m, 2H), 3.32-3.37 (m, 2H), 1.78-1.96 (m, 2H), 1.75 (s, 3H), 1.50-1.60 (m, 2H), 1.42 (s, 3H), 1.15-1.38 (m, 30H), 0.89 (t, J=6.54 Hz, 3H). ESI MS: 798.51 $[M+H]^+$, 820.56 $[M+Na]^+$.

To a solution of 5c (60 mg, 0.075 mmol) in THF (2 mL), concentrated HCl (0.1 mL) was added at 0° C. After 20 minutes, the ice bath was removed and the reaction was monitored by TLC. After 3 hours, the ice bath was returned and the mixture was neutralized with sat. $NaHCO_3$. The mixture was concentrated under vacuum and the residue was purified by column chromatography (silica gel, dichloromethane/methanol 10-20%) to give 35 mg (62% yield) of 6c. $^1H$ NMR (400 MHz, $CDCl_3$+methanol $d_4$) δ ppm 7.84-7.90 (m, 1H), 7.29-7.38 (m, 5H), 6.89-6.93 (m, 1H), 6.82-6.86 (m, 1H), 5.03 (d, J=11.36 Hz, 2H), 4.76-4.81 (m, 1H), 4.40-4.45 (m, 1H), 4.30-4.37 (m, 1H), 4.17-4.31 (m, 2H), 4.06-4.14 (m, 2H), 3.54-3.60 (m, 2H), 3.39-3.47 (m, 2H), 3.33-3.37 (m, 2H), 3.12-3.18 (m, 2H), 1.82-1.91 (m, 2H), 1.49-1.59 (m, 2H), 1.20-1.37 (m, 30H), 0.89 (t, J=6.60 Hz, 3H). ESI MS: 758.32 $[M+H]^+$, 780.43 $[M+Na]^+$.

C. Synthesis of 1-O-Alkyl-2-O-Substituted-Sn-Glyceryl Esters of GS-441524 5'-Monophosphate The following scheme (Scheme 2) depicts embodiments of synthesis methods that were used to produce the following embodiments of 1-O-alkyl-2-O-substituted-sn-glyceryl esters of GS-441524 5'-monophosphate.

Scheme 2. Synthesis of 1-O-alkyl-2-O-substituted-sn-glycerols. Reagents: a) $R_1$ bromides or methanesulfonates, NaH, DMF; b) 80% $CH_3COOH$, reflux; c) trityl chloride, TEA, DMAP, $CH_2Cl_2$; d) $R_2$ bromides or methanesulfonates, NaH, DMF e) acidic deprotection.

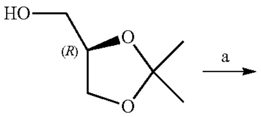

(R)-(2,2-dimethyl-1,3-dioxolan-4-yl)methanol

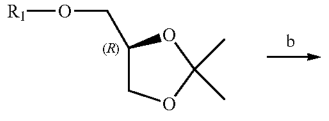

$R_1$

9a $CH_3(CH_2)_{13}$—
9b $CH_3(CH_2)_{15}$—
9c $CH_3(CH_2)_{17}$—
9d $CH_3(CH_2)_7CH{=}CH(CH_2)_8$—

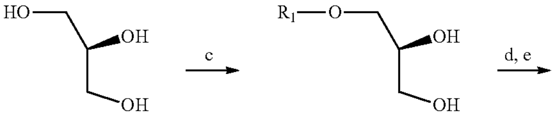

10a-d 11a-d

-continued

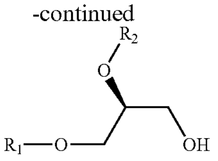

| $R_1$ | $R_2$ |
|---|---|
| 12a $CH_3(CH_2)_{13}$— | 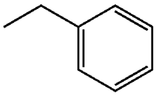 |
| 12b $CH_3(CH_2)_{15}$— | 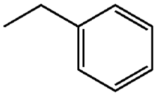 |
| 12c $CH_3(CH_2)_{15}$— | 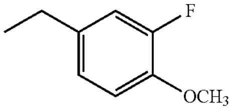 |
| 12d $CH_3(CH_2)_{17}$— | 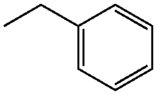 |
| 12e $CH_3(CH_2)_{17}$— | 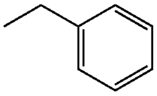 (racemic glycerol) |
| 12f $CH_3(CH_2)_{17}$— | —$(CH_2)_7CH_3$ |
| 12g $CH_3(CH_2)_{17}$— | 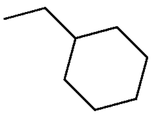 |
| 12h $CH_3(CH_2)_{17}$— | 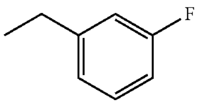 |
| 12i $CH_3(CH_2)_{17}$— | 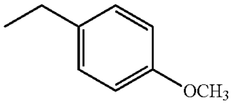 |
| 12j $CH_3(CH_2)_{17}$— | 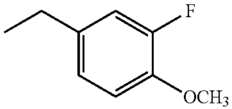 |
| 12k $CH_3(CH_2)_{17}$— | 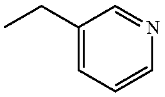 |
| 12l $CH_3(CH_2)_7CH{=}CH(CH_2)_8$— | 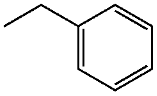 |
| 12m $CH_3(CH_2)_7CH{=}CH(CH_2)_8$— | 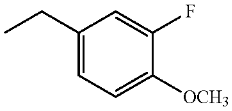 |
| 12n $CH_3(CH_2)_{17}$— | 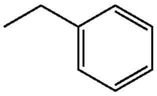 (3-O-octadecyl Isomer) |
| 12o $CH_3(CH_2)_{17}$— | 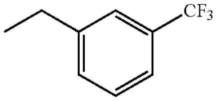 |

-continued

12p $CH_3(CH_2)_{17}$— 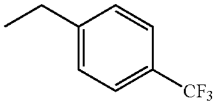

Synthesis of 1-O-Alkyl-sn-glycerols (Scheme 2, 10 a-d)

General Method F. In this embodiment, alkylation of 2,3-isopropylideneglycerol using an alkylmethanesulfonate was performed as described in the literature (Fernández, D. M.; Contreras, L. J.; Moreno, B. M.; Silva, E. G.; Mayorga, H. W. Enantiomeric synthesis of natural alkylglycerols and their antibacterial and antibiofilm activities. *Nat. Prod. Res.* 2019, 1-7).

Sodium hydride and DMF were stirred in a flask. Isopropylidene glycerol was added slowly, due to expected hydrogen evolution, while cooling, if necessary, to keep the temperature less than 35° C. After stirring an additional 30 minutes, alkyl methanesulfonate was added all at once and stirred vigorously for 5 hours. The reaction mix was poured onto crushed ice and stirred gently. The solid was collected on a frit funnel, and then washed with water. To achieve deprotection, the filter cake was added to 80% acetic acid and heated at 80° C. for 1 hour. The flask was cooled and the product crystallized, and was collected via vacuum filtration and dried. Crude product was recrystallized in hexanes or purified by flash column chromatography on silica gel 60.

General Method G. (Alkylation using a 1-bromoalkane alkene as described in the literature: (Halldorsson, A., et al. *Tetrahedron: Asymmetry,* 2004, 15, 2893-2899)).

Isopropylideneglycerol (1 eq), 1-bromoalkane/alkene (1 eq) and tetrabutylammonium bromide (0.2 eq) were stirred vigorously in a round-bottomed flask. Ground potassium hydroxide (2 eq) was added slowly, and the mixture stirred for about 15 hours at 35-40° C. in an oil bath. The alkylated product was extracted into hexanes and the organic phase was washed with $H_2O$, then evaporated to yield the 1-O-alkyl-2,3-isopropylidene-sn-glycerol.

Deprotection: The products were refluxed overnight with p-toluenesulfonic acid (10 mol %) in THF/water. After concentration under vacuum, the residue was dissolved in diethyl ether, washed with water and brine solution, dried over anhydrous magnesium sulfate, and solvent removal was achieve in vacuo on a rotary evaporator to afford the 1-O-alkyl-sn-glycerol.

10a. 1-O-Tetradecyl-sn-glycerol. Synthesized according to General Method F. Analytical data was consistent with literature values (Barragin, C. A.; Silva, E. G.; Moreno, B. M.; Mayorga, H. W. Inhibition of quorum sensing by compounds from two Eunicea species and synthetic saturated alkylglycerols. *Vitae* 2018, 25, 92-103.)

10b. 1-O-Hexadecyl-sn-glycerol was purchased from Bachem America 10c. 1-O-Octadecyl-sn-glycerol was purchased from Bachem America 10d. 1-O-Oleyl-sn-glycerol. Synthesized according to General Method G. A mixture of oleyl bromide (541 mg, 1.63 mmol), $Bu_4NBr$ (0.2 eq), 2,3-isopropylidene-sn-glycerol (1 eq), and KOH (powder, 2.5 eq) was stirred at 40° C. overnight. A subsequent work up gave 583 mg crude 9d as an oil. Crude 9d was treated with p-TsOH·$H_2O$ (0.15 eq.) in refluxing THF (6 mL) and $H_2O$ (2.5 mL) overnight. Purification of the crude oil (540 mg) by flash column chromatography (MeOH in DCM 0-8%) afforded 420 mg 1-O-oleyl-sn-glycerol 10d as an oil. Yield 75% (two steps). $^1H$ NMR ($CDCl_3$) δ 5.36-5.33 (m, 2H), 3.86-3.85 (m, 1H), 3.72 (dd, 1H), 3.62 (dd, 1H), 3.52 (dd, 1H), 3.46 (dd, 1H), 3.50-3.42 (m, 2H), 2.02-1.99 (m, 4H), 1.59-1.55 (quintet, 2H), 1.35-1.26 (m, 22H), 0.88 (t, 3H) ESI-MS: 343.67 $[M+H]^+$, 365.61 $[M+Na]^+$.

Synthesis of 1-O-Alkyl-2-O-Substituted-sn-glycerols (Scheme 2, 12a-p)

General Method H. Protection of the 3-hydroxy group of 1-O-substituted-sn-glycerols was carried out as described in the literature (e.g., Kini, G. D., Hostetler, S. E., Beadle, J. R., Aldem, K. A. Synthesis and antiviral activity of 1-O-octadecyl-2-O-alkyl-sn-glycero-3-foscarnet conjugates in human cytomegalovirus-infected cells, *Antiviral Research,* 1997, 36, 115; and Huang, Z., Szoka, Z. (2008); Sterol-Modified Phospholipids: Cholesterol and Phospholipid Chimeras with Improved Biomembrane Properties. *J. Am. Chem. Soc.,* 130, 15702-15712). Triethylamine (1.5 eq) was added to a solution of 1-O-alkyl-sn-glycerol (1 eq), N,N-dimethylaminopyridine (DMAP, 0.1 eq), and triphenyl chloride (TrCl, 1.5 eq) in anhydrous dichloromethane, and the mixture was stirred 18 hours. The reaction mixture was then quenched with water, evaporated, and adsorbed onto silica gel and purified by flash column chromatography over silica gel. An increasing gradient of ethyl acetate in hexanes (0-20%) eluted the proper fractions.

11a 1-O-Tetradecyl-3-O-trityl-sn-glycerol—Prepared as described in the literature (Huang, Z., Szoka, Z. (2008). Sterol-Modified Phospholipids: Cholesterol and Phospholipid Chimeras with Improved Biomembrane Properties. *J. Am. Chem. Soc.,* 130, 15702-15712).

11b 1-O-Hexadecyl-3-O-trityl-sn-glycerol—Prepared as described in the literature (Huang, Z., Szoka, Z. (2008). Sterol-Modified Phospholipids: Cholesterol and Phospholipid Chimeras with Improved Biomembrane Properties. *J. Am. Chem. Soc.,* 130, 15702-15712).

11c 1-O-octadecyl-3-O-trityl-sn-glycerol. Prepared from 10c according to General Method H. Yield 87%. $^1H$ NMR ($CDCl_3$): δ 0.9 (t, 3H), 1.3 (bs, 30H), 1.55 (m, 4H) 3.2 (m, 2H), 3.4-3.6 (m, 3H), 3.95 (m, 1H) 7.2-7.5 (m, 15H).

11d 1-O-oleyl-3-O-trityl-sn-glycerol. Prepared from 10d according to General Method H. Yield 77%. $^1H$ NMR ($CDCl_3$), δ 0.88 (t, J=7.2, 3H); 1.27 (br, 22H); 1.55 (m, 2H); 2.0 (m, 4H); 2.40 (br, 1H); 3.20 (m, 2H); 3.41-3.56 (m, 4H); 3.95 (m, 1H); 5.35 (m, 2H); 7.25 (m, 9H); 7.45 (m, 6H). ESI-MS 607.75 $[M+Na]^+$ General Method I. Alkylation and deprotection of 1-O-alkyl-3-O-trityl-sn-glycerols was done as described previously (Kini, G. D., Hostetler, S. E., Beadle, J. R., Aldem, K. A. Synthesis and antiviral activity of 1-O-octadecyl-2-O-alkyl-sn-glycero-3-foscarnet conjugates in human cytomegalovirus-infected cells, Antiviral Research, 1997, 36, 115). Briefly, sodium hydride (2.5 eq.) was added to a stirred solution of 1-O-alkyl-3-O-trityl-sn-glycerol (1 eq) in DMF at 0° C. After 20 minutes, a bromo or methanesulfonate derivative of $R_2$— (1.8 eq.) was added. The reaction mixture was then stirred at room temperature for 5 hours, or until the reaction was substantially complete by TLC. Work up and column chromatography gave 1-O-alkyl-2-O-substituted-3-O-trityl-sn-glycerols, which were detritylated with acid. Work up and column chromatography afforded 1-O-alkyl-2-O-substituted-sn-glycerols.

12a 1-O-Tetradecyl-2-O-benzyl-sn-glycerol—Prepared from 11a and benzyl bromide according to General Method I. Structure was confirmed by ESI-MS: 401.51 $[M+Na]^+$ 12b 1-O-Hexadecyl-2-O-benzyl-sn-glycerol—Prepared from 11b and benzyl bromide according to General Method I. $^1H$ NMR (300 MHz, $CDCl_3$): δ 7.36-7.27 (m, 5H), 4.65 (m, 2H), 3.79-3.59 (m, 5H), 3.55 (t, 2H), 1.57-1.51 (m, 2H), 1.29 (br s, 26H), 0.89 (t, 3H).

12c 1-O-Hexadecyl-2-O-(3-fluoro-4-methoxybenzyl)-sn-glycerol was prepared from 11b and 3-fluoro-4-methoxybenzyl bromide according to General Method I.

12d 1-O-Octadecyl-2-O-benzyl-sn-glycerol, 12e 1-O-Octadecyl-2-O-benzyl-rac-glycerol, 12f 1-O-Octadecyl-2-O-octyl-sn-glycerol, 12g 1-O-Octadecyl-2-O-(cyclohexylmethyl)-sn-glycerol, 12h 1-O-Octadecyl-2-O-(3-fluorobenzyl)-sn-glycerol, 12i 1-O-Octadecyl-2-O-(4-methoxybenzyl)-sn-glycerol, 12j 1-O-Octadecyl-2-O-(3-fluoro-4-methoxybenzyl)-sn-glycerol, and 12k 1-O-Octadecyl-2-O-(pyridine-3-yl-methyl)-sn-glycerol were prepared from 11c and the appropriate bromide according to General Method I.

12l 1-O-Oleyl-2-O-benzyl-sn-glycerol. Sodium hydride (1.3 eq.) was added to 11d (531 mg, 0.91 mmol) in DMF (4 mL) at 0° C. The resulting mixture was stirred at room temperature for 1 hour before benzyl bromide (1.3 eq.) was added. The reaction mixture was stirred at room temperature overnight. Work up and column chromatography afforded 354 mg crude product and 200 mg of 11d was also recovered. Deprotection afforded 12l. $^1H$ NMR (300 MHz, Chloroform-d) δ 7.35-7.26 (m, 4H), 5.36-5.32 (m, 2H), 3.84-3.62 (m, 5H), 3.54-3.46 (m, 2H), 3.44 (t, 2H), 2.88-2.75 (m, 2H), 2.02 (m, 4H), 1.54-1.50 (pentet 2H), 1.29 (br s, 22H), 0.88 (t, 3H). 455.73 $[M+Na]^+$ 12m 1-O-Oleyl-2-O-(3-fluoro-4-methoxybenzyl)-sn-glycerol. Prepared from 11d and 3-fluoro-4-methoxybenzyl bromide according to General Method I. $^1H$ NMR (300 MHz, Chloroform-d) δ 7.12 (m, 2H), 6.95 (t, 1H), 5.36-5.32 (m, 2H), 4.65-4.52 (dd, 2H), 3.75-3.70 (m, 2H), 3.67-3.60 (m, 2H), 3.57-3.55 (m, 2H), 3.45 (t, 2H), 2.01-1.97 (m, 2H), 1.28 (br s, 16H), 0.87 (t, 3H). ESI-MS: 503.79 $[M+Na]^+$ 12n 3-O-Octadecyl-2-O-benzyl-sn-glycerol.

12o 1-O-Octadecyl-2-O-(3-trifluoromethyl)benzyl)-sn-glycerol ESI-MS 525.47 $[M+Na]^+$.

12p 1-O-Octadecyl-2-O-(4-trifluoromethyl)benzyl)-sn-glycerol. ESI-MS 503.35 $[M+H]^+$.

Synthesis of 1-O-Alkyl-2-O-substituted-sn-glyceryl esters of GS-441524 5'-monophosphate (Scheme 3, 15a-p)

The following scheme depicts embodiments of synthesis steps used to produce 1-O-alkyl-2-O-substituted-sn-glyceryl esters of GS-441524 5'-monophosphate.

Scheme 3. Synthesis of 1-O-Alkyl-2-O-substituted-sn-glyceryl esters of GS-441524 5'-minophosphate. Reagents: a) $POCl_3$ or bis(trichloroethyl) chlorophosphate/zinc powder; b) DCC/DMAP or DIC/NMI, pyridine; c) formic acid or con HCl/THF.

12a-p

-continued

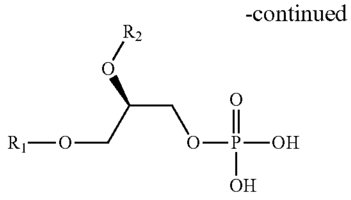

13a-p

+ a

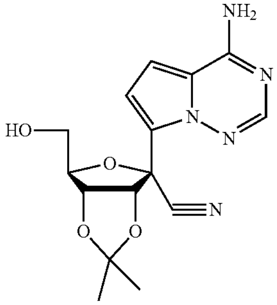

GS-441524 acetonide

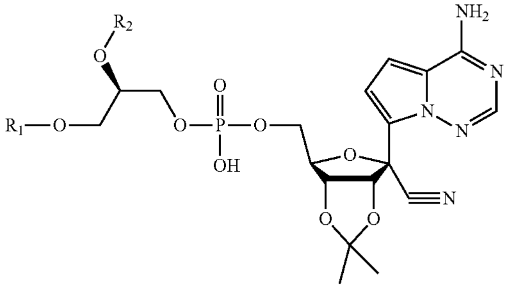

14 a-p b

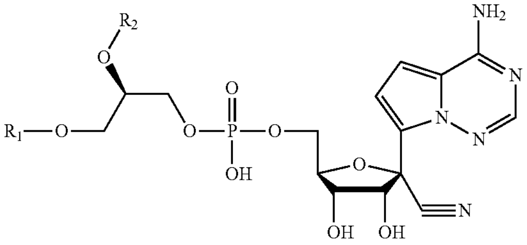

| R1 | R2 |
| --- | --- |
| 15a $CH_3(CH_2)_{13}$— | 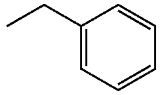 |
| 15b $CH_3(CH_2)_{15}$— | 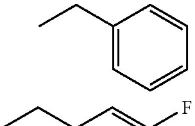 |
| 15c $CH_3(CH_2)_{15}$— | 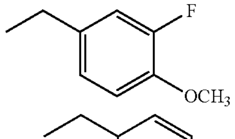 |
| 15d $CH_3(CH_2)_{17}$— | 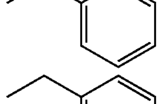 |
| 15e $CH_3(CH_2)_{17}$— | 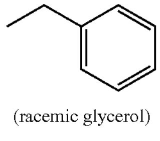 (racemic glycerol) |

-continued

15f $CH_3(CH_2)_{17}$— —$(CH_2)_7CH_3$

15g $CH_3(CH_2)_{17}$—
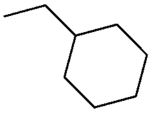

15h $CH_3(CH_2)_{17}$—
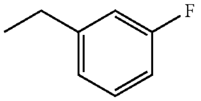

15i $CH_3(CH_2)_{17}$—
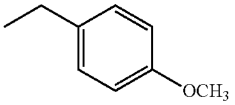

15j $CH_3(CH_2)_{17}$—
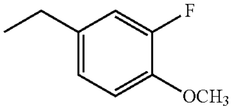

15k $CH_3(CH_2)_{17}$—
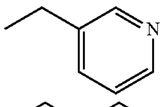

15l $CH_3(CH_2)_7CH{=}CH(CH_2)_8$—
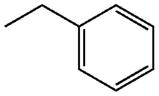

3-O-octadecyl Isomer

15m $CH_3(CH_2)_7CH{=}CH(CH_2)_8$—
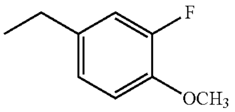

15n $CH_3(CH_2)_{17}$—
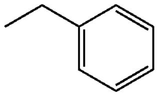

15o $CH_3(CH_2)_{17}$—
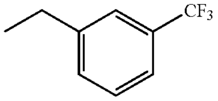

15p $CH_3(CH_2)_{17}$—
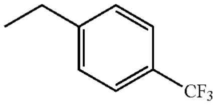

General Method J. Phosphorylation of 1-O-alkyl-2-O-substituted-sn-glycerols was accomplished as described in the literature (Kates, M., Adams, G. A., Blank, M. L., Snyder, F. M. (1991), Chemical synthesis and physiological activity of sulfonium analogues of platelet activating factor. Lipids, 26, 1095-1101). 1-O-alkyl-2-O-substituted-sn-glycerols (11.5 mmol) and 1-methylimidazole (14.4 mmol) were dissolved in dry pyridine (100 mL) and stirred at room temperature. A solution of bis(trichloroethyl) chlorophosphate (5.5 g, 14.4 mmol) in diethyl ether (20 mL) was added dropwise over 10 minutes, then the mixture was stirred overnight. Analysis by TLC showed complete phosphorylation. Water (10 mL) was added to quench excess reagent and then the mixture was concentrated by rotary evaporation, and co-evaporated with toluene to remove pyridine. The residue was adsorbed onto silica gel 60 (ca. 30 g) and purified by flash column chromatography. Gradient elution 100% hexanes to 25% EtOAc/hexanes was used to isolate protected phosphorylated product.

The products (9.65 mmol) were dissolved in a mixture of chloroform (50 mL) and glacial acetic acid (90 mL), and then vigorously stirred and cooled with an ice water bath. Zinc powder (5 g) was added to the mixture, stirred for 1 hour and then the ice water bath was removed, and stirring was continued for another 2 hours. The remaining zinc was removed by vacuum filtration and the clear filtrate was concentrated by rotary evaporation. The residue was taken up in 20% $MeOH/CH_2Cl_2$ (250 mL) and extracted with 1 M HCl (3×50 mL), then the organic layer was concentrated and co-evaporated with ethanol (2×50 mL). The waxy residue was dissolved in 1,4-dioxane, frozen, then lyophilized in vacuo (18 h) to provide glyceryl phosphates.

Compounds 13a, 13b, 13c, 13d, 13e, 13f, 13g, 13 h, 13i, 13j, and 13k were prepared according to General Method J.

13l 1-O-Oleyl-2-O-benzyl-sn-glyceryl-3-phosphate. Prepared according to General Method A. $^1$H NMR (300 MHz, Chloroform-d) δ 7.36-7.23 (m, 5H), 5.36-5.32 (m, 2H), 4.69 (d, J=11.9 Hz, 1H), 4.62 (d, J=11.8 Hz, 1H), 4.11-4.09 (m, 2H), 3.80-3.77 (m, 2H), 3.76-3.69 (m, 1H), 3.53-3.47 (m, 1H), 3.42 (t, 2H), 2.00 (tq, J=7.1, 3.7 Hz, 4H), 1.50 (m, 2H), 1.26 (br s, 22H), 0.87 (t, 3H). ESI-MS: 513.72 $[M+1]^+$ 13m 1-O-Oleyl-2-O-(3-fluoro-4-methoxybenzyl)-sn-glyceryl-3-phosphate. Prepared according to General Method A.

13n 3-O-Octadecyl-2-O-benzyl-sn-glyceryl-1-phosphate. Prepared according to General Method A.

13o 1-O-Octadecyl-2-O-(3-trifluoromethyl)benzyl-sn-glyceryl-3-phosphate. Prepared according to General Method A. ESI-MS 581.49 $[M-H]^-$.

13p 1-O-Octadecyl-2-O-(4-trifluoromethyl)benzyl-sn-glyceryl-3-phosphate. Prepared according to General Method A. ESI-MS 581.47 $[M-H]^-$.

Coupling of Phosphates 13a-p to GS-441524 Acetonide (Remdesivir Nucleoside, RVn Acetonide)

14a 1-O-Tetradecyl-2-O-benzyl-sn-glyceryl-phospho-RVn acetonide—Prepared from GS-441524 acetonide and 13a according to General Method C. Structure was confirmed by ESI-MS 770.50 $[M-H]^-$.

14b 1-O-Hexadecyl-2-O-benzyl-sn-glyceryl-phospho-RVn acetonide—Prepared from GS-441524 acetonide and 13b according to General Method C.

14c 1-O-Hexadecyl-2-O-(3-fluoro-4-methoxy-benzyl)-sn-glyceryl-phospho-RVn acetonide—Prepared from GS-441524 acetonide and 13c according to General Method C.

14d 1-O-Octadecyl-2-O-benzyl-sn-glyceryl-phospho-RVn acetonide—Prepared from GS-441524 acetonide and 13d according to General Method B. N,N-Dicyclohexylcarbodiimide (DCC, 310 mg, 1.5 mmol) was added to a mixture of acetonide (300 mg, 0.91 mmol), phosphate 13d (515 mg, 1.0 mmol), and 4-dimethylaminopyridine (DMAP, 122 mg, 1.0 mmol) in 25 mL of dry pyridine, and then the mixture was heated to 90° C. and stirred for 24 h. Pyridine was then evaporated and the residue was purified by flash column chromatography on silica gel 60. Gradient elution ($CH_2Cl_2$/methanol 10-20%) afforded 210 mg (28% yield) of compound 14d. ESI MS 826.58 $[M-H]^-$.

14e 1-O-Octadecyl-2-O-benzyl-rac-glyceryl-phospho-RVn acetonide.—Prepared from GS-441524 acetonide and 13e according to General Method C.

14f 1-O-Octadecyl-2-O-octyl-sn-glyceryl-phospho-RVn acetonide—Prepared from GS-441524 acetonide and 13f according to General Method C.

14g 1-O-Octadecyl-2-O-(cyclohexylmethyl)-sn-glyceryl-phospho-RVn acetonide—May be prepared from GS-441524 acetonide and 13g according to General Method C.

14h 1-O-Octadecyl-2-O-(3-fluoro-benzyl)-sn-glyceryl-phospho-RVn acetonide—Prepared from GS-441524 acetonide and 13h according to General Method C.

14i 1-O-Octadecyl-2-O-(4-methoxy-benzyl)-sn-glyceryl-phospho-RVn acetonide—May be prepared from GS-441524 acetonide and 13i according to General Method C.

14j 1-O-Octadecyl-2-O-(3-fluoro-4-methoxy-benzyl)-sn-glyceryl-phospho-RVn acetonide—Prepared from GS-441524 acetonide and 13j according to General Method C.

14k 1-O-Octadecyl-2-O-(pyridine-3-yl-methyl)-sn-glyceryl-phospho-RVn acetonide—May be prepared from GS-441524 acetonide and 13k according to General Method C.

14l 1-O-Oleyl-2-O-benzyl-sn-glyceryl-phospho-RVn acetonide Prepared from GS-441524 acetonide and 13l according to General Method B.

14m 1-O-Oleyl-2-O-(3-fluoro-4-methoxy-benzyl)-sn-glyceryl-phospho-RVn acetonide Prepared from GS-441524 acetonide and 13m according to General Method B.

14n 3-O-Octadecyl-2-O-benzyl-sn-glyceryl-1-phospho-RVn acetonide Prepared from GS-441524 acetonide and 13n according to General Method B.

14o 1-O-Octadecyl-2-O-(3-trifluoromethyl)benzyl-sn-glyceryl-phospho-RVn acetonide Prepared from GS-441524 acetonide and 13o according to General Method B. ESI-MS 894.66 $[M-H]^-$.

14p 1-O-Octadecyl-2-O-(4-trifluoromethyl)benzyl-sn-glyceryl-phospho-RVn acetonide Prepared from GS-441524 acetonide and 13p according to General Method B. ESI-MS 894.53 $[M-H]^-$.

Removal of Acetonide Protecting Group 15a 1-O-Tetradecyl-2-O-benzyl-sn-glyceryl-phospho-RVn—Prepared from Compound 14a according to General Method E and isolated as an off-white powder. Structure was confirmed by ESI-MS $[M-H]^-$=730.41.

15b 1-O-Hexadecyl-2-O-benzyl-sn-glyceryl-phospho-RVn. Prepared from Compound 14b according to General Method E. $^1$H NMR (500 MHz, DMSO-$d_6$) δ 7.94 (s, 1H), 7.89 (s, 1H), 7.81 (s, 1H), 7.32-7.25 (m, 3H), 7.22 (ddd, J=8.7, 5.4, 2.6 Hz, 1H), 6.88 (d, J=4.5 Hz, 1H), 6.80 (d, J=4.5 Hz, 1H), 6.24 (s, 1H), 5.95 (d, J=4.0 Hz, 1H), 4.55 (q, J=12.1, 12.1, 12.1 Hz, 3H), 4.09 (dt, J=6.7, 4.3, 4.3 Hz, 1H), 3.92 (d, J=4.5 Hz, 1H), 3.78 (dtt, J=24.4, 7.8, 7.8, 4.4, 4.4 Hz, 2H), 3.66-3.55 (m, 3H), 3.43 (dd, J=10.6, 3.5 Hz, 1H), 3.32-3.28 (m, 2H), 1.42 (q, J=6.5, 6.5, 6.0 Hz, 2H), 1.20 (d, J=7.7 Hz, 24H), 0.83 (t, J=7.0, 7.0 Hz, 3H). LC/MS purity=99.8%; $[M+H]^+$ 760.6.

15c 1-O-Hexadecyl-2-O-(3-fluoro, 4-methoxybenzyl)-sn-glyceryl-phospho-RVn. Prepared from Compound 14c according to General Method E. $^1$H NMR (500 MHz, DMSO-d6) δ 7.89 (s, 1H), 7.80 (s, 1H), 7.11 (d, J=12.3 Hz, 1H), 7.04 (d, J=6.1 Hz, 2H), 6.87 (d, J=4.6 Hz, 1H), 6.81 (d, J=4.5 Hz, 1H), 6.17 (s, 1H), 4.56 (d, J=5.0 Hz, 1H), 4.52-4.41 (m, 2H), 4.10 (s, 1H), 3.93 (q, J=5.4, 5.2, 5.2 Hz, 1H). 3.78 (s, 3H), 3.63 (s. 2H), 3.57 (d, J=4.6 Hz, 1H), 3.41 (dd, J=10.4, 3.5 Hz, 1H), 3.29 (s, 3H), 1.41 (d, J=6.5 Hz, 2H), 1.25-1.17 (m, 24H), 0.83 (t, J=7.0, 7.0 Hz, 3H). LC/MS purity 99.8%; $[M+H]^+$ 808.9.

15f 1-O-Octadecyl-2-O-octyl-sn-glyceryl-phospho-RVn—Prepared from Compound 14f according to General Method E. $^1$H NMR (500 MHz, DMSO-d6) δ 7.89 (s, 1H), 7.79 (s, 1H), 6.88 (d, J=4.5 Hz, 1H), 6.80 (d, J=4.5 Hz, 1H), 6.10 (s, 1H), 5.92 (s, 1H), 4.56 (t, J=5.2, 5.2 Hz, 1H). 4.08 (t. J=5.7, 5.7 Hz, 1H), 3.91 (q, J=5.0, 4.9, 4.9 Hz, 1H), 3.79 (d, J=18.1 Hz, 3H), 3.54 (d, J=19.3 Hz, 3H), 3.46-3.35 (m, 5H), 3.33 (s, 2H), 3.27-3.23 (m, 1H), 1.41 (dt, J=16.0, 7.4, 7.4 Hz, 4H), 1.21 (d, J=4.5 Hz, 36H), 0.83 (td, J=7.1, 7.0, 5.7 Hz. 6H). LC/MS purity 99.7%; $[M+H]^+$ 810.7.

15g 1-O-Octadecyl-2-O-(ethylcyclohexyl)-sn-glyceryl-phospho-RVn—May be prepared from Compound 14g according to General Method E.

15h 1-O-Octadecyl-2-O-(3-fluoro-benzyl)-sn-glyceryl-phospho-RVn—Prepared from Compound 14h according to General Method E. $^1$H NMR (500 MHz, DMSO-$d_6$) δ 8.47 (s, 2H), 7.88 (s, 2H), 7.36-7.26 (m, 1H), 7.12 (q, J=8.4, 6.9, 6.9 Hz, 2H), 7.03 (td, J=8.5, 8.4, 2.9 Hz, 1H). 6.88 (d, J=4.5 Hz, 1H), 6.80 (d, J=4.5 Hz, 1H), 6.30 (s, 1H), 5.97 (s, 1H), 4.64-4.50 (m, 3H), 4.13-4.07 (m, 1H), 3.92 (t, J=5.8, 5.8 Hz, 1H), 3.79 (dddd, J=33.7, 12.0, 7.6, 4.3 Hz, 2H), 3.63 (dtt, J=14.0, 10.1, 10.1, 5.7, 5.7 Hz, 3H), 3.43 (dd, J=10.7, 3.4 Hz, 2H), 1.43 (p, J=6.5, 6.5, 6.5, 6.5 Hz, 2H), 1.20 (d, J=11.1 Hz, 30H), 0.83 (t, J=6.9, 6.9 Hz, 3H). LC/MS purity 98.7%; $[M+H]^+$ 806.8.

15i 1-O-Octadecyl-2-O-(4-methoxybenzyl)-sn-glyceryl-phospho-RVn—May be prepared from Compound 14i according to General Method E.

15j 1-O-Octadecyl-2-O-(3-fluoro-4-methoxy-benzyl)-sn-glyceryl-phospho-RVn—Prepared from Compound 14j according to General Method E. $^1$H NMR (500 MHz, DMSO-$d_6$) δ 8.43 (d, J=6.7 Hz, 2H), 7.99-7.73 (m, 2H), 7.04 (d, J=5.5 Hz, 1H), 6.87 (q, J=3.7, 3.7, 3.2 Hz, 1H), 6.82 (dd, J=7.3, 4.3 Hz, 1H), 6.17-5.74 (m, 1H), 4.59 (t, J=4.9, 4.9 Hz, 1H), 4.53-4.41 (m, 1H), 4.11 (q, J=4.9, 4.9, 4.9 Hz, 1H), 3.93 (q, J=5.4, 5.4, 5.4 Hz, 1H), 3.84 (dq, J=11.3, 6.5, 5.1, 5.1 Hz, 1H), 3.80-3.70 (m, 3H), 3.61 (ddd, J=27.7, 10.9, 5.2 Hz, 3H), 3.30 (dd, J=6.6, 3.0 Hz, 3H), 3.21 (dq, J=9.8, 5.1, 5.1, 4.9 Hz, 1H), 1.43 (p, J=6.6, 6.6, 6.5, 6.5 Hz, 2H), 1.27-1.16 (m, 30H), 0.83 (t, J=6.8, 6.8 Hz, 3H). LC/MS purity 94.7%; $[M+H]^+$ 836.8.

15k 1-O-Octadecyl-2-O-(pyridine-3-yl-methyl)-sn-glyceryl-phospho-RVn—May be prepared from Compound 14k according to General Method E.

15l 1-O-Oleyl-2-O-benzyl-sn-glyceryl-phospho-RVn Prepared from Compound 14l according to General Method D and isolated as an off-white solid in 84% yield. $^1$H NMR (300 MHz, $CDCl_3$+$CD_3OD$) δ 7.79 (s, 1H), 7.38 (s, 2H), 7.27-7.21 (m, 5H), 6.92 (d, J=6.0 Hz, 1H), 6.90 (d, J=6.0 Hz, 1H), 5.30 (t, J=6.0 Hz, 2H), 4.70 (d, J=11 Hz, 1H), 4.62 (d, J=5 Hz, 1H), 4.34-4.49 (m, 1H), 4.20 (m, 1H), 3.90-3.87 (m, 2H), 4.18-4.06 (m, 2H), 3.71-3.69 (m, 2H), 3.52 (ddd, J=11.7, 3.1, 1.3 Hz, 1H), 3.35 (t, 2H), 1.96-1.93 (m, 4H) 1.49-1.47 (m, 2H), 1.33-1.23 (m, 20H), 0.83 (t, 2H). LC/MS purity 99%; $[M+H]^+$ 786.78, 15m 1-O-Oleyl-2-O-(3-fluoro, 4-methoxybenzyl)-sn-glyceryl-phospho-RVn Prepared from Compound 14m according to General Method D and isolated as an off white solid. Yield was 92%. $^1$H NMR (300 MHz, $CD_3OD$) δ 7.74 (s, 1H), 7.32 (s, 2H), 6.99 (d, J=6.0 Hz, 1H), 6.92-6.77 (m, 3H), 5.23 (t, J=6.0 Hz, 2H), 4.67 (d, J=11 Hz, 1H), 4.49 (d, J=5 Hz, 2H), 4.30 (m, 1H), 4.20 (m, 1H), 3.83-3.81 (m, 2H), 3.75 (s, 3H), 3.63 (m, 1H), 3.31 (t, 2H), 1.91-1.89 (m, 4H), 1.44 (m, 2H), 1.18 (br s, 22H), 0.77 (t, 2H). LC/MS purity 99%; $[M+H]^+$ 834.87.

15n 3-O-Octadecyl-2-O-benzyl-sn-glyceryl-1-phospho-RVn Prepared from Compound 14n according to General Method D and isolated as an off white solid.

15o 1-O-Octadecyl-2-O-(3-trifluoromethyl)benzyl-sn-glyceryl-phospho-RVn Prepared from Compound 14o according to General Method D and isolated as an off white solid. ESI-MS 854.48 $[M-H]^-$.

15p 1-O-Octadecyl-2-O-(4-trifluoromethyl)benzyl-sn-glyceryl-phospho-RVn Prepared from Compound 14p according to General Method D and isolated as an off white solid. ESI-MS 854.46 [M–H]$^-$.

D. Synthesis of 1-O-Octadecyl-2-O-benzyl-sn-glyceryl-benzyl-phospho-RVn

Scheme 4. Reagents: a) benzyl alcohol, PyBOP, DIEA, DMF; b) formic acid, rt

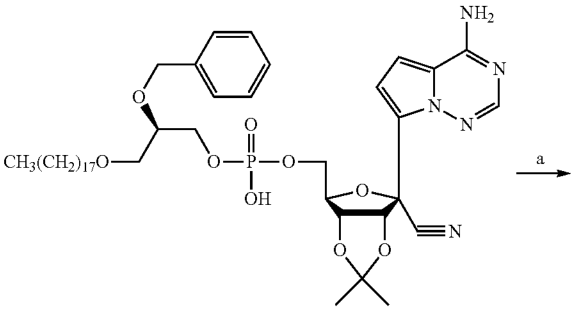

14d

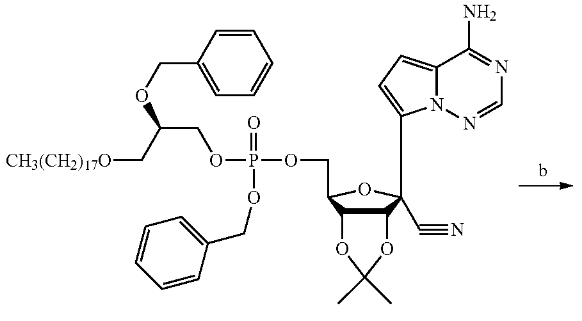

16

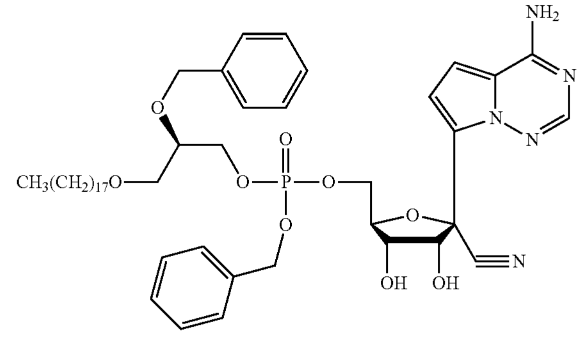

17

Compound 14d (160 mg, 0.22 mmol), benzyl alcohol (48 mg, 0.45 mmol), diisopropylethylamine (DIEA, 58 mg, 0.45 mmol), and (1H-benzotriazol-1-yloxy)-tripyrrolidinophosphonium hexafluorophosphate (PyBOP, 230 mg, 0.45 mmol) in dry DMF (5 mL) were stirred at room temperature for 3 h. DMF was then evaporated, and the residue was dissolved in ethyl acetate (50 mL) and washed with saturated $NaHCO_3$ (3×10 mL). The organic layer was dried over $MgSO_4$ and concentrated. The residue was purified by column chromatography on silica gel, eluting with chloroform/methanol (0-15%) to yield 16. ESI-MS 918.33 [M–H]$^-$.

Compound 16 was added to formic acid and the deprotection was monitored by TLC. The mixture was concentrated under vacuum and the residue was purified by column chromatography (silica gel, dichloromethane/methanol 10-20%) to give Compound 17. Structure was confirmed by ESI-MS: 878.35 [M+H]$^+$, 900.43 [M+Na]$^+$.

E. Synthesis of GS-441524-3',5'-cyclic monophosphate, octadecyloxyethyl and 1-O-octadecyl-2-O-benzyl-sn-glyceryl Esters In another embodiment, compounds of the disclosure are 3',5'-cyclic phosphates. The 3',5'-cyclic phosphates were prepared from known or readily prepared starting materials, following methods known to one skilled in the art of organic synthesis. As an example, 3',5'-cyclic phosphates 18-eq, 18-ax, 19-eq and 19-ax are prepared from phosphodiesters 15d and 4c by an intramolecular esterification reaction:

A solution of 1-O-octadecyl-2-O-benzyl-sn-glyceryl-phospho-RVn (15d, 1 mmol) in dry DMF (5 mL) was added to a solution of diisopropylethylamine (DIEA, 58 mg, 0.45 mmol), and (1H-benzotriazol-1-yloxy)-tripyrrolidinophosphonium hexafluorophosphate (PyBOP, 230 mg, 0.45 mmol) in dry DMF (5 mL) and stirred at room temperature for 3 hours until TLC indicated substantial conversion to the 3',5'-cyclic phosphate. Water (mL) was added and the solvents were evaporated under vacuum. The residue was purified by column chromatography on silica gel to yield compounds 18-eq (ESI-MS: 770.18 [M+H]$^+$), and 18-ax (ESI-MS: 770.29 [M+H]*).

Similarly, a solution of octadecyloxyethyl-phospho-RVn (4c, 1 mmol) in dry DMF (5 mL) was added to a solution of diisopropylethylamine (DIEA, 160 mg, 1.5 mmol), and (1H-benzotriazol-1-yloxy)-tripyrrolidinophosphonium hexafluorophosphate (PyBOP, 780 mg, 1.5 mmol) in dry DMF (5 mL) and stirred at room temperature for 3 hours until TLC indicated substantial conversion to the 3',5'-cyclic phosphate. Water (1 mL) was added and the solvents were evaporated under vacuum. The residue was purified by column chromatography on silica gel to yield compounds 19-eq (ESI-MS: 650.41 [M+H]$^+$) and 19-ax (ESI-MS: 650.42 [M+H]$^+$).

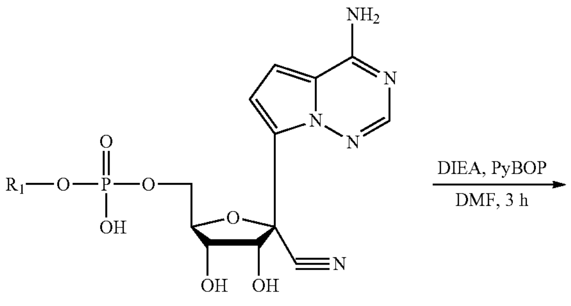

4c or 15d

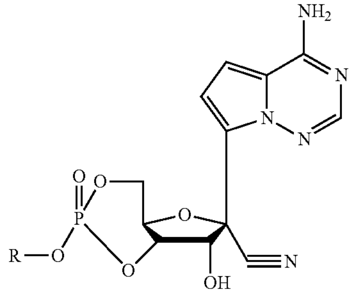

+ equatorial

-continued

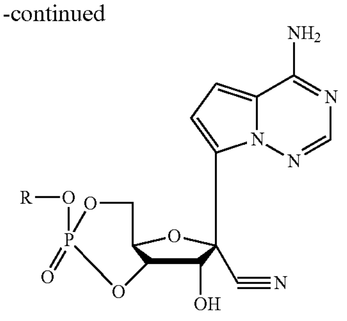

axial

R =

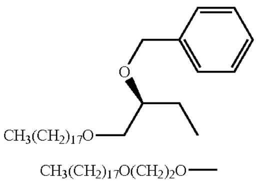

18-eq, 18-ax 19-eq,19-x

F. Synthesis of 1-O-Octadecyl-2-O-(4-cyano)benzyl-sn-glyceryl-phospho-RVn

OD-4-CN-Bn-P-RVn was prepared using the Methods outlined above in Section C. 1-O-octadecyl-3-O-trityl-sn-glycerol was alkylated with 4-cyanobenzyl chloride and the trityl removed (Method I) to provide 1-O-octadecyl-2-O-(4-cyano)benzyl)-sn-glycerol. The alcohol was then phosphorylated (Method A), and coupled to GS-441524 acetonide (Method C) and deprotected (Method E) to give the title compound.

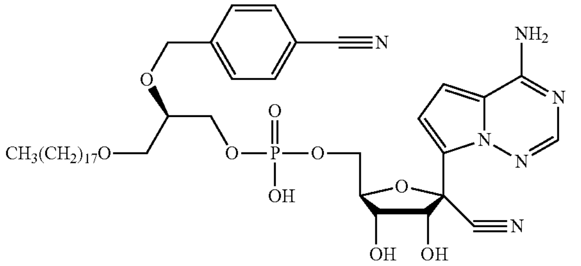

1-O-octadecyl-2-O-(4-cyano)benzyl-sn-glyceryl-phospho-RVn

Example 2—Assay for Anti-Coronavirus Activity in Vero E6 Cells

In this example, reference is made to the following compounds, which include remdesivir nucleoside analogs and related intermediates:

1

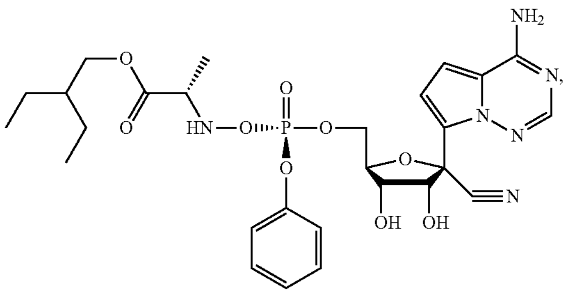

remdesivir, RDV

2

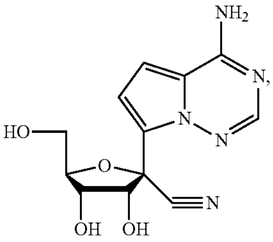

remdesivir nucleoside, RVn

2a

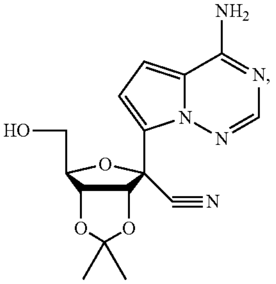

2,3-isopropylidene-RVn, RVa

3

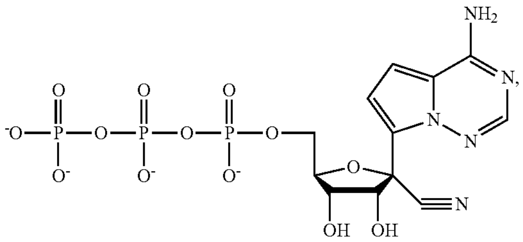

RVn triphosphate

The compounds of this example were assayed for anti-coronavirus activity in Vero E6 cells in comparison with remdesivir (RDV) and the remdesivir nucleoside (RVn). Ten thousand Vero E6 cells were seeded in 100 microliters of culture medium in 96 well plates. The following day serial two-fold dilutions of antiviral compounds or the DMSO-containing vehicle were added to each well. The USA WA-01 strain of SARS CoV-2 was added to each well at a multiplicity of infection of 0.1 thirty minutes later. Cells were incubated for 48 hours, washed twice in PBS and lysed with TRIzol. RNA was extracted using Directzol micro RNA columns. RNA was made into cDNA and assayed for the SARS CoV-2 spike protein and for a housekeeping gene (RPLPO) RNA by qPCR. Data represents the average of duplicate wells. Cellular cytotoxicity was also measured in VERO E6 cells. As below, each of the synthesized compounds exhibited enhanced anti-SARS CoV-2 activity compared to remdesivir or the remdesivir nucleoside with selectivity indices ranging from 22.8 to >227. Cytotoxicity ($CC_{50}$) was assessed using a commercially available MTT assay.

As shown in the following table, ODE-P-RVn (4c) and ODBG-P-RVn (15d) were 9 to 15 times more active against the USA WA-1 strain of SARS-CoV-2019 in Vero E6 cells. Likewise, HDP-P-RVn (4b) was 3.3-fold more active than remdesivir.

Antiviral activity in Vero E6 cells infected with SARS-CoV-2

| Compound | $EC_{50}$ (μM) | $EC_{90}$ (μM) | $CC_{50}$ (μM) | Selectivity Index |
|---|---|---|---|---|
| RDV | 3.16 | 5.50 | >50 | >15.8 |
| ODE-P-RVn (4c) | 0.35 | 0.53 | >50 | >143 |
| ODBG-P-RVn (15d) | 0.21 | 0.56 | >50 | >238 |
| HDP-P-RVn (4b) | 0.84 | 1.58 | 21 | 25.0 |
| RVn | 1.56 | 2.69 | >50 | >32.0 |

Abbreviations: $EC_{50}$, 50% effective concentration; $EC_{90}$, 90% effective concentration; $CC_{50}$, 50% cytotoxic concentration. Selective Index = $CC_{50}/EC_{50}$.

Example 3. Additional Synthesis and Testing of RVn Monophosphate Prodrugs

Figure 1F:
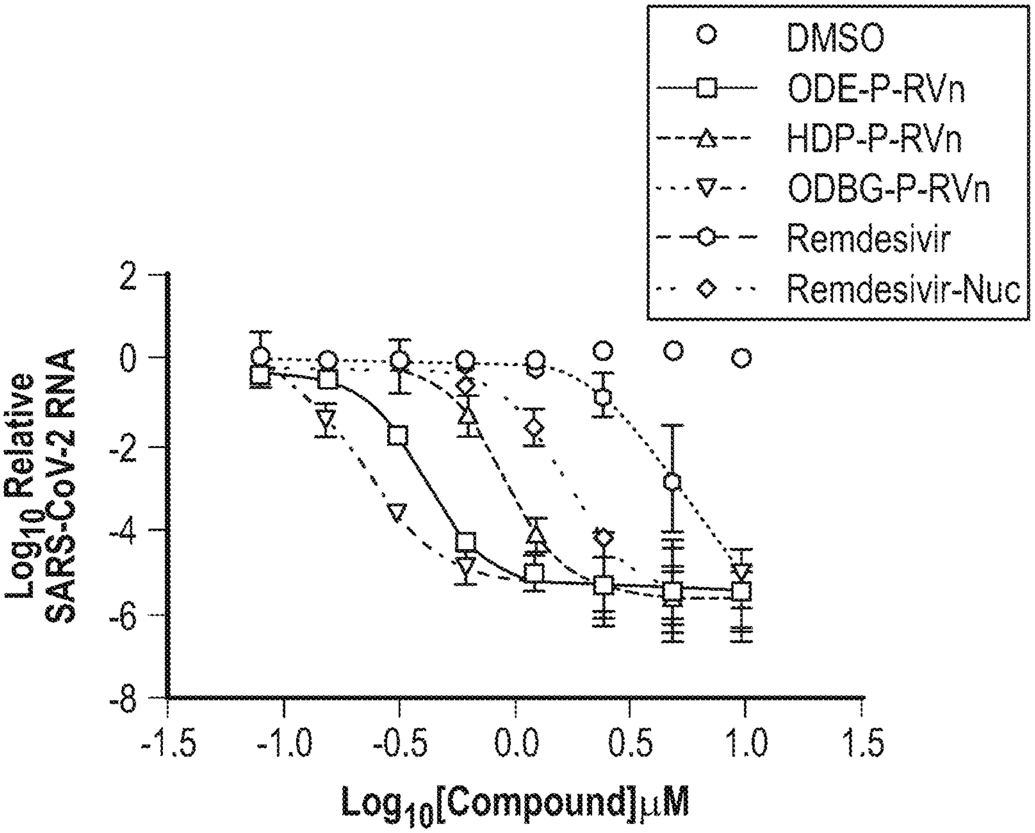

Antiviral Activity: Also generated were concentration-response curves for ODBG-P-RVn (15d), ODE-P-RVn (4c), and HDP-P-RVn (4b), remdesivir (RDV) and remdesivir nucleoside (RVn) for SARS-CoV-2 infection in Vero E6 cells in two separate experiments performed in duplicate (FIG. 1A-FIG. 1F). Dose response curves for three remdesivir analogs (FIG. 1A, FIG. 1B, and FIG. 1C), remdesivir (GS-5734) (FIG. 1D), and remdesivir nucleoside (GS-441524) (FIG. 1E) against SARS-CoV-2 infection in Vero E6 cells. Vero E6 cells were pretreated with the indicated dose of the indicated drug for thirty minutes and then infected with SARS-CoV-2 isolate USA-WA1/2020 for 48 hours. The relative SARS-CoV-2 Spike RNA expression was determined by qRT-PCR. Each dose-response comparison was conducted simultaneously for all drugs on 2 separate occasions. Data from both experiments are shown at FIG. 1A-FIG. 1F. Data points indicate the mean relative expression from duplicate wells. Error bars represent the standard deviations (SDs). The black vertical dashed line indicates the concentrations at which there is 50% inhibition ($EC_{50}$). (FIG. 1F). Combined inhibition curves for all five compounds and DMSO on a single chart. DMSO, which was the vehicle for all compounds, had no effect on SARS-CoV-2 replication at the concentrations used. The three lipid esters of RVn-monophosphate were all substantially more active than RDV and RVn.

The following table shows the effective concentrations ($EC_{50}$, $EC_{90}$), 50% cytotoxic concentration ($CC_{50}$), and selectivity index of the compounds, mean±SD. Cytotoxicity ($CC_{50}$) was assessed using Cell Titer Glo. The $EC_{50}$ values of RDV and RVn were 4.6 and 1.7 μM, respectively. The lipid prodrugs were more active with $EC_{50}$s of ranging from 0.19±0.023 to 0.96±0.17. ODBG-P-RVn and ODE-P-RVn were the most active and selective compounds. Based on the $EC_{50}$ values the most active compound, ODBG-P-RVn, was 24 times more active than RDV and 8.9 times more active than RVn (p<0.001 and 0.005) with a selectivity index of 240.

Antiviral activity, cytotoxicity and selectivity of the compounds in Vero E6 cells

| Compound | $EC_{50}$ (μM) | $EC_{90}$ (μM) | $CC_{50}$ (μM) | Selectivity | p value vs RDV, RVn |
|---|---|---|---|---|---|
| Remdesivir | 4.6 ± 2.1 | 8.9 ± 4.9 | >100 | >21.7 | — |
| Remdesivir nucleoside | 1.7 ± 0.13 | 3.2 ± 0.77 | >100 | >58.8 | — |
| HDP-P-RVn, 5a | 0.96 ± 0.17 | 2.1 ± 0.78 | 51 | 52 | 0.02, 0.59 |
| ODE-P-RVn, 5b | 0.47 ± 0.18 | 1.1 ± 0.80 | >100 | >212 | 0.004, 0.047 |
| ODBG-P-RVn, 5c | 0.19 ± 0.023 | 0.56 ± 0.0002 | 46 | 240 | <0.001, 0.005 |

A graph showing the $CC_{50}$ results by Cell Titer Glo is shown in the Supplemental Materials. Abbreviations: RDV, Remdesivir (GS-5734); RVn, Remdesivir nucleoside (GS-441524); HDP-P-, hexadecyloxypropyl-P-; ODE-P-, octadecyloxyethyl-P-; ODBG-P-, 1-O-octadecyl-2-O-benzyl-glycero-3-P-; Selectivity index, $CC_{50}/EC_{50}$; statistical analysis comparing Log$IC_{50}$ values from separate experiments by one-way ANOVA.

Of all the perceived disadvantages of RDV, it was chosen in this example to design prodrugs of RVn which could provide oral bioavailability because an effective oral drug would allow for much earlier treatment of persons diagnosed with SARS-CoV-2 infection. As shown in this example, this was accomplished by constructing liponucleotides of RVn resembling lysophospholipids that are normally absorbed in the GI tract. The RVn liponucleotides were not metabolized rapidly in plasma and gain rapid entry to the cell often exhibiting greatly increased antiviral activity.

In contrast to the activation of RDV, which required four transformations, intracellular kinase bypass with this kind of compound generated the nucleoside monophosphate when the lipid ester moiety was cleaved in a single reaction catalyzed by acid phospholipase C or acid sphingomyelinase (sphingomyelin phosphodiesterase I).

One of the compounds, ODBG-P-RVn (15d) was likely to deliver relatively more drug to lung and less to liver as shown previously in lethal mousepox infection (Hostetler K Y, Beadle J R, et al. Oral 1-O-octadecyl-2-O-benzyl-sn-glycero-3-cidofovir targets the lung and is effective against a lethal respiratory challenge with ectromelia virus in mice; Antiviral Res. 2007 March; 73(3):212-8).

The synthesis of the lipid prodrugs of this example was much simpler than RDV and was readily scalable.

In this example, three lipid prodrugs of RVn were synthesized that were substantially more active than RDV or RVn in Vero E6 cells. The two most active compounds ODBG-P-RVn and ODE-P-RVn were 24 and 9.8 times more active than RDV. These compounds were expected to be orally bioavailable, stable in plasma and provide significant exposure and antiviral activity to all tissues infected with SARS-CoV-2.

Compounds: Remdesivir (GS-5734) and remdesivir nucleoside (GS-441524) were purchased from AA Blocks (San Diego, CA and Mason-Chem (Palo Alto, CA), respectively.

Cells: Vero E6 were obtained from ATCC and grown in DMEM (Corning) with 10% FBS and Penicillin-Streptomycin (Gibco).

SARS-CoV-2 infection: SARS-CoV-2 isolate USA-WA1/2020 (BEI Resources) was propagated and infectious units quantified by plaque assay using Vero E6 (ATCC) cells. Approximately $10^4$ Vero E6 cells per well were seeded in a 96 well plate and incubated overnight. Compounds or controls were added at the indicated concentrations 30 minutes prior to infection followed by the addition of SARS-CoV-2 at a multiplicity of infection equal to 0.01. After incubation for 48 hours at 37° C. and 5% $CO_2$, cells were washed twice with PBS and lysed in 200 ul TRIzol (ThermoFisher).

RNA extraction, cDNA synthesis and qPCR: RNA was purified from TRIzol lysates using Direct-zol RNA Microprep kits (Zymo Research) according to manufacturer recommendations that included DNase treatment. RNA was converted to cDNA using the iScript cDNA synthesis kit (BioRad) and qPCR was performed using iTaq universal SYBR green supermix (BioRad) and an ABI 7300 real-time pcr system. cDNA was amplified using the following primers RPLP0 F—GTGTTCGACAATGGCAGCAT (SEQ ID NO: 1); RPLP0 R—GACACCCTCCAGGAAGCGA (SEQ ID NO: 2); SARS-CoV-2 Spike F—CCTACTAAATTAAATGATCTCTGCTTTACT (SEQ ID NO: 3); SARS-CoV-2 Spike R—CAAGCTATAACGCAGCCTGTA (SEQ ID NO: 4). Relative expression of SARS-CoV-2 Spike RNA was calculated by delta-delta-Ct by first normalizing to the housekeeping gene RPLP0 and then comparing to SARS-CoV-2 infected Vero E6 cells that were untreated (reference control). Curves were fit and 50 and 90% effective concentrations $EC_{50}$ and $EC_{90}$ values calculated using Prism 8.

CellTiter-glo luminescent cell viability assay: Approximately $10^4$ Vero E6 cells per well were seeded in opaque walled 96 well cell culture plates and incubated overnight. Compounds or controls were added at the indicated concentrations. After incubation for 48.5 hours at 37° C. and 5% $CO_2$, an equal volume of CellTiter-Glo reagent (Cat. #G7570, Promega, Madison, WI) was added, mixed and luminescence recorded on an EnSpire Multimode Plate Reader (PerkinElmer) according to manufacturer recommendations. Viability was calculated compared to untreated controls and $CC_{50}$ values were calculated using Prism 8.

Determination of Cytotoxicity: The 50% cytotoxic concentrations ($CC_{50}$) were determined with Cell Titer Glo (Cat. #G7570, Promega, Madison, WI) according to the manufacturer's instructions. The calculated $CC_{50}$ values are shown in the foregoing table.

Figure 2:
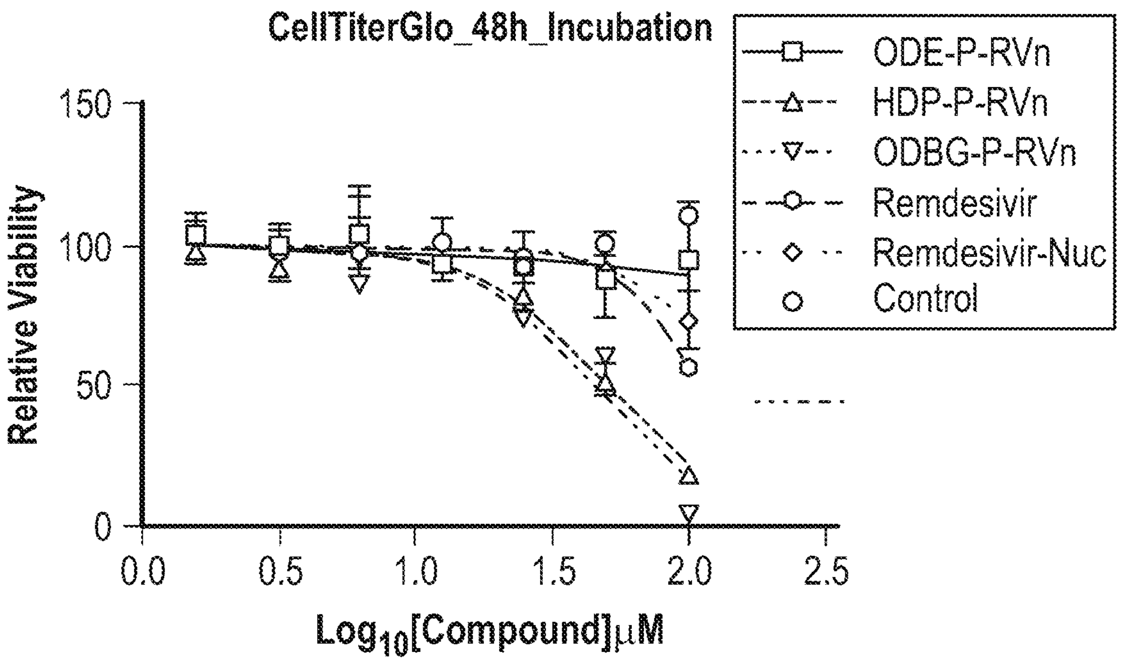
FIG. 2 depicts relative viabilities of embodiments of treated Vero E6 cells, as measured by CellTiter-Glo luminescent cell viability assay.

Vero E6 cells were treated with increasing concentrations of remdesivir analogs, remdesivir (GS-5734), remdesivir nucleoside (GS441524) or DMSO vehicle (control) for 48.5 hrs. Relative viability was measured by CellTiter-Glo luminescent cell viability assay, as depicted at FIG. 2.

Example 4—Generation of Remdesivir Triphosphate in Vero E6 Cells

In this example, Vero E6 cells were plated in 6 well plates at about $3.4\times10^5$ cells per well in 2 mL of media (DMEM, 10% FBS).

Cells were then incubated at 37° C. for 24 hours. Media was then aspirated and replaced with 2 mL of control media (fresh Dulbecco's Modified Eagle's Medium (DMEM), 10% FBS) or 2 mL of media with drug at a concentration of 1 μM. Cell were incubated with the various drugs for 48 hours. The media was aspirated, the cells rinsed twice with phosphate-buffered saline (PBS), trypsinized for 5 minutes with 1 mL ATV, triturated and removed to a 15 mL centrifuge tube, rinsed with 1 mL PBS, which was also then removed to the 15 mL centrifuge tube, and the cells were triturated again. Cells were counted in a Reichert hemocytometer using two 10 μL samples, and the number of cells in each sample was determined.

Figure 3:
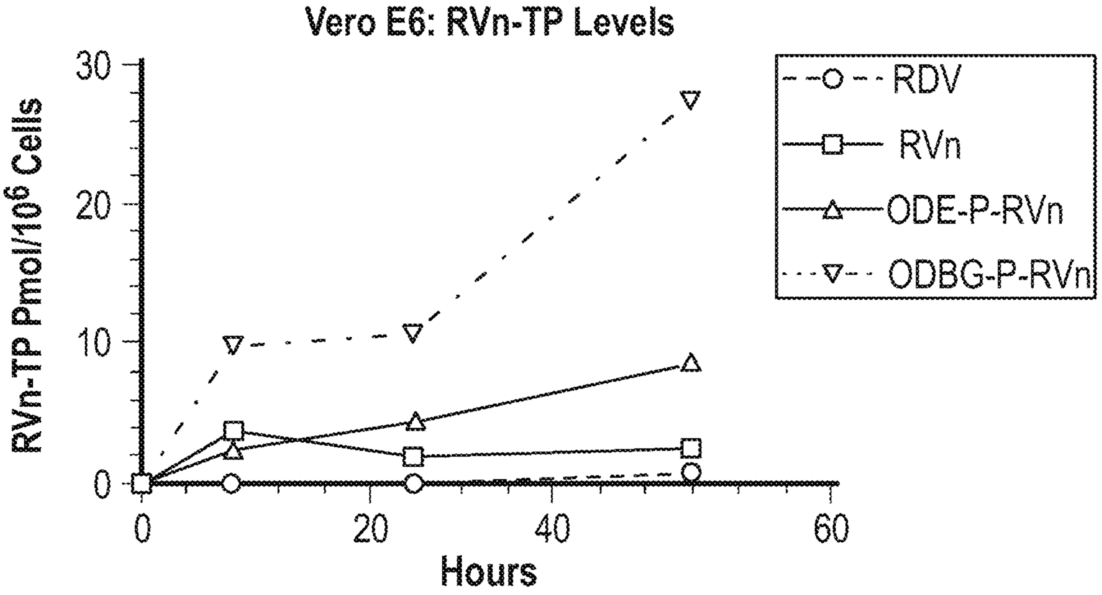
FIG. 3 depicts LC/MS/MS analysis of cells that were centrifuged at 1200 rpm for 10 minutes, diluent aspirated, and resuspended in 250 μL of methanol/distilled water (70/30).

Cells were centrifuged at 1200 rpm for 10 minutes, diluent aspirated and the pellet resuspended in 250 μL of methanol/distilled water (70/30) and analyzed by LC/MS/MS. The results, which are depicted at FIG. 3, were in picomoles/$10^6$ cells and were the average of two or three determinations. Abbreviations for FIG. 3: RDV, remdesivir; RVn, remdesivir nucleoside (GS-441524); ODE-P-RVn, octadecyloxyethyl-phospho-RVn (4c); ODBG-P-RVn, 1-O-octadecyl-2-O-benzyl-glyceryl-sn-3-phospho-RVn (15d)

As depicted at FIG. 3, in Vero E6 cells, the synthesis of remdesivir triphosphate (RVn-TP) increased progressively to 48 hours with exposure to 1 micromolar ODE-P-RVn and OBDG-P-RVn. With RVn the levels of RVn-TP peaked at 8 hours and declined thereafter. Levels of RVn-TP with RDV were below the level of quantification at 8 and 24 hours.

Example 5—Human Coronavirus 229E Infection

In this example, human Coronavirus 229E (ATCC) was propagated and infectious units quantified by $TCID_{50}$ using MRC-5 cells. For antiviral testing, approximately 104 MRC-5 cells were seeded per well in EMEM (10% FCS) at 37° C. in a 96 well plate overnight. Medium from each well was removed and cells were infected with 100 $TCID_{50}$ virus in 100 μL medium for two hours.

Cells were washed one time with medium and then compounds or controls added at the indicated concentrations. After three days, CPE was observed under microscope and quantified using an MTT cell proliferation assay kit (Abcam) read on an ELx800, Universal Microplate reader (BIO-TEK Instruments, INC).

Effect of Compounds on HCoV-229E Replication in MRC-5 Cells

| | | | | HCoV-229E in MRC-5 Cells | | |
|---|---|---|---|---|---|---|
| Entry | Compd | $R_1$ | $R_2$ | $EC_{50}$ (μM) | $EC_{90}$ (μM) | $CC_{50}$ (μM) |
| 1 | 4a | eicosyl | H | ±0.91 ± 1.21 | ±1.80 ± 1.87 | ±>50 |
| 2 | 4b | hexadecyloxypropyl | H | 3.02 ± 0.36 | 6.60 ± 1.14 | 32.1 ± 17.9 |
| 3 | 4c | octadecyloxyethyl | H | 0.41 ± 0.012 | 0.84 ± 0.095 | >50 |
| 4 | 6c | octadecyloxyethyl | benzyl | 0.22 ± 0.056 | 0.44 ± 0.085 | >50 |

-continued

| Effect of Compounds on HCoV-229E Replication in MRC-5 Cells | | | | | | |
|---|---|---|---|---|---|---|
| | | | | HCoV-229E in MRC-5 Cells | | |
| Entry | Compd | $R_1$ | $R_2$ | $EC_{50}$ (μM) | $EC_{90}$ (μM) | $CC_{50}$ (μM) |
| 5 | 15a | 1-O-tetradecyl-2-O-benzyl-sn-glyceryl | H | 0.76 ± 0.34 | ±3.25 ± 2.18 | ±>50 |
| 6 | 15b | 1-O-hexadecyl-2-O-benzyl-sn-glyceryl | H | 0.56 ± 0.27 | 0.98 ± 0.38 | >50 |
| 7 | 15c | 1-O-hexadecyl-2-O-(3-F,4-MeO-Bn)-sn-glyceryl | H | 0.36 ± 0.054 | 1.12 ± 0.10 | >50 |
| 8 | 15d | 1-O-octadecyl-2-O-benzyl-sn-glyceryl | H | 0.10 ± 0 | 0.28 ± 0.013 | 43.1 ± 18.9 |
| 9 | 15e | 1-O-octadecyl-2-O-benzyl-rac-glyceryl | H | 0.21 ± 0.004 | 0.35 ± 0.006 | 30.9 ± 7.7 |
| 10 | 15f | 1-O-octadecyl-2-O-octyl-sn-glyceryl | H | 0.12 ± 0.057 | 0.29 ± 0.058 | ±>50 |
| 11 | 15g | 1-O-octadecyl-2-O-(methylcyclohexyl)-sn-glyceryl | H | nd | nd | nd |
| 12 | 15h | 1-O-octadecyl-2-O-(3-F-Bn)-sn-glyceryl | H | 1.40 ± 0.058 | 2.80 ± 0.04 | 22.9 ± 0.1 |
| 13 | 15i | 1-O-octadecyl-2-O-(4-MeO-Bn)-sn-glyceryl | H | nd | nd | nd |
| 14 | 15j | 1-O-octadecyl-2-O-(3-F,4-MeO-Bn)-sn-glyceryl | H | 0.074 ± 0.01 | 0.17 ± 0.014 | >50 |
| 15 | 15k | 1-O-octadecyl-2-O-methylpyridinyl-sn-glyceryl | H | nd | nd | nd |
| 16 | 15l | 1-O-oleyl-2-O-benzyl-sn-glyceryl | H | 0.13 ± 0.029 | 0.26 ± 0.0037 | >50 |
| 17 | 15m | 1-O-oleyl-2-O-(3-F,4-MeO-Bn)-sn-glyceryl | H | 0.06 ± 0.014 | 0.11 ± 0.02 | >50 |
| 18 | 17 | 1-O-octadecyl-2-O-benzyl-sn-glyceryl | benzyl | 1.50 ± 0.93 | 4.27 ± 0.88 | >50 |
| 19 | 15o | 1-O-octadecyl-2-O-(3-$CF_3$-Bn)-sn-glyceryl | H | 0.16 ± 0.046 | 0.46 ± 0.27 | 16.0 ± 2.8 |
| 20 | 15p | 1-O-octadecyl-2-O-(4-CF3-Bn)-sn-glyceryl | H | 0.16 ± 078 | 0.33 ± 0.039 | 13.9 ± 8.8 |

nd = not determined;

The % inhibition was calculated as (Atv−Acv)/(Acd−Acv)×100% where Atv indicates the absorbance of the test compounds with virus infected cells and Acv and Acd indicate the absorbance of the virus control and the absorbance of the cell control, respectively. The average half-maximal effective concentration ($EC_{50}$) was defined as the concentration which achieved 50% inhibition of virus-induced cytopathic effects.

Example 6—SARS-CoV-2 Infection Assay

About 12e3 TMPRSS2-Vero cells or 20e3 Huh7.5 cells were seeded per well in black with clear flat bottom 96 well plates and incubated overnight. Compounds or controls were added about 30 to about 60 minutes prior to infection at the indicated concentrations with addition of SARS-CoV-2 at a multiplicity of infection (FFU/cell) equal to 0.01 for TMPRSS2-Vero and 0.1 for Huh7.5.

After incubation for 32 hours for TMPRSS2-Vero or 48 hours for Huh7.5 at 37° C. and 5% $CO_2$, the medium was removed and cells were incubated in 4% formaldehyde for 30 minutes at room temperature. Formaldehyde fixed cells were washed with PBS and permeabilized for immunofluorescence in 0.1% Triton-X 100 in PBS with 1% bovine serum albumin (BSA) fraction V (Millipore-Sigma) and stained for SARS-CoV-2 with a primary anti-Nucleocapsid antibody (GeneTex GTX135357) followed by AlexaFluor 594 secondary antibody (Thermo Fisher Scientific A-11012) with nuclear counterstain Sytox Green (Thermo Fisher Scientific).

Five images per well were obtained at 10× magnification using an Incucyte S3 (Sartorius). The percent infected cells and nuclei count were calculated using built-in image analysis tools for the Incucyte S3. Calculations for $EC_{50}$, $EC_{90}$ and $CC_{50}$ were carried out using the nonlinear regression analysis in GraphPad Prism 9 with the bottom and top parameters constrained to 0 and 100, respectively.

Effect of Compounds on SARS CoV-2 Replication in Huh7.5 and TMPRSS2-Vero Cells

| | | | | Huh7.5 Cells | | | TMPRSS2-Vero Cells | | |
|---|---|---|---|---|---|---|---|---|---|
| Entry | - Compd | $R_1$ | $R_2$ | $EC_{50}$ (μM) | $EC_{90}$ (μM) | $CC_{50}$ (μM) | $EC_{50}$ (μM) | $EC_{90}$ (μM) | $CC_{50}$ (μM) |
| 1 | 4a | eicosyl | H | 1.411 ± 0.089 | 4.746 ± 0.626 | >20 | 1.171 ± 0.060 | 2.185 ± 0.201 | >20 |
| 2 | 4b | hexadecyloxypropyl | H | 0.19[a] | 0.40[a] | >20 | nd | nd | nd |
| 3 | 4c | octadecyloxyethyl | H | 0.19[a] | 0.37[a] | >20 | nd | nd | nd |
| 4 | 6c | octadecyloxyethyl | benzyl | nd | nd | nd | nd | nd | nd |
| 5 | 15a | 1-O-tetradecyl-2-O-benzyl-sn-glyceryl | H | 0.156 ± 0.008 | 0.493 ± 0.051 | >20 | 0.901 ± 0.022 | 1.694 ± 0.131 | >20 |
| 6 | 15b | 1-O-hexadecyl-2-O-benzyl-sn-glyceryl | H | 0.130 ± 0.020 | 0.309 ± 0.092 | >20 | 0.395 ± 0.021 | 0.810 ± 0.079 | >20 |
| 7 | 15c | 1-O-hexadecyl-2-O-(3-F,4-MeO-Bn)-sn-glyceryl | H | 0.049 ± 0.005 | 0.113 ± 0.019 | >20 | 0.397 ± 0.026 | 0.869 ± 0.106 | >20 |
| 8 | 15d | 1-O-octadecyl-2-O-benzyl-sn-glyceryl | H | 0.138 ± 0.018 | 0.377 ± 0.098 | >20 | 0.205 ± 0.016 | 0.432 ± 0.075 | >20 |
| 9 | 15e | 1-O-octadecyl-2-O-benzyl-rac-glyceryl | H | 0.163 ± 0.026 | 0.514 ± 0.172 | >20 | 0.242 ± 0.020 | 0.642 ± 0.133 | >20 |
| 10 | 15f | 1-O-octadecyl-2-O-octyl-sn-glyceryl | H | 0.710 ± 0.028 | 1.713 ± 0.183 | >20 | 1.326 ± 0.052 | 2.349 ± 0.123 | >20 |
| 11 | 15g | 1-O-octadecyl-2-O-(methylcyclohexyl)-sn-glyceryl | H | nd | nd | nd | nd | nd | nd |
| 12 | 15h | 1-O-octadecyl-2-O-(3-F-Bn)-sn-glyceryl | H | 0.182 ± 0.018 | 0.444 ± 0.083 | >20 | 0.270 ± 0.016 | 0.629 ± 0.106 | >20 |
| 13 | 15i | 1-O-octadecyl-2-O-(4-MeO-Bn)-sn-glyceryl | H | nd | nd | nd | nd | nd | nd |
| 14 | 15j | 1-O-octadecyl-2-O-(3-F,4-MeO-Bn)-sn-glyceryl | H | 0.056 ± 0.008 | 0.222 ± 0.070 | >20 | 0.174 ± 0.016 | 0.341 ± 0.044 | >20 |
| 15 | 15k | 1-O-octadecyl-2-O-methylpyridinyl-sn-glyceryl | H | nd | nd | nd | nd | nd | nd |
| 16 | 15l | 1-O-oleyl-2-O-benzyl-sn-glyceryl | H | 0.100 ± 0.010 | 0.246 ± 0.062 | >20 | 0.295 ± 0.013 | 0.568 ± 0.080 | >20 |
| 17 | 15m | 1-O-oleyl-2-O-(3-F,4-MeO-Bn)-sn-glyceryl | H | 0.054 ± 0.006 | 0.102 ± 0.013 | >20 | 0.296 ± 0.019 | 0.524 ± 0.115 | >20 |
| 18 | 17 | 1-O-octadecyl-2-O-benzyl-sn-glyceryl | benzyl | 3.537 ± 0.583 | 16.44 ± 5.98 | >20 | 7.443 ± 0.018 | 15.263 ± 5.912 | >20 |

nd = not determined;
[a]Data from Example 7

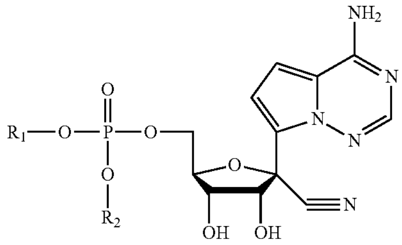

Effect of Compounds on SARS CoV-2 Replication in Calu-3 cells

| | | | | Calu-3 Cells | | |
|---|---|---|---|---|---|---|
| Entry | Compd | $R_1$ | $R_2$ | $EC_{50}$ (μM) | $EC_{90}$ (μM) | $CC_{50}$ (μM) |
| 1 | 4a | eicosyl | H | 0.178 ± 0.035 | 1.316 ± 0.566 | >20 |
| 2 | 4b | hexadecyloxypropyl | H | nd | nd | nd |
| 3 | 4c | octadecyloxyethyl | H | nd | nd | nd |
| 4 | 6c | octadecyloxyethyl | benzyl | nd | nd | nd |
| 5 | 15a | 1-O-tetradecyl-2-O-benzyl-sn-glyceryl | H | 0.212 ± 0.025 | 0.536 ± 0.150 | >20 |
| 6 | 15b | 1-O-hexadecyl-2-O-benzyl-sn-glyceryl | H | 0.101 ± 0.020 | 0.623 ± 0.272 | 88.23 ± 8.89 |

-continued

Effect of Compounds on SARS CoV-2 Replication in Calu-3 cells

| Entry | Compd | $R_1$ | $R_2$ | Calu-3 Cells $EC_{50}$ (μM) | $EC_{90}$ (μM) | $CC_{50}$ (μM) |
|---|---|---|---|---|---|---|
| 7 | 15c | 1-O-hexadecyl-2-O-(3-F,4-MeO-Bn)-sn-glyceryl | H | 0.051 ± 0.006 | 0.221 ± 0.058 | 75.63 ± 3.96 |
| 8 | 15d | 1-O-octadecyl-2-O-benzyl-sn-glyceryl | H | 0.164 ± 0.020 | 0.536 ± 0.138 | >20 |
| 9 | 15e | 1-O-octadecyl-2-O-benzyl-rac-glyceryl | H | 0.210 ± 0.062 | 0.763 ± 0.490 | >20 |
| 10 | 15f | 1-O-octadecyl-2-O-octyl-sn-glyceryl | H | 0.410 ± 0.060 | 2.314 ± 0.738 | >20 |
| 11 | 15g | 1-O-octadecyl-2-O-(methylcyclohexyl)-sn-glyceryl | H | 0.147 ± 0.032 | 1.660 ± 0.798 | >20 |
| 12 | 15h | 1-O-octadecyl-2-O-(3-F-Bn)-sn-glyceryl | H | 0.216 ± 0.062 | 0.548 ± 0.368 | >20 |
| 13 | 15i | 1-O-octadecyl-2-O-(4-MeO-Bn)-sn-glyceryl | H | nd | nd | nd |
| 14 | 15j | 1-O-octadecyl-2-O-(3-F,4-MeO-Bn)-sn-glyceryl | H | 0.080 ± 8.741 | 0.101 ± 4.554 | 50.63 ± 5.42 |
| 15 | 15k | 1-O-octadecyl-2-O-methylpyridinyl-sn-glyceryl | H | nd | nd | nd |
| 16 | 15l | 1-O-oleyl-2-O-benzyl-sn-glyceryl | H | 0.198 ± 0.077 | 0.294 ± 0.093 | 78.96 ± 6.95 |
| 17 | 15m | 1-O-oleyl-2-O-(3-F,4-MeO-Bn)-sn-glyceryl | H | 0.075 ± 4.752 | 0.090 ± 3.487 | 58.53 ± 6.28 |
| 18 | 17 | 1-O-octadecyl-2-O-benzyl-sn-glyceryl | benzyl | 5.320 ± 1.393 | 10.92 ± 5.485 | >20 |
| 19 | 18-eq | 1-O-octadecyl-2-O-benzyl-sn-glyceryl | cyclic-eq | >20 | >20 | >20 |
| 20 | 18-ax | 1-O-octadecyl-2-O-benzyl-sn-glyceryl | cyclic-ax | >20 | >20 | >20 |
| 21 | 19-eq | octadecyloxyethyl | cyclic-eq | 2.758 ± 0.808 | 19.163 ± 12.666 | >20 |
| 22 | 19-ax | octadecyloxyethyl | cyclic-ax | 8.147 ± 8.420 | >20 | >20 |
| 23 | 15n | 3-O-octadecyl-2-O-benzyl-sn-glyceryl | H | 0.163 ± 0.022 | 0.623 ± 0.183 | >20 |
| 24 | 15o | 1-O-octadecyl-2-O-(3-trifluoromethyl)benzyl-sn-glyceryl | H | 0.166 ± 0.068 | 0.278 ± 0.109 | >20 |

SARS-CoV-2 infection assay: Approximately 20k Calu-3 cells were seeded per well in black with clear flat bottom 96 well plates (Corning #3904) and incubated 48-72 h. Compounds or controls were added 30-60 minutes prior to infection at the indicated concentrations with addition of SARS-CoV-2 at a multiplicity of infection (FFU/cell) equal to 0.01. After incubation for 44 hour at 37° C. and 5% $CO_2$, the medium was removed and cells were incubated in 4% formaldehyde for 30 minutes at room temperature. Formaldehyde fixed cells were washed with PBS and permeabilized for immunofluorescence in 0.1% Triton-X 100 in PBS with 1% bovine serum albumin (BSA) fraction V (Millipore-Sigma) and stained for SARS-CoV-2 with a primary anti-Nucleocapsid antibody (GeneTex GTX135357) followed by AlexaFluor 594 secondary antibody (Thermo Fisher Scientific A-11012) with nuclear counterstain Sytox Green (Thermo Fisher Scientific). Five images per well were obtained at 10× magnification using an Incucyte S3 (Sartorius).

The percent infected cells and nuclei count were calculated using built-in image analysis tools for the Incucyte S3. Calculations for $EC_{50}$, $EC_{90}$ and $CC_{50}$ were carried out using the nonlinear regression analysis in GraphPad Prism 9 with the bottom and top parameters constrained to 0 and 100, respectively. All work with authentic SARS-CoV-2 was conducted in Biosafety Level-3 conditions at the University of California San Diego.

Cell viability assay: For select compounds the CC50 was calculated up to a maximum of 100 μM using CellTiter-Glo. For these experiments, approximately 20k Calu-3 cells were seeded per well in opaque white 96-well plates (cat #655073, Greiner Bio-One, Monroe, North Carolina) and incubated 48-72 h. Compounds or controls were added and incubated for 44 h at 37° C. and 5% $CO_2$. After which an equal volume of CellTiter-Glo reagent (Cat. #G7570, Promega, Madison, WI) was added, mixed and luminescence recorded on a Veritas Microplate Luminometer (Turner BioSystems) according to manufacturer recommendations.

Example 7—Antiviral Activity in Various Cell Types Infected with SARS-CoV-2

Vero E6, Caco-2, and Calu-3 cell lines were obtained from ATCC. Huh7.5 cells were obtained from Apath LLC. Calu-3 and Caco-2 cells were propagated in MEM (Corning), 10% FBS, Penicillin-Streptomycin (Gibco). Vero E6 and Huh7.5 cells were propagated in DMEM (Corning) with 10% FBS and Penicillin-Streptomycin (Gibco). Human PSC-lung cell generation, human lung organoids were generated as previously described (Leibel S L, McVicar R N, Winquist A M, Niles W D, Snyder E Y Generation of complete multi-cell type lung organoids from human embryonic and patient-specific induced pluripotent stem cells for infectious disease modeling and therapeutics validation Curr. Protoc. Stem Cell Biol., 54 (1) (2020 September), Article e118). H9 embryonic stem cells (WiCell) were cultured in feeder free conditions upon Matrigel (Corning #354230) coated plates in mTeSR medium (StemCellTech #85850). Media was changed daily, and stem cells were passaged using enzyme free dissociation reagent ReLeSR™ (Stem Cell Tech #05872). Cultures were maintained in an undifferentiated state, in a 5% CO2 incubator at 37° C.

For proximal lung organoid generation, human PSCs were dissociated into single cells, and then seeded on Matrigel-coated plates (BD Biosciences) at a density of $5.3\times10^4$ cells/$cm^2$ in Definitive Endoderm (DE) induction medium (RPMI1640, 2% B27 supplement, 1% HEPES, 1% glutamax, 50 U/mL penicillin/streptomycin), supplemented with 100 ng/mL human activin A (R&D), 5 μM CHIR99021 (Stemgent), and 10 μM ROCK inhibitor, Y-27632 (R&D Systems) on day 1. On days 2 and 3 cells were cultured in DE induction media with only 100 ng/mL human activin A. Anterior Foregut Endoderm (AFE) was generated by supplementing serum free basal medium (3 parts IMDM:1 part F12, B27+N2 supplements, 50 U/mL penicillin/streptomycin, 0.25% BSA, 0.05 mg/mL L-ascorbic acid, 0.4 mM monothioglycerol) with 10 μM SB431542 (R&D) and 2 μM Dorsomorphin (StemGent) on days 4-6. On day 7, AFE medium was changed to Lung Progenitor Cell (LPC) induction medium, containing serum free basal medium supplemented with 10 ng/mL human recombinant BMP4 (R&D), 0.1 μM all-trans retinoic acid (Sigma-Aldrich) and 3 μM CHIR99021. Media was changed every other day for 9-11 days. To generate 3D human proximal lung organoids, we modified a previously published protocol (K. B. McCauley, F. Hawkins, M. Serra, D. C. Thomas, A. Jacob, and D. N. Kotton. (2017) Efficient Derivation of Functional Human Airway Epithelium from Pluripotent Stem Cells via Temporal Regulation of Wnt Signaling. *Cell Stem Cell;* 20(6): 844-857)

LPCs were dissociated in accutase for 10 minutes and resuspended in Matrigel in a 12-well, 0.4 μm pore size Transwell (Corning) culture insert at $5.0\times10^4$ cells/200 ul of Matrigel. Cells were cultured in proximal lung organoid maturation media using serum free basal medium supplemented with 250 ng/mL FGF2, 100 ng/mL rhFGF10, 50 nM dexamethasone (Dex), 100 μM 8-Bromoadenosine 3',5'-cyclic monophosphate sodium salt (Br-cAMP), 100 μM 3-Isobutyl-1-methylxanthine (IBMX) and 10 μM ROCK inhibitor (Y-27632). Proximal lung organoid media was changed every other day for 3 weeks. Human PSC-derived lung organoids were dissociated into single cells and seeded at 20,000 cells per well of a matrigel coated 96-well plate one day before transfection. Transwells containing the proximal organoids in matrigel were incubated in 2 U/ml dispase for 30 minutes at 37° C. Cold PBS was added to the mixture then centrifuged at 400×g for 5 minutes.

Supernatant was carefully removed and resuspended in 2-3 mls of TrypLE Express (Gibco #12605010) for 20 minutes at 37° C. Reaction was quenched with 2% FBS in DMEM/F12 then centrifuged at 400×g for 5 min. The supernatant was aspirated, and the cell pellet resuspended in 1 ml of quenching media supplemented with 10 μM Rock inhibitor (Y-27632). Cell count was performed and the respective volume of cells were transferred into a reagent reservoir trough and resuspended in proximal lung organoid maturation media and plated via multichannel pipette into 96 well plates at 100 ul per well as monolayers.

SARS-CoV-2 infection: SARS-CoV-2 isolate USA-WA1/2020 (BEI Resources) was propagated and infectious units quantified by plaque assay using Vero E6 (ATCC) cells. Approximately 12,000 cells from each cell line were seeded per well in a 96 well plate. Vero E6 and Huh7.5 were seeded approximately 24 hours prior to treatment/infection. Calu-3 and Caco-2 were seeded approximately 48 h prior to treatment/infection. Human PSC lung cell infections and cytotoxicity experiments were performed when cells reached 100% confluency. Compounds or controls were added at the indicated concentrations 30 minutes prior to infection followed by the addition of SARS-CoV-2 at a multiplicity of infection equal to 0.01. After incubation for 48 hours at 37° C. and 5% $CO_2$, cells were washed twice with PBS and lysed in 200 ul TRIzol (ThermoFisher). All work with SARS-CoV-2 was conducted in Biosafety Level 3 conditions at the University of California San Diego with approval from the Institutional Biosafety Committee.

RNA extraction, cDNA synthesis and qPCR: RNA was purified from TRIzol lysates using Direct-zol RNA Microprep kits (Zymo Research) according to manufacturer recommendations that included Dnase treatment. RNA was converted to cDNA using the iScript cDNA synthesis kit (BioRad) and qPCR was performed using iTaq universal SYBR green supermix (BioRad) and an ABI 7300 real-time per system. cDNA was amplified using the following primers RPLP0 F—GTGTTCGACAATGGCAGCAT (SEQ ID NO: 1); RPLP0 R—GACACCCTCCAGGAAGCGA (SEQ ID NOL 2); SARS-CoV-2 Spike F—CCTACTAAATTAAATGATCTCTGCTTTACT (SEQ ID NO: 3); SARS-CoV-2 Spike R—CAAGCTATAACGCAGCCTGTA (SEQ ID NO 4). Relative expression of SARS-CoV-2 Spike RNA was calculated by delta-delta-Ct by first normalizing to the housekeeping gene RPLP0 and then comparing to SARS-CoV-2 infected Vero E6 cells that were untreated (reference control). Curves were fit using the nonlinear regression—log(inhibitor) vs. response (four parameter) model using Prism 9. To calculate effective concentrations $EC_{50}$ and $EC_{90}$ values, qRT-PCR values were normalized to percent inhibition and curves fit using the 20 nonlinear regression—log(agonist) vs. response (four parameter) model with bottom and top constrained to 0 and 100 respectively using Prism 9.

Cell viability assay: Cell type were seeded as per SARS-CoV-2 infection studies in opaque walled 96-well cell culture plates or 229E infection studies in clear 96-well cell culture plates and incubated overnight. Compounds or controls were added at the indicated concentrations. For SARS-CoV-2 related studies, cells were incubated for 48.5 hours at 37° C. and 5% $CO_2$, an equal volume of CellTiter-Glo reagent (Cat. #G7570, Promega, Madison, WI) was added, mixed and luminescence recorded on a Veritas Microplate Luminometer (Turner BioSystems) according to manufacturer recommendations. For 229E related, cells were incubated for 72 hours at 37° C. and 5% $CO_2$, supernatants removed, 50 μL of serum-free media and 50 μL of MTT Reagent (Abcam ab211091) added to each well and incubated for 3 hrs at 37° C. Absorbance was measured on an ELx800, Universal Microplate reader, (1310-TEK Instruments, INC) according to manufacturer recommendations. Percent viability was calculated compared to untreated controls and $CC_{50}$ values were calculated using Prism 9.

Antiviral Activity, Cytotoxicity and Selectivity of the Compounds in five cell types

| Compound | $EC_{50}$ (μM) | $EC_{90}$ (μM) | $CC_{50}$ (μM) | Selectivity | p value $EC_{50}$ vs RDV, RVn |
|---|---|---|---|---|---|
| **Vero E6 cells** | | | | | |
| RDV | 1.13 | 7.05 | 101 | 89.4 | — |
| RVn | 0.38 | 0.77 | >100 | >263 | — |
| HDP-P-RVn, 4b | 0.63 | 0.73 | >100 | >158 | NS |
| ODE-P-RVn, 4c | 0,30 | 0.33 | >100 | >333 | NS |
| ODBG-P-RVn, 15d | 0.14 | 0.16 | 97.9 | 699 | 0.010, 0.311 |
| **PSC-human lung cells** | | | | | |
| RDV | 0.14 | 0.23 | 32.7 * | 234 | — |
| RVn | 0.74 | 2.62 | >100 * | >135 | — |
| HDP-P-RVn * | 0.35 | 0.94 | ND | | — |
| ODE-P-RVn | 0.22 | 0.70 | >100 * | >454 | 0.791, 0.006 |
| ODBG-P-RVn | 0.15 | 0.26 | 61.5 * | 410 | >0.999, 0.002 |
| **Calu-3 cells** | | | | | |
| RDV | 0.23 | 0.31 | >100 | >434 | — |
| RVn | 0.15 | 0.18 | >100 | >666 | — |
| ODE-P-RVn | 0.34 | 0.64 | 98.7 | 290 | NS |
| ODBG-P-RVn | 0.30 | 0.33 | 98.2 | 327 | NS |
| **Huh7.5 cells** | | | | | |
| RDV | 0.06 | 0.12 | 15.2 | 253 | — |
| RVn | 0.32 | 0.73 | >100 | >312 | — |
| HDP-P-RVn | 0.19 | 0.40 | >100 | >526 | NS |
| ODE-P-RVn | 0.19 | 0.37 | >100 | >526 | NS |
| ODBG-P-RVn | 0.14 | 0.15 | 62.9 | 449 | NS |
| **Caco-2 cells** | | | | | |
| RDV | 0.17 | 0.28 | >100 | >588 | — |
| RVn | 0.96 | 1.75 | >100 | >104 | — |
| ODE-P-RVn | 0.77 | 1.25 | >100 | >129 | 0.007, 0.971 |
| ODBG-P-RVn | 0.30 | 0.33 | 88.4 | 295 | 0.968, 0.007 |

Abbreviations: RDV, Remdesivir (GS-5734); RVn, Remdesivir nucleoside (GS-441524); HDP-P-, hexadecyloxypropyl-P-; ODE-P-, octadecyloxyethyl-P-; ODBG-P-, 1-O-octadecyl-2-O-benzyl-glycero-3-P-; $EC_{50}$: half-maximal effective concentration; $CC_{50}$: 50% cytotoxic concentration, Selectivity index, $CC_{50}/EC_{50}$; statistical analysis comparing $LogEC_{50}$ values from separate experiments by one-way ANOVA. $CC_{50}$ results by Cell-Titer-Glo. All experiments performed three times in duplicate except starred (*) were done twice in duplicate.

In all cell lines, there was a dose-dependent inhibition of viral RNA by ODBG-P-RVn, ODE-P-RVn, HDP-P-RVn, remdesivir (RDV) and remdesivir nucleoside (RVn). In Vero E6 cells, the average half-maximal effective concentration ($EC_{50}$) and average 90% effective concentration ($EC_{90}$) of ODBG-P-RVn was 0.14 M and 0.164M, respectively. The $EC_{50}$ of ODBG-P-RVn in Vero E6 cells was significantly lower than RDV. ODE-P-RVn and HDP-P-RVn were also potently antiviral with $EC_{50}$ values of 0.3 μM and 0.63 μM in Vero E6. The $EC_{50}$ of ODBG-P-RVn and ODE-P-RVn were less than 0.35 M in PSC-lung and Calu-3, both models of human lung infection. The antiviral activities of ODBG-P-RVn and ODE-P-RVn were significantly better than RVn in PSC-lung cells. ODBG-P-RVn, ODE-P-RVn and HDP-P-RVn demonstrated strong antiviral activity in Huh7.5 cells with $EC_{50}$ less than 0.2 μM that was not significantly different from RDV or RVn. In the Caco-2 cell line, the $EC_{50}$ of ODBG-P-RVn was 0.3 M which was significantly lower than RVn but similar to RDV. In the same cell line, the $EC_{50}$ of ODE-P-RVn was 0.77 μM, which was significantly higher than RDV.

The cytotoxicity of each compound by incubating each of these cell lines with serial dilutions of each compound from 1.23 μM to 100 μM for 48 hours. The average 50% cytotoxic concentrations ($CC_{50}$) for all compounds were greater than 60 μM in all cell lines except for RDV which had a $CC_{50}$ of 32.7 μM in PSC-lung cells and 15.2 μM in Huh7.5, a human hepatocyte cell line. The selectivity index of ODBG-P-RV ranged from 295 to 699 in the five cell types tested in this example). The range of antiviral activity and cytotoxicity of ODBG-P-RVn ($EC_{50}$ 0.14 μM-0.30 μM and $CC_{50}$ 61.5 μM-98.2 μM) was more consistent across cell types than RDV ($EC_{50}$ 0.06 μM-1.13 μM and $CC_{50}$ 15.2 μM->100 μM) (see table above). Collectively, these data demonstrate that lipid RVn monophosphate prodrugs are potent antivirals against SARS-CoV-2 in vitro with low toxicity and excellent selectivity indexes.

Example 8—Effect of Antivirals in Human Coronavirus 229E Infected Cells

Human Coronavirus 229E (ATCC) was propagated and infectious units quantified by $TCID_{50}$ using MRC-5 cells. For antiviral testing, approximately 10 MRC-5 cells were seeded per well in EMEM (10% FCS) at 37 C in a 96 well plate overnight. Medium from each well was removed and cells were infected with 100 $TCID_{50}$ virus in 100 μL medium for two hours.

Cells were washed one time with medium and then compounds or controls added at the indicated concentrations. After three days, CPE was observed under microscope and quantified using an MTT cell proliferation assay kit (Abcam) read on an ELx800, Universal Microplate reader (BIO-TEK Instruments, INC). The % Inhibition was calculated as $(A_{tv}-A_{cv})/(A_{cd}-A_{cv})\times100\%$ where $A_{tv}$ indicates the absorbance of the test compounds with virus infected cells and $A_{cv}$ and $A_{cd}$ indicate the absorbance of the virus control and the absorbance of the cell control, respectively. The average half-maximal effective concentration ($EC_{50}$) was defined as the concentration which achieved 50% inhibition of virus-induced cytopathic effects.

As described herein, various compounds of the disclosure inhibit the human Alphacoronavirus 229E. Cells were infected with 229E for 2 hours followed by treatment with the indicated dose of the indicated drug for 72 hours. The relative CPE was determined by measuring cell viability using an MTT assay. depicts the cytotoxicity in MRC-5 cells incubated in the presence of the indicated drug at the indicated concentration for 72 hours, after which cell viability was measured by the CellTiter-Glo assay. Data points indicate the averages from 3 independent experiments performed in duplicate. Error bars represent the standard error mean (SEM). Both ODBG-P-RVn and RDV demonstrated a dose-dependent inhibition of cytopathic effect (CPE). The $EC_{50}$ values of ODBG-P-RVn and RDV were 0.15 μM and 0.04 M and the $EC_{90}$s were 0.54 mM and 0.26 mM respectively. The $CC_{50}$ for ODBG-P-RVn and RDV were greater than 50 μM in MRC-5 cells. The most active compounds were compounds which had 3-fluoro,4-methoxy substitutions. Together with the antiviral data for SARS-CoV-2, this demonstrates that ODBG-P-RVn related analogs have antiviral activity against two genetically distinct human pathogenic coronaviruses.

Example 9—Orally Administered ODBG-P-RVn (15d) Achieved Therapeutic Plasma Levels in Syrian Hamsters ODBG-P-RVn in 0.1M sodium carbonate/bicarbonate buffer, pH 9.0, was administered to Syrian Hamsters by oral gavage every 12 hours for seven days. ODBG-P-RVn was present as the sodium salt. It was well tolerated, and no adverse clinical signs were noted. Peak plasma levels of ODBG-P-RVn were noted at 1 hour and fell by 50% in about 5 hours.

Plasma curves were generally similar at day 1 and 7 except at 16.9 mg/kg, the 7 d values were slightly higher than the levels at day 1. At 12 hours ODBG-P-RVn levels were above the $EC_{90}$ for ODBG-P-RVn in all cell lines studied including Vero E6 cells and PSC lung cells on both day 1 and 7. Levels of the RVn, the nucleoside metabolite of ODBG-P-RVn peaked at 3 hours after administration and declined thereafter. Plasma levels of RVn were less than the $EC_{90}$ for RVn in both PSC lung cells and Vero E6 cells. The observed low levels or RVn suggest that antiviral activity attributable to this metabolite will be minimal and are also consistent with finding of OBDG-P-RVn stability in human plasma. Collectively, these results suggest that ODBG-P-RVn will be effective in suppressing viral replication in a variety of tissue types in vivo.

Figure 4A:
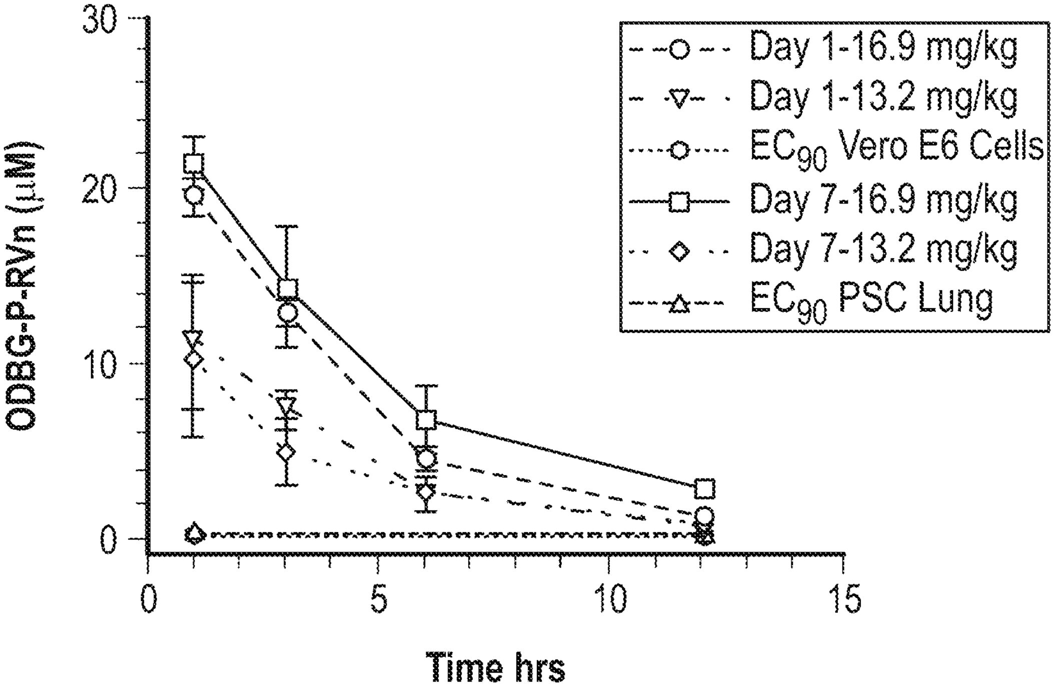
FIG. 4A and FIG. 4B depict plasma levels of ODBG-P-RVn (FIG. 4A) and RVn (FIG. 4B) in a seven day oral pharmacokinetic study in Syrian hamsters.
Figure 4B:
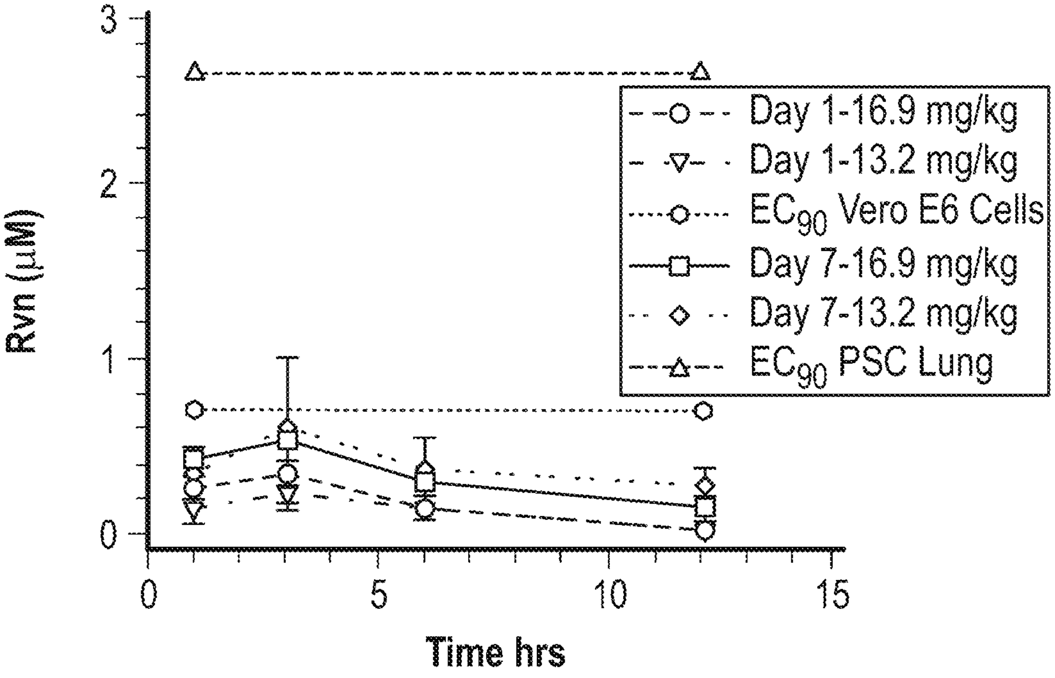

FIG. 4A and FIG. 4B depict the seven day oral pharmacokinetics in Syrian hamsters. Syrian hamsters were given vehicle or ODBG-P-RVn by oral gavage every 12 hours for 7 days. Groups of 3 animals received vehicle or drug at doses of 16.9 and 13.2 mg/kg. Animals were weighed daily and monitored for clinical signs. Plasma samples were obtained at 1, 3, 6 and 12 hours on day 1 and day 7 and frozen for analysis of ODBG-P-RVn (FIG. 4A) and RVn (FIG. 4B) by LC/MS/MS.

Analytical Methods: ODBG-P-RVn: Hamster plasma samples (10 μL) containing ODBG-P-RVn and $K_2$EDTA as the anticoagulant were added to polypropylene tubes containing water (100 μL), internal standard solution (10 μL; 1,000 ng/mL of ODE-P-RVn in ACN:DMF (1:1, v/v)), and 10 μL of ACN:DMF (1:1, v/v). The solutions were mixed, then acidified with phosphoric acid, 85% w/v:water (1:19, v/v; 10 μL), mixed, then diluted with 200 μL of IPA, mixed, then diluted with 500 μL of water, and mixed. The samples were extracted with a Sep-Pak® tC18 96-well solid phase extraction plate (25 mg; Waters, Milford, MA). Extraction occurred under positive pressure conditions using nitrogen. Samples were washed serially with 1 mL of water:acetonitrile:formic acid (475:25:0.5, v/v/v) and 0.4 mL of water: acetonitrile:formic acid (350:150:0.5, v/v/v) before being serially eluted with 100 μL and 150 μL of water:{acetonitrile:isopropyl alcohol (1:1, v/v)}:formic acid:ammonium formate:citric acid solution, 2% w/v (15:85:0.1:0.1:0.1, v/v/v/w/v). The citric acid solution was prepared as water:citric acid monohydrate (20:0.4, v/w). After elution, 100 μL of water was added to each sample. The ODBG-P-RVn extracts were analyzed using an Agilent 1200 HPLC system (Agilent, Santa Clara, CA) coupled to an API5500 mass analyzer (SCIEX, Foster City, CA). Analytes were chromatographically separated using a Dacapo DX-C18 MF column (100×2 mm, 2.5 μm; ImtaktUSA, Portland, OR) using a mobile phase system consisting of Mobile Phase A (water:formic acid:[water:ammonium formate:citric acid (25:5:0.5, v/w/w)](1.000:1:1, v/v/v) and Mobile Phase B (acetonitrile: isopropyl alcohol:formic acid:[water:ammonium formate: citric acid (25:5:0.5, v/w/w)](800:200:1:1, v/v/v/v). The total analytical run time was 4.5 minutes. The mobile phase was nebulized using heated nitrogen in a Turbo-V source/ interface set to electrospray positive ionization mode. The ionized compounds were detected using multiple reaction monitoring with transitions m/z 788.4>229 (V2043) and 668.4>467.2 (V2041). This method is applicable for measuring ODBG-P-RVn concentrations ranging from 6.25 to 3,000 ng/mL using 10.0 μL of plasma for extraction. The peak areas of ODBG-P-RVn and RVn were acquired using Analyst v. 1.6.2 (SCIEX, Framingham, MA). The calibration curve was obtained by fitting the peak area ratios of the analyte/I.S. and the standard concentrations to a linear equation with 1/x2 weighting, using Analyst. The equation of the calibration curve was then used to interpolate the concentrations of the analyte in the samples using their peak area ratios. The peak areas used for the calculations were not rounded.

Analytical Methods: RVn (GS-441524): Hamster plasma samples (20 μL) containing GS-441524 and $K_2$EDTA as the anticoagulant were added to Eppendorf LoBind microfuge tubes containing acetonitrile (300 μL) and water:acetonitrile (2:8, v/v; 60 μL). The solutions were mixed and centrifuged at 16,000 g for five minutes. The supernatant (300 μL) was then filtered through an Ostro protein precipitation and phospholipid removal plate (25 mg; Waters. Milford, MA). Filtration occurred under positive pressure conditions using nitrogen. Collected filtered samples were capped, mixed and stored at 10° C. pending analysis. The GS-441524 extracts were analyzed using an Acquity UPLC system (Waters, Milford, MA) coupled to a G2-S QTof mass analyzer (Waters, Milford, MA). Analytes were chromatographically separated using a Unison-UK Amino HT column (100×2 mm, 3 μm; ImtaktUSA, Portland, OR) using a mobile phase system consisting of Mobile Phase A (0.008% ammonium hydroxide, 0.012% acetic acid in water, v/v/v) and Mobile Phase B (0.008% ammonium hydroxide, 0.012% acetic acid in acetonitrile, v/v/v). The total analytical run time was 12.5 minutes. The mobile phase was nebulized using heated nitrogen in a Z-spray source/interface set to electrospray positive ionization mode. The ionized compounds were detected using Tof MS scan monitoring in sensitivity mode scanning from 50.0 to 700 m/z. This method is applicable for measuring GS-441524 concentrations ranging from 1.00 to 1,000 ng/mL using 20.0 μL of plasma for extraction. The peak areas of GS-441524 were acquired using MassLynx V4.2 (Waters, Milford, MA). The calibration curve was obtained by fitting the peak area ratios of the analyte and the standard concentrations to a linear equation with $1/x^2$ weighting using MassLynx. The equation of the calibration curve was then used to interpolate the concentrations of the analyte in the samples using their peak areas. The peak areas used for the calculations were not rounded.

Example 10—Stability of ODE-P-RVn (4c) and ODBG-P-RVn (15d) in Human Plasma

One of the disadvantages of remdesivir is instability in plasma where it has been reported to persist at virologically significant levels for less than 2 hours after intravenous infusion. (1, 2). Remdesivir also has limited stability ex vivo in human plasma with a reported $T_{1/2}$ of 69 minutes (Siegel D. Hui H C, Doerftler E. Clarke M O, Chun K, Zhang L, Neville S, Carra E, Lew W, Ross B, Wang Q, Wolfe L. Jordan R. Soloveva V. Knox J. Perry J, Perron M, Stray K M, Barauskas O, Feng J Y, Xu Y, Lee G, Rheingold A L, Ray A S, Bannister R. Strickley R, Swaminathan S, Lee W A, Bavari S, Cihlar T, Lo M K, Warren T K, Macknman R L. Discovery and Synthesis of a Phosphoranidate Prodrug of a Pyrrolo[2,1-f][triazin-4-amino]Adenine C-Nucleoside (GS-5734) for the Treatment of Ebola and Emerging Viruses. J Med Chem. 2017 Mar. 9:60(5):1648-1661).

The stability of ODE-P-RVn and ODBG-P-RVn in human plasma was evaluated with either $K_2$EDTA or sodium heparin as an anticoagulant.

Plasma was spiked with 2 micrograms/ml concentrations of ODE-P-RVn or ODBG-P-RVn and incubated at 37° C.

Figure 5A:
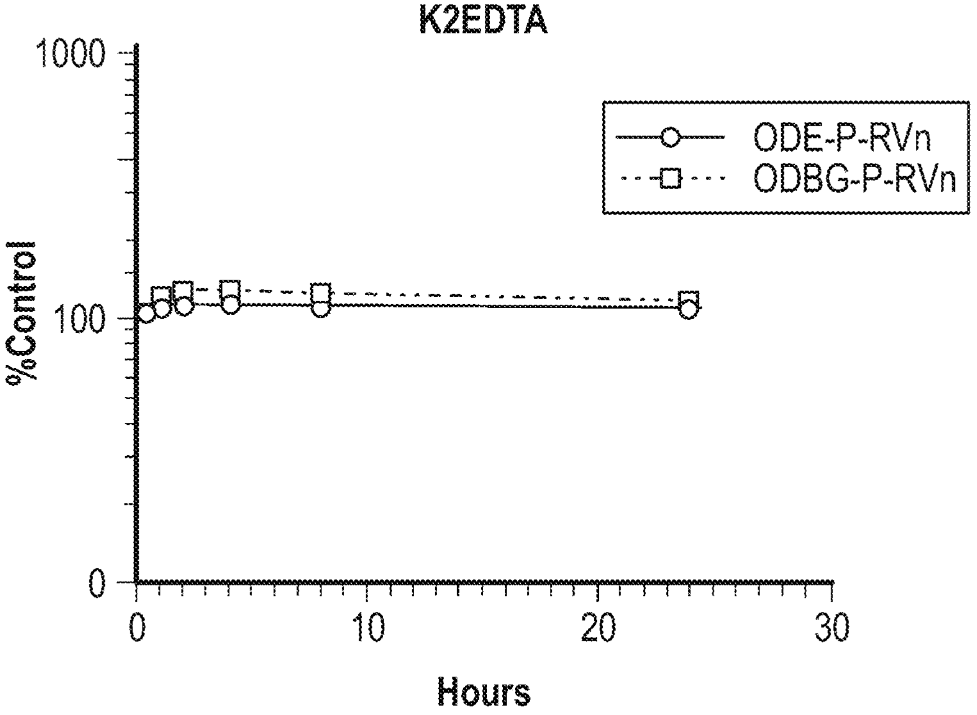
FIG. 5A and FIG. 5B depict the stability of ODE-P-RVn and ODBG-P-RVn in human plasma with either $K_2EDTA$ (FIG. 5A) or sodium heparin (FIG. 5B) as anticoagulants.
Figure 5B:
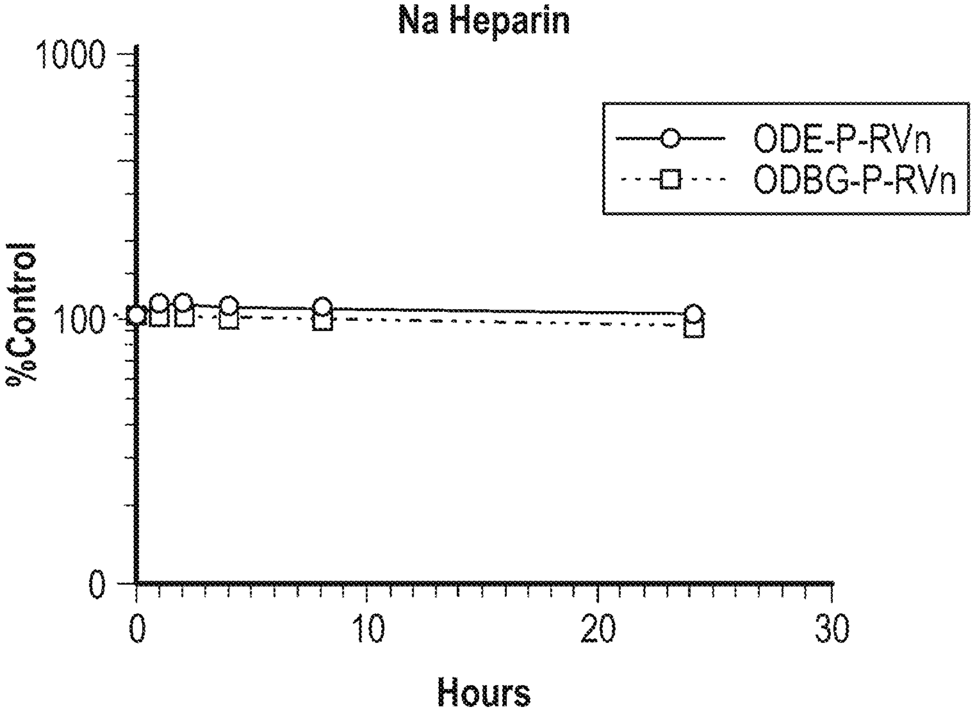

Samples were taken at 0.5, 1, 2, 4, 8 and 24 hours and frozen for later analysis by LC/MS/MS by the method shown in Example C. FIG. 5A and FIG. 5B shows that both ODE-P-RVn and ODBG-P-RVn were stable for at least 24 hours in human plasma with either $K_2EDTA$ (FIG. 5A) or sodium heparin (FIG. 5B) as anticoagulants. (See, e.g., Warren T. K. et al. Nature. 2016 Mar. 17; 531(7594):381-5; and Tempestilli, M. et al. J. Antimicrob Chemother. 2020 Oct. 1; 75(10):2977-2980).

Example 11—Effect of Antivirals of the Replication of the Respiratory Syncytial Virus Methods: The SRV A2 strain of RSV was obtained from the ATCC. Ten thousand Hep-2 cells were seeded into each well of a 96-well plate in EMEM with 10% fetal bovine serum and 1% penicillin and streptomycin. Each well was inoculated with 100 $TCID_{50}$ of virus. Two hours later wells were washed once with medium and serial four-fold dilutions of candidate antiviral drugs were added. Cell cultures were observed for 72 to 96 hours for cytopathic effects. The concentration of drug that reduced CPE by 50 or 90% was calculated using Prism 7 software and expressed as the $EC_{50}$ and $EC_{90}$, respectively.

Cell viability assay: For select compounds the CC50 was calculated up to a maximum of 100 μM using CellTiter-Glo. For these experiments, approximately 20k Calu-3 cells were seeded per well in opaque white 96-well plates (cat #655073, Greiner Bio-One, Monroe, North Carolina) and incubated 48-72 h. Compounds or controls were added and incubated for 44 h at 37° C. and 5% $CO_2$. After which an equal volume of CellTiter-Glo reagent (Cat. #G7570, Promega, Madison, WI) was added, mixed and luminescence recorded on a Veritas Microplate Luminometer (Turner BioSystems) according to manufacturer recommendations.

Antiviral effect of compounds of the present disclosure against RSV infection in Hep-2 cells

| Compd | $R_1$ | $R_2$ | Hep-2 cells $EC_{50}$ (μM) | $EC_{90}$ (μM) | $CC_{50}$ (μM) |
|---|---|---|---|---|---|
| 15d | 1-O-octadecyl-2-O-benzyl-sn-glyceryl | H | 0.010 | 0.019 | 14.7 |
| 15j | 1-O-octadecyl-2-O-(3-F, 4-MeO—Bn)-sn-glyceryl | H | 0.010 | 0.019 | 9.6 |
| 15m | 1-O-oleyl-2-O-(3-F, 4-MeO—Bn)-sn-glyceryl | H | 0.005 | 0.0094 | 12.5 |
| 15c | 1-O-hexadecyl-2-O-(3-F, 4-MeO—Bn)-sn-glyceryl | H | 0.034 | 0.068 | 20.6 |

Not wishing to be bound by any particular theory, it is believed that compounds 15j, 15m, and 15c may be at least 2 to 3 times more active than compound 15d. For example, compound 15m may be more active than remdesivir.

Compounds of the disclosure had very marked antiviral activity in Hep-2 cells infected with RSV A2. Cytotoxicity was moderate and the selectivity (CC50/EC50) ranged from 605 to 2,500.

Example 12—Preparation of Formulations

Synthesis of HIV Antivirals: Synthesis of ((2S,5R)-5-(4-amino-5-fluoro-2-oxo-3,4-dihydropyrimidin-1(2H)-yl)-1,3-oxathiolan-2-yl)methyl benzyl (2-(octadecyloxy)ethyl) phosphate (ODE-Benzyl Phospho-Emtricitabine)

Scheme 5. Example process for synthesis of smtricitabine 5'-monophosphate analogs of the disclosure. Reagents and Conditions: a) emtricitabine, DCC, DMAP, pyridine, 80° C., 72 h; b) benayl alcohol, PyBOP, DIEA, DMF, rt, 3 h.

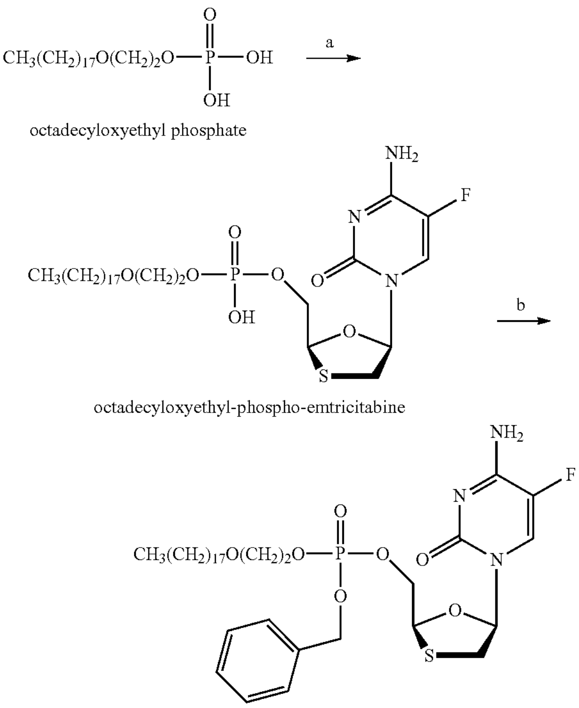

octadecyloxyethyl phosphate octadecyloxyethyl-phospho-emtricitabine octadecyloxyethyl-benzyl-phospho-emtricitabine N,N-Dicyclohexylcarbodiimide (DCC, 410 mg, 2.0 mmol) was added to a solution of emtricitabine (230 mg, 0.9 mmol), octadecyloxyethyl phosphate (320 mg, 0.74 mmol), and 4-dimethylaminopyridine (DMAP, 110 mg, 0.9 mmol) in 10 mL of dry pyridine, and then the mixture was heated to 80° C. and stirred for 3 days. Pyridine was then evaporated and the residue was purified by flash column chromatography on silica gel 60. Gradient elution ($CH_2Cl_2$/methanol 10-20%) afforded 220 mg (47% yield) of, octadecyloxyethyl-phospho-emtricitabine: ESI MS: 622.29 $[M-H]^-$; 624.10 $[M+H]^+$, 646.30 $[M+Na]^+$, 662.26 $[M+K]^+$.

Octadecyloxyethyl-phospho-emtricitabine (220 mg, 0.35 mmol), benzyl alcohol (76 mg, 0.70 mmol), diisopropylethylamine (DIEA. 0.12 ml, 0.70 mmol), and (1H-benzotriazol-1-yloxy)-tripyrrolidinophosphonium hexafluorophosphate (PyBOP. 360 mg, 0.70 mmol) in dry DMF (10 mL) were stirred at room temperature. After 3 h. DMF was evaporated under vacuum. The residue was dissolved in ethyl acetate (50 mL) washed with saturated $NaHCO_3$ (3×10 mL). The organic layer was dried over $MgSO_4$ and ethyl acetate was evaporated. Purification of the residue by silica gel column chromatography using ethyl acetate and ethanol (0-4%) yielded 130 mg (52% yield) of octadecyloxyethyl benzyl phospho-emtricitabine. $^1$H NMR (400 MHz, $CDCl_3$-$CD_3OD$) δ ppm 7.91 (d, J=5.87 Hz, 1H), 7.40-7.48 (m, 4H), 6.27-6.34 (m, 1H), 5.35-5.41 (m, 1H), 5.19 (d, J=8.43 Hz, 2H), 4.33-4.48 (m, 2H), 4.21-4.28 (m, 2H), 3.65-3.71 (m, 2H), 3.48-3.61 (m, 3H), 3.37-3.42 (m, 2H), 3.06-3.18 (m, 1H), 1.53-1.64 (m, 2H), 1.25-1.40 (m, 30H), 0.93 (t, sCJ=6.23 Hz, 3H). ESI MS: 714.32 [M+H]t, 736.43 $[M+Na]^+$.

Synthesis of ((2S,5R)-5-(4-amino-5-fluoro-2-oxo-3,4-dihydropyrimidin-1(2H)-yl)-1,3-oxathiolan-2-yl) methyl benzyl ((R)-2-(benzyloxy)-3-(octadecyloxy) propyl) phosphate (ODBG-benzyl-phospho-emtricitabine)

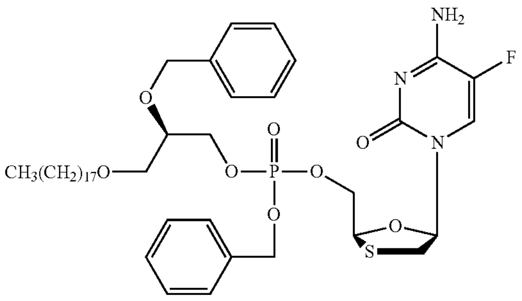

ODBG-benzyl-phospho-emtricitabine

1-O-octadecyl-2-O-benzyl-sn-glyceryl phosphate (ODBG-P-) was coupled to emtricitabine in pyridine using DCC/DMAP as described in Scheme 5 to afford ODBG-phospho-emtricitabine. Esterification of the phosphate diester with benzyl alcohol was accomplished using PyBOP/DIEA as in Scheme 5 to yield the phosphotriester, ODBG-benzyl-phospho-emtricitabine.

Synthesis of benzyl (2-(octadecyloxy)ethyl) ((((R)-1-(2,6-diamino-9H-purin-9-yl)propan-2-yl)oxy) methyl)phosphonate (ODE-benzyl 9-(R)-[2-(phosphonomethoxy)-propyl]2,6-diaminopurine)

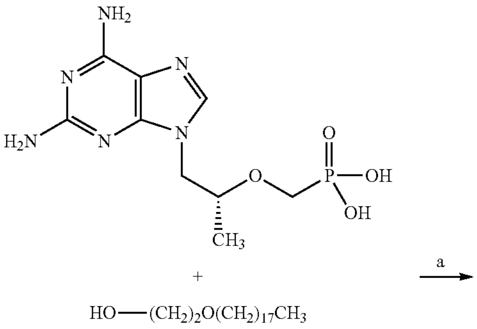

-continued

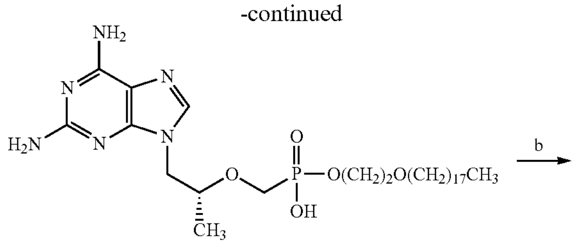

octadecyloxyethyl 9-(R)-[(2-phosphono-methoxy)propyl]2,6-diaminopurine

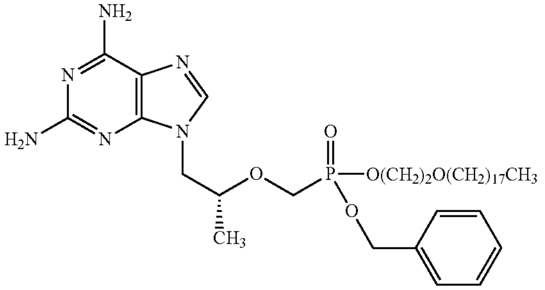

octadecyloxyethyl benzyl 9-(R)-[(2-phosphono-methoxy)propyl]2,6-diaminopurine

Scheme 6. Example process for synthesis of 9-(R)-[2-(phosphonomethoxy)propyl]2,6-diaminopurine) analogs of the disclosure. Reagents and Conditions: a) DCC, DMAP, pyridine, 80° C., 72 h, b) benzyl alcohol, PyBOP, DIEA, DMF, rt, 3h N,N-Dicyclohexylcarbodiimide (3 eq) is added to a mixture of 9-(R)-[2-(phosphonomethoxy)propyl]-2,6-diaminopurine ((R)-PMPDAP, 1 eq, see: Krečmerová, M. Jansa, P., Dračinský, M, Sázelová, P., Kašička, V., Neyts, J., Auwerx, J., Kiss, E., Goris, N., Stepan, G., Janeba, Z. 9-[2-(R)-(Phosphonomethoxy)propyl]-2,6-diarninopurine (R)-PMPDAP and its prodrugs: Optimized preparation, including identification of by-products formed, and antiviral evaluation in vitro, *Bioorganic & Medicinal Chemistry,* 2013, 21: 1199-1208.), octadecyloxyethan-1-ol (1 eq) and 4-dimethylaminopyridine (DMAP, 1 eq) in dry pyridine and the mixture is heated to 80° C. until conversion to the esterified product is complete. The monoester (ODE-(R)-PMPDAP) was isolated after column chromatography. To a mixture of ODE-(R)-PMPDAP (1 eq), benzyl alcohol (1.5 eq) and diisopropylethylamine (DIEA, 1.5 eq) in dry DMF was added (benzotriazol-1-yloxy)tripyrrolidinophosphonium hexafluorophosphate (PyBOP, 1.5 eq) and the mixture was stirred at room temperature until formation of the diester was complete. The pure product, ODE-benzyl-(R)-PMPDAP was isolated by column chromatography.

Synthesis of benzyl (2-(octadec-9-en-1-yloxy)ethyl) ((((R)-1-(2,6-diamino-9H-purin-9-yl)propan-2-yl) oxy)methyl)phosphonate (OLE-benzyl 9-(R)-[2-(phosphonomethoxy)-propyl]2,6-diaminopurine)

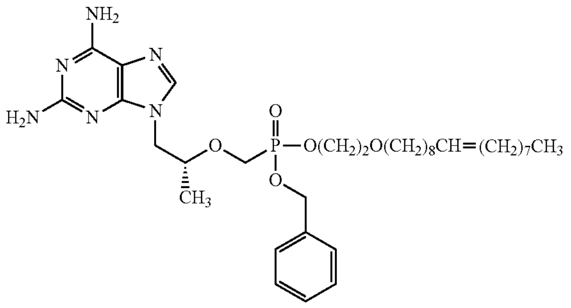

oleyloxyethyl-benzyl 9-(R)-[2-(phosphono-methoxy)propyl]2,6-diaminopurine

A mixture of (R)-PMPDAP and oleyloxyethan-1-ol in pyridine was treated with DCC/DMAP as in Scheme 6 to afford the monoester, OLE-(R)-PMPDAP. OLE-(R)-PMP-DAP was further esterified using benzyl alcohol, PyBOP and DIEA. OLE-benzyl-(R)-PMPDAP was isolated after column chromatography.

Long-acting HIV antivirals: For use in long-acting intramuscular treatment of infection with the human immunodeficiency virus, the antiviral compounds suitable for use are described in this application and in U.S. Pat. No. 8,835,630 and include the following:

Compounds Useful as Long-Acting HIV Antivirals

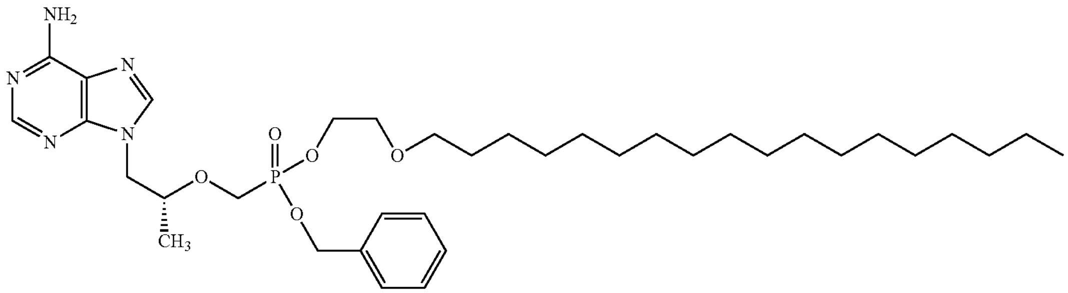

octadecyloxyethyl benzyl tenofovir (ODE-Bn-TFV)

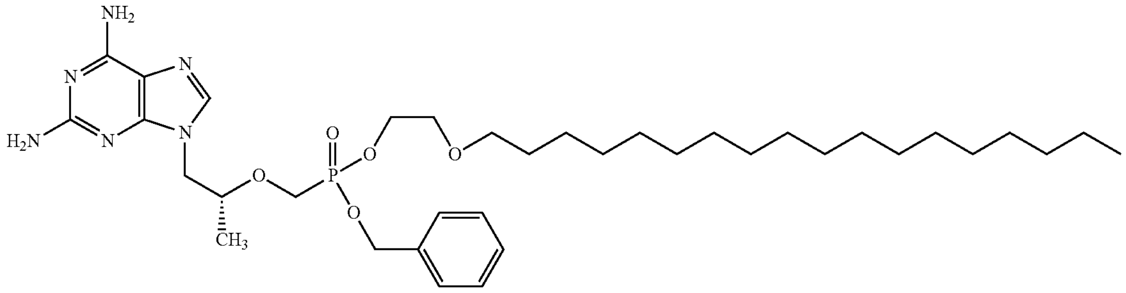

octadecyloxyethyl benzyl 9-[(2-phosphonomethoxy)ethyl]2,6-diaminopurine (ODE-Bn-PMPDAP)

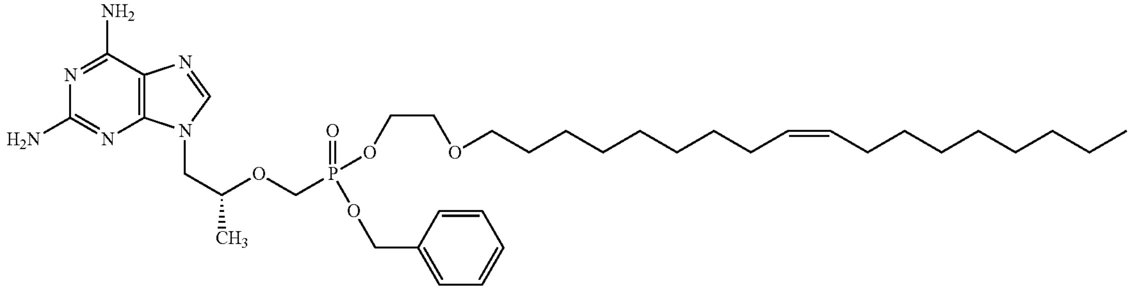

oleyloxyethyl benzyl 9-[(2-phosphonomethoxy)ethyl]2,6-diaminopurine (OLE-Bn-PMPDAP)

-continued

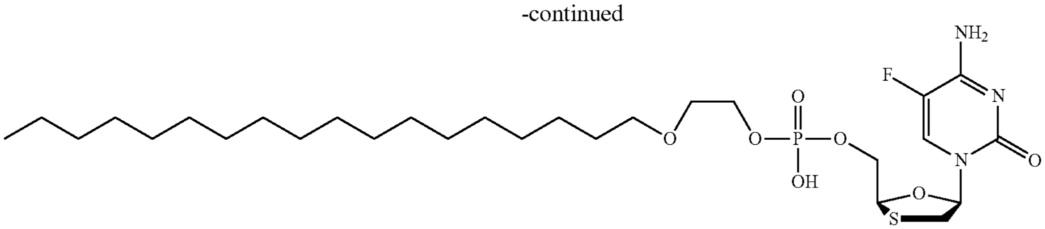

otadecyloxyethyl-phospho-emtricitabine (ODE-P-FTC)

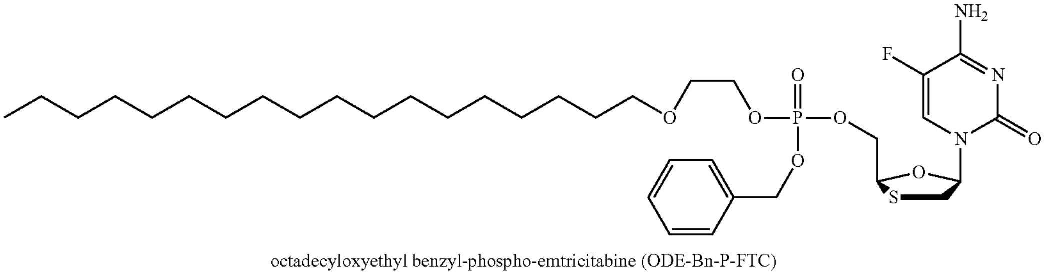

octadecyloxyethyl benzyl-phospho-emtricitabine (ODE-Bn-P-FTC)

| Antiviral activity in HIV infected human PBMCs | | | |
|---|---|---|---|
| Compound | $EC_{50}$, nM | $CC_{50}$, μM | Selectivity index |
| ODE-Bn-Tenofovir | 1.7 ± 1.5 | 8.72 | 5130 |
| ODE-PMPDAP | 0.09 ± 0.05 | 7.0 ± 7.1 | 77,700 |
| OLE-PMPDAP | 0.10 ± 0.03 | 15.0 ± 12.3 | 150,000 |
| ODE-Bn-PMPDAP | active | | |
| OLE-Bn-PMPDAP | active | | |
| ODE-P-Emtricitabine | 9.6 ± 3.1 | 35.6 ± 12.9 | 3708 |
| ODE-Bn-P-Emtricitabine | 18.3 ± 8.7 | 54.7 ± 45.3 | 2989 |

Abbreviations: $EC_{50}$, 50% effective concentration; $CC_{50}$, 50% cytotoxic concentration; SI, selectivity index ($CC_{50}/EC_{50}$). Method: inhibition of antiviral activity was measured in human PBMCs infected with HIV-1 as reported in Beadle et al. Antiviral Research vol. 171 (2019): 104614.

Compounds of this example were active with $EC_{50}$ values in the 0.09 to 18 nanomolar range.

Pharmaceutical Formulations: Also provided herein are pharmaceutical formulations. The pharmaceutical formulations included a compound as described herein, such as a compound of formula (I). In some embodiments, the pharmaceutical formulation was orally bioavailable. In some embodiments, the pharmaceutical formulation is formulated for injection, such as intramuscular injection.

The pharmaceutical formulations included one compound described herein, or more than one (e.g., two, three, etc.) compounds described herein. The pharmaceutical formulations included any one or more pharmaceutically acceptable excipients. Oil based formulations for compounds of the disclosure have the following composition by weight (w/w %):

| Composition of intermediate- and long-acting formulations of compounds for treatment of coronavirus or HIV infections | | | | |
|---|---|---|---|---|
| Components | F3 | F4 | F7 | F8 |
| Sesame oil | 92.65 | 73.67 | — | — |
| Medium chain triglycerides | — | — | 92.65 | 73.67 |
| Benzyl alcohol | 1.22 | 10.67 | 1.22 | 10.67 |
| Benzyl benzoate | — | 15.67 | — | 15.67 |
| Ethyl alcohol | 6.12 | — | 6.12 | — |

The following materials were used in the formulations of the foregoing table:

| Materials and grade | Source and lot | % assay |
|---|---|---|
| Super refined sesame oil, NF | Croda, 0001095029 | N/A |
| Medium chain triglycerides, USP | IOI Oleochemical, 190104 | N/A |
| Benzyl alcohol, USP | EMD, K43136587447 | 98.0-100.5 |
| Benzyl benzoate | Sigma-Aldrich, MKBQ9481V | 99.5 |
| Ethanol, USP 200 proof | Decon labs, | 100 |

In some embodiments, one or more of the compounds described herein, such as those of formula (I), were soluble in an oil, such as one of formulations F3, F4, F7, and F8. When an amount of one or more compounds described herein, such as those of formula (I), were soluble in an oil, then the resulting pharmaceutical formulation may be used in any of the methods herein, including a method of treating coronavirus with a single dose of the pharmaceutical formulation.

Formulations of the foregoing table were prepared using compounds of the disclosure. Antiviral prodrugs of the disclosure employing HIV antivirals or RNA virus antiviral compounds described in PCT/US2021/043094 may be utilized in the formulations. As a non limiting example the following pharmacokinetic experiments were done using ODE-Bn-Tenofovir as the antiviral prodrug.

Comparison of Formulations F3, F4, F7 and F8 following a single IM administration in rats—Groups: Vehicle control, 10 mg/kg, 30 mg/kg and 100 mg/kg of formulations 3, 4, 7, 8.

Procedure: At time zero rats were injected intramuscularly with 100 microliters of vehicle and formulations as noted. The animals were observed for general health and weights were obtained at the start and twice a week thereafter. Blood was obtained at 6, 24 and 48 hours, and at 7, 14, 28, 35 and 42 days and the plasma levels of ODE-Bn-TFV and ODE-TFV (the first metabolite, also an active anti-HIV compound) were determined by LC/MS/MS.

Figure 6A:
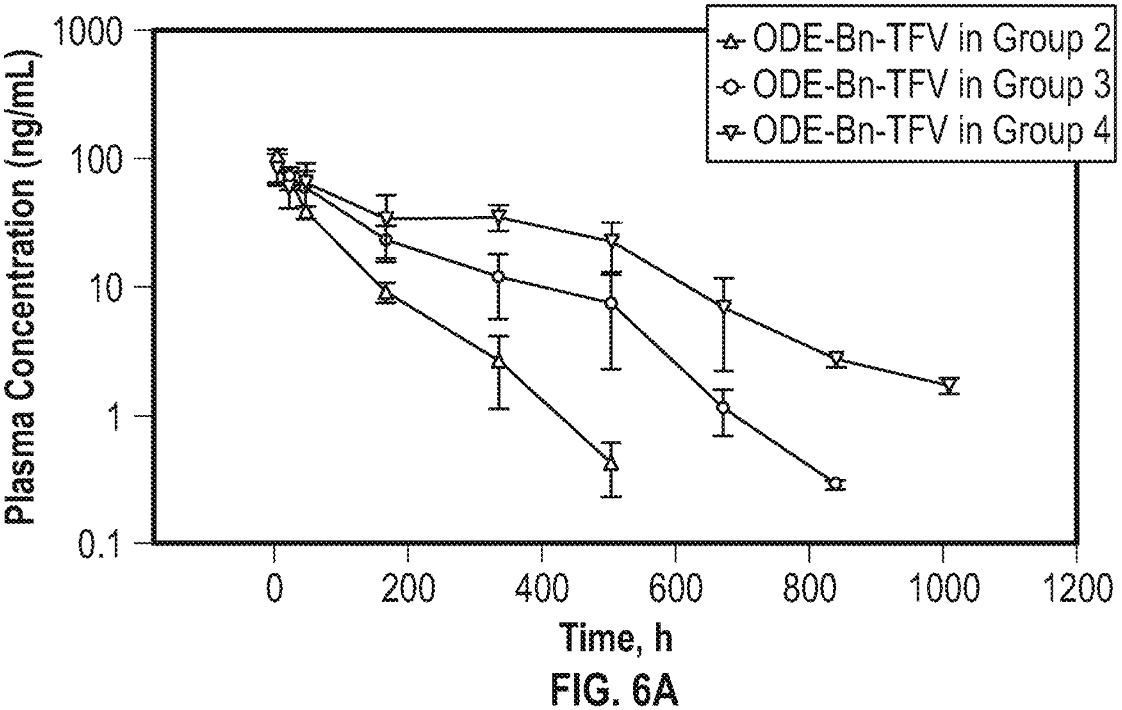
FIG. 6A and FIG. 6B depict pharmacokinetics of ODE-Bn-TFV and ODE-TFV, respectively, after intramuscular administration of 100 mg/kg in formulation F3 to rats.
Figure 6B:
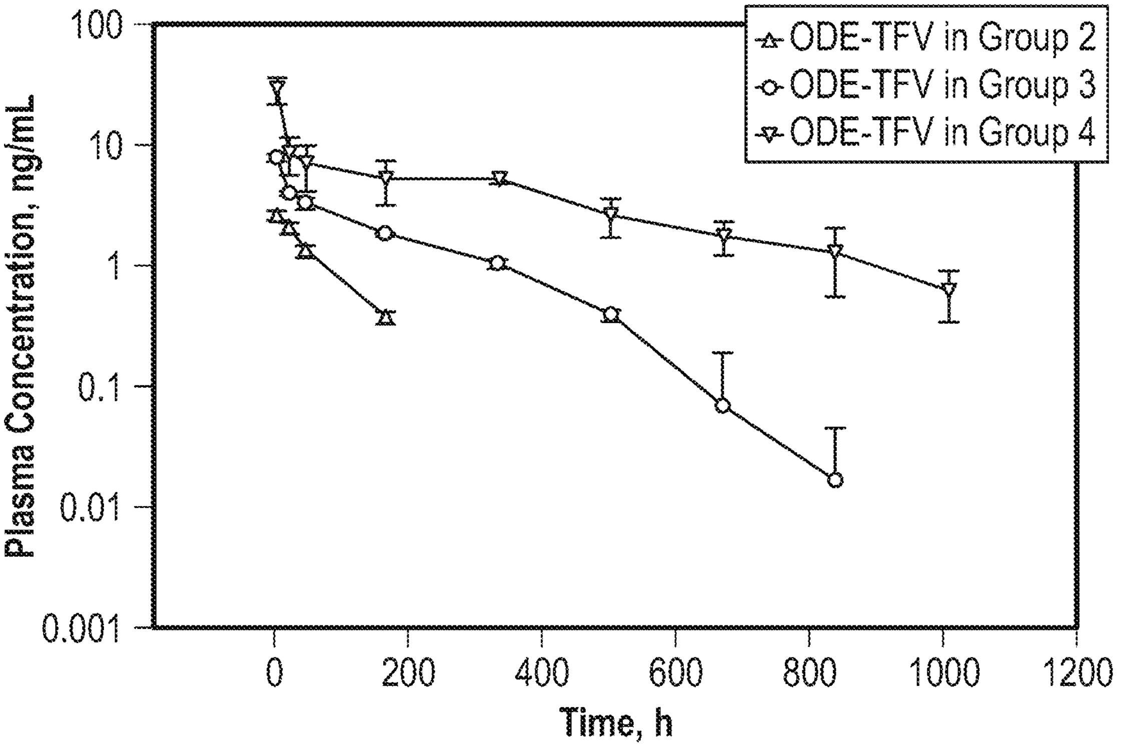

FIG. 6A and FIG. 6B depict pharmacokinetics of ODE-Bn-TFV and ODE-TFV, respectively, after intramuscular administration of 100 mg/kg in formulation F3 to rats.

Results: Rats were injected IM at day zero and weights and clinical observations were acquired twice a week for 42 days. The increases in body weight in vehicle and drug treated rats were identical and no clinical signs were noted. Comprehensive metabolic panels at study termination did not show any abnormalities in liver or kidney functions tests. CBCs were normal controls and all drug dosage groups. After administration ODE-Bn-TFV was metabolized to the more active metabolite, ODE-TFV. Clearly as seen in the ODE-Bn-TFV curves (left) and the curves for the active first metabolite, ODE-TFV (right), doses of 10 and 30 mg/kg (groups 2 & 3) were not adequate to provide antivirally significant levels of compound for 30 days and beyond. Only the 100 mg/kg dose (group 4) provided levels of ODE-Bn-TFV and ODE-TFV at a virally significant level for 28 days.

The two $log_{10}$ panels below show various formulations at doses of 100 mg/kg (formulation drug concentrations of 200 mg/ml). The left panel was ODE-Bn-TFV and the right panel shows plasma levels of ODE-TFV (nM/L). All four formulations given at 100 mg/kg allow for maximal plasma levels of ODE-Bn-TFV at 6 to 48 hours followed by a gradual decline to 2.87 ng/ml (F8) to 6.95 (F3). The highest values at day 28 were noted in F3, ODE-Bn-TFV 6.95 ng/ml (10.3 nM) and ODE-TFV 1.78 ng/ml (3.05 nM). These values were above the $EC_{50}$s for these two compounds (1.7 and 1.1 nM).

Figure 7A:
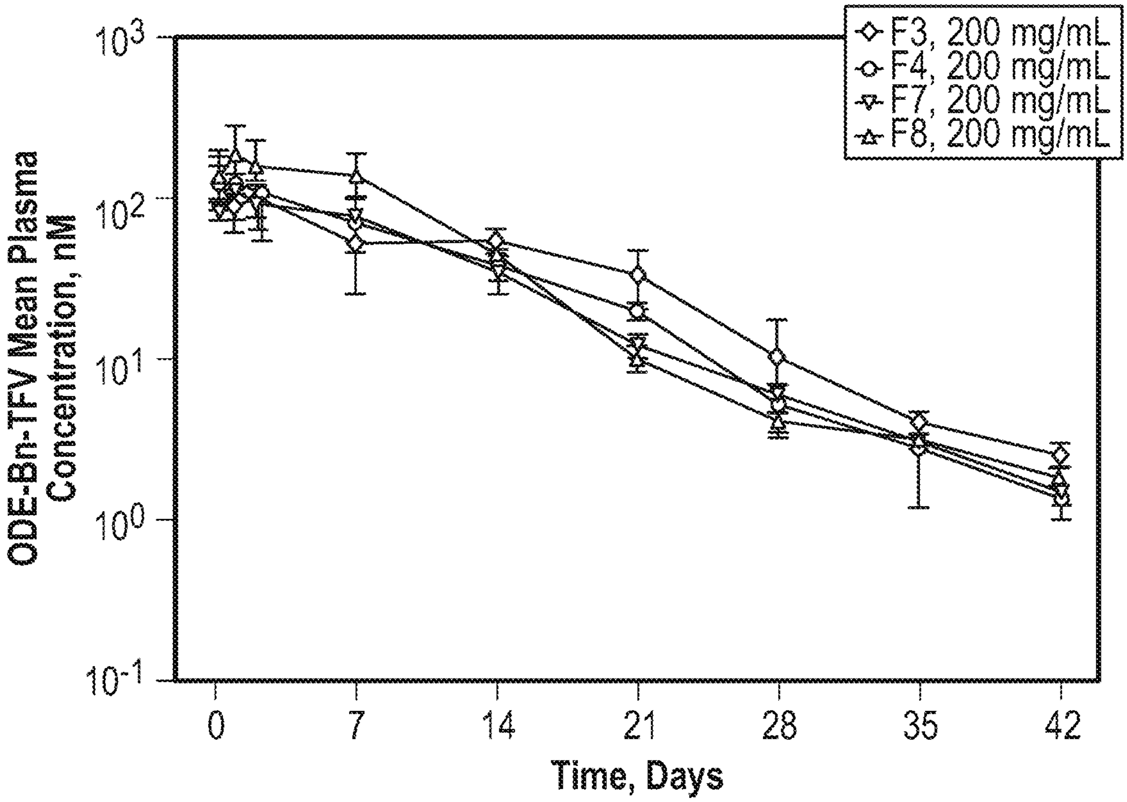
FIG. 7A and FIG. 7B are plots of the effects of 4 different formulations on the pharmacokinetics of ODE-Bn-TFV and ODE-TFV, respectively, after intramuscular administration of 100 mg/kg to rats.
Figure 7B:
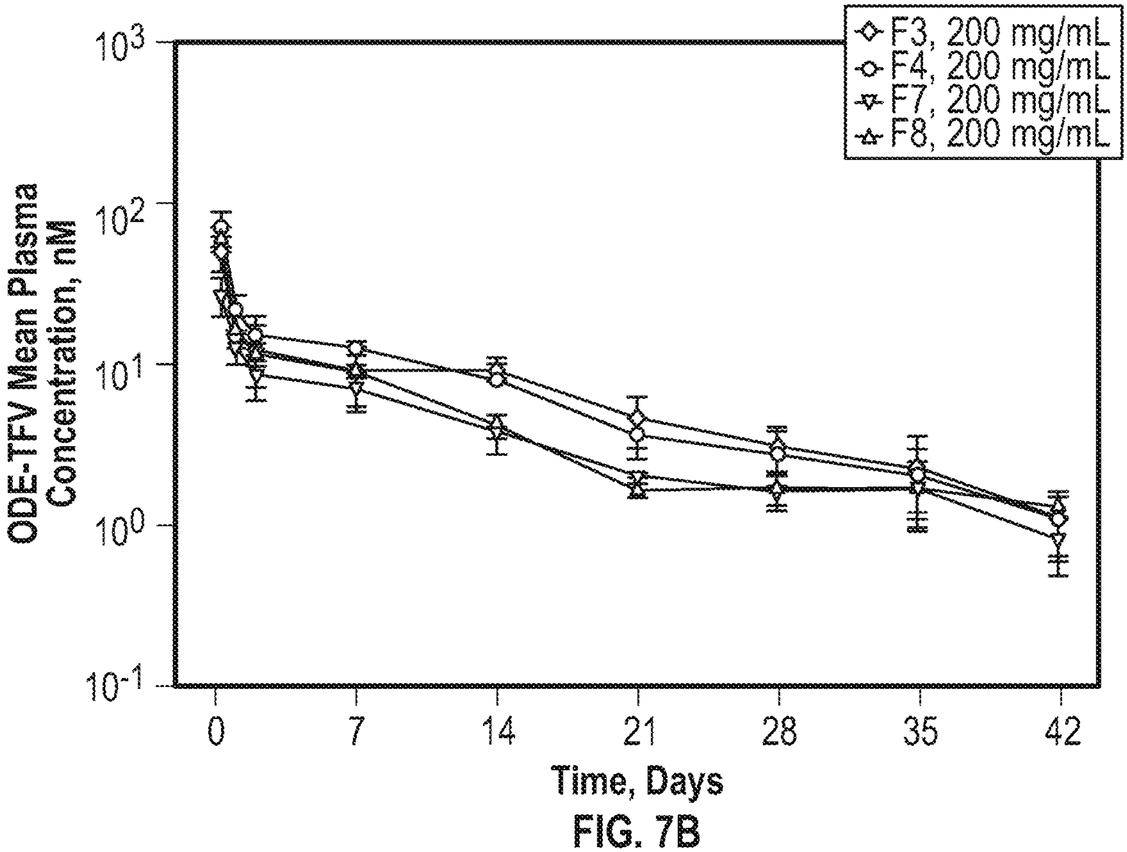

FIG. 7A and FIG. 7B are plots of the effects of 4 different formulations on the pharmacokinetics of ODE-Bn-TFV and ODE-TFV, respectively, after intramuscular administration of 100 mg/kg to rats.

Pharmacokinetic parameters
Pharmacokinetic Parameters

| | F3 | F4 | F7 | F8 |
|---|---|---|---|---|
| Cmax, nM | 130 | 139 | 76 | 187 |
| T½ hr | 142 | 171 | 168 | 278 |
| AUC (0-inf) nM · hr | 35200 | 33800 | 21400 | 48100 |
| AUC (14-28 hr) nM · hr | 10900 | 6900 | 3640 | 5420 |

The following figures shows the comparison between intramuscular ODE-Bn-TFV in Formulation F3 versus formulation F8 in rats. ODE-Bn-TFV in F3 provided lower early levels of drug in comparison with F8 but levels persisted longer, remaining above the HIV $EC_{90}$ for 28 days. The F8 formulation produced higher drug levels until day 15 and was more suitable for treatment courses of 5 to 14 days.

Figure 8:
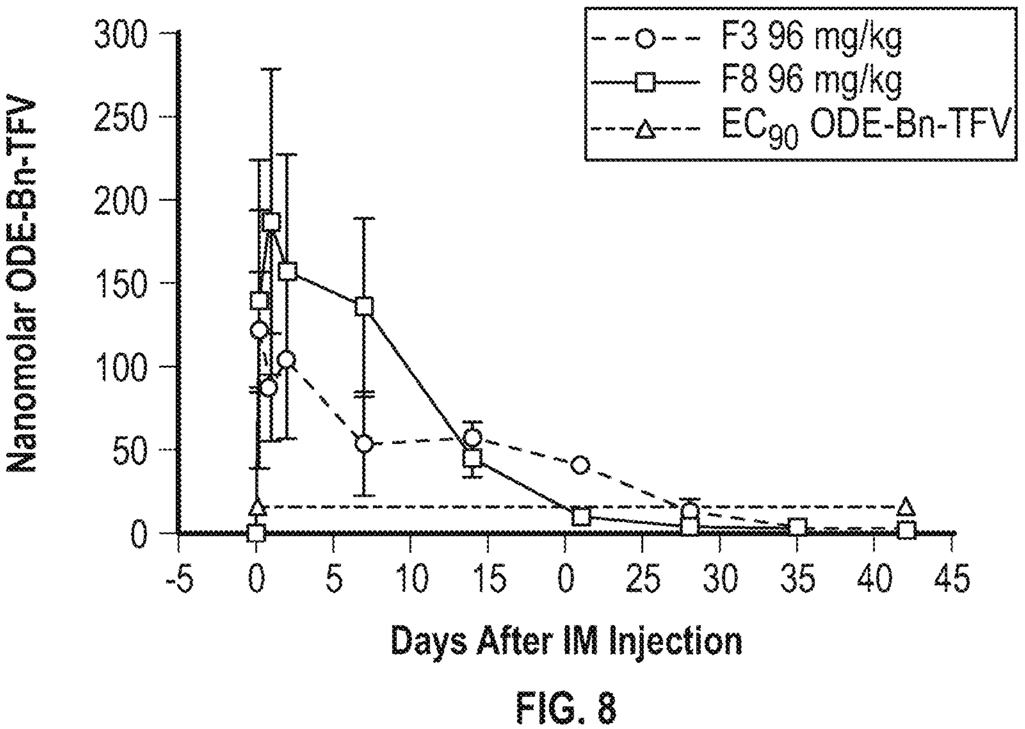
FIG. 8 depicts a comparison of 96 mg/kg ODE-Bn-TFV pharmacokinetics in rats using formulation F3 versus F8.

FIG. 8 depicts a comparison of 96 mg/kg ODE-Bn-TFV pharmacokinetics in rats using formulation F3 versus F8.

Calculated area under curve (AUC) percentages during the first and second 14 days showing the release profile are shown in the table below.

Release profile: First 14 days versus second 14 days.

| Formulation | % AUC first 14 days | % AUC second 14 days |
|---|---|---|
| F3 | 69 | 31 |
| F4 | 79 | 21 |
| F7 | 83 | 17 |
| F8 | 89 | 11 |

Formulation F3 provided the greatest exposure during the second 14 days. Formulation F8 and F7 showed the highest percentage exposures, 89 and 83%, during the first 14 days.

3 Month study of Formulations F3 in rats with measurements of plasma levels at 15 and 30 days following monthly IM injections of ODE-Bn-TFV—Since the initial plasma values were very high (~100 ng/ml) and declined progressively to slightly suboptimal values at day 28, it was considered important to know the PBMC TFVpp levels in a longer multi-dose study. A 3-month study was designed to test mid and trough plasma levels of ODE-Bn-TFV and ODE-TFV in male Sprague Dawley rats following monthly IM injections of F3 containing ODE-Bn-TFV.

Maximal volume IM injections of 100 microliters were given at day 0, 30 and 60 to groups of 3 rats. There were 3 groups of control animals who received monthly injections of F3 vehicle. Plasma drug levels were analyzed by LC/MS/MS. Weights were assessed over the 3-month period. Rats increased weight from 355 mg to 705 mg at study termination at 105 days. Because a constant (maximal) IM volume of 100 microliters was given, the initial dose was 90 mg/kg and the two following injections at days 30 and 60 were lower, 62 mg/kg, due to weight increases of the rats. There were no clinical observations of significance during the 3 month study and metabolic panels and CBCs showed no abnormalities at day 105.

Figure 9:
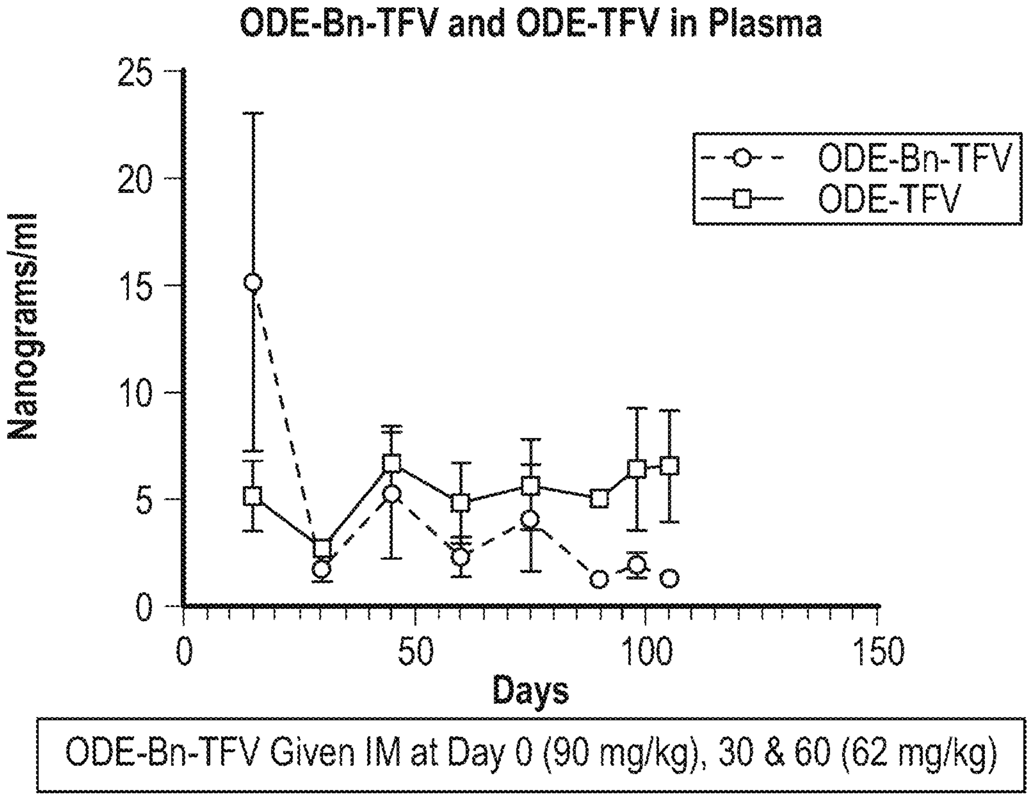
FIG. 9 depicts rat plasma levels of ODE-Bn-TFV and ODE-TFV during a 3-month exposure to monthly intramuscular doses of ODE-Bn-TFV in formulation F3.

FIG. 9 depicts rat plasma levels of ODE-Bn-TFV and ODE-TFV during a 3 month exposure to monthly intramuscular doses of ODE-Bn-TFV in formulation F3.

Plasma drug levels: 15 days following the first dose ODE-Bn-TFV levels were high and the first metabolite, ODE-TFV, were about 30% of the parent compound. However, as the 3 month study proceeded, ODE-TFV levels gradually became the dominant active compound in plasma. After the last dose at 60 days, levels of ODE-TFV remained substantial until day 105 at which time they were 11 nanomolar. The $EC_{90}$ of ODE-TFV is 10 nM (Beadle J R, Aldem K A, Zhang X Q, Valiaeva N, Hostetler K Y, Schooley R T. Octadecyloxyethyl benzyl tenofovir: A novel tenofovir diester provided sustained intracellular levels of tenofovir diphosphate. (Antiviral Res. 2019 November; 171: 104614). Therapeutic levels of ODE-Bn-TFV and ODE-TFV were maintained to 105 days following 3 monthly IM doses at 0, 30 and 60 days. Rats received maximal (volume) doses of 100 microliters. Since their weight doubled during treatment, the second and third doses were only 62 mg/kg. Even with the lower $2^{nd}$ and $3^{rd}$ doses, therapeutic levels of drug were maintained for 105 days. Therapeutic levels of the ODE-TFV metabolite persisted for 105 days.

Figure 10:
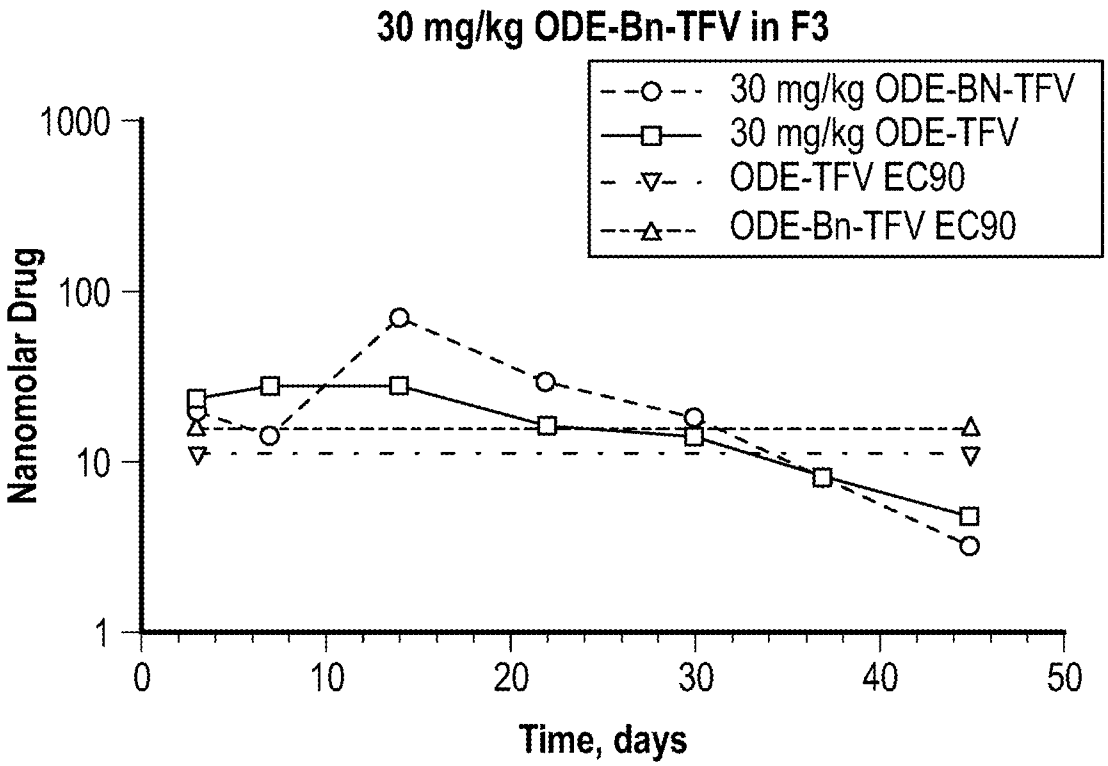
FIG. 10 depicts plasma levels of ODE-Bn-TFV and ODE-TFV in beagle dogs treated with 100 mg/kg with ODE-Bn-TFV in formulation F3.
Figure 11A:
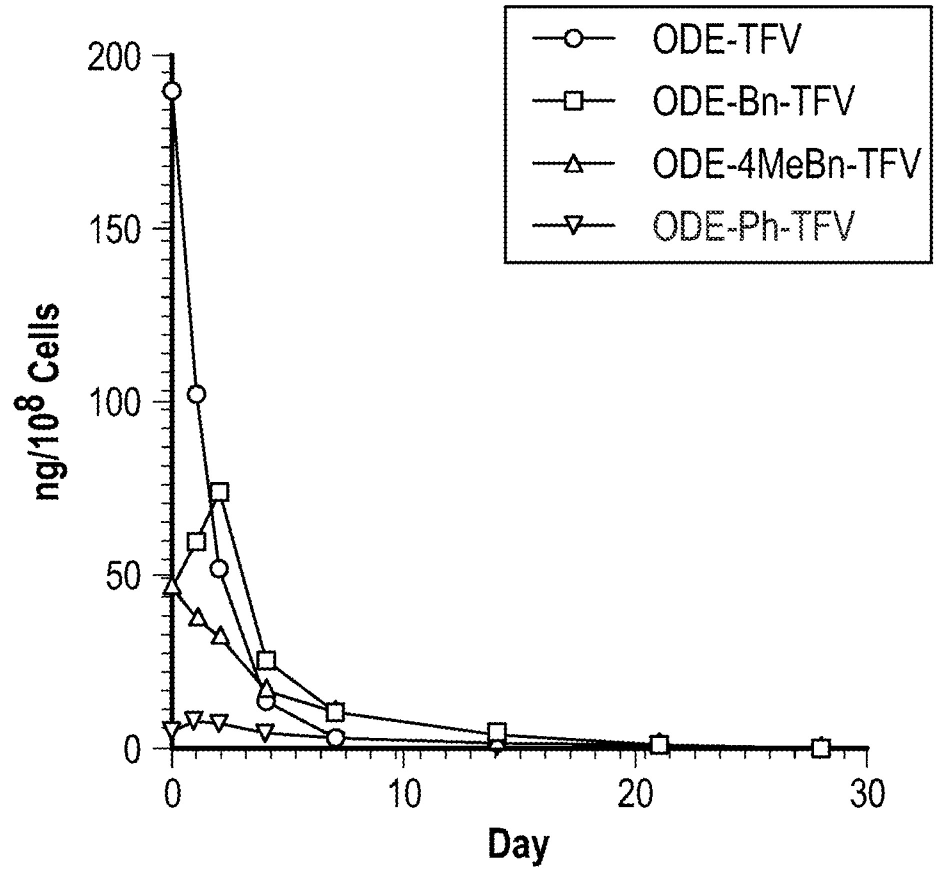
FIG. 11A and FIG. 11B depict the TFVpp persistence in HFF cells of ODE-TFV (FIG. 11A) and ODE-Et-TFV (FIG. 1111).
Figure 11B:
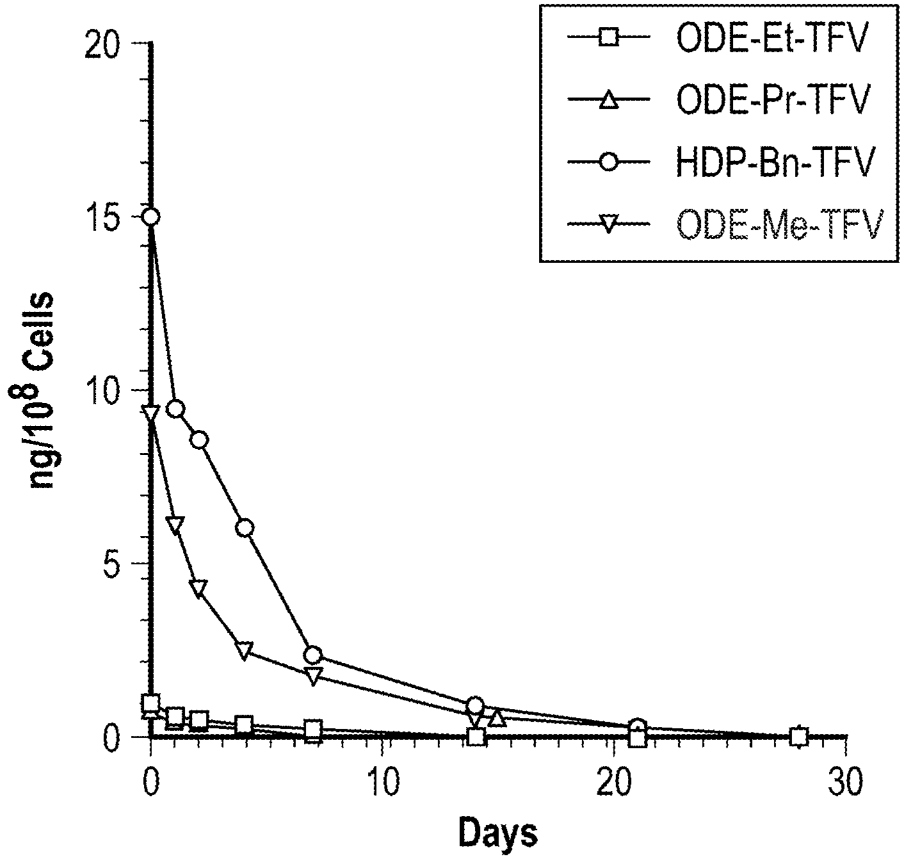

Canine Pharmacokinetics of ODE-Bn-TFV in Formulation F3—A 30 day study in beagle dogs was done with 30 mg/kg IM doses of ODE-Bn-TFV in formulation F3. FIG. 10 shows the levels of ODE-Bn-TFV (circles) and ODE-TFV (squares). $EC_{90}$ values are shown in triangles to indicate when the plasma drug levels pass below the 90% effective level. At 30 mg/kg intramuscular ODE-Bn-TFV in formulation F3 provided 30 to 34 days above the $EC_{90}$ values for both ODE-Bn-TFV and its active metabolite, ODE-TFV.

FIG. 10 depicts plasma levels of ODE-Bn-TFV and ODE-TFV in beagle dogs treated with 100 mg/kg with ODE-Bn-TFV in formulation F3.

There were no adverse effects except for some transient swelling at the injection sites. Pre and Post CBCs and metabolic panels before and after the study did not show any abnormalities. Of note, no abnormal liver or kidney function tests were noted. Other compounds of the disclosure may be used in formulation F3 to provide prolonged protection from HIV infection.

Antiviral Compounds and Formulations for Intramuscular Treatment of Coronavirus Infections—In SARS-CoV-2 infection active viral replication usually lasts for 5 to 10 days. To treat with an intramuscular dose, antiviral prodrugs in formulation F8 at 200 to 400 mg/ml were expected to provide effective drug levels for at least 7 days. Non-limiting examples of effective antiviral prodrugs of the remdesivir nucleoside monophosphate may be selected from the structures shown below:

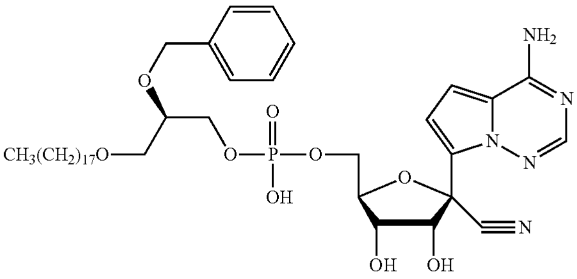

1-O-octadecyl-2-O-benzyl-sn-glyceryl-phospho-RVn

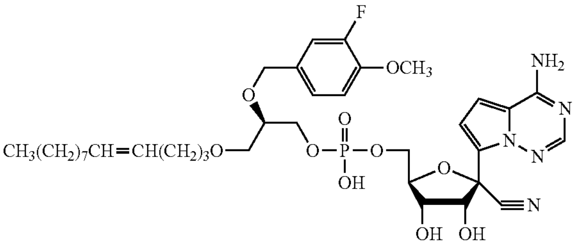

1-O-oleyl-2-O-(3-fluoro, 4-methoxybenzyl)-sn-glyceryl-phospho-RVn

-continued

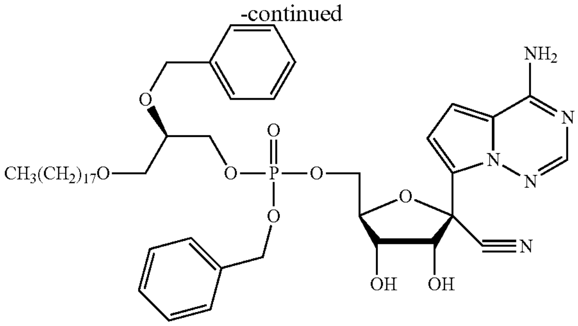

1-O-octadecyl-2-O-benzyl-sn-glyceryl-benzyl-phospho-RVn

Antiviral Compounds and Formulations for Intramuscular Treatment of Human immunodeficiency infections—For use in long-acting intramuscular treatment of infection with the human immunodeficiency virus, the antiviral compounds suitable for use are described in U.S. Pat. No. 8,835,630. These compounds may be used in formulations F3 or F4.

Non-limiting examples that may be used in the formulations described herein include the following compounds:

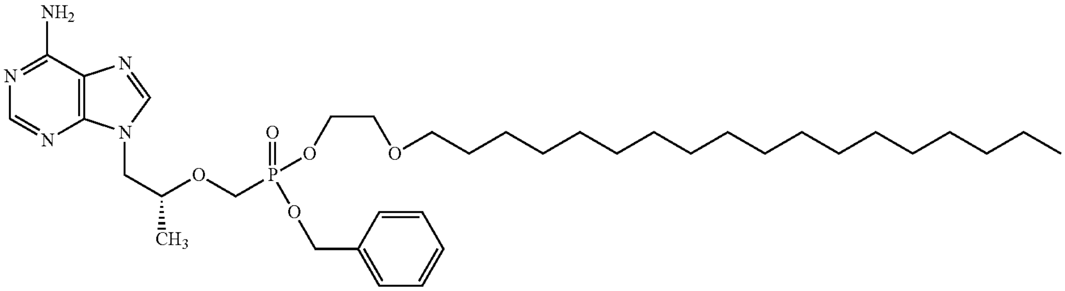

octadecyloxyethyl benzyl tenofovir (ODE-Bn-TFV)

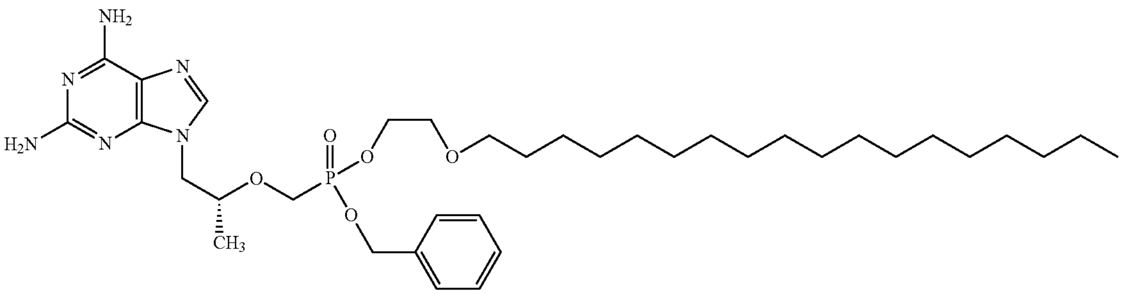

octadecyloxyethyl benzyl 9-[(2-phosphonomethoxy)ethyl]2,6-diaminopurine (ODE-Bn-PMPDAP)

-continued

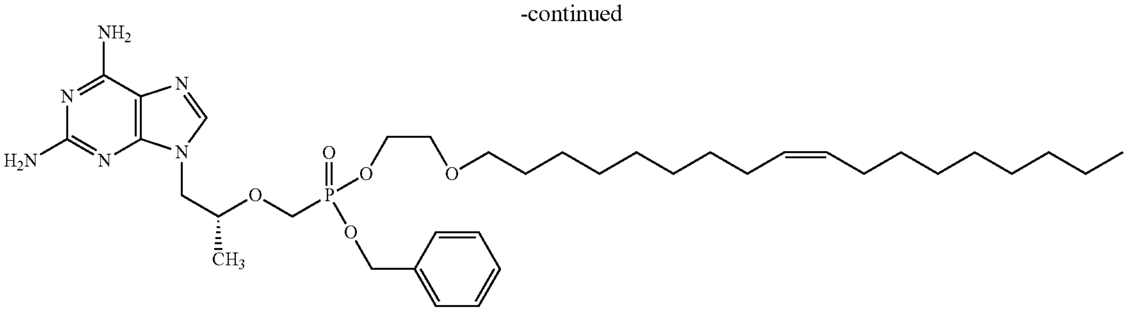

oleyloxyethyl benzyl 9-[(2-phosphonomethoxy)ethyl]2,6-diaminopurine (OLE-Bn-PMPDAP)

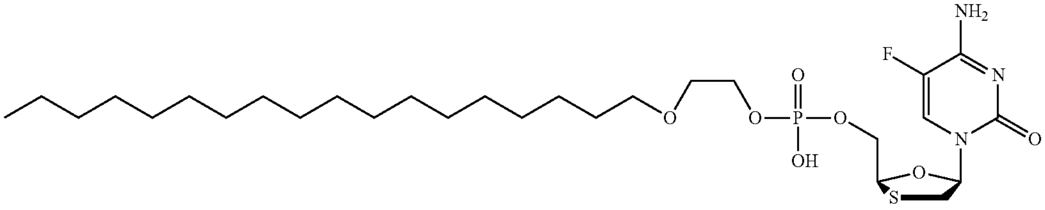

otadecyloxyethyl-phospho-emtricitabine (ODE-P-FTC)

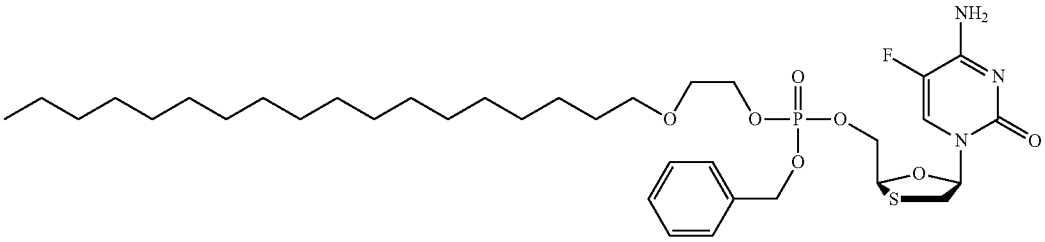

octadecyloxyethyl benzyl-phospho-emtricitabine (ODE-Bn-P-FTC)

Antiviral activity of compounds suitable for use in long-acting formulations in in human PBMCs infected with HIV-1

| Compound | $EC_{50}$, nM | $CC_{50}$, μM | Selectivity index |
|---|---|---|---|
| ODE-Bn-Tenofovir | 1.7 ± 1.5 | 8.72 | 5130 |
| ODE-PMPDAP | 0.09 ± 0.05 | 7.0 ± 7.1 | 77,700 |
| OLE-PMPDAP | 0.10 ± 0.03 | 15.0 ± 12.3 | 150,000 |
| ODE-Bn-PMPDAP | active | | |
| OLE-Bn-PMPDAP | active | | |
| ODE-P-Emtricitabine | 9.6 ± 3.1 | 35.6 ± 12.9 | 3708 |
| ODE-Bn-P-Emtricitabine | 18.3 ± 8.7 | 54.7 ± 45.3 | 2989 |

Abbreviations: ODE-, octadecyloxyethyl; OLE-, oleyloxyethyl; PMP-, phosphonylpropyloxy; DAP, 2,6-diaminopurine; $EC_{50}$, 50% effective concentration; $CC_{50}$, 50% cytotoxic concentration. Method: inhibition of antiviral activity was measured in human PBMCs infected with HIV-1 as reported in Beadle et al. Antiviral Research vol. 171 (2019): 104614.

As explained herein and in this example, 22 analogs of ODE-TFV were synthesized to determine effective diester substituents in comparison with benzyl in ODE-Bn-TFV. Antiviral activities were determined in HIV infected human PBMCs. The pharmacokinetics of TFVpp were determined in HFF cells over a 28 day period.

The variation of the diester substituent on anti-HIV activity of ODE-TFV is depicted in the following table:

| Substituent | $EC_{50}$ nM | CC50 nM | Selectivity Index |
|---|---|---|---|
| H | 1.1 | 1284 | 1170 |
| Benzyl | 1.7 | 8720 | 5130 |
| Phenyl | 2.4 | 3930 | 1640 |
| 4-methyl benzyl | 2.1 | 3410 | 1620 |
| 3-methyl benzyl | 3.2 | 3860 | 1210 |
| 2-methyl benzyl | 2.7 | 1440 | 532 |
| Methyl | 5.2 | 2980 | 677 |
| Ethyl | 57 | 5365 | 95 |
| Iso-propyl | 183 | 1730 | 94 |
| Cyclopropyl | 413 | 5280 | 13 |

FIG. A and FIG. Cm depict the TFVpp persistence in HFF cells of ODE-TFV (FIG. EA) and ODE-Et-TFV (FIG. 1).

The persistence of TFVpp in HFF cells after a 3 day exposure is depicted at the following table. HFF cells were exposed to 1 micromolar drug for 3 days. At days 0, 1, 2, 4, 7, 14, 21, and 28, cells were trypsinized, counted, and processed for LC/MS measurement of TFVpp. Data were expressed at ftg/cell. nm=not meaningful; ftg—gemtogram.

| Compound | Cmax, ftg/cell | $T_{max}$, d | $T_{1/2}$ | $T_{1/10}$ | AUC |
|---|---|---|---|---|---|
| ODE-TFV | 189 | 0 | 1.2 | 2.1 | 323 |
| ODE-Bn-TFV | 72.5 | 2 | 3.7 | 8.7 | 324 |
| ODE-4MeBN-TFV | 49.5 | 0 | 3.1 | 11.8 | 233 |
| HDP-Bn-TFV | 15.0 | 0 | 1.8 | 10.2 | 66.3 |
| ODE-Me-TFV | 9.3 | 0 | 2.0 | 11.3 | 37.2 |
| ODE-Ph-TFV | 8.1 | 1 | 3.0 | 15.1 | 49.2 |
| ODE-Et-TFV | 0.91 | 0 | nm | nm | 4.2 |
| ODE-iPr-TFV | 0.69 | 0 | nm | nm | 2.0 |

In this example, 6 oil-based formulations for ODE-Bn-TFV were prepared. The accelerated stability of 20 mg/mL formulations was determined. API loadings were assessed.

In this example, formulations of ODE-Bn-TFV for IM usage (20 mg/mL formulations) were prepared, and included the components of the following table (w/w %):

| Components | F3V | F4V | F5V |
|---|---|---|---|
| Sesame Oil | 92.65 | 73.67 | 89.765 |
| Benzyl alcohol | 1.22 | 10.67 | 10.20 |
| Benzyl benzoate | 0 | 15.67 | 0 |
| Alcohol | 6.12 | 0 | 0 |
| BHT | 0 | 0 | 0.0306 |

In this example, a two month accelerated stability study was conducted. The results and observations of this study are provided at the following tables:

| 2-8° C. | Appearance | Concentration (mg/g) | Recover over $T_0$ |
|---|---|---|---|
| F3 | Colorless and Clear | 20.09 | 99.0 |
| F4 | Light Yellow and Clear | 20.45 | 102.1 |
| F5 | Colorless and Clear | 19.85 | 100.7 |

| 25° C. | Appearance | Concentration (mg/g) | Recover over $T_0$ |
|---|---|---|---|
| F3 | Colorless and Clear | 20.52 | 101.1 |
| F4 | Yellow and Clear | 19.57 | 97.7 |
| F5 | Colorless and Clear | 19.79 | 100.3 |

| 40° C. | Appearance | Concentration (mg/g) | Recover over $T_0$ |
|---|---|---|---|
| F3 | Colorless and Clear | 20.56 | 101.3 |
| F4 | Yellow and Clear | 19.08 | 95.3 |
| F5 | Colorless and Clear | 19.15 | 97.10 |

Additional formulations were prepared for tested, as provided in the following table (w/w %):

| Components | F3V | F4V | F7V | F8V |
|---|---|---|---|---|
| Sesame Oil | 92.65 | 73.67 | — | — |
| Med. Chain TGs | — | — | 92.65 | 73.67 |
| Benzyl alcohol | 1.22 | 10.67 | 1.22 | 10.67 |
| Benzyl benzoate | — | 15.67 | — | 15.67 |
| Alcohol | 6.12 | — | 6.12 | — |

A 42 days pharmacokinetic study of formulations 3, 4, 7, and 8 of this example in rats was conducted. In the study, 100, 30, and 10 mg/kg of each formulation was administered by intramuscular (IM) injection to male Sprague Dawley rates (100 microliters). Blood was taken at 0.25, 1, 2, 7, 14, 21, 28, 35, and 42 days after injection, and plasma levels of ODE-Bn-TFV and ODE-TFV were determined. The rats were subjected to twice weekly clinical observations, and weights were collected.

Figure 12A:
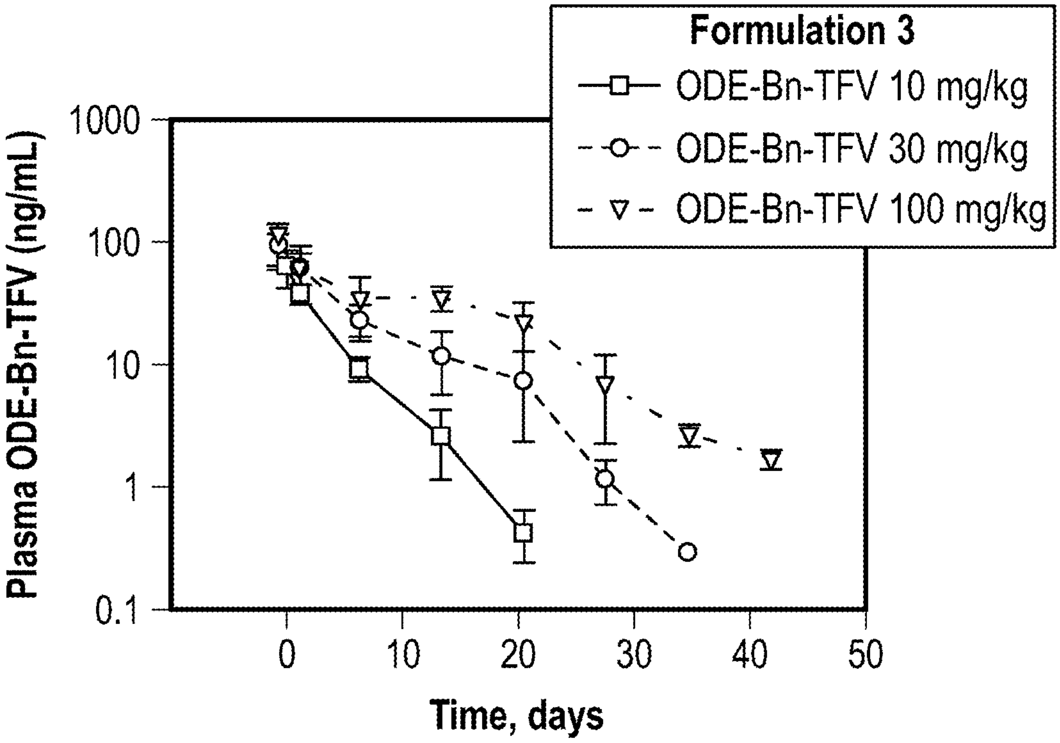
FIG. 12A and FIG. 12B depict plasma concentrations of an embodiments of formulations containing ODE-Bn-TFV (FIG. 12A) or ODE-TFV (FIG. 12B) (ODE-Bn-TFV $ED_{90}$ 10.9 ng/mL; ODE-TFV $ED_{90}$ 6.3 nm/mL).
Figure 12B:
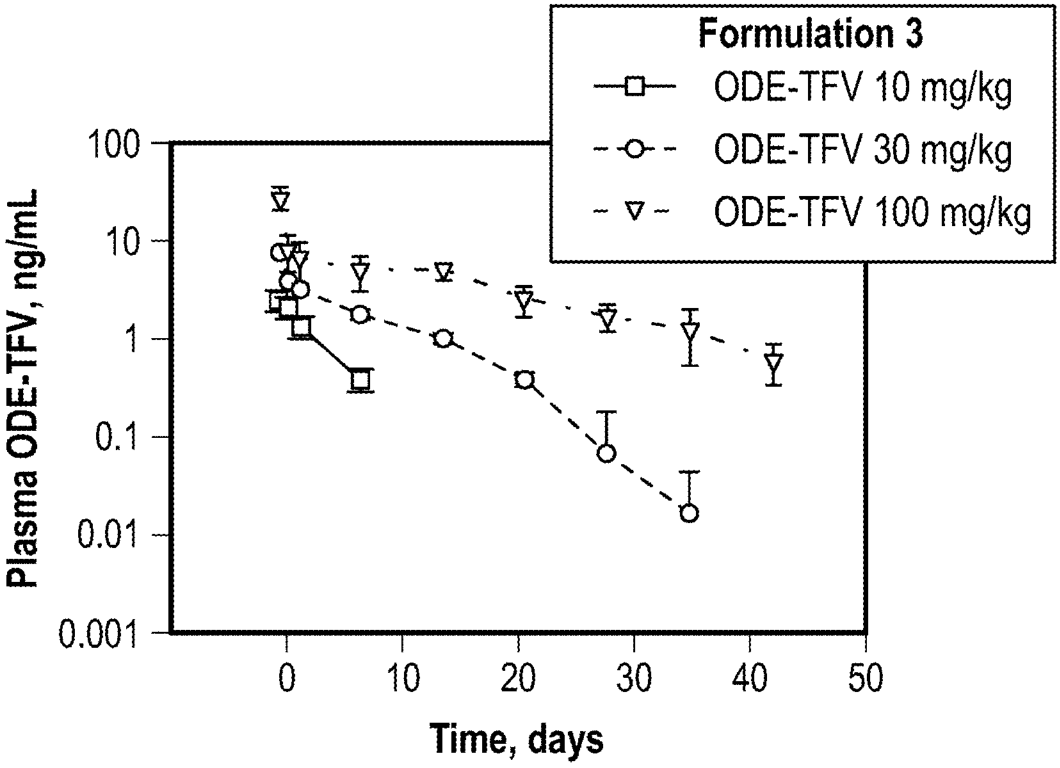

FIG. 12A and FIG. 12B depict plasma concentrations of formulation F3V containing ODE-Bn-TFV (FIG. 12A) and ODE-TFV (FIG. 121B) (ODE-Bn-TFV $ED_{90}$ 10.9 ng/mL; ODE-TFV $ED_{90}$ 6.3 nm/mL).

Figure 12C:
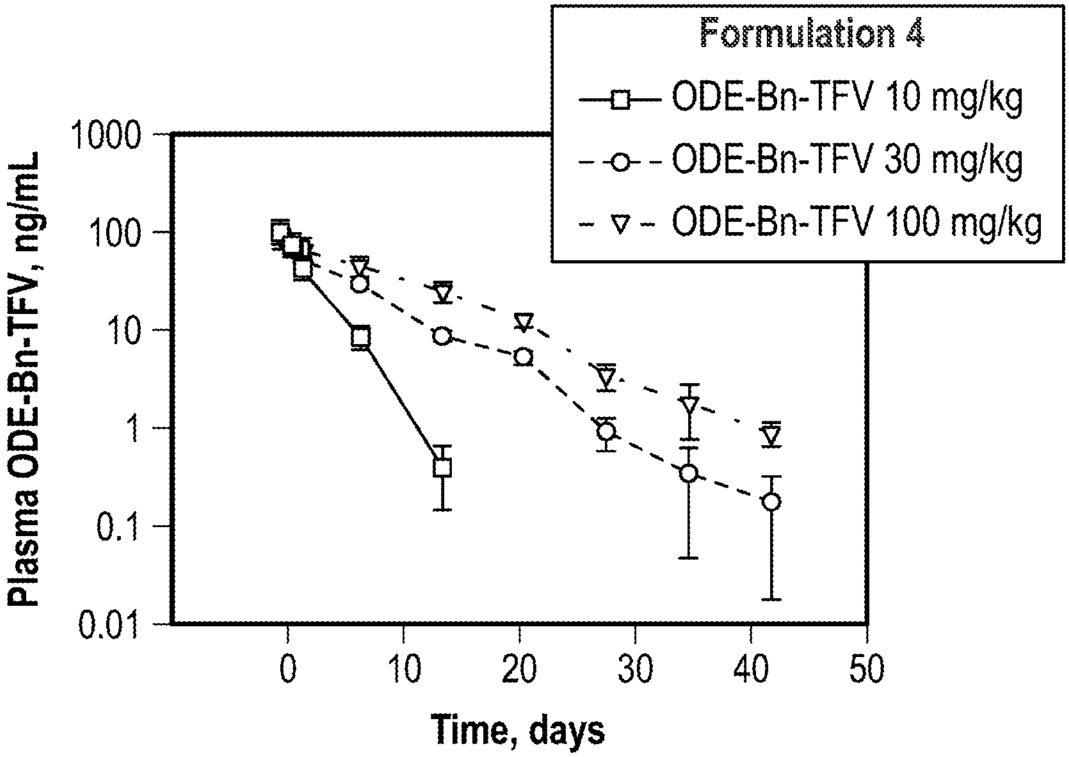
FIG. 12C and FIG. 12D depict plasma concentrations of embodiments of formulations containing ODE-Bn-TFV (FIG. 12C) and ODE-TFV (FIG. 12D).
Figure 12D:
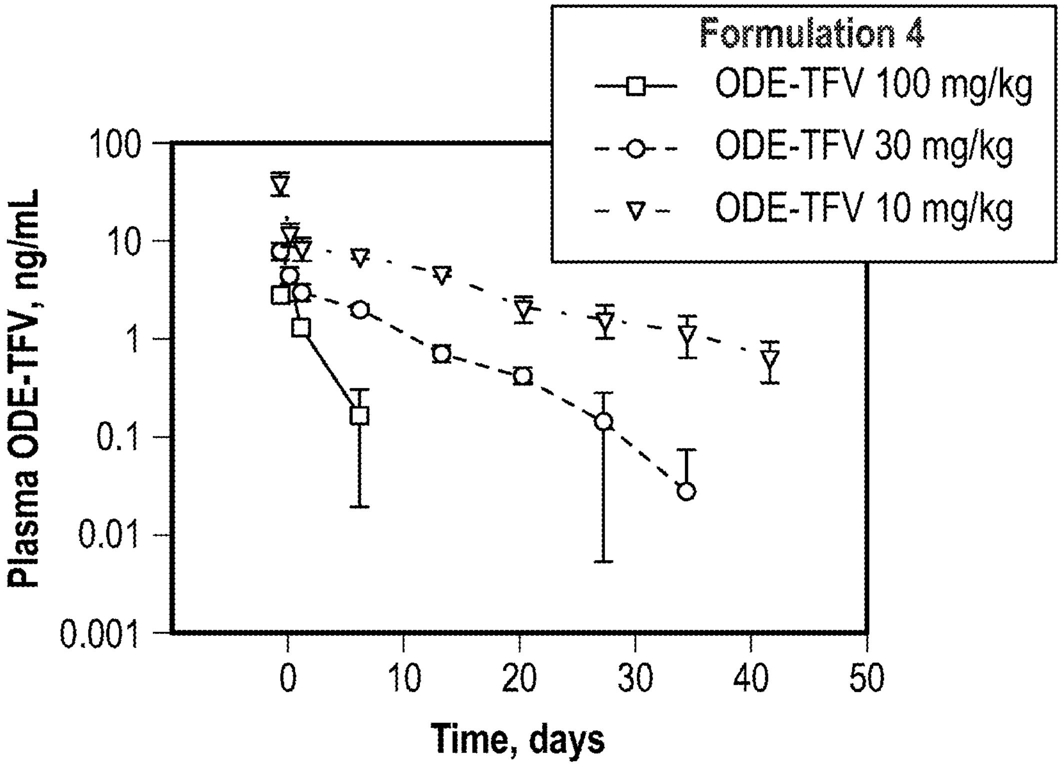

FIG. 12C and FIG. 12D depict plasma concentrations of formulation F4V containing ODE-Bn-TFV (FIG. 12C) and ODE-TFV (FIG. 12D).

Figure 12E:
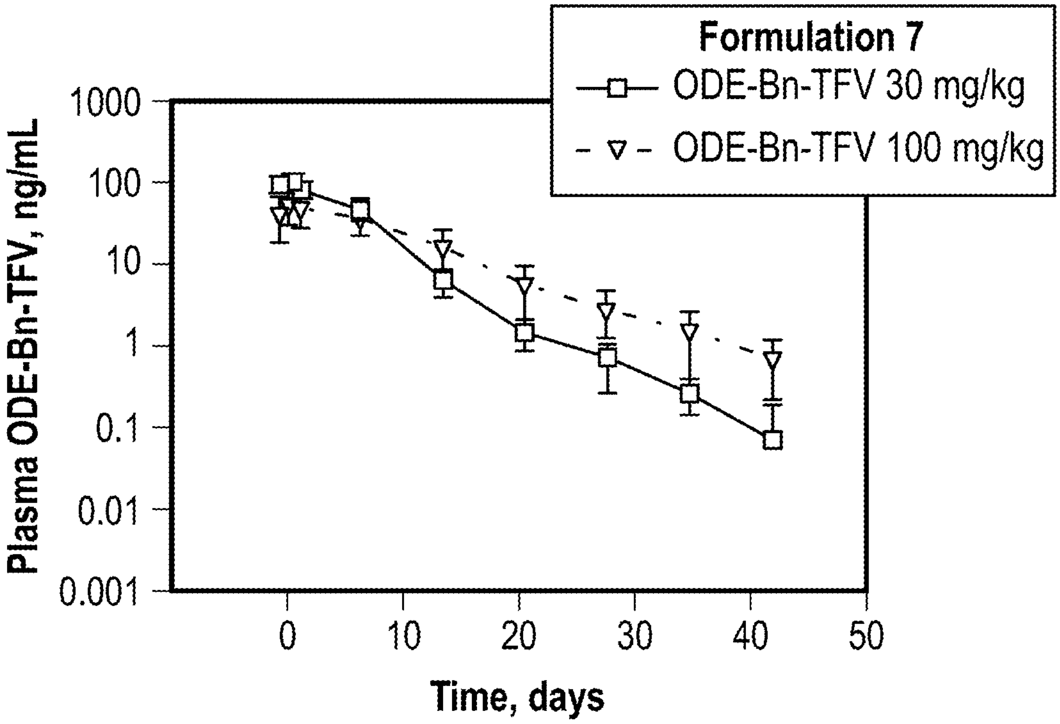
FIG. 12E and FIG. 12F depict plasma concentrations of embodiments of formulations containing ODE-Bn-TFV (FIG. 12E) and ODE-TFV (FIG. 12F).
Figure 12F:
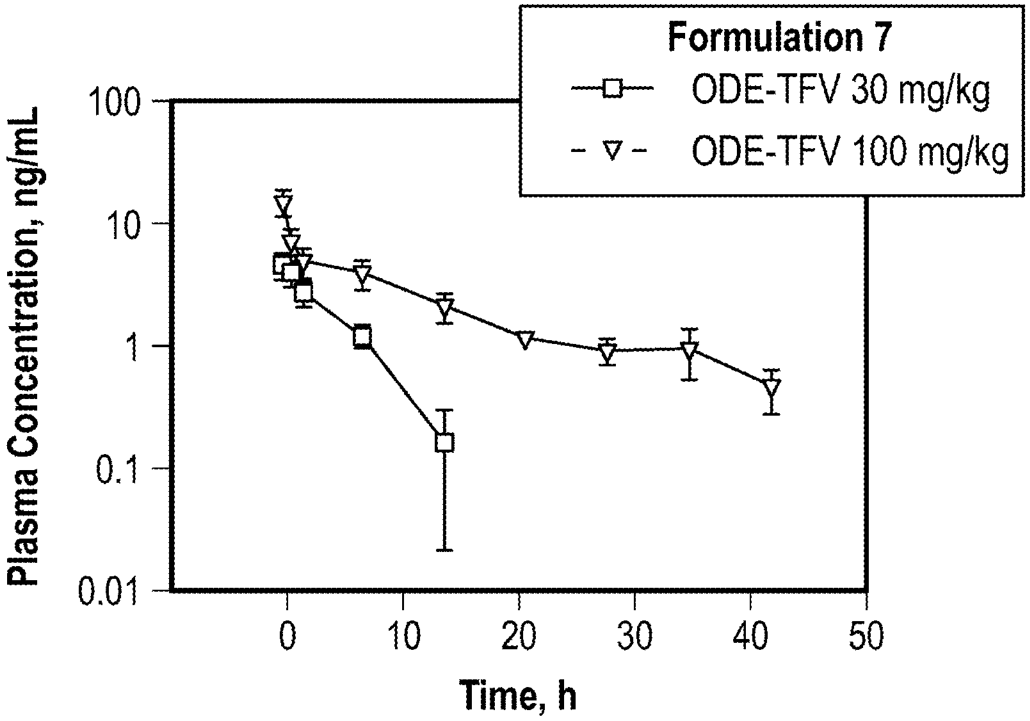

FIG. 12E and FIG. 12F depict plasma concentrations of formulation F7V containing ODE-Bn-TFV (FIG. 12E) and ODE-TFV (FIG. 12F).

Figure 12G:
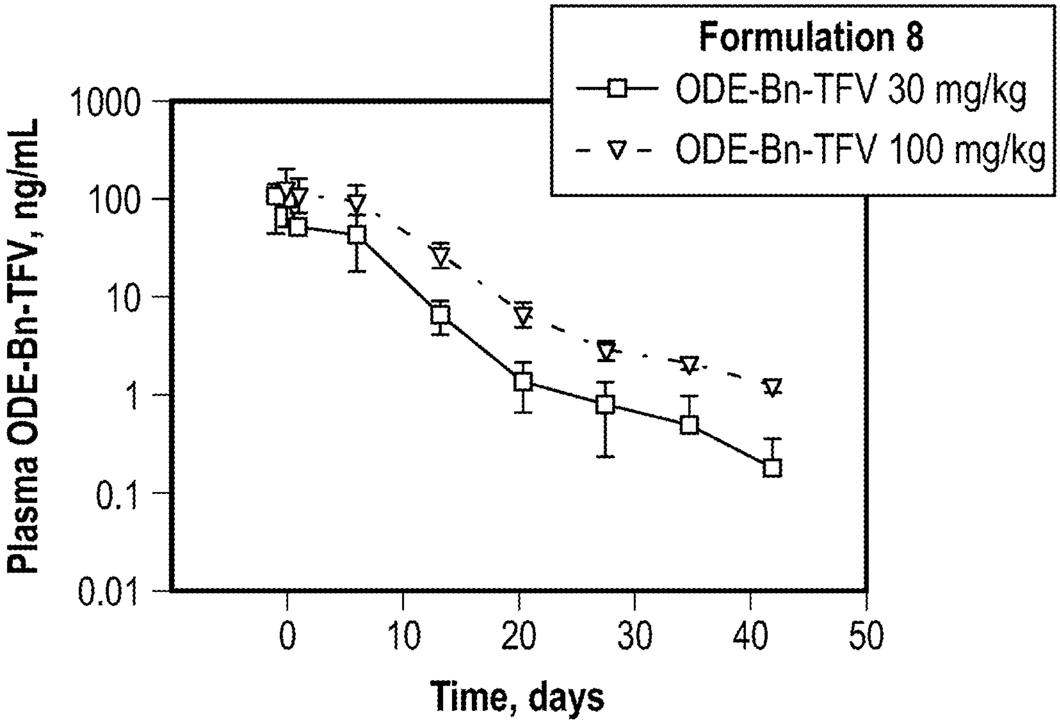
FIG. 12G and FIG. 12H depict plasma concentrations of embodiments of formulations containing ODE-Bn-TFV (FIG. 12G) and ODE-TFV (FIG. 12H).
Figure 12H:
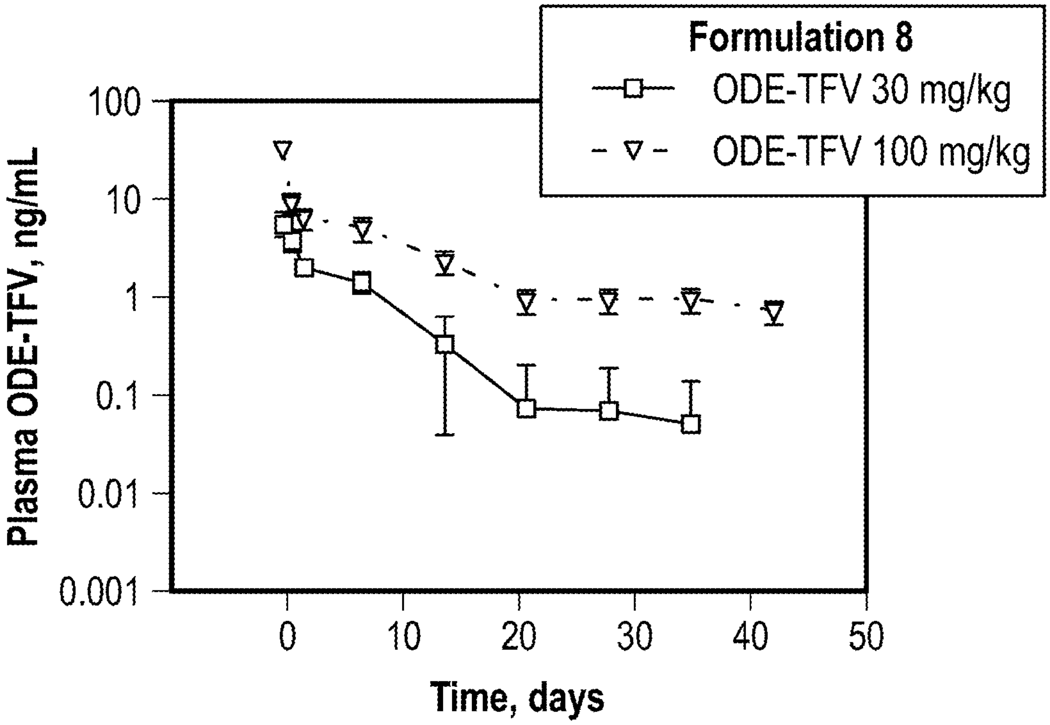

FIG. 12G and FIG. 12H depict plasma concentrations of formulation F8V containing ODE-Bn-TFV (FIG. 12G) and ODE-TFV (FIG. 12H).

Figure 12I:
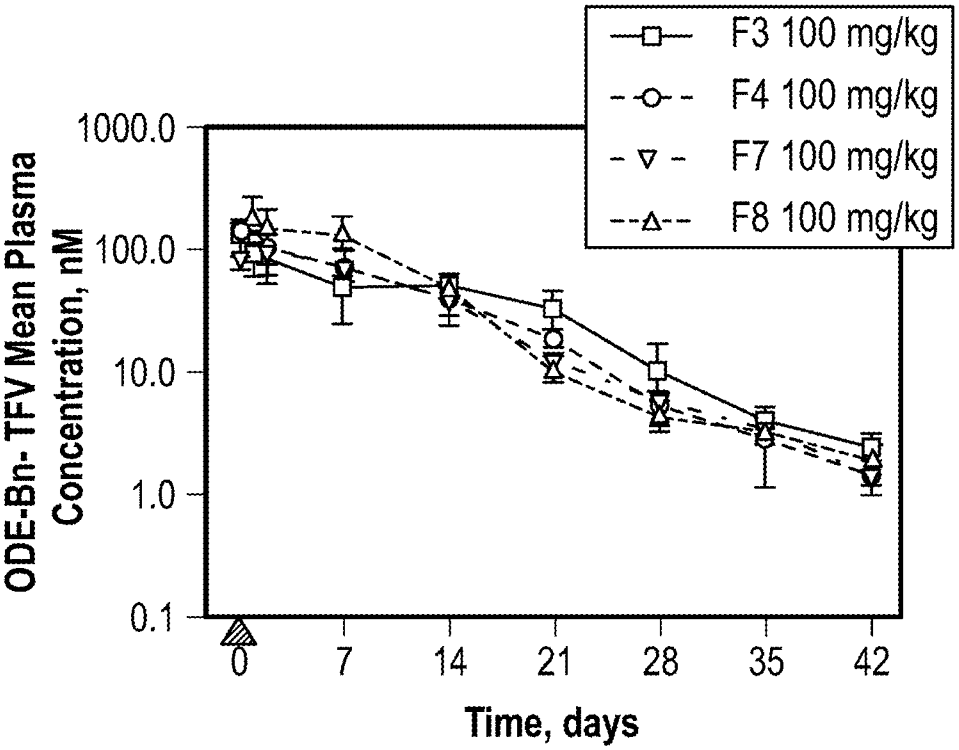
FIG. 12I depicts mean plasma concentrations of embodiments of formulations.

FIG. 12I depicts mean plasma concentrations of formulations F3V, F4V, F7V, and F8V.

The API pharmacokinetic parameters of this example are provided at the following table:

| | F3 | F4 | F7 | F8 |
|---|---|---|---|---|
| Cmax, nm | 130 | 139 | 76 | 187 |
| T½ hour | 142 | 171 | 168 | 278 |
| AUC (0-inf) nM · hr | 35200 | 33800 | 21400 | 48100 |
| AUC (14-28 hr)nM · hr | 10900 | 6900 | 3460 | 5420 |

The ODE-BN-TFV release provided observed in this example is summarized, at least in part, in the following table:

| | First 14 Days verus Second 14 Days | |
|---|---|---|
| Formulation | % AUC first 14 Days | % AUC second 14 Days |
| F3 | 69 | 31 |
| F4 | 79 | 21 |
| F7 | 83 | 17 |
| F8 | 89 | 11 |

The results of this example that through chemical and formulation alterations, TFV was converted to long-acting anti-HIV status. Formulations F3 and F4 of this example released, for example, 69 and 79% of the lead compound in the first 14 days, but this release profile may be modified as described herein. Using formulation F3, a 3 month study was conducted in rats with monthly IM injections of 100 microliters, and measuring plasma drug levels and PBMC levels of TFVpp.

105 Days Pharmacokinetic Study (Monthly IM Injections of F3 in Rats): 100 microliters of the API of formulation 3 was administered monthly by IM injection to male Sprague Dawley rats. Due to the fact that the rats gained significant weight over the 105 day period, the actual dosages based on weight were as follows: 90, 62, and 60 mg/kg. Blood was collected at 15, 30, 45, 60, 75, 90, 98, and 105 days. Plasma levels of ODE-Bn-TFV and ODE-TFV were determined. PBMCs also were obtained at the foregoing days, and fmol/$10^6$ cells was determined.

Figure 13:
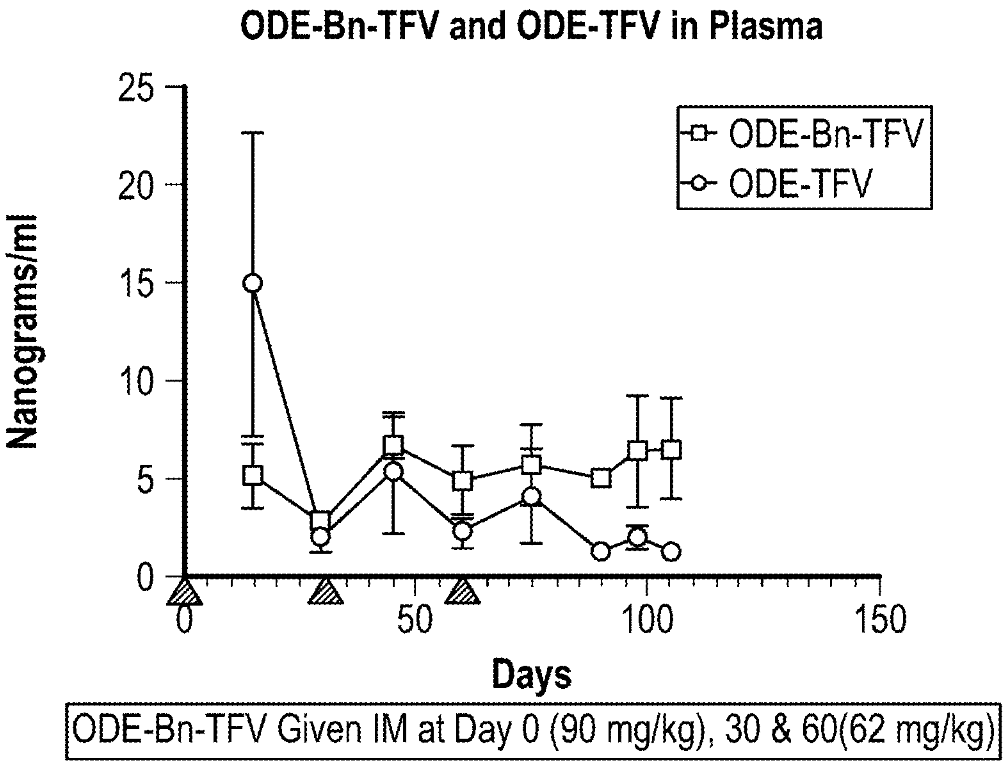
FIG. 13 depicts the nanograms/mL of embodiments of active ingredients present in rat plasma after administration of embodiments of formulations herein.
Figure 14:
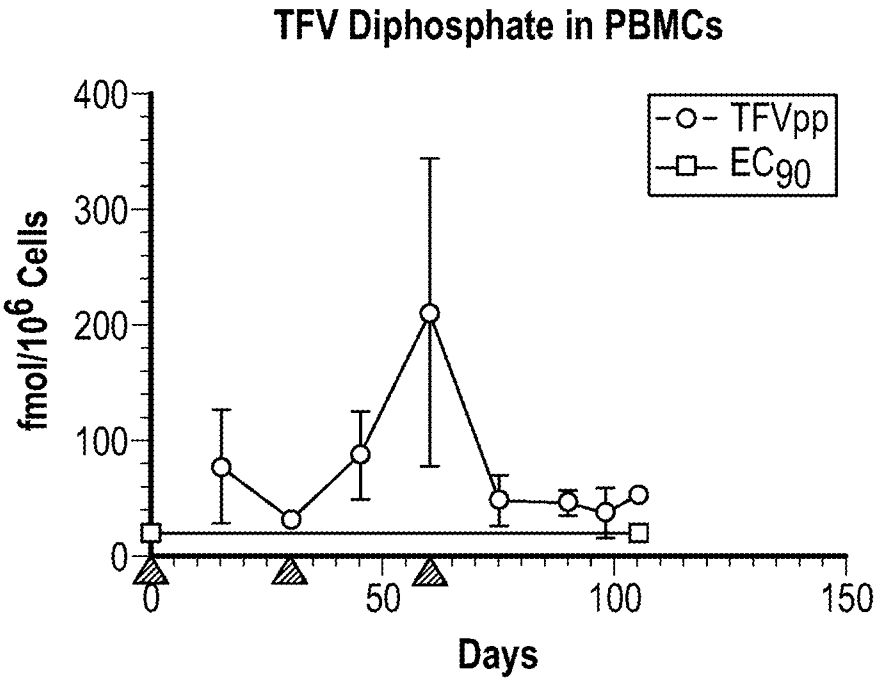
FIG. 14 depicts amounts of an embodiment of a disphosphate in PBMCs after administration of an embodiment of a formulation herein.

FIG. 13 depicts the nanograms/mL of ODE-Bn-TFV and ODE-TFV in plasma. FIG. 14 depicts TFV disphosphate in PBMCs.

The rats of this example gained weight during the 105 day study; about 350 grams to about 670 grams. There was no difference in growth curves between the control and treated rats. There also were not reported clinical observations in either group. CBCs in treated and control animals were normal. Complete metabolic panels were normal in both groups. Of importance was the fact that there were no changes noted in BUN or creatinine.

Example 13—Synthesis of 2-, 3-, and 4-cyanobenzyl Analogs

The following is a scheme depicting embodiments of the synthesis of 2-, 3-, and 4-cyanobenzyl analogs.

Scheme 7. Synthesis of 2, 3 and 4-cyanobenzyl analogs. Reagents: a) sodium hydride, 2,3 or 4-(bromomethylbenzonitrile, tetrabutyl ammoniumiodide, THF; b) p-TsOH (cat.), $CH_2Cl_2$, MeOH; c) i) $POCl_3$,triethylamine, $CH_2Cl_2$, ii) acetone/ice water; d) RVn (GS-441524)acetonide, DIC/NMI, pyridine, 35° C.;e) formic acid, rt.

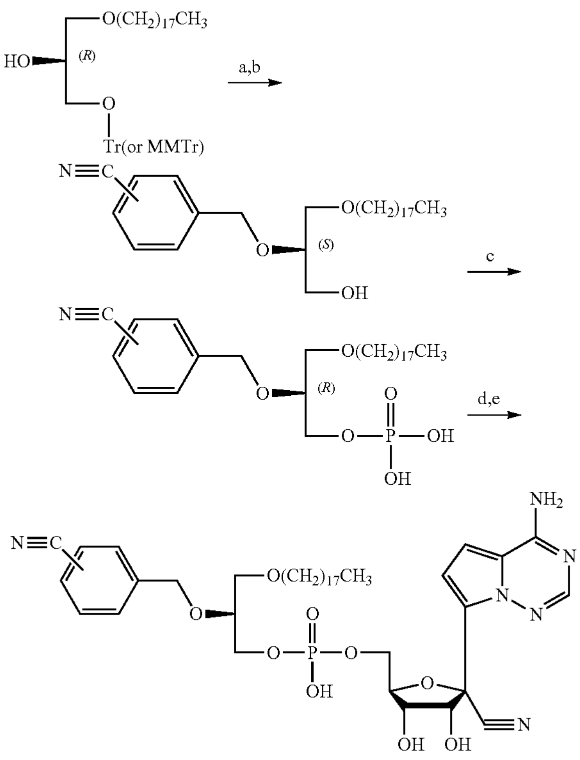

Example 13a. Synthesis of 1-O-Octadecyl-2-O-(4-cyanobenzyl)-sn-glyceryl-phospho-RVn (OD(4-CN-Bn)G-P-RVn)

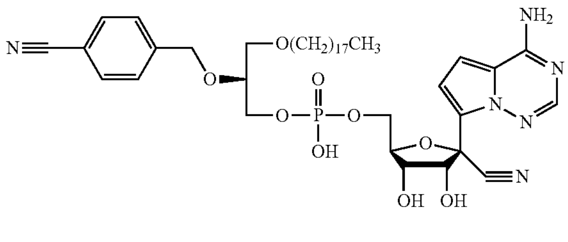

Sodium hydride (440 mg, 11 mmol) was added to a cooled (0° C.) solution of (R)-1-((4-methoxyphenyl)diphenyl-methoxy)-3-(octadecyloxy)propan-2-ol (3.39 g, 5.5 mmol) and tetrabutylammonium iodide (600 mg, 1.65 mmol) in dry THF (30 mL). After stirring vigorously for 20 min., 4-(bromomethyl)benzonitrile (1.61 g, 8.2 mmol) was added and the mixture was allowed to warm to ambient temperature and stirred overnight. The reaction was then quenched with ice (25 mL), diluted with ethyl ether (75 mL), washed with $H_2O$ (2×25 mL) and dried over anhydrous $MgSO_4$. The residue was adsorbed onto silica gel and purified by flash column chromatography (gradient: 0 to 50% EtOAc—in hexanes) to yield (R)-4-(((1-((4-methoxyphenyl)diphenyl-methoxy)-3-(octadecyloxy)propan-2-yl)oxy)methyl)benzonitrile (610 mg, 15%) as a white solid. MS (ESI) m/z $[M+Na]^+$ 754.54.

To a solution of (R)-4-(((1-((4-methoxyphenyl)diphenyl-methoxy)-3-(octadecyloxy)propan-2-yl)oxy)methyl)benzonitrile (400 mg, 0.54 mmol) in 1:1 $CH_2Cl_2$/MeOH (30 mL) was added p-toluenesulfonate monohydrate (5 mg, 0.03 mmol) and the mixture was stirred at room temperature until deprotection was complete (approx. 3 h) according to TLC analysis. Saturated aq $NaHCO_3$ (200 mg) was added, and the solvent evaporated under vacuum. The residue was adsorbed onto silica gel and purified by flash column chromatography (gradient: 0 to 10% EtOAc in hexanes) to afford (S)-4-(((1-hydroxy-3-(octadecyloxy)propan-2-yl)oxy)methyl)benzonitrile, as clear oil (80 mg, 32%). MS (ESI) m/z $[M+Na]^+$ 482.55.

A solution of (S)-4-(((1-hydroxy-3-(octadecyloxy)propan-2-yl)oxy)methyl)benzonitrile (80 mg, 0.17 mmol) and triethylamine (0.08 mg, 0.8 mmol) was added to a cooled (0° C.) solution of $POCl_3$ (30 mg, 0.20 mmol), in $CH_2Cl_2$ (3 mL) and stirred for 3 h. The mixture was added to acetone/ice water, stirred 1 h, then extracted with $CH_2Cl_2$. (R)-2-((4-cyanobenzyl)oxy)-3-(octadecyloxy)propyl dihydrogen phosphate was isolated (80 mg, 87%) and used without further purification. MS (ESI) m/z $[M-H]^-$ 538.47.

The phosphate (200 mg, 0.37 mmol) was coupled to RVn (GS-441524)-acetonide (132 mg, 0.40 mmol) using diisopropylcabodiimide (DIC, 100 mg, 0.80 mmol), N-methyl-imidazole (NMI, 98 mg, 1.2 mmol) in pyridine (10 mL) to yield ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((4-cyanobenzyl)oxy)-3-(octadecyloxy)propyl) hydrogen phosphate (60 mg, 19%, MS m/z $[M-H]^-$ 851.55) which was then treated with formic acid (1 mL) and stirred 6 h. Evaporation of the solvent and purification by flash column chromatography yielded ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((4-cyanobenzyl)oxy)-3-(octadecyloxy)propyl) hydrogen phosphate (20 mg, 35%) as an off white solid. $^1H$ NMR (400 MHz, $CD_3OD+CDCl_3$) δ 7.76 (s, 1H, H2), 7.60 (d, J=8.0 Hz, 2H, —$CH_2$-aryl-H3+H5), 7.49 (d, J=7.9 Hz, 2H, —$CH_2$-aryl-H2+H6), 6.96 (d, J=4.4 Hz, 1H, H9), 6.86 (d, J=4.5 Hz, 1H, H8), 4.80 (d, J=5.3 Hz, 1H, H2'), 4.77-4.63 (m, 2H, —$CH_2$-aryl), 4.37 (d, J=4.7 Hz, 1H, H4'), 4.25 (t, J=5.4 Hz, 1H, H3'), 4.11 (d, J=18.7 Hz, 2H, H5'), 3.90 (s, 2H, H3"), 3.80-3.68 (m, 1H, H2"), 3.49 (qd, J=10.6, 4.9 Hz, 2H, H1"), 3.39 (tt, J=6.0, 3.0 Hz, 2H, —$OCH_2CH_2(CH_2)_{15}$—), 1.52 (p, J=6.9 Hz, 2H, —$OCH_2CH_2(CH_2)_{15}$—), 1.26 (br s, J=5.7 Hz, 30H, —$OCH_2CH_2(CH_2)_{15}$—), 0.89 (t, J=6.8 Hz, 3H). $^{13}C$ NMR (101 MHz, $CD_3OD+CDCl_3$) δ 156.63 (C6), 145.57 (C2), 132.62, (—$CH_2$-aryl-C1), 128.47 (—$CH_2$-aryl-C3+C5), 125.14 (—$CH_2$-aryl-C2+C6), 119.38 (—CN), 117.29 (C7), 111.95 (C5), 111.28 (—CN'), 84.60 (C4), 80.18 (C1'), 75.38 (C2'), 72.24 (C2"), 71.57 (—$CH_2$-aryl), 71.40 (—$OCH_2CH_2(CH_2)_{14}$—), 71.12 (C1"), 65.75 (C3"), 65.20 (C5'), 32.57 (—$OCH_2CH_2(CH_2)_{14}$—), 30.89-29.57 (m) (m, —$OCH_2CH_2(CH_2)_{14}$—), 26.75 (—$CH_2CH_2CH_3$), 23.26 (—$CH_2CH_2CH_3$), 14.21 (—$CH_3$). HRMS (ESI) m/z $[M-H]^-$ calcd for $C_{41}H_{60}N_6O_9P$, 811.4165. found 811.4178, HPLC purity 98.6%.

Example 13b. Synthesis of 1-O-Octadecyl-2-O-(3-cyanobenzyl)-sn-glyceryl-phospho-RVn (OD(3-CN-Bn)G-P-RVn)

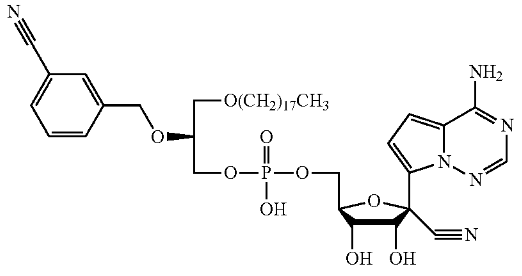

Sodium hydride (60 mg, 2.5 mmol) was added to a cooled (0° C.) solution of (R)-1-(octadecyloxy)-3-(trityloxy)propan-2-ol (540 mg, 0.92 mmol) and tetrabutylammonium iodide (180 mg, 0.5 mmol) in dry THF (30 mL). The mixture was stirred vigorously for 20 min before 3-(bromomethyl) benzonitrile (480 mg, 2.6 mmol) was added, and then the mixture was allowed to warm to ambient temperature and stirred overnight. The reaction was then quenched with ice (25 mL), diluted with ethyl ether (75 mL), washed with $H_2O$ (2×25 mL) and dried over anhydrous $MgSO_4$. The residue was adsorbed onto silica gel and purified by flash column chromatography (gradient: 0 to 50% EtOAc—in hexanes) to yield (R)-3-(((1-(octadecyloxy)-3-(trityloxy)propan-2-yl) oxy)methyl)benzonitrile (600 mg, 93%) as a white solid. MS (ESI) m/z $[M+Na]^+$724.57.

To a solution of (R)-3-(((1-(octadecyloxy)-3-(trityloxy) propan-2-yl)oxy)methyl)benzonitrile (600 mg, 0.85 mmol) in 1:1 $CH_2Cl_2$/MeOH (30 mL) was added p-toluene-sulfonate monohydrate (8 mg, 0.04 mmol) and the mixture was stirred at room temperature until deprotection was complete according to TLC analysis (approx. 3 h). Saturated aq $NaHCO_3$ (200 mg) was added, and the solvent evaporated under vacuum. The residue was adsorbed onto silica gel and purified by flash column chromatography (gradient: 0 to 10% EtOAc in hexanes) to afford (S)-3-(((1-hydroxy-3-(octadecyloxy)propan-2-yl)oxy)methyl)benzonitrile as clear oil (380 mg, 97%). MS (ESI) m/z $[M+H]^+$ 460.57, $[M+Na]^+$ 482.52.

A solution of (S)-3-(((1-hydroxy-3-(octadecyloxy)propan-2-yl)oxy)methyl)benzonitrile (360 mg, 0.78 mmol) and triethylamine (340 mg, 3.0 mmol) was added to a cooled (0° C.) solution of $POCl_3$ (140 mg, 2.0 mmol) in $CH_2Cl_2$ (5 mL) and stirred for 3 h. The mixture was added to acetone/ice water, stirred 1 h, then extracted with $CH_2Cl_2$. Evaporation of the organic phase gave (R)-2-((3-cyanobenzyl)oxy)-3-(octadecyloxy)propyl dihydrogen phosphate (850 mg, 1.57 mmol, MS (ESI) m/z $[M-H]^-$ 538.46), which was then coupled to RVn (GS-441524)-acetonide (600 mg, 1.8 mmol) using DIC (450 mg, 3.6 mmol), NMI (440 mg, 5.4 mmol) in pyridine (30 mL). Reaction at 35° C. overnight followed by chromatographic purification yielded ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((3-cyanobenzyl)oxy)-3-(octadecyloxy)propyl) hydrogen phosphate (360 mg, 26%) MS (ESI) m/z $[M+Na]^+$875.49.

The acetonide (340 mg, 0.39 mmol) was added to formic acid (7 mL) at room temperature and stirred 3 h. Evaporation of the solvent and purification by flash column chromatography afforded ((2R,3S,4R,5R)-5-(4-aminopyrrolo[2,1-f][1,2,4]triazin-7-yl)-5-cyano-3,4-dihydroxytetrahydrofuran-2-yl)methyl ((R)-2-((3-cyanobenzyl)oxy)-3-(octadecyloxy) propyl) hydrogen phosphate (290 mg, 90%) as an off white solid. $^1$H NMR (400 MHz, $CD_3OD+CDCl_3$) δ 7.71 (s, 1H, H2), 7.70 (s, 1H, —$CH_2$-aryl-H2), 7.62 (d, J=7.8 Hz, 1H, —$CH_2$-aryl-H4), 7.56 (d, J=7.8 Hz, 1H, —$CH_2$-aryl-H5), 7.44 (t, J=7.6 Hz, 1H, —$CH_2$-aryl-H6), 6.96 (d, J=4.5 Hz, 1H, H9), 6.86 (d, J=4.5 Hz, 1H, H8), 4.72 (d, J=5.3 Hz, 1H, H2'), 4.72 (d, J=12.4 Hz, 1H, —$CH_2$-aryl), 4.65 (d, J=12.4 Hz, 1H, —$CH_2$-aryl), 4.39 (q, J=4.4 Hz, 1H, H4'), 4.27 (t, J=5.5 Hz, 1H, H3'), 4.10 (d, J=11.5 Hz, 1H, H5'), 3.89 (d, J=11.2 Hz, 1H, H5'), 3.78 (m, 2H, H3'), 3.71 (q, J=5.0 Hz, 1H, H2'), 3.51-3.40 (m, 2H, H1"), 3.41 (tt, J=5.5, 2.7 Hz, 2H, —$OCH_2CH_2(CH_2)_{15}$—), 1.54 (p, J=6.6 Hz, 2H, —$OCH_2CH_2(CH_2)_{15}$—), 1.26 (br s, 30H, —$OCH_2CH_2$ $(CH_2)_{15}$), 0.89 (t, 3H, —$CH_3$). $^{13}$C NMR (101 MHz, $CD_3OD+CDCl_3$) δ 156.64 (C6), 147.68 (C2), 141.50 (—$CH_2$-aryl-C1), 132.77 (—$CH_2$-aryl-C2), 131.73 (—$CH_2$-aryl-C4), 131.57 (—$CH_2$-aryl-C6), 129.88 (—$CH_2$-aryl-C5), 125.25 (C7), 119.50 (C5), 117.41 (—CN), 112.62 (—CN'), 111.98 (C8), 102.47 (C9), 84.91 (C4'), 80.07 (C1'), 75.57 (C2"), 72.40 (—$CH_2$-aryl), 71.58 (—$OCH_2CH_2$ $(CH_2)_{14}$—), 71.44 (C1"), 71.23 (C3'), 65.73 (C3"), 65.21 (C5'), 32.67 (—$OCH_2CH_2(CH_2)_{14}$—), 31.02-29.33 (m, —$OCH_2CH_2(CH_2)_{14}$—), 26.85 (—$CH_2CH_2CH_3$), 23.37 (—$CH_2CH_2CH_3$), 14.39 (—$CH_3$). HRMS (ESI) m/z $[M-H]^-$ calcd for $C_{41}H_{60}N_6O_9P$, 811.4165. found 811.4178. HPLC purity 98.6%.

Example 13c. Synthesis of 1-O-Octadecyl-2-O-(2-cyanobenzyl)-sn-glyceryl-phospho-RVn (OD(2-CN-Bn)G-P-RVn)

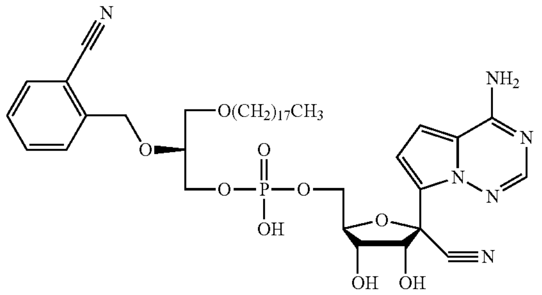

Sodium hydride (60 mg, 2.5 mmol) was added to a cooled (0° C.) solution of (R)-1-(octadecyloxy)-3-(trityloxy)propan-2-ol (587 mg, 1.0 mmol) and tetrabutylammonium iodide (180 mg, 0.5 mmol) in dry THF (30 mL). The mixture was stirred vigorously for 20 minutes. before 2-(bromomethyl)benzonitrile (455 mg, 2.5 mmol) was added, and then the solution was allowed to warm to ambient temperature overnight. The reaction was then quenched with ice (25 mL), diluted with ethyl ether (75 mL), washed with $H_2O$ (2×25 mL) and dried over anhydrous $MgSO_4$. The residue was adsorbed onto silica gel and purified by flash column chromatography (gradient: 0 to 50% EtOAc—in hexanes) to yield (R)-2-(((1-(octadecyloxy)-3-(trityloxy)propan-2-yl) oxy)methyl)benzonitrile (580 mg, 83%) as a white solid. MS (ESI) m/z $[M+Na]^+$ 724.62.

To a solution of (R)-2-(((1-(octadecyloxy)-3-(trityloxy) propan-2-yl)oxy)methyl)benzonitrile (580 mg, 0.83 mmol) in 1:1 $CH_2Cl_2$/MeOH (15 mL) was added p-toluene-sulfonate monohydrate (8 mg, 0.04 mmol) and the mixture was stirred at room temperature until deprotection was complete (approx. 3 h) according to TLC analysis. Saturated aq $NaHCO_3$ (200 mg) was added, and the solvent evaporated under vacuum. The residue was adsorbed onto silica gel and purified by flash column chromatography (gradient: 0 to 10% EtOAc in hexanes) to afford compound (S)-2-(((1-hydroxy-3-(octadecyloxy)propan-2-yl)oxy)methyl)benzonitrile as clear oil (380 mg, 97%). MS (ESI) m/z $[M+H]^+$ 460.57, $[M+Na]^+$482.52.

A solution of (S)-2-(((l-hydroxy-3-(octadecyloxy)propan-2-yl)oxy)methyl)benzonitrile (360 mg, 0.78 mmol) and triethylamine (340 mg, 3.0 mmol) was added to cooled (0° C.) solution of $POCl_3$ (140 mg, 2.0 mmol) in $CH_2Cl_2$ (5 mL) and stirred for 3 h. The mixture was added to ice water, stirred 1 h, then extracted with $CH_2Cl_2$. Evaporation of the organic phase gave phosphate (R)-2-((2-cyanobenzyl)oxy)-3-(octadecyloxy)propyl dihydrogen phosphate (850 mg) which was used without further purification. MS (ESI) m/z $[M-H]^-$ 538.46.

The phosphate (460 mg, 0.85 mmol) was coupled to RVn (GS-441524)-acetonide (280 mg, 0.85 mmol) using DIC (210 mg, 1.7 mmol), NMI (140 mg, 1.7 mmol) in dry pyridine (15 mL). Reaction at 35° C. for 23 h followed by chromatographic purification yielded ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl ((R)-2-((2-cyanobenzyl)oxy)-3-(octadecyloxy)propyl) hydrogen phosphate (190 mg, 22%) MS (ESI) m/z $[M+H]^+$ 851.47.

The coupled acetonide (190 mg, 0.22 mmol) was added to formic acid (5 mL) and stirred 3 h. Formic acid was evaporated and the residue purified by flash column chromatography to give ((2R,3S,4R,5R)-5-(4-aminopyrrolo[2,1-J][1,2,4]triazin-7-yl)-5-cyano-3,4-dihydroxytetrahydrofuran-2-yl)methyl ((R)-2-((2-cyanobenzyl)oxy)-3-(octadecyloxy)propyl) hydrogen phosphate as an off white solid (120 mg, 67%). $^1$H NMR (400 MHz, $CD_3OD+CDCl_3$) δ 7.73 (s, 1H, H2), 7.65 (d, J=7.6, Hz, 2H, —$CH_2$-aryl-H3+H5), 7.59 (td, J=7.6, 1.3 Hz, 1H, H4), 7.39 (td, J=7.6, 1.3 Hz, 1H, H6), 6.97 (d, J=4.6 Hz, 1H, H9), 6.86 (d, J=4.5 Hz, 1H, H8), 4.81 (d, J=5.7 Hz, 1H, H2'), 4.38 (q, J=4.2 Hz, 1H, H4'), 4.28 (t, J=5.3 Hz, 1H, H3'), 4.19-3.84 (m, 2H, H5'), 3.93 (tp, J=10.7, 4.7 Hz, 2H, H3"), 3.85-3.70 (m, 1H, H2"), 3.54 (qd, J=10.6, 5.0 Hz, 2H, H1"), 3.41 (td, J=6.6, 2.7 Hz, 2H, —$OCH_2CH_2(CH_2)_{15}$—), 1.52 (p, J=6.6 Hz, 2H, —$OCH_2CH_2(CH_2)_{15}$—), 1.26 (m, J=7.2 Hz, 30H, —$OCH_2CH_2(CH_2)_{15}$—), 0.89 (t, 3H, —$CH_3$). $^{13}$C NMR (101 MHz, $CD_3OD+CDCl_3$) δ 156.53 (C6), 147.49 (C2), 142.96 (—$CH_2$-aryl-C1), 133.62, (—$CH_2$-aryl-C3), 133.23, (—$CH_2$-aryl-C6), 129.66, (—$CH_2$-aryl-C5), 128.68, (—$CH_2$-aryl-C4), 125.15, (C7), 117.85, (C5), 117.26, (—CN), 111.84, (—CN'), 111.58, (C8), 102.35, (C9), 84.75, (C4'), 79.89 (C1'), 78.99 (C2'), 75.45 (C2"), 72.21 (—$CH_2$-aryl), 71.30 ($OCH_2CH_2(CH_2)_{14}$—), 71.09 (C1"), 70.45 (C3'), 65.73 (C3"), 65.03 (C5'), 32.51 (—$OCH_2CH_2(CH_2)_{14}$—), 31.09-29.39 (m, —$OCH_2CH_2(CH_2)_{14}$—), 26.67, (—$CH_2CH_2CH_3$), 23.21 (—$CH_2CH_2CH_3$), 14.19 (—$CH_3$). HRMS (ESI) m/z $[M+H]^+$ calcd for $C_{41}H_{62}N_6O_9P$, 813.4310. found 8813.4302. HPLC purity 99.4%.

Example 13d. Antiviral Evaluation of Cyanobenzyl Analogs

| | Calu 3 | | | | Huh7.5 | | | |
|---|---|---|---|---|---|---|---|---|
| Compound | $EC_{50}$ (μM) | $EC_{90}$(μM) | $CC_{50}$ (μM) | SI | $EC_{50}$ (μM) | $EC_{90}$ (μM) | $CC_{50}$ (μM) | SI |
| OD(4-CN-Bn)G-P-RVn | 0.043 ± 0.013 | 0.082 ± 0.022 | 60.20 | 1400 | 0.024 ± 0.002 | 0.070 ± 0.010 | 47.2 | 1966 |
| OD(3-CN-Bn)G-P-RVn | 0.034 ± 0.007 | 0.065 ± 0.036 | 61.55 | 1810 | 0.024 ± 0.006 | 0.077 ± 0.017 | 49.6 | 2066 |
| OD(2-CN-Bn)G-P-RVn | 0.091 ± 0.025 | 0.186 ± 0.047 | *82.8 | 909 | 0.0102 ± 0.017 | 0.281 ± 0.030 | >100 | >980 |

The invention claimed is:

1. A compound of the following structure or a pharmaceutically acceptable salt thereof:

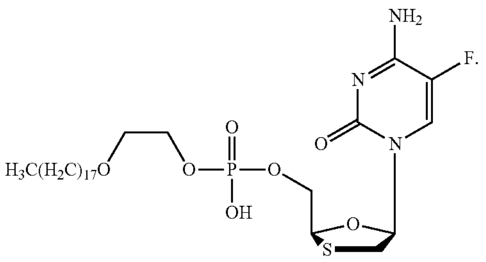

2. A compound of the following structure or a pharmaceutically acceptable salt thereof:

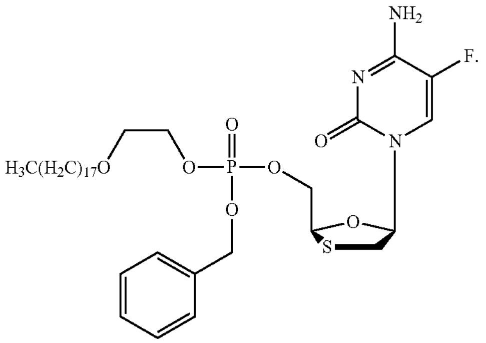

3. A compound of the following structure or a pharmaceutically acceptable salt thereof:

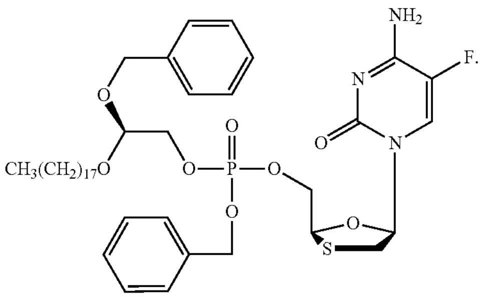

4. A compound of the following structure or a pharmaceutically acceptable salt thereof:

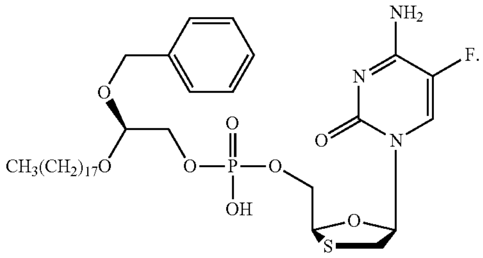

5. A compound of the following structure or a pharmaceutically acceptable salt thereof:

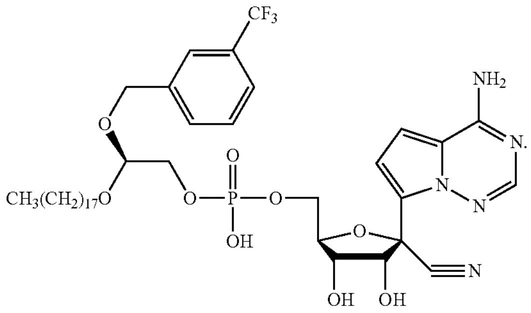

6. A compound of the following structure or a pharmaceutically acceptable salt thereof:

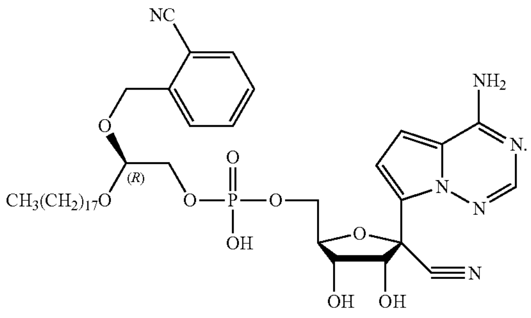

7. A compound of following structure or a pharmaceutically acceptable salt thereof:
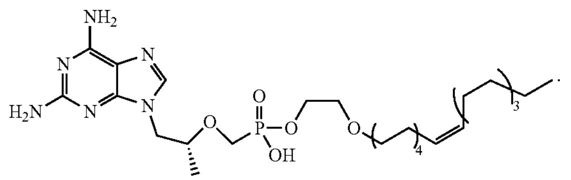
8. A compound the following structure or a pharmaceutically acceptable salt thereof:
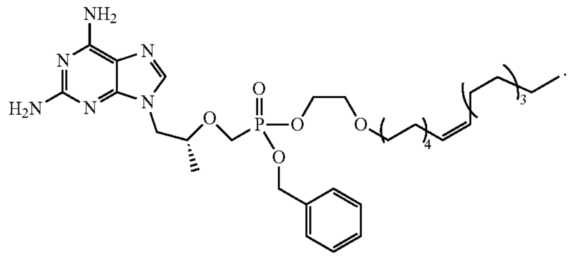
* * * * *

SEQUENCE LISTING

```
Sequence total quantity: 4
SEQ ID NO: 1            moltype = DNA  length = 20
FEATURE                 Location/Qualifiers
source                  1..20
                        mol_type = other DNA
                        organism = synthetic construct
SEQUENCE: 1
gtgttcgaca atggcagcat                                            20

SEQ ID NO: 2            moltype = DNA  length = 19
FEATURE                 Location/Qualifiers
source                  1..19
                        mol_type = other DNA
                        organism = synthetic construct
SEQUENCE: 2
gacaccctcc aggaagcga                                             19

SEQ ID NO: 3            moltype = DNA  length = 30
FEATURE                 Location/Qualifiers
source                  1..30
                        mol_type = other DNA
                        organism = synthetic construct
SEQUENCE: 3
```

-continued

```
cctactaaat taaatgatct ctgctttact                         30

SEQ ID NO: 4          moltype = DNA  length = 21
FEATURE               Location/Qualifiers
source                1..21
                      mol_type = other DNA
                      organism = synthetic construct
SEQUENCE: 4
caagctataa cgcagcctgt a                                  21
```